(12) United States Patent
Muto et al.

(10) Patent No.: US 7,626,042 B2
(45) Date of Patent: Dec. 1, 2009

(54) O-SUBSTITUTED HYDROXYARYL DERIVATIVES

(75) Inventors: Susumu Muto, Tokyo (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 678 days.

(21) Appl. No.: 10/515,622

(22) PCT Filed: Jun. 5, 2003

(86) PCT No.: PCT/JP03/07127

§ 371 (c)(1), (2), (4) Date: Aug. 24, 2005

(87) PCT Pub. No.: WO03/103656

PCT Pub. Date: Dec. 18, 2003

(65) Prior Publication Data
US 2006/0094718 A1 May 4, 2006

(30) Foreign Application Priority Data
Jun. 6, 2002 (JP) ............................. 2002-165482

(51) Int. Cl.
*A61K 31/40* (2006.01)
*A61K 31/445* (2006.01)
*A61K 31/495* (2006.01)
*A61K 31/5375* (2006.01)
*C07D 207/16* (2006.01)
*C07D 241/04* (2006.01)
*C07D 265/30* (2006.01)

(52) U.S. Cl. .................. 548/531; 514/423; 514/330; 514/255.01; 514/237.5; 544/172; 544/389; 546/239

(58) Field of Classification Search ................. 548/531
See application file for complete search history.

(56) References Cited

U.S. PATENT DOCUMENTS

| | | | |
|---|---|---|---|
| 3,331,874 A | 7/1967 | Stecker | |
| 3,906,023 A | 9/1975 | Buchel et al. | |
| 4,358,443 A | 11/1982 | Coburn et al. | |
| 4,560,549 A | 12/1985 | Ritchey | |
| 4,659,710 A | 4/1987 | Sato et al. | |
| 4,661,630 A | 4/1987 | Harigaya et al. | |
| 4,690,924 A | 9/1987 | Sato et al. | |
| 4,725,590 A | 2/1988 | Ritchey | |
| 4,742,083 A | 5/1988 | Ritchey | |
| 4,786,644 A | 11/1988 | Glamkowski et al. | |
| 4,939,133 A | 7/1990 | Connor et al. | |
| 4,952,588 A | 8/1990 | Glamkowski et al. | |
| 4,966,906 A | 10/1990 | Glamkowski et al. | |
| 5,126,341 A | 6/1992 | Suzuki et al. | |
| 5,589,514 A | 12/1996 | Naik et al. | |
| 5,776,977 A | 7/1998 | Naik et al. | |
| 5,811,428 A | 9/1998 | Suto et al. | |
| 5,852,028 A | 12/1998 | Suto et al. | |
| 5,935,966 A | 8/1999 | Suto et al. | |
| 6,002,884 A | 12/1999 | Okumura et al. | |
| 6,117,859 A | 9/2000 | Evans et al. | |
| 6,159,988 A | 12/2000 | Naik et al. | |
| 6,225,329 B1 | 5/2001 | Richter et al. | |
| 6,262,044 B1 | 7/2001 | Møller et al. | |

(Continued)

FOREIGN PATENT DOCUMENTS

DE 996074 6/1965

(Continued)

OTHER PUBLICATIONS

Woohsmann et al., CA 62:45186, 1965.*

(Continued)

*Primary Examiner*—Laura L. Stockton
(74) *Attorney, Agent, or Firm*—Greenblum & Bernstein, P.L.C.

(57) ABSTRACT

A medicament having inhibitory activity against NF-κB activation which comprises as an active ingredient a substance selected from the group consisting of a compound represented by the following general formula (I) and a pharmacologically acceptable salt thereof, and a hydrate thereof and a solvate thereof:

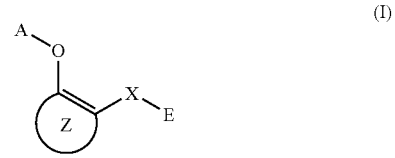

(I)

wherein X represents a connecting group whose number of atoms in a main chain is 2 to 5 (said connecting group may be substituted), "A" represents an acyl group which may be substituted, (provided that unsubstituted acetyl group and unsubstituted acryloyl group are excluded,) or a $C_1$ to $C_6$ alkyl group which may be substituted, or A may bind to connecting group X to form a cyclic structure which may be substituted, "E" represents an aryl group which may be substituted or a heteroaryl group which may be substituted, ring Z represents an arene which may have one or more substituents in addition to the group represented by formula —O-A wherein A has the same meaning as that defined above and the group represented by formula —X-E wherein each of X and E has the same meaning as that defined above, or a heteroarene which may have one or more substituents in addition to the group represented by formula —O-A wherein A has the same meaning as that defined above and the group represented by formula —X-E wherein each of X and E has the same meaning as that defined above.

15 Claims, No Drawings

U.S. PATENT DOCUMENTS

| | | |
|---|---|---|
| 6,410,586 B1 | 6/2002 | Møller et al. |
| 6,414,013 B1 | 7/2002 | Fancelli et al. |
| 6,566,394 B1 | 5/2003 | Takeuchi et al. |
| 6,653,309 B1 | 11/2003 | Saunders et al. |
| 6,734,180 B1 | 5/2004 | Nunokawa et al. |
| 6,787,652 B1 | 9/2004 | Dow et al. |
| 2002/0002199 A1 | 1/2002 | Jeppesen et al. |
| 2002/0019412 A1 | 2/2002 | Andresen et al. |
| 2002/0165398 A1 | 11/2002 | Jeppesen et al. |
| 2003/0069267 A1 | 4/2003 | Moller et al. |
| 2003/0083386 A1 | 5/2003 | Yuan et al. |
| 2004/0048891 A1 | 3/2004 | Kato et al. |
| 2004/0087650 A1 | 5/2004 | Saunders et al. |
| 2004/0122244 A1 | 6/2004 | Suzuki et al. |
| 2004/0157844 A1 | 8/2004 | Dow et al. |
| 2004/0259877 A1 | 12/2004 | Muto et al. |
| 2006/0014811 A1 | 1/2006 | Muto et al. |
| 2006/0019958 A1 | 1/2006 | Muto et al. |

FOREIGN PATENT DOCUMENTS

| | | |
|---|---|---|
| EP | 0 081 782 | 6/1983 |
| EP | 0198456 | 10/1986 |
| EP | 0221211 | 5/1987 |
| EP | 0221346 | 5/1987 |
| EP | 0317991 | 5/1989 |
| EP | 0452873 | 10/1991 |
| EP | 0483881 | 5/1992 |
| EP | 0551849 | 7/1993 |
| EP | 0 931 544 | 7/1999 |
| EP | 1 008 346 | 6/2000 |
| EP | 1018514 | 12/2000 |
| EP | 1 113 000 | 4/2001 |
| EP | 1088819 | 4/2001 |
| EP | 1205478 | 5/2002 |
| EP | 1219596 | 7/2002 |
| EP | 1314712 | 5/2003 |
| EP | 1344525 | 9/2003 |
| EP | 1352650 | 10/2003 |
| EP | 1510210 | 3/2005 |
| EP | 1512396 | 3/2005 |
| EP | 1514544 | 3/2005 |
| EP | 1535610 | 6/2005 |
| EP | 1555018 | 7/2005 |
| FR | 1481713 | 6/1966 |
| GB | 1099865 | 7/1969 |
| GB | 2031410 | 4/1980 |
| JP | 37 000 225 | 1/1962 |
| JP | 52-110835 | 9/1977 |
| JP | 56/073054 A * | 6/1981 |
| JP | 56/156251 A * | 12/1981 |
| JP | 62-30780 | 2/1987 |
| JP | 62-081359 | 4/1987 |
| JP | 63-104912 | 5/1988 |
| JP | 10-87491 | 9/1989 |
| JP | 2-138260 | 5/1990 |
| JP | 11-21225 | 1/1991 |
| JP | 4-217916 | 8/1992 |
| JP | 4-217981 | 8/1992 |
| JP | 6-009476 | 1/1994 |
| JP | 62-99329 | 10/1994 |
| JP | 8-175990 | 7/1996 |
| JP | 9-227561 | 2/1997 |
| JP | 9-169747 | 6/1997 |
| JP | 10-45738 | 2/1998 |
| JP | 11-021243 | 1/1999 |
| JP | 11-217361 | 8/1999 |
| JP | 11 0512399 | 10/1999 |
| JP | 2000-80041 | 3/2000 |
| JP | 2000-169479 | 6/2000 |
| JP | 2001-114768 | 1/2001 |
| JP | 2001-522834 | 11/2001 |
| JP | 2002-506072 | 2/2002 |
| JP | 2004-501146 | 1/2004 |
| WO | 93/24115 | 12/1993 |
| WO | 96/17832 | 6/1996 |
| WO | 97/09315 | 3/1997 |
| WO | 98/20864 | 5/1998 |
| WO | 98/32017 | 7/1998 |
| WO | 99/24404 | 5/1999 |
| WO | 99/40907 | 8/1999 |
| WO | 99/46236 | 9/1999 |
| WO | 99/46244 | 9/1999 |
| WO | 99/46267 | 9/1999 |
| WO | 99/55663 | 11/1999 |
| WO | 99/65449 | 12/1999 |
| WO | 00/03991 | 1/2000 |
| WO | 00/05234 | 5/2000 |
| WO | 00/35442 | 6/2000 |
| WO | 01/00213 | 1/2001 |
| WO | 01/10865 | 2/2001 |
| WO | 01/12588 | 2/2001 |
| WO | 01/44217 | 6/2001 |
| WO | 01/68648 | 9/2001 |
| WO | 01/98290 | 12/2001 |
| WO | 02/16633 | 2/2002 |
| WO | 02/76918 | 3/2002 |
| WO | 02/28819 | 4/2002 |
| WO | 02/49632 | 6/2002 |
| WO | 02/051397 | 7/2002 |
| WO | 02/067919 | 9/2002 |
| WO | 02/076926 | 10/2002 |
| WO | 03/103647 | 12/2003 |
| WO | 03/103648 | 12/2003 |
| WO | 03/103654 | 12/2003 |
| WO | 03/103655 | 12/2003 |
| WO | 03/103657 | 12/2003 |
| WO | 03/103658 | 12/2003 |
| WO | 03/103665 | 12/2003 |
| WO | 2004/006906 | 1/2004 |

OTHER PUBLICATIONS

Vippagunta et al. (Advanced Drug Delivery Reviews, 48 (2001), pp. 3-26.*
Souillac, et al., Characterization of Delivery Systems, Differential Scanning Calorimetry in Encyclopedia of Controlled Drug Delivery, 1999, John Wiley & Sons, pp. 212-227.*
Golub et al., Science, vol. 286, Oct. 15, 1999, pp. 531-537.*
Matsuzaki, et al., "Amer. J. Reproductive Immunol.," 1986, vol. 40, p. 291-294.
Uchiide, et al., "Nikkei Medical," 2002, No. 415, p. 28, with English translation.
Uchiide, et al., "Fertility and Sterility," 2002, vol. 78, No. 4, p. 782-786.
Chegini, "Frontiers in Bioscience," 2002, vol. 7, p. e91-115.
English language Abstract of JP 11-21225, 1999.
Berking, et al., American Journal of Pathology, 2001, vol. 158, No. 3, pp. 943-953.
Singh, et al., Histology and Histopathology, 2000, vol. 15, pp. 843-849.
Recio, et al., Cancer Research, 2002, vol. 62, No. 22, pp. 6724-6730.
Kim, et al., "The Journal of Clinical Investigation," 2001, vol. 108, No. 3, p. 437-446.
Yuan, et al., "Science," 2001, vol. 293, p. 1673-1677.
Macielag, et al., "The Journal of Medicinal Chemistry," 1998, vol. 41, No. 16 p. 2939-2945.
Waisser, et al., "Archiv der Pharmazie," 1998, vol. 331, No. 1, p. 3-6.
Inaba, et al., "Chemical and Pharmaceutical Bulletin," 2000, vol. 48, p. 131-139.
Yamamoto, et al., "Chemical and Pharmaceutical Bulletin," 1996, vol. 44, p. 734-745.
Hunt, et al., "The Journal of the Chemical Society," 1956, p. 3099-3107.

Zwaagstra, et al., "European The Journal of Medicinal Chemistry," 1996, vol. 31, p. 861-874.
Sharanin, et al., "Zhournal Organicheskoi Khimii: Russian The Journal of Organic Chemistry," 1980, vol. 16, p. 2185-2188.
South, et al., "The Journal of Heterocyclic Chemistry ," 1991, vol. 28, p. 1017-1024.
Tajika, "Yakugaku Zasshi: The Journal of the Pharmaceutical Society of Japan," 1961, vol. 81, p. 1456-1459, together with partial English language translation of the same.
Okamiya, "Nihon Kagaku Zasshi," 1962, vol. 83, p. 209-211, together with partial English language translation of the same.
Yura, et al., "Chemical and Pharmaceutical Bulletin," 1962, vol. 10, p. 376-382.
Diez-Barra, et al., "Tetrahedron," 1997, vol. 53, No. 33, p. 11437-11448.
Djuric, et al., "The Journal of Medicinal Chemistry," 2000, vol. 43, No. 16, p. 2975-2981.
English language Abstract of JP 2000-80041, 2000.
English language Abstract of JP 9-169747, 1997.
English language Abstract of JP 63-104912, 1988.
English language Abstract of JP 11-21243, 1999.
Aisen, "Journal of Pain and Symptom Management," 2002, vol. 23, No. 4, p. S35-40.
Baud, et al., "Trends in Cell Biology," 2001, vol. 11, No. 9, p. 372-377.
Clark, et al., "Nucleic Acids Research," 1986, vol. 14, No. 20, p. 7897-7914.
Daidone, et al., "Farmaco," 1989, vol. 44, No. 5, p. 465-473.
DiDonato, et al., "Nature," 1997, vol. 388, p. 548-554.
Dou, et al., "Proceedings of The National Academy of Sciences of the United States of America," 2003, vol. 100, No. 2, p. 721-726.
Dumas, et al., "Bioorganic and Medicinal Chemistry Letters," 1999, vol. 9, No. 17, p. 2531-2536.
Eldar-Finkelman, "Trends of Molecular Medicine," 2002, vol. 8, No. 3, p. 126-132.
Frame, et al., "The Biochemical Journal," 2001, vol. 359, No. PT1, p. 1-16.
Hill, et al., "Cell," 1993, vol. 73, No. 2, p. 395-406.
Hoshi, et al., "Proceedings of The National Academy of Sciences of the United States of America," 1996, vol. 93, No. 7, p. 2719-2723.
Hsi, et al., "The Journal of Organic Chemistry," 1972, vol. 37, No. 22, p. 3427-3431.
Ishige, et al., "Yakugaku Zasshi," 1999, vol. 119, No. 7, p. 510-518.
Kang, et al., "Neuroreport," 2001, vol. 12, No. 7, p. 1449-1452.
Karin, et al., "Proceedings of The National Academy of Science of the United States of America," 1998, vol. 95, No. 16, p. 9067-9069.
Karttunen, et al., "Proceedings of the National Academy of Sciences of United States of America," 1991, vol. 88, No. 9, p. 3972-3976.
Kaytor, et al., "Current Opinion of Neurobiology," 2002, vol. 12, No. 3, p. 275-278.
Klosa, "Journal fuer Praktische Chemie," 1964, vol. 25, No. 1-2, p. 48-55, together with English language Abstract(Chemical Abstract) of the same, col. 4022, paragraph 6-col. 4023.
Konta, et al., "The Journal of Biological Chemistry," 2001, vol. 276, No. 16, p. 12697-12701.
Kopp, et al., "Science," 1994, vol. 265, p. 956-959.
Ladva, et al., "Indian Journal of Chemistry, Section B," 1996, vol. 35B, No. 10, p. 1062-1066.
Lee, et al., "Proceedings of The National Academy of Science of The United States of America," 1998, vol. 95, No. 16, p. 9319-9324.
Madan et al., "Molecular Pharmacology", 2000, vol. 58, No. 3., pp. 526-534.
Mailliot, et al., "Annals of The New York Academy of Science," 2000, vol. 920, p. 107-114.
Manna, et al., "The Journal of Immunology," 1999, vol. 162, No. 4, p. 2095-2102.
Matsumoto, et al., "Bioorganic and Medicinal Chemistry Letters," 2000, vol. 10, No. 9, p. 865-869.
Mattson, et al., "The Journal of Clinical Investigation," 2001, vol. 107, No. 3, p. 247-254.
Mattson, et al., "Cell and Tissue Research," 2000, vol. 301, No. 1, p. 173-187.
Millet, et al., "The Journal of Biological Chemistry," 2000, vol. 275, No. 20, p. 15114-15121.
Mori, et al., "Yakugaku Zasshi," 1975, vol. 95, No. 12, p. 1477-1482, together with an English language abstract of the same.
Nedospasov et al., "Cold Spring Harbor Symposia on Quantitative Biology,"1986, vol. 51, No. 1, p. 611-624.
Noble, et al., "Neuron," 2003, vol. 38, No. 4, p. 555-565.
Ohsugi, et al., "Yakugaku Zasshi," 1976, vol. 96, No. 2, p. 165-169, together with an English language abstract of the same.
Okamoto, 18th Meeting of the Japanese Inflammatory Society, Symposium "Mechanism of Antirheumatic Pharmaceutical Composition and New Development," Tokyo, 2000, Presentation Abstract p. 57, with English translation.
Palanki, et al., "Current Medicinal Chemistry," 2002, vol. 9, No. 2, p. 219-227.
Phlel, et al., "Nature," 2003, vol. 423, No. 6938, p. 435-439.
Piu, et al., "Molecular and Cellular Biology," 2001, vol. 21, No. 9, p. 3012-3024.
Régnier, et al., "Cell," 1997, vol. 90, No. 2, p. 373-383.
Robert-Piessard, et al., "Pharmaceutical Science," 1997, vol. 3, No. 5/6, p. 295-299.
Sato, et al., "The Journal of Biological Chemistry," 2002, vol. 277, No. 44, p. 42060-42065.
Scheinman, et al., "Science," 1995, vol. 270, p. 283-286.
Sullivan, et al., "The Journal of Medicinal Chemistry," 1998, vol. 41, No. 4, p. 413-419.
Umezawa, "Surgery Frontier," 2002, vol. 9, No. 2, p. 88-91, together with English language translation of the same.
Upadhyay, et al., "Indian Journal of Heterocyclic Chemistry," 1991, vol. 1, No. 2, p. 71-74.
Verma, et al., "Genes and Development" 1995, vol. 9 No. 22, p. 2723-2735.
Wajant, "Cellular Signaling," 2001, vol. 13, No. 6, p. 389-400.
West, et al., "Analytical Biochemistry," 1990, vol. 190, No. 2, p. 254-258.
Won, et al., "Neuroscience," 1999, vol. 94, No. 1, p. 83-91.
Woronicz, et al., "Science," 1997, vol. 278, p. 866-869.
Xu, et al., "The Journal of Neuroscience," 2001, vol. 21, No. 1, RC118, 5 pages.
Yamamoto, et al., "The Journal of Clinical Investigation," 2001, vol. 107, No. 2, p. 135-142.
Yin, et al., "Cell," 1998, vol. 93, No. 5, p. 875-884.
Yin, et al., "Nature," 1998, vol. 396, p. 77-80.
Zandi, et al., "Cell," 1997, vol. 91, No. 2, p. 243-252.
English language Abstract of JP 10-45738, 1988.
English language Abstract of JP9-227561, 1997.
English language Abstract of JP 10-87491, 1998.
English language Abstract of JP 11-217361, 1999.
English language Abstract of JP 8-175990, 1996.
English language Abstract of JP 4-217916, 1992.
English language Abstract of JP 62-30780, 1987.
English language Abstract of JP 2000-169479, 2000.
English language Abstract of JP 52-110835, 1977.
U.S. Appl. No. 10/433,619, to Muto et al., 2003.
U.S. Appl. No. 10/515,343, to Muto et al., 2004.
U.S. Appl. No. 10/515,623, to Muto et al., 2004.
U.S. Appl. No. 10/515,341, to Muto et al., 2004.
U.S. Appl. No. 10/515,342, to Muto et al., 2004.
U.S. Appl. No. 10/516,294, to Muto et al., 2004.
U.S. Appl. No. 10/516,692, to Muto et al., 2004.
U.S. Appl. No. 10/516,293, to Muto et al., 2004.
English language abstract of JP 37 000 225, 1962.

* cited by examiner

O-SUBSTITUTED HYDROXYARYL DERIVATIVES

FIELD OF INVENTION

The present invention relates to pharmaceutical compositions having inhibitory activity against the production and release of inflammatory cytokines such as interleukin (IL)-1, IL-6, IL-8 and tumor necrosis factor (TNF-α), and having inhibitory activity against the activation of NF-κB.

BACKGROUND ART

Inflammation is a basic defense mechanism to various infestations, where inflammatory cytokine such as interleukin (IL)-1 and TNF-α (tumor necrosis factor) are known to play important roles. On the basis of the progress of gene analysis of inflammatory cytokines and inflammatory cell adhesion factors, it has been revealed that these cytokines are controlled by a common transcription factor (also called as transcription regulatory factor). This transcription factor is a protein called as NF-κB (also described as NFκB, Nucleic Acids Research, (England), 1986, Vol. 14, No. 20, p. 7897-1914; Cold Spring Harbor Symposia on Quantitative Biology, (USA), 1986, Vol. 51, No. 1, p. 611-624).

This NF-κB is a hetero dimer (also called as complex) of p65 (also called as Rel A) and p50 (also called as NF-κB-1), usually binds to I-κB when external stimulation does not exist, and exists in cytoplasm as an inactive type. I-κB is phosphorated by various external stimulations such as oxidative stress, cytokine, lipopolysaccharide, virus, UV, free radical, protein kinase C to become ubiquitin, and then decomposed by proteasome (Genes & Development, (USA), 1995, Vol. 9, No. 22, p. 2723-2735). NF-κB separated from I-κB immediately move into nucleus, and plays a role as a transcription factor by binding to promoter region which has recognition sequence of NF-κB.

In 1997, phosphoenzyme (called as IκB kinase abbreviated as "IKK"), which participates in phosphorylation of I-κB, was identified (Nature, (England), 1997, Vol. 388, p. 548-554; Cell, (USA), 1997, Vol. 90, No. 2, p. 373-383). IKK-α (also called as IKK1) and IKK-β (also called as IKK2) which resemble each other exist among a class of IKK, and they are known to form a complex to bind directly to IκB and phosphorize IκB (Science, (USA), 1997, Vol. 278, p. 866-869; Cell, (USA), 1997, Vol. 91, No. 2, p. 243-252).

Recently, a mechanism except cyclooxygenase inhibition is suggested for aspirin which is a widely used anti-inflammatory agent, which is known to be based on inhibition of NF-κB activation (Science, (USA), 1994, Vol. 265, p. 956-959). Moreover, it was revealed that aspirin regulates release and activation of NF-κB by binding reversibly to IKK-β which is I-κB kinase competing with ATP and by inhibiting phosphorylation of I-κB (Nature, (England), 1998, Vol. 396, p. 77-80). However, a huge amount of aspirin needs to be administered to sufficiently suppress NF-κB activation, and as a result, side effects such as gastrointestinal disorders by prostaglandin synthesis inhibition and increase of bleeding tendency by anticoagulation action are expected to be caused with high probability.

Besides aspirin, some pharmaceuticals are known to have inhibitory action against NF-κB activation. Glucocorticoids (steroid hormones) such as dexamethasone suppress NF-κB activation by binding to their receptors (called as "glucocorticoid receptor," Science, (USA), 1995, Vol. 270, p. 283-286). However, long term use is not suitable, because they have serious side effects such as aggravation of an infectious disease, generation of peptic ulcer, degradation of bone density, and central action. Leflunomide as an immunosuppressive agent, an isoxazole-type agent, also has NF-κB inhibitory action (Journal of Immunology, (USA), 1999, Vol. 162, No. 4, p. 2095-2102). However, this drug is also not suitable for long term use due to serious side effects. Furthermore, substituted pyrimidine derivatives (Japanese Patent Publication of International Application (KOHYO) No. (Hei) 11-512399, and Journal of Medicinal Chemistry, (USA), 1998, Vol. 41, No. 4, p. 413-419), xanthine derivatives (Japanese Patent Unexamined Publication (KOKAI) No. (Hei) 9-227561), isoquinoline derivatives (Japanese Patent Unexamined Publication (KOKAI) No. (Hei) 10-87491), indan derivatives (International Publication WO00/05234 pamphlet), epoxyquinomycin C, D, and their derivatives (Japanese Patent Unexamined Publication (KOKAI) No. (Hei) 10-45738, and Bioorganic & Medicinal Chemistry Letters, (England), 2000, Vol. 10, No. 9, p. 865-869) are known as inhibitors against NF-κB activation.

As for salicylamide derivatives, N-phenylsalicylamide derivatives are disclosed as a plant growth inhibitor in the specification of U.S. Pat. No. 4,358,443. Moreover, as medicaments, said derivatives are disclosed as anti-inflammatory agents in the specification of European Patent No. 0,221,211, Japanese Patent Unexamined Publication (KOKAI) No. (Sho) 62-99329, and the specification of U.S. Pat. No. 6,117,859. N-Phenylsalicylamide derivatives having NF-κB inhibitory action are disclosed in the pamphlet of International Publication WO99/65449. However, only a small number of compounds were subjected to measurements of anti-inflammatory activity or inhibitory activity against NF-κB. Moreover, as for a structure of the aniline moiety, studies were made merely on limited kinds of substituents and substituting positions. The pamphlet of International Publication WO02/49632 discloses that hydroxyaryl derivatives including N-arylsalicylamide derivatives have NF-κB inhibitory action. However, the descriptions of O-substituted compounds of hydroxyaryl derivatives are limited to O-acetyl compounds of N-substituted salicylamides. The pamphlet of International Publication WO02/076918 discloses N-phenylsalicylamide derivatives having NF-κB inhibitory action. The pamphlet of International Publication WO02/051397 discloses N-phenylsalicylamide derivatives as inhibitors against the production of cytokines.

DISCLOSURE OF THE INVENTION

An object of the present invention is to provide a medicament having inhibitory activity against the activation of NF-κB.

The inventors of the present invention synthesized O-substituted compounds for various hydroxyaryl derivatives and studied inhibitory activity of those compounds against NF-κB activation by a reporter assay method under TNF-α stimulation. As a result, they found that O-substituted hydroxyaryl derivatives had potent inhibitory activity against NF-κB activation. The present invention was achieved on the basis of these findings.

The present invention thus provides:

(1) A medicament having inhibitory activity against NF-κB activation which comprises as an active ingredient a substance selected from the group consisting of a compound represented by the general formula (I) and a pharmacologically acceptable salt thereof, and a hydrate thereof and a solvate thereof:

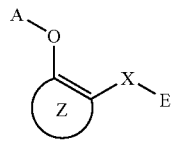

(I)

wherein X represents a connecting group whose number of atoms in a main chain is 2 to 5 (said connecting group may be substituted), A represents an acyl group which may be substituted, (provided that unsubstituted acetyl group and unsubstituted acryloyl group are excluded,) or a $C_1$ to $C_6$ alkyl group which may be substituted, or A may bind to connecting group X to form a cyclic structure which may be substituted, E represents an aryl group which may be substituted or a heteroaryl group which may be substituted, ring Z represents an arene which may have one or more substituents in addition to the group represented by formula —O-A wherein A has the same meaning as that defined above and the group represented by formula —X-E wherein each of X and E has the same meaning as that defined above, or a heteroarene which may have one or more substituents in addition to the group represented by formula —O-A wherein A has the same meaning as that defined above and the group represented by formula —X-E wherein each of X and E has the same meaning as that defined above.

Examples of preferred medicaments of the present invention include:

(2) the aforementioned medicament which comprises as an active ingredient a substance selected from the group consisting of the compound and a pharmacologically acceptable salt thereof, and a hydrate thereof and a solvate thereof, wherein X is a group selected from the following connecting group α (said group may be substituted):

[Connecting group α] The groups of the following formulas:

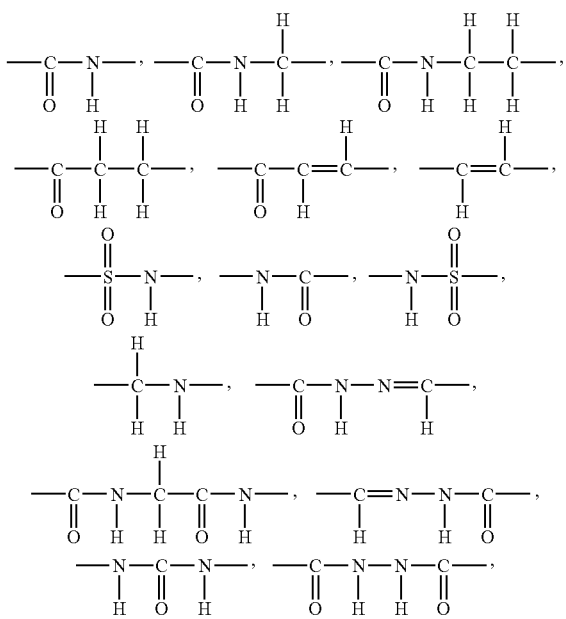

wherein a bond at the left end binds to ring Z and a bond at the right end binds to E;

(3) the aforementioned medicament which comprises as an active ingredient a substance selected from the group consisting of the compound and a pharmacologically acceptable salt thereof, and a hydrate thereof and a solvate thereof, wherein X is a group represented by the following formula (said group may be substituted):

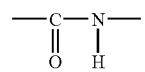

wherein a bond at the left end binds to ring Z and a bond at the right end binds to E;

(4) the aforementioned medicament which comprises as an active ingredient a substance selected from the group consisting of the compound and a pharmacologically acceptable salt thereof, and a hydrate thereof and a solvate thereof, wherein A is a group selected from the following substituent group ω:

[Substituent group ω] a hydrocarbon-carbonyl group which may be substituted, a heterocyclic ring-carbonyl group which may be substituted, a hydrocarbon-oxy-carbonyl group which may be substituted, a hydrocarbon-sulfonyl group which may be substituted, a sulfamoyl group which may be substituted, a sulfo group which may be substituted, a phosphono group which may be substituted, and a carbamoyl group which may be substituted provided that unsubstituted acetyl group and unsubstituted acryloyl group are excluded;

(5) the aforementioned medicament which comprises as an active ingredient a substance selected from the group consisting of the compound and a pharmacologically acceptable salt thereof, and a hydrate thereof and a solvate thereof, wherein ring Z is a $C_6$ to $C_{10}$ arene which may have one or more substituents in addition to the group represented by formula —O-A wherein A has the same meaning as that defined in the general formula (I) and the group represented by formula —X-E wherein each of X and E has the same meaning as that defined in the general formula (I);

(6) the aforementioned medicament which comprises as an active ingredient a substance selected from the group consisting of the compound and a pharmacologically acceptable salt thereof, and a hydrate thereof and a solvate thereof, wherein ring Z is a benzene ring which may have one or more substituents in addition to the group represented by formula —O-A wherein A has the same meaning as that defined in the general formula (I) and the group represented by formula —X-E wherein each of X and E has the same meaning as that defined in the general formula (I);

(7) the aforementioned medicament which comprises as an active ingredient a substance selected from the group consisting of the compound and a pharmacologically acceptable salt thereof, and a hydrate thereof and a solvate thereof, wherein ring Z is a benzene ring which is substituted with halogen atom(s) in addition to the group represented by formula —O-A wherein A has the same meaning as that defined in the general formula (I) and the group represented by formula —X-E wherein each of X and E has the same meaning as that defined in the general formula (I);

(8) the aforementioned medicament which comprises as an active ingredient a substance selected from the group consisting of the compound and a pharmacologically acceptable salt thereof, and a hydrate thereof and a solvate thereof, wherein ring Z is a naphthalene ring which may have one or more substituents in addition to the group represented by formula —O-A wherein A has the same meaning as that defined in the general formula (I) and the group represented by formula —X-E wherein each of X and E has the same meaning as that defined in the general formula (I);

(9) the aforementioned medicament which comprises as an active ingredient a substance selected from the group consisting of the compound and a pharmacologically acceptable salt thereof, and a hydrate thereof and a solvate thereof, wherein E is a $C_6$ to $C_{10}$ aryl group which may be substituted or a 5-membered heteroaryl group which may be substituted;

(10) the aforementioned medicament which comprises as an active ingredient a substance selected from the group consisting of the compound and a pharmacologically acceptable salt thereof, and a hydrate thereof and a solvate thereof, wherein E is a phenyl group which may be substituted;

(11) the aforementioned medicament which comprises as an active ingredient a substance selected from the group consisting of the compound and a pharmacologically acceptable salt thereof, and a hydrate thereof and a solvate thereof, wherein E is 3,5-bis(trifluoromethyl)phenyl group;

(12) the aforementioned medicament which comprises as an active ingredient a substance selected from the group consisting of the compound and a pharmacologically acceptable salt thereof, and a hydrate thereof and a solvate thereof, wherein E is a thiazolyl group which may be substituted.

From another aspect, the present invention provides: use of each of the aforementioned substances for manufacture of the medicament according to the aforementioned (1) to (12); an inhibitor which comprises each of the aforementioned substances against the activation of NF-κB; and a method for inhibiting activation of NF-κB in a mammal including a human, which comprises the step of administering effective amount of each of the aforementioned substances to a mammal including a human.

The present invention further provides:

(1) a compound represented by the general formula (I-1) or a salt thereof, or a hydrate thereof or a solvate thereof:

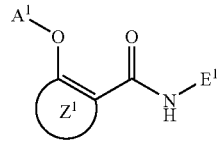

(I-1)

wherein $A^1$ represents an acyl group which may be substituted, (provided that unsubstituted acetyl group and unsubstituted acryloyl group are excluded,) or an acyl-oxy-methylene group which may be substituted, $E^1$ represents an aryl group which may be substituted or a heteroaryl group which may be substituted, ring $Z^1$ represents an arene which may have one or more substituents in addition to the group represented by formula —O-$A^1$ wherein A has the same meaning as that defined above and the group represented by formula —CONH-$E^1$ wherein $E^1$ has the same meaning as that defined above, or a heteroarene which may have one or more substituents in addition to the group represented by formula —O-$A^1$ wherein $A^1$ has the same meaning as that defined above and the group represented by formula —CONH-$E^1$ wherein $E^1$ has the same meaning as that defined above.

According to preferred embodiments of the present invention, provided are:

(2) the aforementioned compound or a salt thereof, or a hydrate thereof or a solvate thereof, wherein $A^1$ is a N,N-di-substituted carbamoyl group (two substituents of said carbamoyl group may combine to each other, together with the nitrogen atom to which they bind, to form a nitrogen-containing heterocyclic group which may be substituted);

(3) the aforementioned compound or a salt thereof, or a hydrate thereof or a solvate thereof, wherein $A^1$ is (morpholin-4-yl)carbonyl group;

(4) the aforementioned compound or a salt thereof, or a hydrate thereof or a solvate thereof, wherein $A^1$ is a phosphono group which may be substituted;

(5) the aforementioned compound or a salt thereof, or a hydrate thereof or a solvate thereof, wherein ring $Z^1$ is a benzene ring which may have one or more substituents in addition to the group represented by formula —O-$A^1$ wherein $A^1$ has the same meaning as that defined in the general formula (I-1) and the group represented by formula —CONH-$E^1$ wherein $E^1$ has the same meaning as that defined in the general formula (I-1);

(6) the aforementioned compound or a salt thereof, or a hydrate thereof or a solvate thereof, wherein ring $Z^1$ is a benzene ring which is substituted with halogen atom(s) in addition to the group represented by formula —O-$A^1$ wherein $A^1$ has the same meaning as that defined in the general formula (I-1) and the group represented by formula —CONH-$E^1$ wherein $E^1$ has the same meaning as that defined in the general formula (I-1);

(7) the aforementioned compound or a salt thereof, or a hydrate thereof or a solvate thereof, wherein ring $Z^1$ is a naphthalene ring which may have one or more substituents in addition to the group represented by formula —O-$A^1$ wherein $A^1$ has the same meaning as that defined in the general formula (I-1) and the group represented by formula —CONH-$E^1$ wherein $E^1$ has the same meaning as that defined in the general formula (I-1);

(8) the aforementioned compound or a salt thereof, or a hydrate thereof or a solvate thereof, wherein $E^1$ is a phenyl group which may be substituted;

(9) the aforementioned compound or a salt thereof, or a hydrate thereof or a solvate thereof, wherein $E^1$ is a 2,5-di-substituted phenyl group or a 3,5-di-substituted phenyl group;

(10) the aforementioned compound or a salt thereof, or a hydrate thereof or a solvate thereof, wherein $E^1$ is 3,5-bis (trifluoromethyl)phenyl group; and

(11) the aforementioned compound or a salt thereof, or a hydrate thereof or a solvate thereof, wherein $E^1$ is a thiazolyl group which may be substituted.

From another aspect, the present invention provides: a medicament which comprises the compound according to the aforementioned (1) to (11) or a pharmacologically acceptable salt thereof, or a hydrate thereof or a solvate thereof; use of the compound according to the aforementioned (1) to (11) or a pharmacologically acceptable salt thereof, or a hydrate thereof or a solvate thereof for manufacture of the medicament according to the aforementioned (1) to (11); a medicament having inhibitory activity against NF-κB activation which comprises as an active ingredient the compound according to the aforementioned (1) to (11) or a pharmacologically acceptable salt thereof, or a hydrate thereof or a solvate thereof; an inhibitor against the activation of NF-κB which comprises as an active ingredient the compound according to the aforementioned (1) to (11) or a pharmacologically acceptable salt thereof, or a hydrate thereof or a solvate thereof; and a method for inhibiting activation of NF-κB in a mammal including a human, which comprises the step of administering effective amount of the compound according to the aforementioned (1) to (11) or a pharmacologically acceptable salt thereof, or a hydrate thereof or a solvate thereof to a mammal including a human.

BEST MODE FOR CARRYING OUT THE INVENTION

Reference to the disclosure of the pamphlet of International Publication WO02/49632 is useful for better understanding of the present invention. The entire disclosure of the aforementioned pamphlet of International Publication WO02/49632 is incorporated by reference in the disclosures of the present specification.

The terms used in the present specification have the following meanings.

As the halogen atom, any of fluorine atom, chlorine atom, bromine atom, or iodine atom may be used unless otherwise specifically referred to.

Examples of the hydrocarbon group include, for example, an aliphatic hydrocarbon group, an aryl group, an arylene group, an aralkyl group, a bridged cyclic hydrocarbon group, a spiro cyclic hydrocarbon group, and a terpene hydrocarbon.

Examples of the aliphatic hydrocarbon group include, for example, alkyl group, alkenyl group, alkynyl group, alkylene group, alkenylene group, alkylidene group and the like which are straight chain or branched chain monovalent or bivalent acyclic hydrocarbon groups; cycloalkyl group, cycloalkenyl group, cycloalkanedienyl group, cycloalkyl-alkyl group, cycloalkylene group, and cycloalkenylene group, which are saturated or unsaturated monovalent or bivalent alicyclic hydrocarbon groups.

Examples of the alkyl group include, for example, methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-ethylbutyl, 1-ethyl-1-methylpropyl, n-heptyl, n-octyl, n-nonyl, n-decyl, n-undecyl, n-dodecyl, n-tridecyl, n-tetradecyl, and n-pentadecyl, which are $C_1$ to $C_{15}$ straight chain or branched chain alkyl groups.

Examples of the alkenyl group include, for example, vinyl, prop-1-en-1-yl, allyl, isopropenyl, but-1-en-1-yl, but-2-en-1-yl, but-3-en-1-yl, 2-methylprop-2-en-1-yl, 1-methylprop-2-en-1-yl, pent-1-en-1-yl, pent-2-en-1-yl, pent-3-en-1-yl, pent-4-en-1-yl, 3-methylbut-2-en-1-yl, 3-methylbut-3-en-1-yl, hex-1-en-1-yl, hex-2-en-1-yl, hex-3-en-1-yl, hex-4-en-1-yl, hex-5-en-1-yl, 4-methylpent-3-en-1-yl, 4-methylpent-3-en-1-yl, hept-1-en-1-yl, hept-6-en-1-yl, oct-1-en-1-yl, oct-7-en-1-yl, non-1-en-1-yl, non-8-en-1-yl, dec-1-en-1-yl, dec-9-en-1-yl, undec-1-en-1-yl, undec-10-en-1-yl, dodec-1-en-1-yl, dodec-11-en-1-yl, tridec-1-en-1-yl, tridec-12-en-1-yl, tetradec-1-en-1-yl, tetradec-13-en-1-yl, pentadec-1-en-1-yl, and pentadec-14-en-1-yl, which are $C_2$ to $C_{15}$ straight chain or branched chain alkenyl groups.

Examples of the alkynyl group include, for example, ethynyl, prop-1-yn-1-yl, prop-2-yn-1-yl, but-1-yn-1-yl, but-3-yn-1-yl, 1-methylprop-2-yn-1-yl, pent-1-yn-1-yl, pent-4-yn-1-yl, hex-1-yn-1-yl, hex-5-yn-1-yl, hept-1-yn-1-yl, hept-6-yn-1-yl, oct-1-yn-1-yl, oct-7-yn-1-yl, non-1-yn-1-yl, non-8-yn-1-yl, dec-1-yn-1-yl, dec-9-yn-1-yl, undec-1-yn-1-yl, undec-10-yn-1-yl, dodec-1-yn-1-yl, dodec-11-yn-1-yl, tridec-1-yn-1-yl, tridec-12-yn-1-yl, tetradec-1-yn-1-yl, tetradec-13-yn-1-yl, pentadec-1-yn-1-yl, and pentadec-14-yn-1-yl, which are $C_2$ to $C_{15}$ straight chain or branched chain alkynyl groups.

Examples of the alkylene group include, for example, methylene, ethylene, ethane-1,1-diyl, propane-1,3-diyl, propane-1,2-diyl, propane-2,2-diyl, butane-1,4-diyl, pentane-1,5-diyl, hexane-1,6-diyl, and 1,1,4,4-tetramethylbutane-1,4-diyl group, which are $C_1$ to $C_8$ straight chain or branched chain alkylene groups.

Examples of the alkenylene group include, for example, ethene-1,2-diyl, propene-1,3-diyl, but-1-ene-1,4-diyl, but-2-ene-1,4-diyl, 2-methylpropene-1,3-diyl, pent-2-ene-1,5-diyl, and hex-3-ene-1,6-diyl, which are $C_1$ to $C_6$ straight chain or branched chain alkylene groups.

Examples of the alkylidene group include, for example, methylidene, ethylidene, propylidene, isopropylidene, butylidene, pentylidene, and hexylidene, which are $C_1$ to $C_6$ straight chain or branched chain alkylidene groups.

Examples of the cycloalkyl group include, for example, cyclopropyl, cyclobutyl, cyclopentyl, cyclohexyl, cycloheptyl, and cyclooctyl, which are $C_3$ to $C_8$ cycloalkyl groups.

The aforementioned cycloalkyl group may be fused with benzene ring, naphthalene ring and the like, and examples include, for example, 1-indanyl, 2-indanyl, 1,2,3,4-tetrahydronaphthalen-1-yl, and 1,2,3,4-tetrahydronaphthalen-2-yl.

Examples of the cycloalkenyl group include, for example, 2-cyclopropen-1-yl, 2-cyclobuten-1-yl, 2-cyclopenten-1-yl, 3-cyclopenten-1-yl, 2-cyclohexen-1-yl, 3-cyclohexen-1-yl, 1-cyclobuten-1-yl, and 1-cyclopenten-1-yl, which are $C_3$ to $C_6$ cycloalkenyl groups.

The aforementioned cycloalkenyl group may be fused with benzene ring, naphthalene ring and the like, and examples include, for example, 1-indanyl, 2-indanyl, 1,2,3,4-tetrahydronaphthalen-1-yl, 1,2,3,4-tetrahydronaphthalen-2-yl, 1-indenyl, and 2-indenyl.

Examples of the cycloalkanedienyl group include, for example, 2,4-cyclopentadien-1-yl, 2,4-cyclohexanedien-1-yl, and 2,5-cyclohexanedien-1-yl, which are $C_5$ to $C_6$ cycloalkanedienyl groups.

The aforementioned cycloalkanedienyl group may be fused with benzene ring, naphthalene ring and the like, and examples include, for example, 1-indenyl and 2-indenyl.

Examples of the cycloalkyl-alkyl group include the groups in which one hydrogen atom of the alkyl group is substituted with a cycloalkyl group, and include, for example, cyclopropylmethyl, 1-cyclopropylethyl, 2-cyclopropylethyl, 3-cyclopropylpropyl, 4-cyclopropylbutyl, 5-cyclopropylpentyl, 6-cyclopropylhexyl, cyclobutylmethyl, cyclopentylmethyl, cyclobutylmethyl, cyclopentylmethyl, cyclohexylmethyl, cyclohexylpropyl, cyclohexylbutyl, cycloheptylmethyl, cyclooctylmethyl, and 6-cyclooctylhexyl, which are $C_4$ to $C_{14}$ cycloalkyl-alkyl groups.

Examples of the cycloalkylene group include, for example, cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,1-diyl, cycloheptane-1,2-diyl, cyclooctane-1,1-diyl, and cyclooctane-1,2-diyl, which are $C_3$ to $C_8$ cycloalkylene groups.

Examples of the cycloalkenylene group include, for example, 2-cyclopropene-1,1-diyl, 2-cyclobutene-1,1-diyl, 2-cyclopentene-1,1-diyl, 3-cyclopentene-1,1-diyl, 2-cyclohexene-1,1-diyl, 2-cyclohexene-1,2-diyl, 2-cyclohexene-1,4-diyl, 3-cyclohexene-1,1-diyl, 1-cyclobutene-1,2-diyl, 1-cyclopentene-1,2-diyl, and 1-cyclohexene-1,2-diyl, which are $C_3$ to $C_6$ cycloalkenylene groups.

Examples of the aryl group include a monocyclic or a fused polycyclic aromatic hydrocarbon group, and include, for example, phenyl, 1-naphthyl, 2-naphthyl, anthryl, phenanthryl, and acenaphthylenyl, which are $C_6$ to $C_{14}$ aryl groups.

The aforementioned aryl group may be fused with the aforementioned $C_3$ to $C_8$ cycloalkyl group, $C_3$ to $C_6$ cycloalkenyl group, $C_5$ to $C_6$ cycloalkanedienyl group or the like, and examples include, for example, 4-indanyl, 5-indanyl, 1,2,3,4-tetrahydronaphthalen-5-yl, 1,2,3,4-tetrahydronaphthalen-6-yl, 3-acenaphthenyl, 4-acenaphthenyl, inden-4-yl, inden-5-yl, inden-6-yl, inden-7-yl, 4-phenalenyl, 5-phenalenyl, 6-phenalenyl, 7-phenalenyl, 8-phenalenyl, and 9-phenalenyl.

Examples of the arylene group include, for example, 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,4-diyl, naphthalene-2,5-diyl, naphthalene-2,6-diyl, naphthalene-2,7-diyl, naphthalene-2,8-diyl, and anthracene-1,4-diyl, which are $C_6$ to $C_{14}$ arylene groups.

Examples of the aralkyl group include the groups in which one hydrogen atom of the alkyl group is substituted with an aryl group, and include, for example, benzyl, 1-naphthylmethyl, 2-naphthylmethyl, anthracenylmethyl, phenanthrenylmethyl, acenaphthylenylmethyl, diphenylmethyl, 1-phenethyl, 2-phenethyl, 1-(1-naphthyl)ethyl, 1-(2-naphthyl)ethyl, 2-(1-naphthyl)ethyl, 2-(2-naphthyl)ethyl, 3-phenylpropyl, 3-(1-naphthyl)propyl, 3-(2-naphthyl)propyl, 4-phenylbutyl, 4-(1-naphthyl)butyl, 4-(2-naphthyl)butyl, 5-phenylpentyl, 5-(1-naphthyl)pentyl, 5-(2-naphthyl)pentyl, 6-phenylhexyl, 6-(1-naphthyl)hexyl, and 6-(2-naphthyl)hexyl, which are $C_7$ to $C_{16}$ aralkyl groups.

Examples of the bridged cyclic hydrocarbon group include, for example, bicyclo[2.1.0]pentyl, bicyclo[2.2.1]heptyl, bicyclo[2.2.1]octyl, and adamantyl.

Examples of the spiro cyclic hydrocarbon group include, for example, spiro[3.4]octyl, and spiro[4.5]deca-1,6-dienyl.

Examples of the terpene hydrocarbon include, for example, geranyl, neryl, linalyl, phytyl, menthyl, and bornyl.

Examples of the halogenated alkyl group include the groups in which one hydrogen atom of the alkyl group is substituted with a halogen atom, and include, for example, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, 2,2,2-trifluoroethyl, pentafluoroethyl, 3,3,3-trifluoropropyl, heptafluoropropyl, heptafluoroisopropyl, nonafluorobutyl, and perfluorohexyl, which are $C_1$ to $C_6$ straight chain or branched chain halogenated alkyl groups substituted with 1 to 13 halogen atoms.

Examples of the heterocyclic group include, for example, a monocyclic or a fused polycyclic hetero aryl group which comprises at least one atom of 1 to 3 kinds of hetero atoms selected from oxygen atom, sulfur atom, nitrogen atom and the like as ring-constituting atoms (ring forming atoms), and a monocyclic or a fused polycyclic non-aromatic heterocyclic group which comprises at least one atom of 1 to 3 kinds of hetero atoms selected from oxygen atom, sulfur atom, nitrogen atom and the like as ring-constituting atoms (ring forming atoms).

Examples of the monocyclic heteroaryl group include, for example, 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1-imidazolyl, 2-imidazolyl, 4-imidazolyl, 5-imidazolyl, 1-pyrazolyl, 3-pyrazolyl, 4-pyrazolyl, 5-pyrazolyl, (1,2,3-oxadiazol)-4-yl, (1,2,3-oxadiazol)-5-yl, (1,2,4-oxadiazol)-3-yl, (1,2,4-oxadiazol)-5-yl, (1,2,5-oxadiazol)-3-yl, (1,2,5-oxadiazol)-4-yl, (1,3,4-oxadiazol)-2-yl, (1,3,4-oxadiazol)-5-yl, furazanyl, (1,2,3-thiadiazol)-4-yl, (1,2,3-thiadiazol)-5-yl, (1,2,4-thiadiazol)-3-yl, (1,2,4-thiadiazol)-5-yl, (1,2,5-thiadiazol)-3-yl, (1,2,5-thiadiazol)-4-yl, (1,3,4-thiadiazolyl)-2-yl, (1,3,4-thiadiazolyl)-5-yl, (1H-1,2,3-triazol)-1-yl, (1H-1,2,3-triazol)-4-yl, (1H-1,2,3-triazol)-5-yl, (2H-1,2,3-triazol)-2-yl, (2H-1,2,3-triazol)-4-yl, (1H-1,2,4-triazol)-1-yl, (1H-1,2,4-triazol)-3-yl, (1H-1,2,4-triazol)-5-yl, (4H-1,2,4-triazol)-3-yl, (4H-1,2,4-triazol)-4-yl, (1H-tetrazol)-1-yl, (1H-tetrazol)-5-yl, (2H-tetrazol)-2-yl, (2H-tetrazol)-5-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, (1,2,3-triazin)-4-yl, (1,2,3-triazin)-5-yl, (1,2,4-triazin)-3-yl, (1,2,4-triazin)-5-yl, (1,2,4-triazin)-6-yl, (1,3,5-triazin)-2-yl, 1-azepinyl, 2-azepinyl, 3-azepinyl, 4-azepinyl, (1,4-oxazepin)-2-yl, (1,4-oxazepin)-3-yl, (1,4-oxazepin)-5-yl, (1,4-oxazepin)-6-yl, (1,4-oxazepin)-7-yl, (1,4-thiazepin)-2-yl, (1,4-thiazepin)-3-yl, (1,4-thiazepin)-5-yl, (1,4-thiazepin)-6-yl, and (1,4-thiazepin)-7-yl, which are 5 to 7-membered monocyclic heteroaryl groups.

Examples of the fused polycyclic heteroaryl group include, for example, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzo[b]thienyl, 3-benzo[b]thienyl, 4-benzo[b]thienyl, 5-benzo[b]thienyl, 6-benzo[b]thienyl, 7-benzo[b]thienyl, 1-benzo[c]thienyl, 4-benzo[c]thienyl, 5-benzo[c]thienyl, 1-indolyl, 1-indolyl, 2-indolyl, 3-indolyl, 4-indolyl, 5-indolyl, 6-indolyl, 7-indolyl, (2H-isoindol)-1-yl, (2H-isoindol)-2-yl, (2H-isoindol)-4-yl, (2H-isoindol)-5-yl, (1H-indazol)-1-yl, (1H-indazol)-3-yl, (1H-indazol)-4-yl, (1H-indazol)-5-yl, (1H-indazol)-6-yl, (1H-indazol)-7-yl, (2H-indazol)-1-yl, (2H-indazol)-2-yl, (2H-indazol)-4-yl, (2H-indazol)-5-yl, 2-benzoxazolyl, 2-benzoxazolyl, 4-benzoxazolyl, 5-benzoxazolyl, 6-benzoxazolyl, 7-benzoxazolyl, (1,2-benzisoxazol)-3-yl, (1,2-benzisoxazol)-4-yl, (1,2-benzisoxazol)-5-yl, (1,2-benzisoxazol)-6-yl, (1,2-benzisoxazol)-7-yl, (2,1-benzisoxazol)-3-yl, (2,1-benzisoxazol)-4-yl, (2,1-benzisoxazol)-5-yl, (2,1-benzisoxazol)-6-yl, (2,1-benzisoxazol)-7-yl, 2-benzothiazolyl, 4-benzothiazolyl, 5-benzothiazolyl, 6-benzothiazolyl, 7-benzothiazolyl, (1,2-benzisothiazol)-3-yl, (1,2-benzisothiazol)-4-yl, (1,2-benzisothiazol)-5-yl, (1,2-benzisothiazol)-6-yl, (1,2-benzisothiazol)-7-yl, (2,1-benzisothiazol)-3-yl, (2,1-benzisothiazol)-4-yl, (2,1-benzisothiazol)-5-yl, (2,1-benzisothiazol)-6-yl, (2,1-benzisothiazol)-7-yl, (1,2,3-benzoxadiazol)-4-yl, (1,2,3-benzoxadiazol)-5-yl, (1,2,3-benzoxadiazol)-6-yl, (1,2,3-benzoxadiazol)-7-yl, (2,1,3-benzoxadiazol)-4-yl, (2,1,3-benzoxadiazol)-5-yl, (1,2,3-benzothiadiazol)-4-yl, (1,2,3-benzothiadiazol)-5-yl, (1,2,3-benzothiadiazol)-6-yl, (1,2,3-benzothiadiazol)-7-yl, (2,1,3-benzothiadiazol)-4-yl, (2,1,3-benzothiadiazol)-5-yl, (1H-benzotriazol)-1-yl, (1H-benzotriazol)-4-yl, (1H-benzotriazol)-5-yl, (1H-benzotriazol)-6-yl, (1H-benzotriazol)-7-yl, (2H-benzotriazol)-2-yl, (2H-benzotriazol)-4-yl, (2H-benzotriazol)-5-yl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolinyl, 4-cinnolinyl, 5-cinnolinyl, 6-cinnolinyl, 7-cinnolinyl, 8-cinnolinyl, 2-quinazolinyl, 4-quinazolinyl, 5-quinazolinyl, 6-quinazolinyl, 7-quinazolinyl, 8-quinazolinyl, 2-quinoxalinyl, 5-quinoxalinyl, 6-quinoxalinyl, 1-phthalazinyl, 5-phthalazinyl, 6-phthalazinyl, 2-naphthyridinyl, 3-naphthyridinyl, 4-naphthyridinyl, 2-purinyl, 6-purinyl, 7-purinyl, 8-purinyl, 2-pteridinyl, 4-pteridinyl, 6-pteridinyl, 7-pteridinyl, 1-carbazolyl, 2-carbazolyl, 3-carbazolyl, 4-carbazolyl, 9-carbazolyl, 2-(α-carbolinyl), 3-(α-carbolinyl), 4-(α-carbolinyl), 5-(α-carbolinyl), 6-(α-carbolinyl), 7-(α-carbolinyl), 8-(α-carbolinyl), 9-(α-carbolinyl), 1-(β-carbolinyl), 3-(β-carbolinyl), 4-(β-carbolinyl), 5-(β-carbolinyl), 6-(β-carbolinyl), 7-(β-carbolinyl), 8-(β-carbolinyl), 9-(β-carbolinyl), 1-(γ-carbolinyl), 2-(γ-carbolinyl), 4-(γ-carbolinyl), 5-(γ-carbolinyl), 6-(γ-carbolinyl), 7-(γ-carbolinyl), 8-(γ-carbolinyl), 9-(γ-carbolinyl), 1-acridinyl, 2-acridinyl, 3-acridinyl, 4-acridinyl, 9-acridinyl, 1-phenoxazinyl, 2-phenoxazinyl, 3-phenoxazinyl, 4-phenoxazinyl, 10-phenoxazinyl, 1-phenothiazinyl, 2-phenothiazinyl, 3-phenothiazinyl, 4-phenothiazinyl, 10-phenothiazinyl, 1-phenazinyl, 2-phenazinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 2-phenanthrolinyl, 3-phenanthrolinyl, 4-phenanthrolinyl, 5-phenanthrolinyl, 6-phenanthrolinyl, 7-phenanthrolinyl, 8-phenanthrolinyl, 9-phenanthrolinyl, 10-phenanthrolinyl, 1-thianthrenyl, 2-thianthrenyl, 1-indolizinyl, 2-indolizinyl, 3-indolizinyl, 5-indolizinyl, 6-indolizinyl, 7-indolizinyl, 8-indolizinyl, 1-phenoxathiinyl, 2-phenoxathiinyl, 3-phenoxathiinyl, 4-phenoxathiinyl, thieno[2,3-b]furyl, pyrrolo[1,2-b]pyridazinyl, pyrazolo[1,5-a]pyridyl, imidazo[11,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-a]pyridazinyl, which are 8 to 14-membered fused polycyclic heteroaryl groups.

Examples of the monocyclic non-aromatic heterocyclic group include, for example, 1-aziridinyl, 1-azetidinyl, 1-pyrrolidinyl, 2-pyrrolidinyl, 3-pyrrolidinyl, 2-tetrahydrofuryl, 3-tetrahydrofuryl, thiolanyl, 1-imidazolidinyl, 2-imidazolidinyl, 4-imidazolidinyl, 1-pyrazolidinyl, 3-pyrazolidinyl, 4-pyrazolidinyl, 1-(2-pyrrolinyl), 1-(2-imidazolinyl), 2-(2-imidazolinyl), 1-(2-pyrazolinyl), 3-(2-pyrazolinyl), piperidino, 2-piperidinyl, 3-piperidinyl, 4-piperidinyl, 1-homopiperidinyl, 2-tetrahydropyranyl, morpholino, (thiomorpholin)-4-yl, 1-piperazinyl, and 1-homopiperazinyl, which are 3 to 7-membered saturated or unsaturated monocyclic non-aromatic heterocyclic groups.

Examples of the fused polycyclic non-aromatic heterocyclic group include, for example, 2-quinuclidinyl, 2-chromanyl, 3-chromanyl, 4-chromanyl, 5-chromanyl, 6-chromanyl, 7-chromanyl, 8-chromanyl, 1-isochromanyl, 3-isochromanyl, 4-isochromanyl, 5-isochromanyl, 6-isochromanyl, 7-isochromanyl, 8-isochromanyl, 2-thiochromanyl, 3-thiochromanyl, 4-thiochromanyl, 5-thiochromanyl, 6-thiochromanyl, 7-thiochromanyl, 8-thiochromanyl, 1-isothiochromanyl, 3-isothiochromanyl, 4-isothiochromanyl, 5-isothiochromanyl, 6-isothiochromanyl, 7-isothiochromanyl, 8-isothiochromanyl, 1-indolinyl, 2-indolinyl, 3-indolinyl, 4-indolinyl, 5-indolinyl, 6-indolinyl, 7-indolinyl, 1-isoindolinyl, 2-isoindolinyl, 4-isoindolinyl, 5-isoindolinyl, 2-(4H-chromenyl), 3-(4H-chromenyl), 4-(4H-chromenyl), 5-(4H-chromenyl), 6-(4H-chromenyl), 7-(4H-chromenyl), 8-(4H-chromenyl), 1-isochromenyl, 3-isochromenyl, 4-isochromenyl, 5-isochromenyl, 6-isochromenyl, 7-isochromenyl, 8-isochromenyl, 1-(1H-pyrrolidinyl), 2-(1H-pyrrolidinyl), 3-(1H-pyrrolidinyl), 5-(1H-pyrrolidinyl), 6-(1H-pyrrolidinyl), and 7-(1H-pyrrolidinyl), which are 8 to 10-membered saturated or unsaturated fused polycyclic non-aromatic heterocyclic groups.

Among the aforementioned heterocyclic groups, a monocyclic or a fused polycyclic hetero aryl groups which may have 1 to 3 kinds of hetero atoms selected from oxygen atom, sulfur atom, nitrogen atom and the like, in addition to the nitrogen atom that has the bond, as ring-constituting atoms (ring forming atoms), and a monocyclic or a fused polycyclic non-aromatic heterocyclic groups which may have 1 to 3 kinds of hetero atoms selected from oxygen atom, sulfur atom, nitrogen atom and the like, in addition to the nitrogen atom that has the bond, as ring-constituting atoms (ring forming atoms) are referred to as "cyclic amino group." Examples include, for example, 1-pyrrolidinyl, 1-imidazolidinyl, 1-pyrazolidinyl, 1-oxazolidinyl, 1-thiazolidinyl, piperidino, morpholino, 1-piperazinyl, thiomorpholin-4-yl, 1-homopiperidinyl, 1-homopiperazinyl, 2-pyrolin-1-yl, 2-imidazolin-1-yl, 2-pyrazolin-1-yl, 1-indolinyl, 2-isoindolinyl, 1,2,3,4-tetrahydroquinolin-1-yl, 1,2,3,4-tetrahydroisoquinolin-2-yl, 1-pyrrolyl, 1-imidazolyl, 1-pyrazolyl, 1-indolyl, 1-indazolyl, and 2-isoindolyl.

The aforementioned cycloalkyl group, cycloalkenyl group, cycloalkanedienyl group, aryl group, cycloalkylene group, cycloalkenylene group, arylene group, bridged cyclic hydrocarbon group, spiro cyclic hydrocarbon group, and heterocyclic group are generically referred to as "cyclic group." Furthermore, among said cyclic groups, particularly, aryl group, arylene group, monocyclic heteroaryl group, and fused polycyclic heteroaryl group are generically referred to as "aromatic ring group."

Examples of the hydrocarbon-oxy group include the groups in which a hydrogen atom of the hydroxy group is substituted with a hydrocarbon group, and examples of the hydrocarbon include similar groups to the aforementioned hydrocarbon groups. Examples of the hydrocarbon-oxy group include, for example, alkoxy group (alkyl-oxy group), alkenyl-oxy group, alkynyl-oxy group, cycloalkyl-oxy group, cycloalkyl-alkyl-oxy group and the like, which are aliphatic hydrocarbon-oxy groups; aryl-oxy group; aralkyl-oxy group; and alkylene-dioxy group.

Examples of the alkoxy (alkyl-oxy group) include, for example, methoxy, ethoxy, n-propoxy, isopropoxy, n-butoxy, isobutoxy, sec-butoxy, tert-butoxy, n-pentyloxy, isopentyloxy, 2-methylbutoxy, 1-methylbutoxy, neopentyloxy, 1,2-dimethylpropoxy, 1-ethylpropoxy, n-hexyloxy, 4-methylpentyloxy, 3-methylpentyloxy, 2-methylpentyloxy, 1-methylpentyloxy, 3,3-dimethylbutoxy, 2,2-dimethybutoxy, 1,1-dimethylbutoxy, 1,2-dimethylbutoxy, 1,3-dimethylbutoxy, 2,3-dimethylbutoxy, 2-ethylbutoxy, 1-ethylbutoxy, 1-ethyl-1-methylpropoxy, n-heptyloxy, n-octyloxy, n-nonyloxy, n-decyloxy, n-undecyloxy, n-dodecyloxy, n-tridecyloxy, n-tetradecyloxy, and n-pentadecyloxy, which are $C_1$ to $C_{15}$ straight chain or branched chain alkoxy groups.

Examples of the alkenyl-oxy group include, for example, vinyloxy, (prop-1-en-1-yl)oxy, allyloxy, isopropenyloxy, (but-1-en-1-yl)oxy, (but-2-en-1-yl)oxy, (but-3-en-1-yl)oxy, (2-methylprop-2-en-1-yl)oxy, (1-methylprop-2-en-1-yl)oxy, (pent-1-en-1-yl)oxy, (pent-2-en-1-yl)oxy, (pent-3-en-1-yl)oxy, (pent-4-en-1-yl)oxy, (3-methylbut-2-en-1-yl)oxy, (3-methylbut-3-en-1-yl)oxy, (hex-1-en-1-yl)oxy, (hex-2-en-1-yl)oxy, (hex-3-en-1-yl)oxy, (hex-4-en-1-yl)oxy, (hex-5-en-1-yl)oxy, (4-methylpent-3-en-1-yl)oxy, (4-methylpent-3-en-1-yl)oxy, (hept-1-en-1-yl)oxy, (hept-6-en-1-yl)oxy, (oct-1-en-1-yl)oxy, (oct-7-en-1-yl)oxy, (non-1-en-1-yl)oxy, (non-8-en-1-yl)oxy, (dec-1-en-1-yl)oxy, (dec-9-en-1-yl)oxy, (undec-1-en-1-yl)oxy, (undec-10-en-1-yl)oxy, (dodec-1-en-1-yl)oxy, (dodec-11-en-1-yl)oxy, (tridec-1-en-1-yl)oxy, (tridec-12-en-1-yl)oxy, (tetradec-1-en-1-yl)oxy, (tetradec-13-en-1-yl)oxy, (pentadec-1-en-1-yl)oxy, and (pentadec-14-en-1-yl)oxy, which are $C_2$ to $C_{15}$ straight chain or branched chain alkenyl-oxy groups.

Examples of the alkynyl-oxy group include, for example, ethynyloxy, (prop-1-yn-1-yl)oxy, (prop-2-yn-1-yl)oxy, (but-1-yn-1-yl)oxy, (but-3-yn-1-yl)oxy, (1-methylprop-2-yn-1-yl)oxy, (pent-1-yn-1-yl)oxy, (pent-4-yn-1-yl)oxy, (hex-1-yn-1-yl)oxy, (hex-5-yn-1-yl)oxy, (hept-1-yn-1-yl)oxy, (hept-6-yn-1-yl)oxy, (oct-1-yn-1-yl)oxy, (oct-7-yn-1-yl)oxy, (non-1-yn-1-yl)oxy, (non-8-yn-1-yl)oxy, (dec-1-yn-1-yl)oxy, (dec-9-yn-1-yl)oxy, (undec-1-yn-1-yl)oxy, (undec-10-yn-1-yl)oxy, (dodec-1-yn-1-yl)oxy, (dodec-11-yn-1-yl)oxy, (tridec-1-yn-1-yl)oxy, (tridec-12-yn-1-yl)oxy, (tetradec-1-yn-1-yl)oxy, (tetradec-13-yn-1-yl)oxy, (pentadec-1-yn-1-yl)oxy, and (pentadec-14-yn-1-yl)oxy, which are $C_2$ to $C_{15}$ straight chain or branched chain alkynyl-oxy groups.

Examples of the cycloalkyl-oxy group include, for example, cyclopropoxy, cyclobutoxy, cyclopentyloxy, cyclohexyloxy, cycloheptyloxy, and cyclooctyloxy, which are $C_3$ to $C_8$ cycloalkyl-oxy groups.

Examples of the cycloalkyl-alkyl-oxy group include, for example, cyclopropylmethoxy, 1-cyclopropylethoxy, 2-cyclopropylethoxy, 3-cyclopropylpropoxy, 4-cyclopropylbutoxy, 5-cyclopropylpentyloxy, 6-cyclopropylhexyloxy, cyclobutylmethoxy, cyclopentylmethoxy, cyclobutylmethoxy, cyclopentylmethoxy, cyclohexylmethoxy, 2-cyclohexylethoxy, 3-cyclohexylpropoxy, 4-cyclohexylbutoxy, cycloheptylmethoxy, cyclooctylmethoxy, and 6-cyclooctylhexyloxy, which are $C_4$ to $C_{14}$ cycloalkyl-alkyl-oxy groups.

Examples of the aryl-oxy group include, for example, phenoxy, 1-naphthyloxy, 2-naphthyloxy, anthryloxy, phenanthryloxy, and acenaphthylenyloxy, which are $C_6$ to $C_{14}$ aryl-oxy groups.

Examples of the aralkyl-oxy group include, for example, benzyloxy, 1-naphthylmethoxy, 2-naphthylmethoxy, anthracenylmethoxy, phenanthrenylmethoxy, acenaphthylenylmethoxy, diphenylmethoxy, 1-phenethyloxy, 2-phenethyloxy, 1-(1-naphthyl)ethoxy, 1-(2-naphthyl)ethoxy, 2-(1-naphthyl)ethoxy, 2-(2-naphthyl)ethoxy, 3-phenylpropoxy, 3-(1-naphthyl)propoxy, 3-(2-naphthyl)propoxy, 4-phenylbutoxy, 4-(1-naphthyl)butoxy, 4-(2-naphthyl)butoxy, 5-phenylpentyloxy, 5-(1-naphthyl)pentyloxy, 5-(2-naphthyl)pentyloxy, 6-phenylhexyloxy, 6-(1-naphthyl)hexyloxy, and 6-(2-naphthyl)hexyloxy, which are $C_7$ to $C_{16}$ aralkyl-oxy groups.

Examples of the alkylenedioxy group include, for example, methylenedioxy, ethylenedioxy, 1-methylmethylenedioxy, and 1,1-dimethylmethylenedioxy.

Examples of the halogenated alkoxy group (halogenated alkyl-oxy group) include the groups in which a hydrogen atom of the hydroxy group is substituted with a halogenated alkyl group, and include, for example, fluoromethoxy, difluoromethoxy, chloromethoxy, bromomethoxy, iodomethoxy, trifluoromethoxy, trichloromethoxy, 2,2,2-trifluoroethoxy, pentafluoroethoxy, 3,3,3-trifluoropropoxy, heptafluoropropoxy, heptafluoroisopropoxy, nonafluorobutoxy, and perfluorohexyloxy, which are $C_1$ to $C_6$ straight chain or branched chain halogenated alkoxy groups substituted with 1 to 13 halogen atoms.

Examples of the heterocyclic-oxy group include the groups in which a hydrogen atom of the hydroxy group is substituted with a heterocyclic group, and examples of the heterocyclic ring include similar groups to the aforementioned heterocyclic groups. Examples of the heterocyclic-oxy group include, for example, a monocyclic heteroaryl-oxy group, a fused polycyclic heteroaryl-oxy group, a monocyclic non-aromatic heterocyclic-oxy group, and a fused polycyclic non-aromatic heterocyclic-oxy group.

Examples of the monocyclic heteroaryl-oxy group include, for example, 3-thienyloxy, (isoxazol-3-yl)oxy, (thiazol-4-yl)oxy, 2-pyridyloxy, 3-pyridyloxy, 4-pyridyloxy, and (pyrimidin-4-yl)oxy.

Examples of the fused polycyclic heteroaryl-oxy group include, for example, 5-indolyloxy, (benzimidazol-2-yl)oxy, 2-quinolyloxy, 3-quinolyloxy, and 4-quinolyloxy.

Examples of the monocyclic non-aromatic heterocyclic-oxy group include, for example, 3-pyrrolidinyloxy, and 4-piperidinyloxy.

Examples of the fused polycyclic non-aromatic heterocyclic-oxy group include, for example, 3-indolynyloxy, and 4-chromanyloxy.

Examples of the hydrocarbon-sulfanyl group include the groups in which a hydrogen atom of the sulfanyl group is substituted with a hydrocarbon group, and examples of the hydrocarbon include similar groups to the aforementioned hydrocarbon groups. Examples of the hydrocarbon-sulfanyl groups include, for example, alkyl-sulfanyl group, alkenyl-sulfanyl group, alkynyl-sulfanyl group, cycloalkyl-sulfanyl group, cycloalkyl-alkyl-sulfanyl group and the like, which are aliphatic hydrocarbon-sulfanyl groups; aryl-sulfanyl group, and aralkyl-sulfanyl group.

Examples of the alkyl-sulfanyl group include, for example, methylsulfanyl, ethylsulfanyl, n-propylsulfanyl, isopropylsulfanyl, n-butylsulfanyl, isobutylsulfanyl, sec-butylsulfanyl, tert-butylsulfanyl, n-pentylsulfanyl, isopentylsulfanyl, (2-methylbutyl)sulfanyl, (1-methylbutyl)sulfanyl, neopentylsulfanyl, (1,2-dimethylpropyl)sulfanyl, (1-ethylpropyl)sulfanyl, n-hexylsulfanyl, (4-methylpentyl)sulfanyl, (3-methylpentyl)sulfanyl, (2-methylpentyl)sulfanyl, (1-methylpentyl)sulfanyl, (3,3-dimethylbutyl)sulfanyl, (2,2-dimethylbutyl)sulfanyl, (1,1-dimethylbutyl)sulfanyl, (1,2-dimethylbutyl)sulfanyl, (1,3-dimethylbutyl)sulfanyl, (2,3-dimethylbutyl)sulfanyl, (2-ethylbutyl)sulfanyl, (1-ethylbutyl)sulfanyl, (1-ethyl-1-methylpropyl)sulfanyl, n-heptylsulfanyl, n-octylsulfanyl, n-nonylsulfanyl, n-decylsulfanyl, n-undecylsulfanyl, n-dodecylsulfanyl, n-tridecylsulfanyl, n-tetradecylsulfanyl, and n-pentadecylsulfanyl, which are $C_1$ to $C_{15}$ straight chain or branched chain alkyl-sulfanyl groups.

Examples of the alkenyl-sulfanyl group include, for example, vinylsulfanyl, (prop-1-en-1-yl)sulfanyl, allylsulfanyl, isopropenylsulfanyl, (but-1-en-1-yl)sulfanyl, (but-2-en-1-yl)sulfanyl, (but-3-en-1-yl)sulfanyl, (2-methylprop-2-en-1-yl)sulfanyl, (1-methylprop-2-en-1-yl)sulfanyl, (pent-1-en-1-yl)sulfanyl, (pent-2-en-1-yl)sulfanyl, (pent-3-en-1-yl)sulfanyl, (pent-4-en-1-yl)sulfanyl, (3-methylbut-2-en-1-yl)sulfanyl, (3-methylbut-3-en-1-yl)sulfanyl, (hex-1-en-1-yl)sulfanyl, (hex-2-en-1-yl)sulfanyl, (hex-3-en-1-yl)sulfanyl, (hex-4-en-1-yl)sulfanyl, (hex-5-en-1-yl)sulfanyl, (4-methylpent-3-en-1-yl)sulfanyl, (4-methylpent-3-en-1-yl)sulfanyl, (hept-1-en-1-yl)sulfanyl, (hept-6-en-1-yl)sulfanyl, (oct-1-en-1-yl)sulfanyl, (oct-7-en-1-yl)sulfanyl, (non-1-en-1-yl)sulfanyl, (non-8-en-1-yl)sulfanyl, (dec-1-en-1-yl)sulfanyl, (dec-9-en-1-yl)sulfanyl, (undec-1-en-1-yl)sulfanyl, (undec-10-en-1-yl)sulfanyl, (dodec-1-en-1-yl)sulfanyl, (dodec-11-en-1-yl)sulfanyl, (tridec-1-en-1-yl)sulfanyl, (tridec-12-en-1-yl)sulfanyl, (tetradec-1-en-1-yl)sulfanyl, (tetradec-13-en-1-yl)sulfanyl, (pentadec-1-en-1-yl)sulfanyl, and (pentadec-14-en-1-yl)sulfanyl, which are $C_2$ to $C_{15}$ straight chain or branched chain alkenyl-sulfanyl groups.

Examples of the alkynyl-sulfanyl group include, for example, ethynylsulfanyl, (prop-1-yn-1-yl)sulfanyl, (prop-2-yn-1-yl)sulfanyl, (but-1-yn-1-yl)sulfanyl, (but-3-yn-1-yl)sulfanyl, (1-methylprop-2-yn-1-yl)sulfanyl, (pent-1-yn-1-yl)sulfanyl, (pent-4-yn-1-yl)sulfanyl, (hex-1-yn-1-yl)sulfanyl, (hex-5-yn-1-yl)sulfanyl, (hept-1-yn-1-yl)sulfanyl, (hept-6-yn-1-yl)sulfanyl, (oct-1-yn-1-yl)sulfanyl, (oct-7-yn-1-yl)sulfanyl, (non-1-yn-1-yl)sulfanyl, (non-8-yn-1-yl)sulfanyl, (dec-1-yn-1-yl)sulfanyl, (dec-9-yn-1-yl)sulfanyl, (undec-1-yn-1-yl)sulfanyl, (undec-10-yn-1-yl)sulfanyl, (dodec-1-yn-1-yl)sulfanyl, (dodec-11-yn-1-yl)sulfanyl, (tridec-1-yn-1-yl)sulfanyl, (tridec-12-yn-1-yl)sulfanyl, (tetradec-1-yn-1-yl)sulfanyl, (tetradec-13-yn-1-yl)sulfanyl, (pentadec-1-yn-1-yl)sulfanyl, and (pentadec-14-yn-1-yl)sulfanyl, which are $C_2$ to $C_{15}$ straight chain or branched chain alkynyl-sulfanyl groups.

Examples of the cycloalkyl-sulfanyl group include, for example, cyclopropylsulfanyl, cyclobutylsulfanyl, cyclopentylsulfanyl, cyclohexylsulfanyl, cycloheptylsulfanyl, and cyclooctylsulfanyl, which are $C_3$ to $C_8$ cycloalkyl-sulfanyl groups.

Examples of the cycloalkyl-alkyl-sulfanyl group include, for example, (cyclopropylmethyl)sulfanyl, (1-cyclopropylethyl)sulfanyl, (2-cyclopropylethyl)sulfanyl, (3-cyclopropylpropyl)sulfanyl, (4-cyclopropylbutyl)sulfanyl, (5-cyclopropylpentyl)sulfanyl, (6-cyclopropylhexyl)sulfanyl, (cyclobutylmethyl)sulfanyl, (cyclopentylmethyl)sulfanyl, (cyclobutylmethyl)sulfanyl, (cyclopentylmethyl)sulfanyl, (cyclohexylmethyl)sulfanyl, (2-cyclohexylethyl)sulfanyl, (3-cyclohexylpropyl)sulfanyl, (4-cyclohexylbutyl)sulfanyl, (cycloheptylmethyl)sulfanyl, (cyclooctylmethyl)sulfanyl, and (6-cyclooctylhexyl)sulfanyl, which are $C_4$ to $C_{14}$ cycloalkyl-alkyl-sulfanyl groups.

Examples of the aryl-sulfanyl group include, for example, phenylsulfanyl, 1-naphthylsulfanyl, 2-naphthylsulfanyl, anthrylsulfanyl, fenanthrylsulfanyl, and acenaphthylenylsulfanyl, which are $C_6$ to $C_{14}$ aryl-sulfanyl groups.

Examples of the aralkyl-sulfanyl group include, for example, benzylsulfanyl, (1-naphthylmethyl)sulfanyl, (2-naphthylmethyl)sulfanyl, (anthracenylmethyl)sulfanyl, (phenanthrenylmethyl)sulfanyl, (acenaphthylenylmethyl)sulfanyl, (diphenylmethyl)sulfanyl, (1-phenethyl)sulfanyl, (2-phenethyl)sulfanyl, (1-(1-naphthyl)ethyl)sulfanyl, (1-(2-naphthyl)ethyl)sulfanyl, (2-(1-naphthyl)ethyl)sulfanyl, (2-(2-naphthyl)ethyl)sulfanyl, (3-phenylpropyl)sulfanyl, (3-(1-naphthyl)propyl)sulfanyl, (3-(2-naphthyl)propyl)sulfanyl, (4-phenylbutyl)sulfanyl, (4-(1-naphthyl)butyl)sulfanyl, (4-(2-naphthyl)butyl)sulfanyl, (5-phenylpentyl)sulfanyl, (5-(1-naphthyl)pentyl)sulfanyl, (5-(2-naphthyl)pentyl)sulfanyl, (6-phenylhexyl)sulfanyl, (6-(1-naphthyl)hexyl)sulfanyl, and (6-(2-naphthyl)hexyl)sulfanyl, which are $C_7$ to $C_{16}$ aralkyl-sulfanyl groups.

Examples of the halogenated alkyl-sulfanyl group include the groups in which a hydrogen atom of the sulfanyl group is substituted with a halogenated alkyl group, and include, for example, (fluoromethyl)sulfanyl, (chloromethyl)sulfanyl, (bromomethyl)sulfanyl, (iodomethyl)sulfanyl, (difluoromethyl)sulfanyl, (trifluoromethyl)sulfanyl, (trichloromethyl)sulfanyl, (2,2,2-trifluoroethyl)sulfanyl, (pentafluoroethyl)sulfanyl, (3,3,3-trifluoropropyl)sulfanyl, (heptafluoropropyl)sulfanyl, (heptafluoroisopropyl)sulfanyl, (nonafluorobutyl)sulfanyl, and (perfluorohexyl)sulfanyl, which are $C_1$ to $C_6$ straight chain or branched chain halogenated alkyl-sulfanyl groups substituted with 1 to 13 halogen atoms.

Examples of the heterocyclic-sulfanyl group include the groups in which a hydrogen atom of the sulfanyl group is substituted with a heterocyclic group, and examples of the heterocyclic ring include similar groups to the aforementioned heterocyclic groups. Examples of the heterocyclic-sulfanyl group include, for example, a monocyclic heteroaryl-sulfanyl group, a fused polycyclic heteroaryl-sulfanyl group, a monocyclic non-aromatic heterocyclic-sulfanyl group, and a fused polycyclic non-aromatic heterocyclic-sulfanyl group.

Examples of the monocyclic heteroaryl-sulfanyl group include, for example, (imidazol-2-yl)sulfanyl, (1,2,4-triazol-2-yl)sulfanyl, (pyridin-2-yl)sulfanyl, (pyridin-4-yl)sulfanyl, and (pyrimidin-2-yl)sulfanyl.

Examples of the fused polycyclic heteroaryl-sulfanyl group include, for example, (benzimidazol-2-yl)sulfanyl, (quinolin-2-yl)sulfanyl, and (quinolin-4-yl)sulfanyl.

Examples of the monocyclic non-aromatic heterocyclic-sulfanyl groups include, for example, (3-pyrrolidinyl)sulfanyl, and (4-piperidinyl)sulfanyl.

Examples of the fused polycyclic non-aromatic heterocyclic-sulfanyl group include, for example, (3-indolinyl)sulfanyl, and (4-chromanyl)sulfanyl.

Examples of the acyl group include, for example, formyl group, glyoxyloyl group, thioformyl group, carbamoyl group, thiocarbamoyl group, sulfamoyl group, sulfinamoyl group, carboxy group, sulfo group, phosphono group, and groups represented by the following formulas:

(ω-1A)

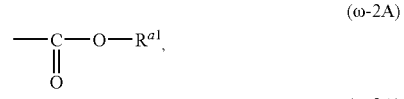
(ω-2A)

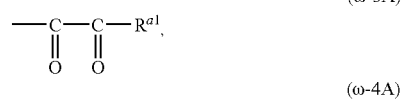
(ω-3A)

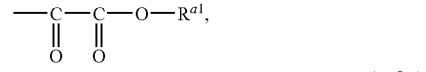
(ω-4A)

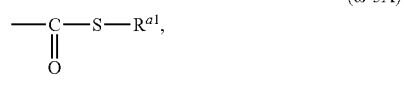
(ω-5A)

-continued

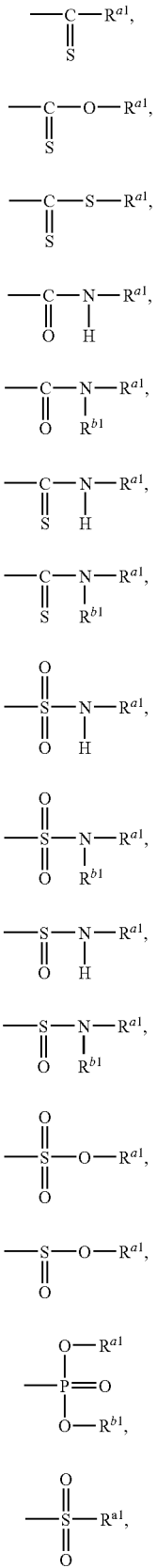

(ω-6A)

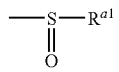

(ω-7A)

(ω-8A)

(ω-9A)

(ω-10A)

(ω-11A)

(ω-12A)

(ω-13A)

(ω-14A)

(ω-15A)

(ω-16A)

(ω-17A)

(ω-18A)

(ω-19A)

(ω-20A)

-continued (ω-21A)

wherein $R^{a1}$ and $R^{b1}$ may be the same or different and represent a hydrocarbon group or a heterocyclic group, or $R^{a1}$ and $R^{b1}$ combine to each other, together with the nitrogen atom to which they bind, to form a cyclic amino group.

In the definition of the aforementioned acyl group, among the groups represented by the formula (ω-1A), those groups in which $R^{a1}$ is a hydrocarbon group are referred to as "hydrocarbon-carbonyl group" whose examples include, for example, acetyl, propionyl, butyryl, isobutyryl, valeryl, isovaleryl, pivaloyl, lauroyl, myristoryl, palmitoyl, acryloyl, propioloyl, methacryloyl, crotonoyl, isocrotonoyl, cyclohexylcarbonyl, cyclohexylmethylcarbonyl, benzoyl, 1-naphthoyl, 2-naphthoyl, and phenylacetyl, and those groups in which $R^{a1}$ is a heterocyclic group are referred to as "heterocyclic ring-carbonyl group" whose examples include, for example, 2-thenoyl, 3-furoyl, nicotinoyl, and isonicotinoyl.

Among the groups represented by the formula (ω-2A), those groups in which $R^{a1}$ is a hydrocarbon group are referred to as "hydrocarbon-oxy-carbonyl group" whose examples include, for example, methoxycarbonyl, ethoxycarbonyl, phenoxycarbonyl, and benzyloxycarbonyl, and those groups in which $R^{a1}$ is a heterocyclic group are referred to as "heterocyclic ring-oxy-carbonyl group" whose examples include, for example, 3-pyridyloxycarbonyl.

Among the groups represented by the formula (ω-3A), those groups in which $R^{a1}$ is a hydrocarbon group are referred to as "hydrocarbon-carbonyl-carbonyl group" whose examples include, for example, pyruvoyl, and those groups in which $R^{a1}$ is a heterocyclic group are referred to as "heterocyclic ring-carbonyl-carbonyl group."

Among the groups represented by the formula (ω-4A), those groups in which $R^{a1}$ is a hydrocarbon group are referred to as "hydrocarbon-oxy-carbonyl-carbonyl group" whose examples include, for example, methoxalyl and ethoxalyl groups, and those groups in which $R^{a1}$ is a heterocyclic group are referred to as "heterocyclic ring-oxy-carbonyl-carbonyl group."

Among the groups represented by the formula (ω-5A), those groups in which $R^{a1}$ is a hydrocarbon group are referred to as "hydrocarbon-sulfanyl-carbonyl group," and those groups in which $R^{a1}$ is a heterocyclic group are referred to as "heterocyclic ring-sulfanyl-carbonyl group."

Among the groups represented by the formula (ω-6A), those groups in which $R^{a1}$ is a hydrocarbon group are referred to as "hydrocarbon-thiocarbonyl group," and those groups in which $R^{a1}$ is a heterocyclic group are referred to as "heterocyclic ring-thiocarbonyl group."

Among the groups represented by the formula (ω-7A), those groups in which $R^{a1}$ is a hydrocarbon group are referred to as "hydrocarbon-oxy-thiocarbonyl group," and those groups in which $R^{a1}$ is a heterocyclic group are referred to as "heterocyclic ring-oxy-thiocarbonyl group."

Among the groups represented by the formula (ω-8A), those groups in which $R^{a1}$ is a hydrocarbon group are referred to as "hydrocarbon-sulfanyl-thiocarbonyl group," and those groups in which $R^{a1}$ is a heterocyclic group are referred to as "heterocyclic ring-sulfanyl-thiocarbonyl group."

Among the groups represented by the formula (ω-9A), those groups in which $R^{a1}$ is a hydrocarbon group are referred to as referred to as "N-hydrocarbon-carbamoyl group" whose examples include, for example, N-methylcarbamoyl group, and those groups in which $R^{a1}$ is a heterocyclic group are referred to as "N-heterocyclic ring-carbamoyl group."

Among the groups represented by the formula (ω-10A), those groups in which both $R^{a1}$ and $R^{b1}$ are hydrocarbon groups are referred to as "N,N-di(hydrocarbon)-carbamoyl group" whose examples include, for example, N,N-dimethylcarbamoyl group, those groups in which both $R^{a1}$ and $R^{b1}$ are heterocyclic groups are referred to as "N,N-di(heterocyclic ring)-carbamoyl group," those groups in which $R^{a1}$ is a hydrocarbon group and $R^{b1}$ is a heterocyclic group are referred to as "N-hydrocarbon-N-heterocyclic ring-substituted carbamoyl group," and those groups in which $R^{a1}$ and $R^{b1}$ combine to each other, together with the nitrogen atom to which they bind, to form a cyclic amino group are referred to as "cyclic amino-carbonyl group" whose examples include, for example, morpholino-carbonyl.

Among the groups represented by the formula (ω-11A), those groups in which $R^{a1}$ is a hydrocarbon group are referred to as "N-hydrocarbon-thiocarbamoyl group," and those groups in which $R^{a1}$ is a heterocyclic group are referred to as "N-heterocyclic ring-thiocarbamoyl group."

Among the groups represented by the formula (ω-12A), those groups in which both $R^{a1}$ and $R^{b1}$ are hydrocarbon groups are referred to as "N,N-di(hydrocarbon)-thiocarbamoyl group," those groups in which both $R^{a1}$ and $R^{b1}$ are heterocyclic groups are referred to as "N,N-di(heterocyclic ring)-thiocarbamoyl group," those groups in which $R^{a1}$ is a hydrocarbon group and $R^{b1}$ is a heterocyclic group are referred to as "N-hydrocarbon-N-heterocyclic ring-thiocarbamoyl group," and those groups in which $R^{a1}$ and $R^{b1}$ combine to each other, together with the nitrogen atom to which they bind, to form a cyclic amino group are referred to as "cyclic amino-thiocarbonyl group."

Among the groups represented by the formula (ω-13A), those groups in which $R^{a1}$ is a hydrocarbon group are referred to as "N-hydrocarbon-sulfamoyl group," and those groups in which $R^{a1}$ is a heterocyclic group are referred to as "N-heterocyclic ring-sulfamoyl group."

Among the groups represented by the formula (ω-14A), those groups in which both $R^{a1}$ and $R^{b1}$ are hydrocarbon groups are referred to as "N,N-di(hydrocarbon)-sulfamoyl group" whose examples include, for example, N,N-dimethylsulfamoyl group, those groups in which both $R^{a1}$ and $R^{b1}$ are heterocyclic groups are referred to as "N,N-di(heterocyclic ring)-sulfamoyl group," those groups in which $R^{a1}$ is a hydrocarbon group and $R^{b1}$ is a heterocyclic group are referred to as "N-hydrocarbon-N-heterocyclic ring-sulfamoyl group," and those groups in which $R^{a1}$ and $R^{b1}$ combine to each other, together with the nitrogen atom to which they bind, to form a cyclic amino group are referred to as "cyclic amino-sulfonyl group" whose examples include, for example 1-pyrrolylsulfonyl.

Among the groups represented by the formula (ω-15A), those groups in which $R^{a1}$ is a hydrocarbon group are referred to as "N-hydrocarbon-sulfinamoyl group," and those groups in which $R^{a1}$ is a heterocyclic group are referred to as "N-heterocyclic ring-sulfinamoyl group."

Among the groups represented by the formula (ω-16A), those groups in which both $R^{a1}$ and $R^{b1}$ are hydrocarbon groups are referred to as "N,N-di(hydrocarbon)-sulfinamoyl group," those groups in which both $R^{a1}$ and $R^{b1}$ are heterocyclic groups are referred to as "N,N-di(heterocyclic ring)-sulfinamoyl group," those groups in which $R^{a1}$ is a hydrocarbon group and $R^{b1}$ is a heterocyclic group are referred to as "N-hydrocarbon-N-heterocyclic ring-sulfinamoyl group," and those groups in which $R^{a1}$ and $R^{b1}$ combine to each other, together with the nitrogen atom to which they bind, to form a cyclic amino group are referred to as "cyclic amino-sulfinyl group."

Among the groups represented by the formula (ω-17A), those groups in which $R^{a1}$ is a hydrocarbon group are referred to as "hydrocarbon-oxy-sulfonyl group," and those groups in which $R^{a1}$ is a heterocyclic group are referred to as "heterocyclic ring-oxy-sulfonyl group."

Among the groups represented by the formula (ω-18A), those groups in which $R^{a1}$ is a hydrocarbon group are referred to as "hydrocarbon-oxy-sulfinyl group," and those groups in which $R^{a1}$ is a heterocyclic group are referred to as "heterocyclic ring-oxy-sulfinyl group."

Among the groups represented by the formula (ω-19A), those groups in which both $R^{a1}$ and $R^{b1}$ are hydrocarbon groups are referred to as "O,O'-di(hydrocarbon)-phosphono group," those groups in which both $R^{a1}$ and $R^{b1}$ are heterocyclic groups are referred to as "O,O'-di(heterocyclic ring)-phosphono group," and those groups in which $R^{a1}$ is a hydrocarbon group and $R^{b1}$ is a heterocyclic group are referred to as "O-hydrocarbon-O'-heterocyclic ring-phosphono group."

Among the groups represented by the formula (ω-20A), those groups in which $R^{a1}$ is a hydrocarbon group are referred to as "hydrocarbon-sulfonyl group" whose examples include, for example, methanesulfonyl and benzenesulfonyl, and those groups in which $R^{a1}$ is a heterocyclic group are referred to as "heterocyclic ring-sulfonyl group."

Among the groups represented by the formula (ω-21A), those groups in which $R^{a1}$ is a hydrocarbon group are referred to as "hydrocarbon-sulfinyl group" whose examples include, for example, methylsulfinyl and benzenesulfinyl, and those groups in which $R^{a1}$ is a heterocyclic group are referred to as "heterocyclic ring-sulfinyl group."

Examples of the hydrocarbon in the groups represented by the aforementioned formulas (ω-1A) through (ω-21A) include the similar groups to the aforementioned hydrocarbon group. Examples of the hydrocarbon-carbonyl group represented by the formula (ω-1A) include, for example, an alkyl-carbonyl group, an alkenyl-carbonyl group, an alkynyl-carbonyl group, a cycloalkyl-carbonyl group, a cycloalkenyl-carbonyl group, a cycloalkanedienyl-carbonyl group, a cycloalkyl-alkyl-carbonyl group, which are aliphatic hydrocarbon-carbonyl groups; an aryl-carbonyl group; an aralkyl-carbonyl group; a bridged cyclic hydrocarbon-carbonyl group; a spirocyclic hydrocarbon-carbonyl group; and a terpene family hydrocarbon-carbonyl group. In the following, groups represented by the formulas (ω-2A) through (ω-21A) are similar to those explained above.

Examples of the heterocyclic ring in the groups represented by the aforementioned formulas (ω-1A) through (ω-21A) include similar groups to the aforementioned heterocyclic group. Examples of the heterocyclic ring-carbonyl group represented by the formula (ω-1A) include, for example, a monocyclic heteroaryl-carbonyl group, a fused polycyclic heteroaryl-carbonyl group, a monocyclic non-aromatic heterocyclic ring-carbonyl group, and a fused polycyclic non-aromatic heterocyclic ring-carbonyl group. In the following, groups represented by the formulas (ω-2A) through (ω-21A) are similar to those explained above.

Examples of the cyclic amino in the groups represented by the aforementioned formulas (ω-10A) through (ω-16A) include similar groups to the aforementioned cyclic amino group.

In the present specification, when a certain functional group is defined as "which may be substituted," the definition means that the functional group may sometimes have one or more substituents at chemically substitutable positions, unless otherwise specifically mentioned. Kind of substituents, number of substituents, and the position of substituents existing in the functional groups are not particularly limited, and when two or more substituents exist, they may be the same or different. Examples of the substituent existing in the functional group include, for example, halogen atoms, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, methooxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, hydrocarbon group, heterocyclic group, hydrocarbon-oxy group, heterocyclic ring-oxy group, hydrocarbon-sulfanyl group, heterocyclic ring-sulfanyl group, acyl group, amino group, hydrazino group, hydrazono group, diazenyl group, ureido group, thioureido group, guanidino group, carbamoimidoyl group (amidino group), azido group, imino group, hydroxyamino group, hydroxyimino group, aminooxy group, diazo group, semicarbazino group, semicarbazono group, allophanyl group, hydantoyl group, phosphano group, phosphoroso group, phospho group, boryl group, silyl group, stannyl group, selanyl group, oxido group and the like.

When two or more substituents exist according to the aforementioned definition of "which may be substituted," said two or more substituents may combine to each other, together with atom(s) to which they bind, to form a ring. For these cyclic groups, as ring-constituting atoms (ring forming atoms), one to three kinds of one or more hetero atoms selected from oxygen atom, sulfur atom, nitrogen atom and the like may be included, and one or more substituents may exist on the ring. The ring may be monocyclic or fused polycyclic, and aromatic or non-aromatic.

The above substituents according to the aforementioned definition of "which may be substituted" may further be substituted with the aforementioned substituents at the chemically substitutable positions on the substituent. Kind of substituents, number of substituents, and positions of substituents are not particularly limited, and when the substituents are substituted with two or more substituents, they may be the same or different. Examples of the substituent include, for example, a halogenated alkyl-carbonyl group whose examples include, for example, trifluoroacetyl, a halogenated alkyl-sulfonyl group whose examples include, for example, trifluoromethanesulfonyl, an acyl-oxy group, an acyl-sulfanyl group, an N-hydrocarbon-amino group, an N,N-di(hydrocarbon)-amino group, an N-heterocyclic ring-amino group, an N-hydrocarbon-N-heterocyclic ring-amino group, an acyl-amino group, and a di(acyl)-amino group. Moreover, substitution on the aforementioned substituents may be repeated multiple orders.

Examples of the acyl-oxy group include the groups in which hydrogen atom of hydroxy group is substituted with acyl group, and include, for example, formyloxy group, glyoxyloyloxy group, thioformyloxy group, carbamoloxy group, thiocarbamoyloxy group, sulfamoyloxy group, sulfinamoloxy group, carboxyoxy group, sulphooxy group, phosphonooxy group, and groups represented by the following formulas:

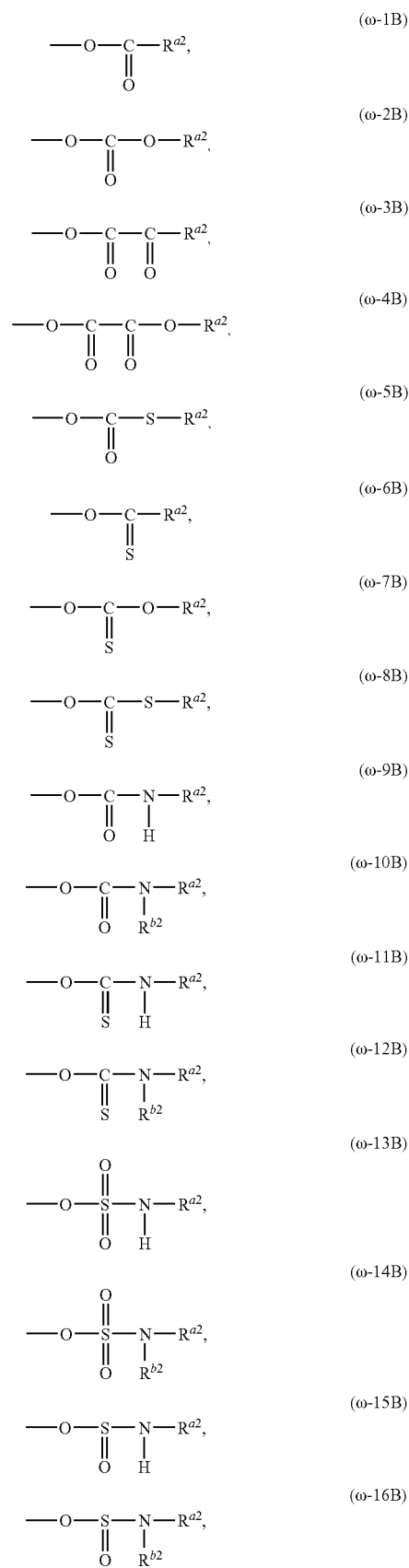

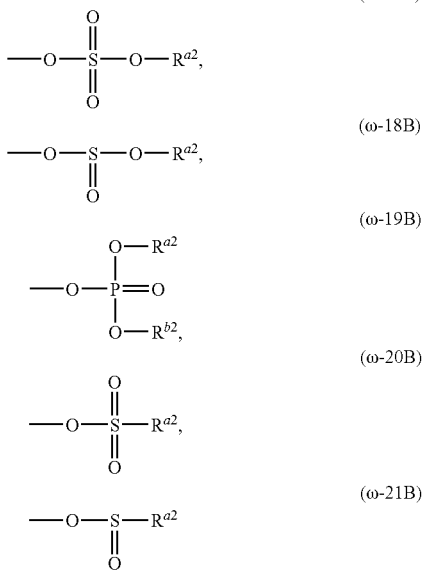

(ω-17B)

(ω-18B)

(ω-19B)

(ω-20B)

(ω-21B)

wherein $R^{a2}$ and $R^{b2}$ may be the same or different and represent a hydrocarbon group or a heterocyclic group, or $R^{a2}$ and $R^{b2}$ combine to each other, together with the nitrogen atom to which they bind, to form a cyclic amino group.

In the definition of the aforementioned acyl-oxy group, among the groups represented by the formula (ω-1B), those groups in which $R^{a2}$ is a hydrocarbon group are referred to as "hydrocarbon-carbonyl-oxy group" whose examples include, for example, acetoxy and benzoyloxy, and those groups in which $R^{a2}$ is a heterocyclic group are referred to as "heterocyclic ring-carbonyl-oxy group."

Among the groups represented by the formula (ω-2B), those groups in which $R^{a2}$ is a hydrocarbon group are referred to as "hydrocarbon-oxy-carbonyl-oxy group," and those groups in which $R^{a2}$ is a heterocyclic group are referred to as "heterocyclic ring-oxy-carbonyl-oxy group."

Among the groups represented by the formula (ω-3B), those groups in which $R^{a2}$ is a hydrocarbon group are referred to as "hydrocarbon-carbonyl-carbonyl-oxy group," and those groups in which $R^{a2}$ is a heterocyclic group are referred to as "heterocyclic ring-carbonyl-carbonyl-oxy group."

Among the groups represented by the formula (ω-4B), those groups in which $R^{a2}$ is a hydrocarbon group are referred to as "hydrocarbon-oxy-carbonyl-carbonyl-oxy group," and those groups in which $R^{a2}$ is a heterocyclic group are referred to as "heterocyclic ring-oxy-carbonyl-carbonyl-oxy group."

Among the groups represented by the formula (ω-5B), those groups in which $R^{a2}$ is a hydrocarbon group are referred to as "hydrocarbon-sulfanyl-carbonyl-oxy group," and those groups where $R^{a2}$ is a heterocyclic group are referred to as "heterocyclic ring-sulfanyl-carbonyl-oxy group."

Among the groups represented by the formula (ω-6B), those groups in which $R^{a2}$ is a hydrocarbon group are referred to as "hydrocarbon-thiocarbonyl-oxy group," and those groups where $R^{a2}$ is a heterocyclic group are referred to as "heterocyclic ring-thiocarbonyl-oxy group."

Among the groups represented by the formula (ω-7B), those groups in which $R^{a2}$ is a hydrocarbon group are referred to as "hydrocarbon-oxy-thiocarbonyl-oxy group," and those groups in which $R^{a2}$ is a heterocyclic group are referred to as "heterocyclic ring-oxy-thiocarbonyl-oxy group."

Among the groups represented by the formula (ω-8B), those groups in which $R^{a2}$ is a hydrocarbon group are referred to as "hydrocarbon-sulfanyl-thiocarbonyl-oxy group," and those groups wherein $R^{a2}$ is a heterocyclic group are referred to as "heterocyclic ring-sulfanyl-thiocarbonyl-oxy group."

Among the groups represented by the formula (ω-9B), those groups in which $R^{a2}$ is a hydrocarbon group are referred to as "N-hydrocarbon-carbamoyl-oxy group," and those groups in which $R^{a2}$ is a heterocyclic group are referred to as "N-heterocyclic ring-carbamoyl-oxy group."

Among the groups represented by the formula (ω-10B), those groups in which both $R^{a2}$ and $R^{b2}$ are hydrocarbon groups are referred to as "N,N-di(hydrocarbon)-carbamoyl-oxy group," those groups in which both $R^{a2}$ and $R^{b2}$ are heterocyclic groups are referred to as "N,N-di(heterocyclic ring)-carbamoyl-oxy group," those groups in which $R^{a2}$ is a hydrocarbon group and $R^{b2}$ is a heterocyclic group are referred to as "N-hydrocarbon-N-heterocyclic ring-carbamoyl-oxy group," and those groups in which $R^{a2}$ and $R^{b2}$ combine to each other, together with the nitrogen atom to which they bind, to form a cyclicic amino group are referred to as "cyclicamino-carbonyl-oxy group."

Among the groups represented by the formula (ω-11B), those groups in which $R^{a2}$ is a hydrocarbon group are referred to as "N-hydrocarbon-thiocarbamoyl-oxy group," and those groups in which $R^{a2}$ is a heterocyclic group are referred to as "N-heterocyclic ring-thiocarbamoyl-oxy group."

Among the groups represented by the formula (ω-12B), those groups in which both $R^{a2}$ and $R^{b2}$ are hydrocarbon groups are referred to as "N,N-di(hydrocarbon)-thiocarbamoyl-oxy group," those groups in which both $R^{a2}$ and $R^{b2}$ are heterocyclic groups are referred to as "N,N-di(heterocyclic ring)-thiocarbamoyl-oxy group," those groups in which $R^{a2}$ is a hydrocarbon group and $R^{b2}$ is a heterocyclic group are referred to as "N-hydrocarbon-N-heterocyclic ring-thiocarbamoyl-oxy group," and those groups in which $R^{a2}$ and $R^{b2}$ combine to each other, together with the nitrogen atom to which they bind, to form a cyclic amino group are referred to as "cyclicamino-thiocarbonyl-oxy group."

Among the groups represented by the formula (ω-13B), those groups in which $R^{a2}$ is a hydrocarbon group are referred to as "N-hydrocarbon-sulfamoyl-oxy group," and those groups in which $R^{a2}$ is a heterocyclic group are referred to as "N-heterocyclic ring-sulfamoyl-oxy group."

Among the groups represented by the formula (ω-14B), those groups in which both $R^{a2}$ and $R^{b2}$ are hydrocarbon groups are referred to as "N,N-di(hydrocarbon)-sulfamoyl-oxy group," those groups in which both $R^{a2}$ and $R^{b2}$ are heterocyclic groups are referred to as "N,N-di(heterocyclic ring)-sulfamoyl-oxy group," those groups in which $R^{a2}$ is a hydrocarbon group and $R^{b2}$ is a heterocyclic group are referred to as "N-hydrocarbon-N-heterocyclic ring-sulfamoyl-oxy group," and those groups in which $R^{a2}$ and $R^{b2}$ combine to each other, together with the nitrogen atom to which they bind, to form a cyclic amino group are referred to as "cyclic amino-sulfonyl-oxy group."

Among the groups represented by the formula (ω-15B), those groups in which $R^{a2}$ is a hydrocarbon group are referred to as "N-hydrocarbon-sulfinamoyl-oxy group," and those groups where $R^{a2}$ is a heterocyclic group are referred to as "N-heterocyclic ring-sulfinamoyl-oxy group."

Among the groups represented by the formula (ω-16B), those groups in which both $R^{a2}$ and $R^{b2}$ are hydrocarbon groups are referred to as "N,N-di(hydrocarbon)-sulfinamoyl-oxy group," those groups in which both $R^{a2}$ and $R^{b2}$ are heterocyclic groups are referred to as "N,N-di(heterocyclic ring)-sulfinamoyl-oxy group," those groups in which $R^{a2}$ is a hydrocarbon group and $R^{b2}$ is a heterocyclic group are referred to as "N-hydrocarbon-N-heterocyclic ring-sulfinamoyl-oxy group," and those groups in which $R^{a2}$ and $R^{b2}$ combine to each other, together with the nitrogen atom to which they bind, to form a cyclic amino group are referred to as "cyclic amino-sulfinyl-oxy group."

Among the groups represented by the formula (ω-17B), those groups in which $R^{a2}$ is a hydrocarbon group are referred to as "hydrocarbon-oxy-sulfonyl-oxy group," and those groups in which $R^{a2}$ is a heterocyclic group are referred to as "heterocyclic ring-oxy-sulfonyl-oxy group."

Among the groups represented by the formula (ω-18B), those groups in which $R^{a2}$ is a hydrocarbon group are referred to as "hydrocarbon-oxy-sulfinyl-oxy group," those groups in which $R^{a2}$ is a heterocyclic group are referred to as "heterocyclic ring-oxy-sulfinyl-oxy group."

Among the groups represented by the formula (ω-19B), those groups in which both $R^{a2}$ and $R^{b2}$ are hydrocarbon groups are referred to as "O,O'-di(hydrocarbon)-phosphono-oxy group," those groups in which both $R^{a2}$ and $R^{b2}$ are heterocyclic groups are referred to as "O,O'-di(heterocyclic ring)-phosphono-oxy group," and those groups in which $R^{a2}$ is a hydrocarbon group and $R^{b2}$ is a heterocyclic group are referred to as "O-hydrocarbon substituted-O'-heterocyclic ring substituted phophono-oxy group."

Among the groups represented by the formula (ωA-20B), those groups in which $R^{a2}$ is a hydrocarbon group are referred to as "hydrocarbon-sulfonyl-oxy group," and those groups in which $R^{a2}$ is a heterocyclic group referred to as "heterocyclic ring-sulfonyl-oxy group."

Among the groups represented by the formula (ω-21B), those groups in which $R^{a2}$ is a hydrocarbon group are referred to as "hydrocarbon-sulfinyl-oxy group," and those groups in which $R^{a2}$ is a heterocyclic group are referred to as "heterocyclic ring-sulfinyl-oxy group."

Examples of the hydrocarbon in the groups represented by the aforementioned formulas (ω-1) through (ω-21B) include the similar groups to the aforementioned hydrocarbon group. Examples of the hydrocarbon-carbonyl-oxy group represented by the formula (ω-1B) include, for example, an alkyl-carbonyl-oxy group, an alkenyl-carbonyl-oxy group, an alkynyl-carbonyl-oxy group, a cycloalkyl-carbonyl-oxy group, a cycloalkenyl-carbonyl-oxy group, a cycloalkanedienyl-carbonyl-oxy group, and a cycloalkyl-alkyl-carbonyl-oxy group, which are aliphatic hydrocarbon-carbonyl-oxy groups; an aryl-carbonyl-oxy group; an aralkyl-carbonyl-oxy group; a bridged cyclic hydrocarbon-carbonyl-oxy group; a spirocyclic hydrocarbon-carbonyl-oxy group; and a terpene family hydrocarbon-carbonyl-oxy group. In the following, groups represented by the formulas (ω-2B) through (ω-21B) are similar to those explained above.

Examples of the heterocyclic ring in the groups represented by the aforementioned formulas (ω-1B) through (ω-21B) include similar groups to the aforementioned heterocyclic group. Examples of the heterocyclic ring-carbonyl group represented by the formula (ω-1B) include, for example, a monocyclic heteroaryl-carbonyl group, a fused polycyclic heteroaryl-carbonyl group, a monocyclic non-aromatic heterocyclic ring-carbonyl group, and a fused polycyclic non-aromatic heterocyclic ring-carbonyl group. In the following, groups represented by the formulas (ω-2B) through (ω-21B) are similar to those groups explained above.

Examples of the cyclic amino in the groups represented by the aforementioned formulas (ω-10B) through (ω-16B) include similar groups to the aforementioned cyclic amino group.

The aforementioned acyl-oxy group, hydrocarbon-oxy group, and heterocyclic-oxy group are generically referred to as "substituted oxy group." Moreover, these substituted oxy group and hydroxy group are generically referred to as "hydroxy group which may be substituted."

Examples of the acyl-sulfanyl group include the groups in which hydrogen atom of sulfanyl group is substituted with acyl group, and include, for example, formylsulfanyl group, glyoxyloylsulfanyl group, thioformylsulfanyl group, carbamoyloxy group, thicarbamoyloxy group, sulfamoyloxy group, sulfinamoyloxy group, carboxyoxy group, sulphooxy group, phosphonooxy group, and groups represented by the following formulas:

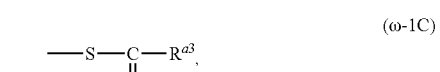

(ω-1C)

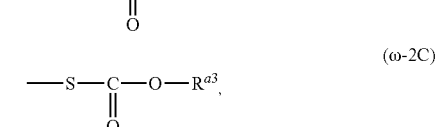

(ω-2C)

(ω-3C)

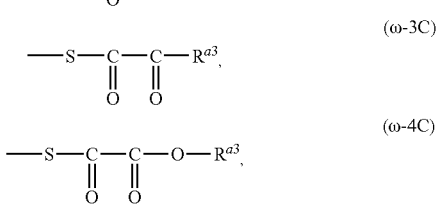

(ω-4C)

(ω-5C)

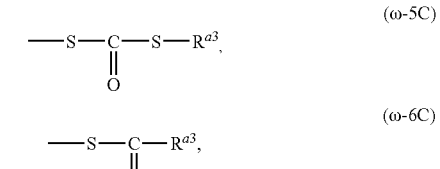

(ω-6C)

(ω-7C)

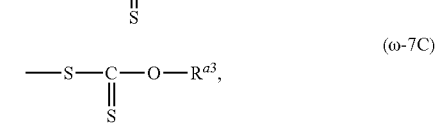

(ω-8C)

(ω-9C)

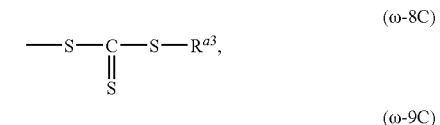

(ω-10C)

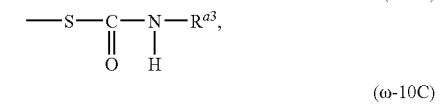

(ω-11C)

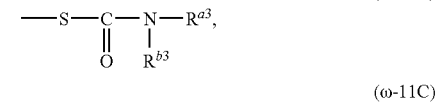

(ω-12C)

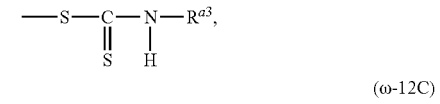

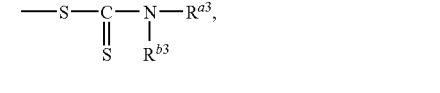

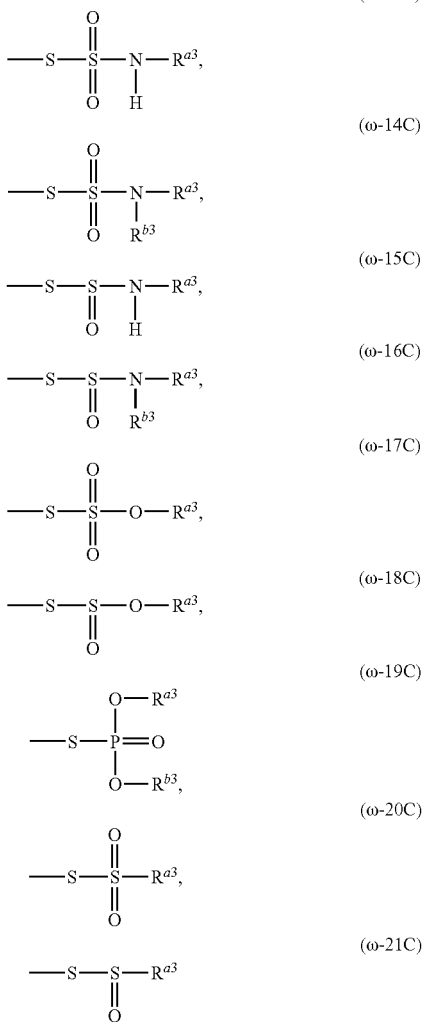

wherein $R^{a3}$ and $R^{b3}$ may be the same or different and represent a hydrocarbon group which may be substituted or a heterocyclic group which may be substituted, or $R^{a3}$ and $R^{b3}$ combine to each other, together with the nitrogen atom to which they bind, to form a cyclic amino group which may be substituted.

In the definition of the aforementioned acyl-sulfanyl group, among the groups represented by the formula (ω-1C), those groups in which $R^{a3}$ is a hydrocarbon group are referred to as "hydrocarbon-carbonyl-sulfanyl group," and those groups in which $R^{a3}$ is a heterocyclic group are referred to as "heterocyclic ring-carbonyl-sulfanyl group."

Among the groups represented by the formula (ω-2C), those groups in which $R^{a3}$ is a hydrocarbon group are referred to as "hydrocarbon-oxy-carbonyl-sulfanyl group," and those groups in which $R^{a3}$ is a heterocyclic group are referred to as "heterocyclic ring-oxy-carbonyl-sulfanyl group."

Among the groups represented by the formula (ω-3C), those groups in which $R^{a3}$ is a hydrocarbon group are referred to as "hydrocarbon-carbonyl-carbonyl-sulfanyl group," and those groups in which $R^{a3}$ is a heterocyclic group are referred to as "heterocyclic ring-carbonyl-carbonyl-sulfanyl group."

Among the groups represented by the formula (ω-4C), those groups in which $R^{a3}$ is a hydrocarbon group are referred to as "hydrocarbon-oxy-carbonyl-carbonyl-sulfanyl group," and those groups in which $R^{a3}$ is a heterocyclic group are referred to as "heterocyclic ring-oxy-carbonyl-carbonyl-sulfanyl group."

Among the groups represented by the formula (ω-5C), those groups in which $R^{a3}$ is a hydrocarbon group are referred to as "hydrocarbon-sulfanyl-carbonyl-sulfanyl group," and those groups in which $R^{a3}$ is a heterocyclic group are referred to as "heterocyclic ring-sulfanyl-carbonyl-sulfanyl group."

Among the groups represented by the formula (ω-6C), those groups in which $R^{a3}$ is a hydrocarbon group are referred to as "hydrocarbon-thiocarbonyl-sulfanyl group," and those groups in which $R^{a3}$ is a heterocyclic group are referred to as "heterocyclic ring-thiocarbonyl-sulfanyl group."

Among the groups represented by the formula (ω-7C), those groups in which $R^{a3}$ is a hydrocarbon group are referred to as "hydrocarbon-oxy-thiocarbonyl-sulfanyl group," and those groups in which $R^{a3}$ is a heterocyclic group are referred to as "heterocyclic ring-oxy-thiocarbonyl-sulfanyl group."

Among the groups represented by the formula (ω-8C), those groups in which $R^{a3}$ is a hydrocarbon group are referred to as "hydrocarbon-sulfanyl-thiocarbonyl-sulfanyl group," and those groups in which $R^{a3}$ is a heterocyclic group are referred to as "heterocyclic ring-sulfanyl-thiocarbonyl-sulfanyl group."

Among the groups represented by the formula (ω-9C), those groups in which $R^{a3}$ is a hydrocarbon group are referred to as "N-hydrocarbon-carbamoyl-sulfanyl group," and those groups in which $R^{a3}$ is a heterocyclic group are referred to as "N-heterocyclic ring-carbamoyl-sulfanyl group."

Among the groups represented by the formula (ω-10C), those groups in which both $R^{a3}$ and $R^{b3}$ are a hydrocarbon groups are referred to as "N,N-di(hydrocarbon)-carbamoyl-sulfanyl group," those groups in which both $R^{a3}$ and $R^{b3}$ are heterocyclic groups are referred to as "N,N-di(heterocyclic ring)-carbamoyl-sulfanyl group," those groups in which $R^{a3}$ is a hydrocarbon group and $R^{b3}$ is a heterocyclic group are referred to as "N-hydrocarbon-N-heterocyclic ring-carbamoyl-sulfanyl group," and those groups in which $R^{a3}$ and $R^{b3}$ combine to each other, together with the nitrogen atom to which they bind, to form a cyclic amino group are referred to as "cyclicamino-carbonyl-sulfamoyl group."

Among the groups represented by the formula (ω-11C), those groups in which $R^{a3}$ is a hydrocarbon group are referred to as "N-hydrocarbon-thiocarbamoyl-sulfanyl group," and those groups in which $R^{a3}$ is a heterocyclic group are referred to as "N-heterocyclic ring-thiocarbamoyl-sulfanyl group."

Among the groups represented by the formula (ω-12C), those groups in which both $R^{a3}$ and $R^{b3}$ are hydrocarbon groups are referred to as "N,N-di(hydrocarbon)-thiocarbamoyl-sulfanyl group," those groups in which and $R^{a3}$ and $R^{b3}$ are heterocyclic groups are referred to as "N,N-di(heterocyclic ring)-thiocarbamoyl-sulfanyl group," those groups in which $R^{a3}$ is a hydrocarbon group and $R^{b3}$ is a heterocyclic group are referred to as "N-hydrocarbon-N-heterocyclic ring-thiocarbamoyl-sulfanyl group," and those groups in which $R^{a3}$ and $R^{b3}$ combine to each other, together with the nitrogen atom to which they bind, to form a cyclic amino group are referred to as "cyclicamino-thiocarbonyl-sulfamoyl group."

Among the groups represented by the formula (ω-13C), those groups in which $R^{a3}$ is a hydrocarbon group are referred to as "N-hydrocarbon-sulfamoyl-sulfanyl group," and those groups in which $R^{a3}$ is a heterocyclic group are referred to as "N-heterocyclic ring-sulfamoyl-sulfanyl group."

Among the groups represented by the formula (ω-14C), those groups in which both $R^{a3}$ and $R^{b3}$ are hydrocarbon groups are referred to as "N,N-di(hydrocarbon)-sulfamoyl-sulfanyl group," those groups in which both $R^{a3}$ and $R^{b3}$ are heterocyclic groups are referred to as "N,N-di(heterocyclic ring)-sulfamoyl-sulfinyl group," those groups in which $R^{a3}$ is a hydrocarbon group and $R^{b3}$ is a heterocyclic group are referred to as "N-hydrocarbon-N-heterocyclic ring-sulfamoyl-sulfanyl group," and those groups in which $R^{a3}$ and $R^{b3}$ combine to each other, together with the nitrogen atom to which they bind, to form a cyclic amino group are referred to as "cyclicamino-sulfonyl-sulfanyl group."

Among the groups represented by the formula (ω-15C), those groups in which $R^{a3}$ is a hydrocarbon group are referred to as "N-hydrocarbon-sulfinamoyl-sulfanyl group," and those groups in which $R^{a3}$ is a heterocyclic group are referred to as "N-heterocyclic ring-sulfinamoyl-sulfanyl group."

Among the groups represented by the formula (ω-16C), those groups in which both $R^{a3}$ and $R^{b3}$ are hydrocarbon groups are referred to as "N,N-di(hydrocarbon)-sulfinamoyl-sulfanyl group," those groups in which both $R^{a3}$ and $R^{b3}$ are heterocyclic groups are referred to as "N,N-di(heterocyclic ring)-sulfinamoyl-sulfanyl group," those groups in which $R^{a3}$ is a hydrocarbon group and $R^{b3}$ is a heterocyclic group are referred to as "N-hydrocarbon-N-heterocyclic ring-sulfinamoyl-sulfanyl group," and those groups in which $R^{a3}$ and $R^{b3}$ combine to each other, together with the nitrogen atom to which they bind, to form a cyclic amino group are referred to as "cyclicamino-sulfanyl-sulfanyl group."

Among the groups represented by the formula (ω-17C), those groups in which $R^{a3}$ is a hydrocarbon group are referred to as "hydrocarbon-oxy-sulfonyl-sulfanyl group," and those groups in which $R^{a3}$ is a heterocyclic group are referred to as "heterocyclic ring-oxy-sulfonyl-sulfanyl group."

Among the groups represented by the formula (ω-18C), those groups in which $R^{a3}$ is a hydrocarbon group are referred to as "hydrocarbon-oxy-sulfinyl-sulfanyl group," and those groups in which $R^{a3}$ is a heterocyclic group are referred to as "heterocyclic ring-oxy-sulfinyl-sulfanyl group."

Among the groups represented by the formula (ω-19C), those groups in which both $R^{a3}$ and $R^{b3}$ are hydrocarbon groups are referred to as "O,O'-di(hydrocarbon)-phosphono-sulfanyl group," those groups in which both $R^{a3}$ and $R^{b3}$ are heterocyclic groups are referred to as "O,O'-di(heterocyclic ring)-phosphono-sulfanyl group," and those groups in which $R^{a3}$ is a hydrocarbon group and $R^{b3}$ is a heterocyclic group are referred to as "O-hydrocarbon-O'-heterocyclic ring-phosphono-sulfanyl group."

Among the groups represented by the formula (ω-20C), those groups in which $R^{a3}$ is a hydrocarbon group are referred to as "hydrocarbon-sulfonyl-sulfanyl group," and those groups in which $R^{a3}$ is a heterocyclic group are referred to as "heterocyclic ring-sulfonyl-sulfanyl group."

Among the groups represented by the formula (ω-21C), those groups in which $R^{a3}$ is a hydrocarbon group are referred to as "hydrocarbon-sulfinyl-sulfanyl group," and those groups in which $R^{a3}$ is a heterocyclic group are referred to as "heterocyclic ring-sulfinyl-sulfanyl group."

Examples of the hydrocarbon in the groups represented by the aforementioned formulas (ω-1C) through (ω-21C) include similar groups to the aforementioned hydrocarbon group. Examples of the hydrocarbon-carbonyl-sulfanyl group represented by the formula (ω-1C) include, for example, an alkyl-carbonyl-sulfanyl group, an alkenyl-carbonyl-sulfanyl group, an alkynyl-carbonyl-sulfanyl group, a cycloalkyl-carbonyl-sulfanyl group, a cycloalkenyl-carbonyl-sulfanyl group, a cycloalkanedienyl-carbonyl-sulfanyl group, a cycloalkyl-alkyl-carbonyl-sulfanyl group which are aliphatic hydrocarbon-carbonyl-sulfanyl groups; an aryl-carbonyl-sulfanyl group; an aralkyl-carbonyl-sulfanyl group; a bridged cyclic hydrocarbon-carbonyl-sulfanyl group; a spiro cyclic hydrocarbon-carbonyl-sulfanyl group; and a terpene family hydrocarbon-carbonyl-sulfanyl group. In the following, groups represented by the formulas (ω-2C) through (ω-21C) are similar to those explained above.

Examples of the heterocyclic ring in the groups represented by the aforementioned formulas (ω-1C) through (ω-21C) include similar groups to the aforementioned heterocyclic group. Examples of the heterocyclic ring-carbonyl-sulfanyl group represented by the formula (ω-1C) include, for example, a monocyclic heteroaryl-carbonyl-sulfanyl group, a fused polycyclic heteroaryl-carbonyl-sulfanyl group, a monocyclic non-aromatic heterocyclic ring-carbonyl-sulfanyl group, and a fused polycyclic non-aromatic heterocyclic ring-carbonyl-sulfanyl group. In the following, groups represented by the formula (ω-2C) through (ω-21C) are similar to those groups explained above.

Examples of the cyclic amino in the groups represented by the aforementioned formulas (ω-10C) through (ω-16C) include similar groups to the aforementioned cyclic amino group.

The aforementioned acyl-sulfanyl group, hydrocarbon-sulfanyl group, and heterocyclic-sulfanyl group are generically referred to as "substituted sulfanyl group." Moreover, these substituted sulfanyl group and sulfanyl group are generically referred to as "sulfanyl group which may be substituted."

Examples of the N-hydrocarbon-amino group include the groups in which one hydrogen atom of amino group is substituted with a hydrocarbon group, and include, for example, an N-alkyl-amino group, an N-alkenyl-amino group, an N-alkynyl-amino group, an N-cycloalkyl-amino group, an N-cycloalkyl-alkyl-amino group, an N-aryl-amino group, and an N-aralkyl-amino group.

Examples of the N-alkyl-amino group include, for example, methylamino, ethylamino, n-propylamino, isopropylamino, n-butylamino, isobutylamino, sec-butylamino, tert-butylamino, n-pentylamino, isopentylamino, (2-methylbutyl)amino, (1-methylbutyl)amino, neopentylamino, (1,2-dimethylpropyl)amino, (1-ethylpropyl)amino, n-hexylamino, (4-methylpentyl)amino, (3-methylpentyl)amino, (2-methylpentyl)amino, (1-methylpentyl)amino, (3,3-dimethylbutyl)amino, (2,2-dimethylbutyl)amino, (1,1-dimethylbutyl)amino, (1,2-dimethylbutyl)amino, (1,3-dimethylbutyl)amino, (2,3-dimethylbutyl)amino, (2-ethylbutyl)amino, (1-ethylbutyl)amino, (1-ethyl-1-methylpropyl)amino, n-heptylamino, n-octylamino, n-nonylamino, n-decylamino, n-undecylamino, n-dodecylamino, n-tridecylamino, n-tetradecylamino, and n-pentadecylamino, which are $C_1$ to $C_{15}$ straight chain or branched chain N-alkyl amino groups.

Examples of the N-alkenyl-amino group include, for example, vinyl amino, (prop-1-en-1-yl)amino, alkylamino, isopropenylamino, (but-1-en-1-yl)amino, (but-2-en-1-yl)amino, (but-3-en-1-yl)amino, (2-methylprop-2-en-1-yl)amino, (1-methylprop-2-en-1-yl)amino, (pent-1-en-1-yl)amino, (pent-2-en-1-yl)amino, (pent-3-en-1-yl)amino, (pent-4-en-1-yl)amino, (3-methylbut-2-en-1-yl)amino, (3-methylbut-3-en-1-yl)amino, (hex-1-en-1-yl)amino, (hex-2-en-1-yl)amino, (hex-3-en-1-yl)amino, (hex-4-en-1-yl)amino, (hex-5-en-1-yl)amino, (4-methylpent-3-en-1-yl)amino, (4-methylpent-3-en-1-yl)amino, (hept-1-en-1-yl)amino, (hept-6-en-1-yl)amino, (oct-1-en-1-yl)amino, (oct-7-en-1-yl)amino, (non-1-en-1-yl)amino, (non-8-en-1-yl)amino, (dec-1-en-1-yl)amino, (dec-9-en-1-yl)amino, (undec- 1-en-1-yl)amino, (undec-10-en-1-yl)amino, (dodec-1-en-1-yl)amino, (dodec-11-en-1-yl)amino, (tridec-1-en-1-yl)amino, (tridec-12-en-1-yl)amino, (tetradec-1-en-1-yl)amino, (tetradec-13-en-1-yl)amino, (pentadec-1-en-1-yl)amino, and (pentadec-14-en-1-yl)amino, which are $C_2$ to $C_{15}$ straight chain or branched chain N-alkenyl amino groups.

Examples of the N-alkynyl-amino group include, for example, ethynylamino, (prop-1-yn-1-yl)amino, (prop-2-yn-1-yl)amino, (but-1-yn-1-yl)amino, (but-3-yn-1-yl)amino, (1-methylprop-2-yn-1-yl)amino, (pent-1-yn-1-yl)amino, (pent-4-yn-1-yl)amino, (hex-1-yn-1-yl)amino, (hex-5-yn-1-yl)amino, (hept-1-yn-1-yl)amino, (hept-6-yn-1-yl)amino, (oct-1-yn-1-yl)amino, (oct-7-yn-1-yl)amino, (non-1-yn-1-yl)amino, (non-8-yn-1-yl)amino, (dec-1-yn-1-yl)amino, (dec-9-yn-1-yl)amino, (undec-1-yn-1-yl)amino, (undec-10-yn-1-yl)amino, (dodec-1-yn-1-yl)amino, (dodec-11-yn-1-yl)amino, (tridec-1-yn-1-yl)amino, (tridec-12-yn-1-yl)amino, (tetradec-1-yn-1-yl)amino, (tetradec-13-yn-1-yl)amino, (pentadec-1-yn-1-yl)amino, and (pentadec-14-yn-1-yl)amino, which are $C_2$ to $C_{15}$ straight chain or branched chain N-alkynyl-amino groups.

Examples of the N-cycloalkyl-amino group include, for example, cyclopropylamino, cyclobutylamino, cyclopentylamino, cyclohexylamino, cycloheptylamino, and cyclooctylamino, which are $C_3$ to $C_8$ N-cycloalkyl-amino groups.

Examples of the N-cycloalkyl-alkyl-amino group include, for example, (cyclopropylmethyl)amino, (1-cyclopropylethyl)amino, (2-cyclopropylethyl)amino, (3-cyclopropylpropyl)amino, (4-cyclopropylbutyl)amino, (5-cyclopropylpentyl)amino, (6-cyclopropylhexyl)amino, (cyclobutylmethyl)amino, (cyclopentylmethyl)amino, (cyclobutylmethyl)amino, (cyclopentylmethyl)amino, (cyclohexylmethyl)amino, (2-cyclohexylethyl)amino, (3-cyclohexylpropyl)amino, (4-cyclohexylbutyl)amino, (cycloheptylmethyl)amino, (cyclooctylmethyl)amino, and (6-cyclooctylhexyl)amino, which are $C_4$ to $C_{14}$ N-cycloalkyl-alkyl-amino groups.

Examples of the N-aryl-amino group include, for example, phenylamino, 1-naphthylamino, 2-naphtylamino, anthrylamino, phenanthrylamino, and acenaphthylenylamino, which are $C_6$ to $C_{14}$ N-mono-arylamino groups.

Examples of the N-aralkyl-amino group include, for example, benzylamino, (1-naphthylmethyl)amino, (2-naphthylmethyl)amino, (anthracenylmethyl)amino, (phenanthrenylmethyl)amino, (acenaphthylenylmethyl)amino, (diphenylmethyl)amino, (1-phenethyl)amino, (2-phenethyl)amino, (1-(1-naphthyl)ethyl)amino, (1-(2-naphthyl)ethyl)amino, (2-(1-naphthyl)ethyl)amino, (2-(2-naphthyl)ethyl)amino, (3-phenylpropyl)amino, (3-(1-naphthyl)propyl)amino, (3-(2-naphthyl)propyl)amino, (4-phenylbutyl)amino, (4-(1-naphthyl)butyl)amino, (4-(2-naphthyl)butyl)amino, (5-phenylpentyl)amino, (5-(1-naphthyl)pentyl)amino, (5-(2-naphthyl)pentyl)amino, (6-phenylhexyl)amino, (6-(1-naphthyl)hexyl)amino, and (6-(2-naphthyl)hexyl)amino, which are $C_7$ to $C_{16}$ N-aralkyl-amino groups.

Examples of the N,N-di(hydrocarbon)-amino group include the groups in which two hydrogen atoms of amino group are substituted with hydrocarbon groups, and include, for example, N,N-dimethylamino, N,N-diethylamino, N-ethyl-N-methylamino, N,N-di-n-propylamino, N,N-diisopropylamino, N-alkyl-N-methylamino, N-(prop-2-yn-1-yl)-N-methylamino, N,N-dicyclohexylamino, N-cyclohexyl-N-methylamino, N-cyclohexylmethylamino-N-methylamino, N,N-diphenylamino, N-methyl-N-phenylamino, N,N-dibenzylamino, and N-benzyl-N-methylamino.

Examples of the N-heterocyclic ring-amino group include the groups in which one hydrogen atom of amino group is substituted with a heterocyclic group, and include, for example, (3-pyrrolizinyl)amino, (4-piperidinyl)amino, (2-tetrahydropyranyl)amino, (3-indolinyl)amino, (4-chromanyl)amino, (3-thienyl)amino, (3-pyridyl)amino, (3-quinolyl)amino, and (5-indolyl)amino.

Examples of the N-hydrocarbon-N-heterocyclic ring-amino group include the groups in which two hydrogen atoms of amino group are substituted with hydrocarbon group and heterocyclic group respectively, and include, for example, N-methyl-N-(4-piperidinyl)amino, N-(4-chromanyl)-N-methylamino, N-methyl-N-(3-thienyl)amino, N-methyl-N-(3-pyridyl)amino, N-methyl-N-(3-quinolyl)amino.

Examples of the acyl-amino group include the groups in which one hydrogen atom of the amino group is substituted with an acyl group, and include, for example, formylamino group, glyoxyloylamino group, thioformylamino group, carbamoylamino group, thiocarbamoylamino group, sulfamoylamino group, sulfinamoylamino group, carboxyamino group, sulphoamino group, phosphonoamino group, and groups represented by the following formulas:

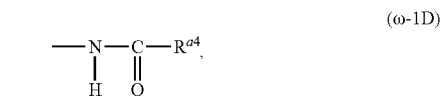
(ω-1D)

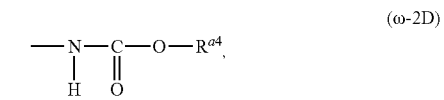
(ω-2D)

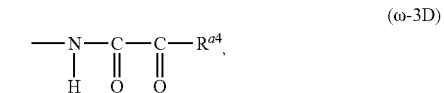
(ω-3D)

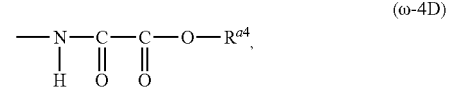
(ω-4D)

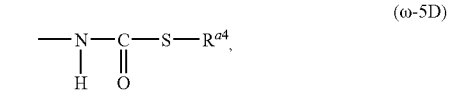
(ω-5D)

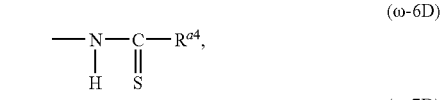
(ω-6D)

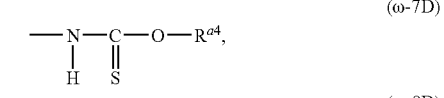
(ω-7D)

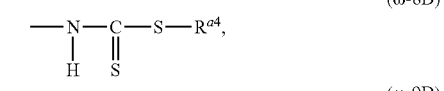
(ω-8D)

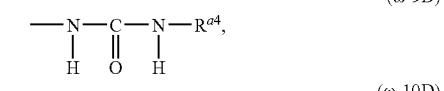
(ω-9D)

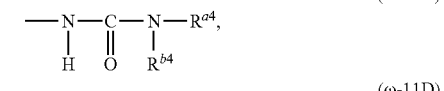
(ω-10D)

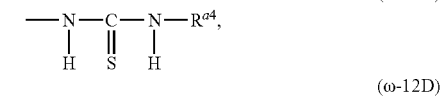
(ω-11D)

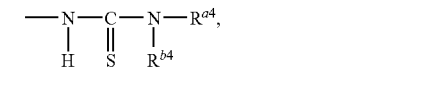
(ω-12D)

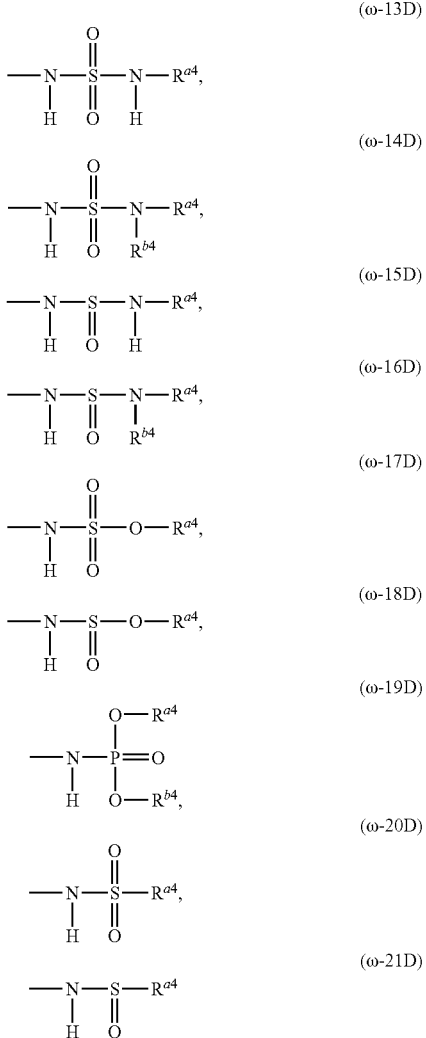

wherein $R^{a4}$ and $R^{b4}$ may be the same or different and represent a hydrocarbon group which may be substituted or a heterocyclic group which may be substituted, or $R^{a4}$ and $R^{b4}$ combine to each other, together with the nitrogen atom to which they bind, to form a cyclic amino group which may be substituted.

In the definition of the aforementioned acyl-amino group, among the groups represented by the formula (ω-1D), those groups in which $R^{a4}$ is a hydrocarbon group are referred to as "hydrocarbon-carbonyl-amino group," and those groups in which $R^{a4}$ is a heterocyclic group are referred to as "heterocyclic ring-carbonyl-amino group."

Among the groups represented by the formula (ω-2D), those groups in which $R^{a4}$ is a hydrocarbon group are referred to as "hydrocarbon-oxy-carbonyl-amino group," and those groups in which $R^{a4}$ is a heterocyclic group are referred to as "heterocyclic ring-oxy-carbonyl-amino group."

Among the groups represented by the formula (ω-3D), those groups in which $R^{a4}$ is a hydrocarbon group are referred to as "hydrocarbon-carbonyl-carbonyl-amino group," and those groups in which $R^{a4}$ is a heterocyclic group are referred to as "heterocyclic ring-carbonyl-carbonyl-amino group."

Among the groups represented by the formula (ω-4D), those groups in which $R^{a4}$ is a hydrocarbon group are referred to as "hydrocarbon-oxy-carbonyl-carbonyl-amino group," and those groups in which $R^{a4}$ is a heterocyclic group are referred to as "heterocyclic ring-oxy-carbonyl-carbonyl-amino group."

Among the groups represented by the formula (ω-5D), those groups in which $R^{a4}$ is a hydrocarbon group are referred to as "hydrocarbon-sulfanyl-carbonyl-amino group," and those groups in which $R^{a4}$ is a heterocyclic group are referred to as "heterocyclic ring-sulfanyl-carbonyl-amino group."

Among the groups represented by the formula (ω-6D), those groups in which $R^{a4}$ is a hydrocarbon group are referred to as "hydrocarbon-thiocarbonyl-amino group," and those groups in which $R^{a4}$ is a heterocyclic group are referred to as "heterocyclic ring-thiocarbonyl-amino group."

Among the groups represented by the formula (ω-7D), those groups in which $R^{a4}$ is a hydrocarbon group are referred to as "hydrocarbon-oxy-thiocarbonyl-amino group," and those groups in which $R^{a4}$ is a heterocyclic group are referred to as "heterocyclic ring-oxy-thiocarbonyl-amino group."

Among the groups represented by the formula (ω-8D), those groups in which $R^{a4}$ is a hydrocarbon group are referred to as "hydrocarbon-sulfanyl-thiocarbonyl-amino group," and those groups in which $R^{a4}$ is a heterocyclic group are referred to as "heterocyclic ring-sulfanyl-thiocarbonyl-amino group."

Among the groups represented by the formula (ω-9D), those groups in which $R^{a4}$ is a hydrocarbon group are referred to as "N-hydrocarbon-carbamoyl group," and those groups in which $R^{a4}$ is a heterocyclic group are referred to as "N-heterocyclic ring-carbamoyl-amino group."

Among the groups represented by the formula (ω-10D), those groups in which both $R^{a4}$ and $R^{b4}$ are hydrocarbon groups are referred to as "N,N-di(hydrocarbon)-carbamoyl-amino group," those groups in which both $R^{a4}$ and $R^{b4}$ are heterocyclic groups are referred to as "N,N-di(heterocyclic ring)-carbamoyl-amino group," those groups in which $R^{a4}$ is a hydrocarbon group and $R^{b4}$ is a heterocyclic group are referred to as "N-hydrocarbon-N-heterocyclic ring-carbamoyl-amino group," and those groups in which $R^{a4}$ and $R^{b4}$ combine to each other, together with the nitrogen atom to which they bind, to form a cyclic amino group are referred to as "cyclic amino-carbonyl-amino group."

Among the groups represented by the formula (ω-11D), those groups in which $R^{a4}$ is a hydrocarbon group are referred to as "N-hydrocarbon-thiocarbamoyl-amino group," and those groups in which $R^{a4}$ is a heterocyclic ring group are referred to as "N-heterocyclic-thiocarbamoyl-amino group."

Among the groups represented by the formula (ω-12D), those groups in which both $R^{a4}$ and $R^{b4}$ are hydrocarbon groups are referred to as "N,N-di(hydrocarbon)-thiocarbamoyl-amino group," those groups in which both $R^{a4}$ and $R^{b4}$ are heterocyclic groups are referred to as "N,N-di(heterocyclic ring)-thiocarbamoyl-amino group," those groups in which $R^{a4}$ is a hydrocarbon group and $R^{b4}$ is a heterocyclic group are referred to as "N-hydrocarbon-N-heterocyclic ring-thiocarbamoyl-amino group," and those groups in which $R^{a4}$ and $R^{b4}$ combine to each other, together with the nitrogen atom to which they bind, to form a cyclic amino group are referred to as "cyclic amino-thiocarbonyl-amino group."

Among the groups represented by the formula (ω-13D), those groups in which $R^{a4}$ is a hydrocarbon group are referred to as "N-hydrocarbon-sulfamoyl-amino group," and those groups in which $R^{a4}$ is a heterocyclic group are referred to as "N-heterocyclic ring-sulfamoyl-amino group."

Among the groups represented by the formula (ω-14D), those groups in which both $R^{a4}$ and $R^{b4}$ are hydrocarbon groups are referred to as "di(hydrocarbon)-sulfamoyl-amino group," those groups in which both $R^{a4}$ and $R^{b4}$ are heterocyclic groups are referred to as "N,N-di(heterocyclic ring)-sulfamoyl-amino group," those groups in which $R^{a4}$ is a hydrocarbon group and $R^{b4}$ is a heterocyclic group are referred to as "N-hydrocarbon-N-heterocyclic ring-sulfamoyl-amino group," and those groups in which $R^{a4}$ and $R^{b4}$ combine to each other, together with the nitrogen atom to which they bind, to form a cyclic amino group are referred to as "cyclic amino-sulfonyl-amino group."

Among the groups represented by the formula (ω-15D), those groups in which $R^{a4}$ is a hydrocarbon group are referred to as "N-hydrocarbon-sulfinamoyl-amino group," and those groups in which $R^{a4}$ is a heterocyclic group are referred to as "N-heterocyclic ring-sulfinamoyl-amino group."

Among the groups represented by the formula (ω-16D), those groups in which both $R^{a4}$ and $R^{b4}$ are hydrocarbon groups are referred to as "N,N-di(hydrocarbon)-sulfinamoyl-amino group," those groups in which both $R^{a4}$ and $R^{b4}$ are heterocyclic groups are referred to as "N,N-di(heterocyclic ring)-sulfinamoyl-amino group," groups in which $R^{a4}$ is a hydrocarbon group and $R^{b4}$ is a heterocyclic group are referred to as "N-hydrocarbon-N-heterocyclic ring-sulfinamoyl-amino group," and those groups in which $R^{a4}$ and $R^{b4}$ combine to each other, together with the nitrogen atom to which they bind, to form a cyclic amino group are referred to as "cyclic amino-sulfinyl-amino group."

Among the groups represented by the formula (ω-17D), those groups in which $R^{a4}$ is a hydrocarbon group are referred to as "hydrocarbon-oxy-sulfonyl-amino group," and those groups in which $R^{a4}$ is a heterocyclic group are referred to as "heterocyclic ring-oxy-sulfoyl-amino group."

Among the groups represented by the formula (ω-18D), those groups in which $R^{a4}$ is a hydrocarbon group are referred to as "hydrocarbon-oxy-sulfinyl-amino group," and those groups in which $R^{a4}$ is a heterocyclic group are referred to as "heterocyclic ring-oxy-sulfinyl-amino group."

Among the groups represented by the formula (ω-19D), those groups in which both $R^{a4}$ and $R^{b4}$ are hydrocarbon groups are referred to as "O,O'-di(hydrocarbon)-phosphono-amino group," those groups in which both $R^{a4}$ and $R^{b4}$ are heterocyclic groups are referred to as "O,O'-di(heterocyclic ring)-phosphono-amino group," and those groups in which $R^{a4}$ is a hydrocarbon group and $R^{b4}$ is a heterocyclic group are referred to as "O-hydrocarbon-O'-heterocyclic ring-phosphono-amino group."

Among the groups represented by the formula (ω-20D), those groups in which $R^{a4}$ is a hydrocarbon group are referred to as "hydrocarbon-sulfonyl-amino group," and those groups in which $R^{a4}$ is a heterocyclic group are referred to as "heterocyclic ring-sulfonyl-amino group."

Among the groups represented by the formula (ω-21D), those groups in which $R^{a4}$ is a hydrocarbon group are referred to as "hydrocarbon-sulfinyl-amino group," and those groups in which $R^{a4}$ is a heterocyclic group are referred to as "heterocyclic ring-sulfinyl-amino group."

Examples of the hydrocarbon in the groups represented by the aforementioned formulas (ω-1D) through (ω-21D) include the similar groups to the aforementioned hydrocarbon group. Examples of the hydrocarbon-carbonyl-amino groups represented by the formula (ω-1D) include, for example, an alkyl-carbonyl-amino group, an alkenyl-carbonyl-amino group, an alkynyl-carbonyl-amino group, a cycloalkyl-carbonyl-amino group, a cycloalkenyl-carbonyl-amino group, a cycloalkanedienyl-carbonyl-amino group, a cycloalkyl-alkyl-carbonyl-amino group which are aliphatic hydrocarbon-carbonyl-amino groups; an aryl-carbonyl-amino group; an aralkyl-carbonyl-amino group; a bridged cyclic hydrocarbon-carbonyl-amino group; a spiro cyclic hydrocarbon-carbonyl-amino group; and a terpene family hydrocarbon-carbonyl-amino group. In the following, groups represented by the formulas (ω-2D) through (ω-21D) are similar to those explained above.

Examples of the heterocyclic ring in the groups represented by the aforementioned formulas (ω-1D) through (ω-21D) include similar groups to the aforementioned heterocyclic group. Examples of the heterocyclic ring-carbonyl-amino group represented by the formula (ω-1D) include, for example, a monocyclic heteroaryl-carbonyl-amino group, a fused polycyclic heteroaryl-carbonyl-amino group, a monocyclic non-aromatic heterocyclic-carbonyl-amino group, and a fused polycyclic non-aromatic heterocyclic-carbonyl-amino group. In the following, groups represented by the formulas (ω-2D) through (ω-21D) are similar to those groups explained above.

Examples of the cyclic amino in the groups represented by the aforementioned formulas (ω-10D) through (ω-16D) include similar groups to the aforementioned cyclic amino group.

Examples of the di(acyl)-amino group include the groups in which two hydrogen atoms of amino group are substituted with acyl groups in the definitions of the aforementioned substituents according to "which may be substituted." Examples include, for example, di(formyl)-amino group, di(glyoxyloyl)-amino group, di(thioformyl)-amino group, di(carbamoyl)-amino group, di(thiocarbamoyl)-amino group, di(sulfamoyl)-amino group, di(sulfinamoyl)-amino group, di(carboxy)-amino group, di(sulfo)-amino group, di(phosphono)-amino group, and groups represented by the following formulas:

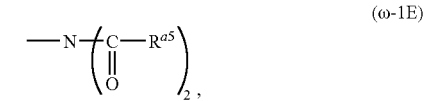

(ω-1E)

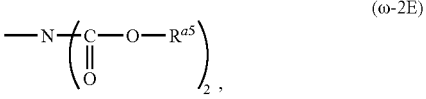

(ω-2E)

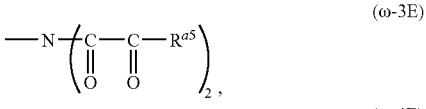

(ω-3E)

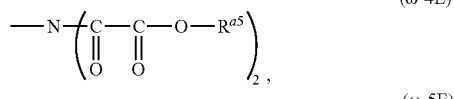

(ω-4E)

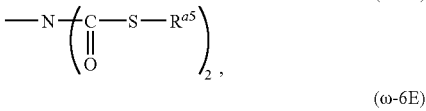

(ω-5E)

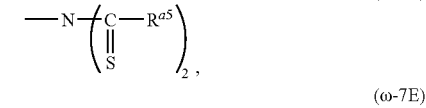

(ω-6E)

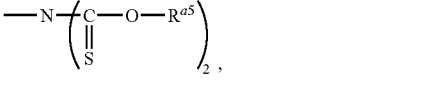

(ω-7E)

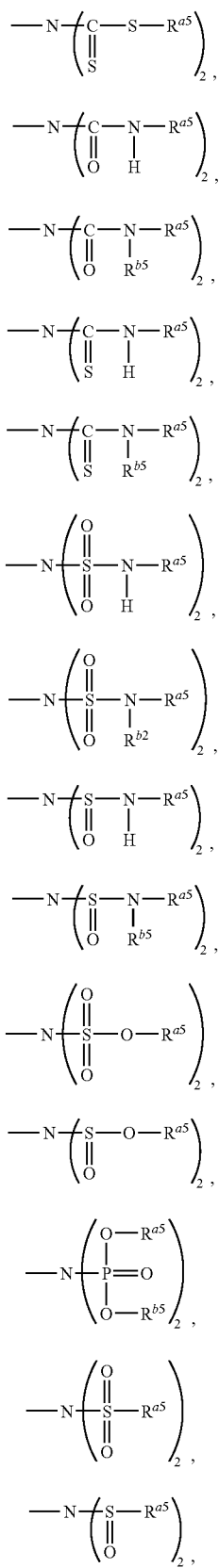

(ω-8E)
(ω-9E)
(ω-10E)
(ω-11E)
(ω-12E)
(ω-13E)
(ω-14E)
(ω-15E)
(ω-16E)
(ω-17E)
(ω-18E)
(ω-19E)
(ω-20E)
(ω-21E)

wherein $R^{a5}$ and $R^{b5}$ may be the same or different and represent hydrogen atom, a hydrocarbon group which may be substituted or a heterocyclic group which may be substituted, or $R^{a5}$ and $R^{b5}$ combine to each other, together with the nitrogen atom to which they bind, to form a cyclic amino group which may be substituted.

In the definition of aforementioned di(acyl)-amino group, among the groups represented by the formula (ω-1E), those groups in which $R^{a5}$ is a hydrocarbon group are referred to as "bis(hydrocarbon-carbonyl)-amino group," and those groups in which $R^{a5}$ is a heterocyclic group are referred to as "bis(heterocyclic ring-carbonyl)-amino group."

Among the groups represented by the formula (ω-2E), those groups in which $R^{a5}$ is a hydrocarbon group are referred to as "bis(hydrocarbon-oxy-carbonyl)-amino group," and those groups in which $R^{a5}$ is a heterocyclic group are referred to as "bis(heterocyclic ring-oxy-carbonyl)-amino group."

Among the groups represented by the formula (ω-3E), those groups in which $R^{a5}$ is a hydrocarbon group are referred to as "bis(hydrocarbon-carbonyl-carbonyl)-amino group," and those groups in which $R^{a5}$ is a heterocyclic group are referred to as "bis(heterocyclic ring-carbonyl-carbonyl)-amino group."

Among the groups represented by the formula (ω-4E), those groups in which $R^{a5}$ is a hydrocarbon group are referred to as "bis(hydrocarbon-oxy-carbonyl-carbonyl)-amino group," and those groups in which $R^{a5}$ is a heterocyclic group are referred to as "bis(heterocyclic ring-oxy-carbonyl-carbonyl)-amino group."

Among the groups represented by the formula (ω-5E), those groups in which $R^{a5}$ is a hydrocarbon group are referred to as "bis(hydrocarbon-sulfanyl-carbonyl)-amino group," and those groups in which $R^{a5}$ is a heterocyclic group are referred to as "bis(heterocyclic ring-sulfanyl-carbonyl)-amino group."

Among the groups represented by the formula (ω-6E), those groups in which $R^{a5}$ is a hydrocarbon group are referred to as "bis(hydrocarbon-thiocarbonyl)-amino group," and those groups in which $R^{a5}$ is a heterocyclic group are referred to as "bis(heterocyclic ring-thiocarbonyl)-amino group."

Among the groups represented by the formula (ω-7E), those groups in which $R^{a5}$ is a hydrocarbon group are referred to as "bis(hydrocarbon-oxy-thiocarbonyl)-amino group," and those groups in which $R^{a5}$ is a heterocyclic group are referred to as "bis(heterocyclic ring-oxy-thiocarbonyl)-amino group."

Among the groups represented by the formula (ω-8E), those groups in which $R^{a5}$ is a hydrocarbon group are referred to as "bis(hydrocarbon-sulfanyl-thiocarbonyl)-amino group," and those groups in which $R^{a5}$ is a heterocyclic group are referred to as "bis(heterocyclic ring-sulfanyl-thiocarbonyl)-amino group."

Among the groups represented by the formula (ω-9E), those groups in which $R^{a5}$ is a hydrocarbon group are referred to as "bis(N-hydrocarbon-carbamoyl)-amino group," and those groups in which $R^{a5}$ is a heterocyclic group are referred to as "bis(N-heterocyclic ring-carbamoyl)-amino group."

Among the groups represented by the formula (ω-10E), those groups in which both $R^{a5}$ and $R^{b5}$ are hydrocarbon groups are referred to as "bis[N,N-di(hydrocarbon)-carbamoyl]-amino group," those groups in which both $R^{a5}$ and $R^{b5}$ are heterocyclic groups are referred to as "bis[N,N-di(heterocyclic ring)-carbamoyl]-amino group," groups in which $R^{a5}$ is a hydrocarbon group and $R^{b5}$ is a heterocyclic group are referred to as "bis(N-hydrocarbon-N-heterocyclic ring-carbamoyl)-amino group," and those groups in which $R^{a5}$ and $R^{b5}$ combine to each other, together with the nitrogen atom to which they bind, to form a cyclic amino groups are referred to as "bis(cyclic amino-carbonyl)amino group."

Among the groups represented by the formula (ω-11E), those groups in which $R^{a5}$ is a hydrocarbon group are referred to as "bis(N-hydrocarbon-thiocarbamoyl)-amino group," and those groups in which $R^{a5}$ is a heterocyclic group are referred to as "bis(N-heterocyclic ring-thiocarbamoyl)-amino group."

Among the groups represented by the formula (ω-12E), those groups in which both $R^{a5}$ and $R^{b5}$ are hydrocarbon groups are referred to as "bis[N,N-di(hydrocarbon)-thiocarbamoyl]-amino group," those groups in which both $R^{a5}$ and $R^{b5}$ are heterocyclic groups are referred to as "bis[N,N-di(heterocyclic ring)-thiocarbamoyl]-amino group," those groups in which $R^{a5}$ is a hydrocarbon group and $R^{b5}$ is a heterocyclic group are referred to as "bis(N-hydrocarbon-N-heterocyclic ring-thiocarbamoyl)-amino group," and those groups in which $R^{a5}$ and $R^{b5}$ combine to each other, together with the nitrogen atom to which they bind, to form a cyclic amino group are referred to as "bis(cyclic amino-thiocarbonyl)-amino group."

Among the groups represented by the formula (ω-13E), those groups in which $R^{a5}$ is a hydrocarbon group are referred to as "bis(N-hydrocarbon-sulfamoyl)-amino group," and those groups in which $R^{a5}$ is a heterocyclic group are referred to as "bis(N-heterocyclic ring-sulfamoyl)-amino group."

Among the groups represented by the formula (ω-14E), those groups in which both $R^{a5}$ and $R^{b5}$ are hydrocarbon groups are referred to as "bis[N,N-di(hydrocarbon)-sulfamoyl]-amino group," those groups in which both $R^{a5}$ and $R^{b5}$ are heterocyclic groups are referred to as "bis[N,N-di(heterocyclic ring)-sulfamoyl]-amino group," those groups in which $R^{a5}$ is a hydrocarbon group and $R^{b5}$ is a heterocyclic group are referred to as "bis(N-hydrocarbon-N-heterocyclic ring-sulfamoyl)-amino group," and those groups in which $R^{a5}$ and $R^{b5}$ combine to each other, together with the nitrogen atom to which they bind, to form a cyclic amino group are referred to as "bis(cyclic amino-sulfonyl)amino group."

Among the groups represented by the formula (ω-15E), those groups in which $R^{a5}$ is a hydrocarbon group are referred to as "bis(N-hydrocarbon-sulfinamoyl)-amino group," and those groups in which $R^{a5}$ is a heterocyclic group are referred to as "bis(N-heterocyclic ring-sulfinamoyl)-amino group."

Among the groups represented by the formula (ω-16E), those groups in which $R^{a5}$ and $R^{b5}$ are hydrocarbon groups are referred to as "bis[N,N-di(hydrocarbon)-sulfinamoyl]-amino group," those groups in which $R^{a5}$ and $R^{b5}$ are heterocyclic groups are referred to as "bis[N,N-di(heterocyclic ring)-sulfinamoyl]-amino group," those groups in which $R^{a5}$ is a hydrocarbon group and $R^{b5}$ is a heterocyclic group are referred to as "bis(N-hydrocarbon-N-heterocyclic ring-sulfinamoyl)-amino group," and those groups in which $R^{a5}$ and $R^{b5}$ combine to each other, together with the nitrogen atom to which they bind, to form a cyclic amino group are referred to as "bis(cyclic amino-sulfinyl)amino group."

Among the groups represented by the formula (ω-17E), those groups in which $R^{a5}$ is a hydrocarbon group are referred to as "bis(hydrocarbon-oxy-sulfonyl)-amino group," and those groups in which $R^{a5}$ is a heterocyclic group are referred to as "bis(heterocyclic ring-oxy-sulfonyl)-amino group."

Among the groups represented by the formula (ω-18E), those groups in which $R^{a5}$ is a hydrocarbon group are referred to as "bis(hydrocarbon-oxy-sulfinyl)-amino group," and those groups in which $R^{a5}$ is a heterocyclic group are referred to as "bis(heterocyclic ring-oxy-sulfinyl)-amino group."

Among the groups represented by the formula (ω-19E), those groups in which both $R^{a5}$ and $R^{b5}$ are hydrocarbon groups are referred to as "bis[O,O'-di(hydrocarbon)-phosphono]-amino group," those groups in which both $R^{a5}$ and $R^{b5}$ are heterocyclic groups are referred to as "bis[O,O'-di(heterocyclic ring)-phosphono]-amino group," and those groups in which $R^{a5}$ is a hydrocarbon group and $R^{b5}$ is a heterocyclic group are referred to as "bis(O-hydrocarbon-O'-heterocyclic ring-phosphono)-amino group."

Among the groups represented by the formula (ω-20E), those groups in which $R^{a5}$ is a hydrocarbon group are referred to as "bis(hydrocarbon-sulfonyl)-amino group," and those groups in which $R^{a5}$ is a heterocyclic group are referred to as "bis(heterocyclic ring-sulfonyl)-amino group."

Among the groups represented by the formula (ω-21E), those groups in which $R^{a5}$ is a hydrocarbon group are referred to as "bis(hydrocarbon-sulfinyl)-amino group," and those groups in which $R^{a5}$ is a heterocyclic group are referred to as "bis(heterocyclic ring-sulfinyl)-amino group."

Examples of the hydrocarbon in the groups represented by the aforementioned formulas (ω-1E) through (ω-21E) include the similar groups to the aforementioned hydrocarbon group. Examples of the bis(hydrocarbon-carbonyl)-amino groups represented by the formula (ω-1E) include, for example, a bis(alkyl-carbonyl)-amino group, a bis(alkenyl-carbonyl)-amino group, a bis(alkynyl-carbonyl)-amino group, a bis(cycloalkyl-carbonyl)-amino group, a bis(cycloalkenyl-carbonyl)-amino group, a bis(cycloalkanedienyl-carbonyl)-amino group, a bis(cycloalkyl-alkyl-carbonyl)-amino group which are bis(aliphatic hydrocarbon-carbonyl)-amino groups; a bis(aryl-carbonyl)-amino group; a bis(aralkyl-carbonyl)-amino group; a bis(bridged cyclic hydrocarbon-carbonyl)-amino group; a bis(spiro cyclic hydrocarbon-carbonyl)-amino group; and a bis(terpene family hydrocarbon-carbonyl)-amino group. In the following, groups represented by the formulas (ω-2E) through (ω-21E) are similar to those explained above.

Examples of the heterocyclic ring in the groups represented by the aforementioned formulas (ω-1E) through (ω-21E) include similar groups to the aforementioned heterocyclic group. Examples of the bis(heterocyclic ring-carbonyl)-amino group represented by the formula (ω-1E) include, for example, a bis(monocyclic heteroaryl-carbonyl)-amino group, a bis(fused polycyclic heteroaryl-carbonyl)-amino group, a bis(monocyclic non-aromatic heterocyclic-carbonyl)-amino group, and a bis(fused polycyclic non-aromatic heterocyclic-carbonyl)-amino group. In the following, groups represented by the formulas (ω-2E) through (ω-21E) are similar to those groups explained above.

Examples of the cyclic amino in the groups represented by the aforementioned formulas (ω-10E) through (ω-16E) include similar groups to the aforementioned cyclic amino group.

The aforementioned acyl-amino group and di(acyl)-amino group are generically referred to as "acyl substituted amino group." Furthermore, the aforementioned N-hydrocarbon-amino group, N,N-di(hydrocarbon)-amino group, N-heterocyclic-amino group, N-hydrocarbon-N-heterocyclic-amino group, cyclic amino group, acyl-amino group, and di(acyl)-amino group are generically referred to as "substituted amino group."

Compounds represented by the aforementioned general formula (I) are explained in details.

"Connecting group whose number of atoms of main chain is 2 to 5" in the definition of X means connecting groups wherein 2 to 5 atoms in a main chain link together between rings Z and E. The aforementioned "number of atoms of the main chain" is counted so as to minimize the number of connecting atoms existing between the rings Z and E, regardless of the presence or absence of hetero atom(s). For example, the number of atoms of 1,2-cyclopentylene is counted as 2, the number of atoms of 1,3-cyclopentylene is counted as 3, the number of atoms of 1,4-phenylene is counted as 4, and the number of atoms of 2,6-pyridine-diyl is counted as 3.

The aforementioned "connecting group whose number of atoms of main chain is 2 to 5" is formed by one functional group selected from the following group of divalent group ζ-1, or formed by combining 2 to 4 functional groups of 1 to 4 kinds selected from the following divalent group ζ-2.

[Divalent Group ζ-1] the Following Formulas:

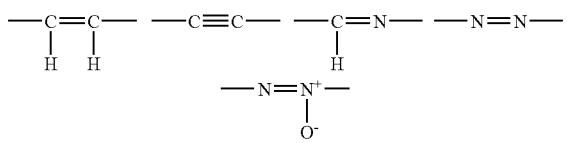

[Divalent Group ζ-2] the Following Formulas:

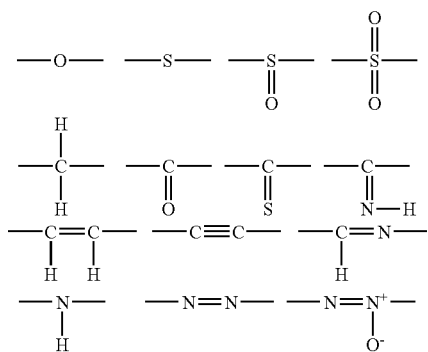

When 2 or more divalent groups combine, each group may be the same or different.

The aforementioned "connecting group wherein the number of atoms of the main chain is 2 to 5," is preferably a group selected from the following "connecting group α."

[Connecting Group α] the Following Formulas:

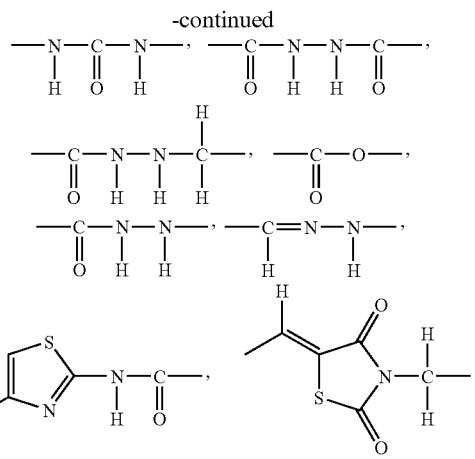

wherein a bond at the left end binds to ring Z and a bond at the right end binds to E.

The group represented by the following formula is most preferred:

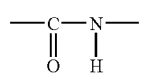

wherein the bond at the left end binds to ring Z and the bond at the right end binds to E.

Examples of the substituent, according to "connecting group which may be substituted" in the definition of "a connecting group whose number of atoms of the main chain is 2 to 5," include similar groups to the substituents in the definition of the aforementioned "which may be substituted." A $C_1$ to $C_6$ alkyl group is preferred, and a methyl group is more preferred. The substituent may combine with a substituent of the ring E or Z, together with atoms to which they bind, to form a cyclic group which may be substituted. Examples include the compounds represented by the general formula (I) being those represented by the following formulas:

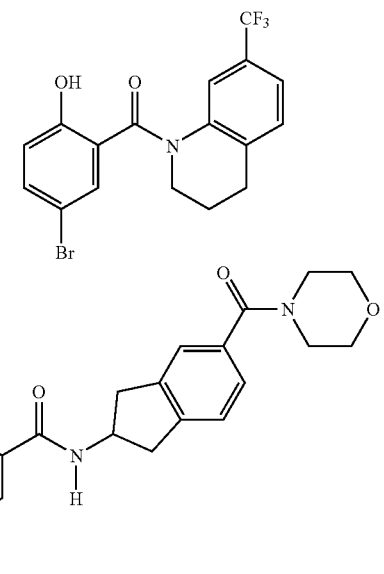

Examples of the substituent in the definition of "an acyl group which may be substituted (provided that unsubstituted acetyl group and unsubstituted acryloyl group are excluded)" in the definition of A include similar groups to the substituent explained for the definition "which may be substituted." The position of substituents existing on the acyl group is not particularly limited, and when two or more substituents exist, they may be the same or different.

Examples of the acyl group of "an acyl group which may be substituted (provided that unsubstituted acetyl group and unsubstituted acryloyl group are excluded)" in the definition of A include similar groups to the acyl group in the aforementioned definition.

Unsubstituted acetyl group and unsubstituted acryloyl group are excluded as "an acyl group which may be substituted" in the definition of A.

A group selected from the following "substituent group ω" is preferred as "an acyl group which may be substituted (provided that unsubstituted acetyl group and unsubstituted acryloyl group are excluded)" in the definition of A, and a heterocyclic ring-carbonyl group which may be substituted, a phosphono group which may be substituted, and a carbamoyl group which may be substituted are more preferred.

[Substituent Group ω] a hydrocarbon-carbonyl group which may be substituted, a heterocyclic ring-carbonyl group which may be substituted, a hydrocarbon-oxy-carbonyl group which may be substituted, a hydrocarbon-sulfonyl group which may be substituted, a sulfamoyl group which may be substituted, a sulfo group which may be substituted, a phosphono group which may be substituted, and a carbamoyl group which may be substituted When "an acyl group which may be substituted" in the definition of A is "a heterocyclic ring-carbonyl group which may be substituted," examples of said heterocyclic ring group include similar groups to the heterocyclic ring group in the aforementioned definition.

When "an acyl group which may be substituted" in the definition of A is "a heterocyclic ring-carbonyl group which may be substituted," preferred examples of the group include groups represented by the following Substituent Group δ-1a.

[Substituent Group δ-1a] nicotinoyl group [(pyridin-3-yl)carbonyl group], isonicotinoyl group [(pyridin-4-yl)carbonyl group], (pyrrolidin-1-yl)carbonyl group, (morpholin-4-yl)carbonyl group [morpholino carbonyl group], (4-methylpiperazin-1-yl)carbonyl group, [4-(ethoxycarbonyl)piperidin-1-yl]carbonyl group, and (4-carboxypiperidin-1-yl)carbonyl group When "an acyl group which may be substituted" in the definition of A is "a heterocyclic ring-carbonyl group which may be substituted," "a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom" is more preferred, (pyrrolidin-1-yl)carbonyl group, (morpholin-4-yl)carbonyl group, (4-methylpiperazin-1-yl)carbonyl group, [4-(ethoxycarbonyl)piperidin-1-yl]carbonyl group and (4-carboxypiperidin-1-yl)carbonyl group are further preferred, and (morpholin-4-yl)carbonyl group is most preferred.

When "an acyl group which may be substituted" in the definition of A is "a phosphono group which may be substituted," phosphono group and dibenzylphosphono group are preferred, and phosphono group is more preferred.

When "an acyl group which may be substituted" in the definition of A is "a carbamoyl group which may be substituted," preferred examples of the group include groups represented by the following Substituent Group δ-2a.

[Substituent Group δ-2a] N-isopropylcarbamoyl group, N-benzylcarbamoyl group, N-(ethoxycarbonylmethyl)carbamoyl group, N-(carbonylmethyl)carbamoyl group, N-(1-methoxycarbonylethyl)carbamoyl group, N-(1-methoxycarbonyl-2-phenylethyl)carbamoyl group, N-[1-methoxycarbonyl-2-(tert-butoxycarbonyl)ethyl]carbamoyl group, N-({N-[1-(tert-butoxycarbonyl)-2-phenylethyl]carbamoyl}methyl)carbamoyl group, N-{[N-(1-carboxy-2-phenylethyl)carbamoyl]methyl}carbamoyl group, N-({N-[1,2-di(tert-butoxycarbonyl)ethyl]carbamoyl}methyl)carbamoyl group, N-{[N-(1,2-dicarboxyethyl)carbamoyl]methyl}carbamoyl group, N-({N-[1,5-di(tert-butoxycarbonyl)pentyl]carbamoyl}methyl)carbamoyl group, N-[(4-methylsulfanyl)phenyl]carbamoyl group, N,N-dimethylcarbamoyl group, N,N-diethylcarbamoyl group, N-methyl-N-phenylcarbamoyl group, N,N-bis[(ethoxycarbonyl)methyl]carbamoyl group, and N,N-bis(carboxymethyl)carbamoyl group When "an acyl group which may be substituted" in the definition of A is "a carbamoyl group which may be substituted," "a N,N-di-substituted carbamoyl group" is more preferred, and N,N-dimethylcarbamoyl group, N,N-diethylcarbamoyl group, N-methyl-N-phenylcarbamoyl group, N,N-bis[(ethoxycarbonyl)methyl]carbamoyl group and N,N-bis(carboxymethyl)carbamoyl group are further preferred.

When "an acyl group which may be substituted" in the definition of A is "a hydrocarbon-carbonyl group which may be substituted," examples of said hydrocarbon group include similar groups to the hydrocarbon group in the aforementioned definition.

When "an acyl group which may be substituted" in the definition of A is "a hydrocarbon-carbonyl group which may be substituted," preferred examples of the group include groups represented by the following Substituent Group δ-3a.

[Substituent Group δ-3a] pivaloyl group [(2,2-dimethyl)propionyl group], Valeryl group, decanoyl group, benzoyl group, 2-acetoxybenzoyl group, phenylacetyl group, (3,4-methylenedioxyphenyl)acetyl group, methoxyacetyl group, acetoxyacetyl group, phenoxyacetyl group, (4-chlorophenoxy)acetyl group, (2,3-dichlorophenoxy)acetyl group, 2-phenoxypropionyl group, 2-(4-chlorophenoxy)isobutyryl group, (tert-butoxycarbonyl)acetyl group, 3-(benzyloxycarbonyl)propionyl group, 3-(piperidinocarbonyl)propionyl group, (acetylamino)acetyl group, [(benzyloxycarbonyl)amino]acetyl group, [(tert-butoxycarbonyl)amino]acetyl group, aminoacetyl group, 2-[(tert-butoxycarbonyl)amino]isovaleryl group, 2-aminoisovaleryl group, 2-[(tert-butoxycarbonyl)amino]-4-methylvaleryl group, 2-amino-4-methylvaleryl group, 2-[(tert-butoxycarbonyl)amino]-3-phenylpropionyl group, 2-amino-3-phenylpropionyl group, 2-[(tert-butoxycarbonyl)amino]-3-(tert-butoxycarbonyl)propionyl group, 2-[(tert-butoxycarbonyl)amino]-4-(tert-butoxycarbonyl)butyryl group, 2-amino-4-carboxybutyryl group, 2,6-bis[(tert-butoxycarbonyl)amino]hexanoyl group, 2,6-diaminohexanoyl group, 2-{2-[(tert-butoxycarbonyl)amino]-3-phenylpropionyl}amino-4-methylvaleryl group, 2-(2-amino-3-phenylpropionyl)amino-4-methylvaleryl group, 2-{2,3-bis[(tert-butoxycarbonyl)amino]propionyl}amino-4-methylvaleryl group, 2-(2-amino-3-carboxypropionyl)amino-4-methylvaleryl group, 2-{2,6-bis[(tert-butoxycarbonyl)amino]hexanoyl}amino-4-methylvaleryl group, 2-(2,6-diaminohexanoyl)amino-4-methylvaleryl group, 2-(2-amino-4-methylvaleryl)amino-3-phenylpropionyl group, and 2-(2-amino-3-carboxypropionyl)amino-3-phenylpropionyl group When "an acyl group which may be substituted" in the definition of A is "a hydrocarbon-oxy-carbonyl group which may be substituted," examples of said hydrocarbon group include similar groups to the hydrocarbon group in the aforementioned definition.

When "an acyl group which may be substituted" in the definition of A is "a hydrocarbon-oxy-carbonyl group which may be substituted," preferred examples of the group include methoxycarbonyl group.

When "an acyl group which may be substituted" in the definition of A is "a hydrocarbon-sulfonyl group which may be substituted," examples of said hydrocarbon group include similar groups to the hydrocarbon group in the aforementioned definition.

When "an acyl group which may be substituted" in the definition of A is "a hydrocarbon-sulfonyl group which may be substituted," preferred examples of the group include methanesulfonyl group [mesyl group], propanesulfonyl group, isopropylsulfonyl group and p-toluenesulfonyl group [tosyl group].

When "an acyl group which may be substituted" in the definition of A is "a sulfamoyl group which may be substituted," preferred examples of the group include N,N-dimethylsulfamoyl group.

When "an acyl group which may be substituted" in the definition of A is "a sulfo group which may be substituted," preferred examples of the group include sulfo group.

When "an acyl group which may be substituted" in the definition of A is "a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom" or "a N,N-di-substituted carbamoyl group," these compounds can be commonly defined as "a N,N-di-substituted carbamoyl group (two substituents of said carbamoyl group may combine to each other, together with the nitrogen atom to which they bind, to form a nitrogen-containing heterocyclic group which may be substituted)." In these compounds, preferred examples of the group include (pyrrolidin-1-yl)carbonyl group, (morpholin-4-yl)carbonyl group, (4-methylpiperazin-1-yl)carbonyl group, (4-ethoxypiperidin-1-yl)carbonyl group, (4-carboxypiperidin-1-yl) carbonyl group, N,N-dimethylcarbamoyl group, N,N-diethylcarbamoyl group, N-methyl-N-phenylcarbamoyl group, N,N-bis[(ethoxycarbonyl)methyl]carbamoyl group and N,N-bis(carboxymethyl)carbamoyl group, and most preferred examples include (morpholin-4-yl)carbonyl group.

Examples of the substituent in the definition of "a $C_1$ to $C_6$ alkyl group which may be substituted" in the definition of A include similar groups to the substituent explained for the definition "which may be substituted." The position of substituents existing on the alkyl group is not particularly limited, and when two or more substituents exist, they may be the same or different.

Examples of the $C_1$ to $C_6$ alkyl group of "a $C_1$ to $C_6$ alkyl group which may be substituted" in the definition of A include, for example, methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-ethylbutyl, and 1-ethyl-1-methylpropyl, which are $C_1$ to $C_6$ straight chain or branched chain alkyl groups.

Preferred examples of "a $C_1$ to $C_6$ alkyl group which may be substituted" in the definition of A include groups represented by the following Substituent Group δ-4a.

[Substituent Group δ-4a] ethyl group, isopropyl group, methoxymethyl group, acetoxymethyl group, (pivaloyloxy)methyl group, 1-(ethoxycarbonyloxy)ethyl group, [(piperidinocarbonyl)oxy]methyl group [{[(piperidin-1-yl)carbonyl]oxy}methyl group], [(morpholinocarbonyl)oxy]methyl group [{[(morpholin-4-yl)carbonyl]oxy}methyl group], ({[4-(ethoxycarbonyl)piperidin-1-yl]carbonyl}oxy)methyl group, {[(4-carboxypiperidin-1-yl)carbonyl]oxy}methyl group, ({n,n-bis[(ethoxycarbonyl)methyl]carbamoyl}oxy)methyl group, {[n,n-bis(carboxymethyl)carbamoyl]oxy}methyl group, 2-hydroxyethyl group, (ethoxycarbonyl)methyl group, carboxymethyl group, (benzyloxycarbonyl)methyl group, 3,4,5,6-tertaacetoxy-tetrahydropyran-2-yl group, and n-phthalylmethyl group An acyl-oxy-methylene group is more preferred as "a $C_1$ to $C_6$ alkyl group which may be substituted" in the definition of A, and acetoxymethyl group, (pivaloyloxy)methyl group, 1-(ethoxycarbonyloxy)ethyl group, [(piperidinocarbonyl)oxy]methyl group, [(morpholinocarbonyl)oxy]methyl group, ({[4-(ethoxycarbonyl)piperidin-1-yl]carbonyl}oxy)methyl group, {[(4-carboxypiperidin-1-yl)carbonyl]oxy}methyl group, ({N,N-bis[(ethoxycarbonyl)methyl]carbamoyl}oxy) methyl group and {[N,N-bis(carboxymethyl)carbamoyl]oxy}methyl group are further preferred.

Symbol "A" may bind to connecting group X to form a cyclic structure which may be substituted. In this embodiment, preferred examples of the compound represented by the general formula (I) include compounds represented by the following formula.

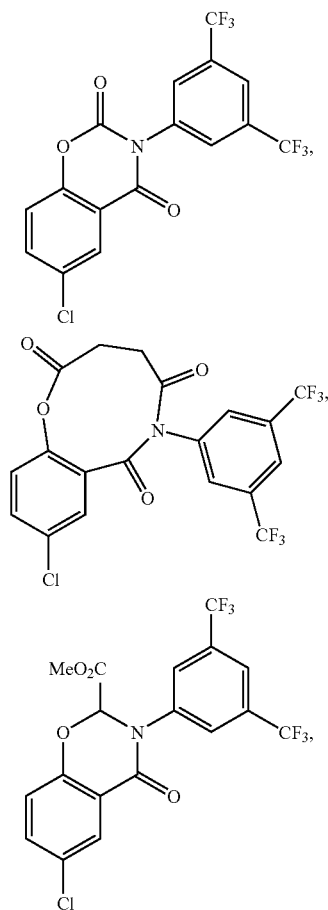

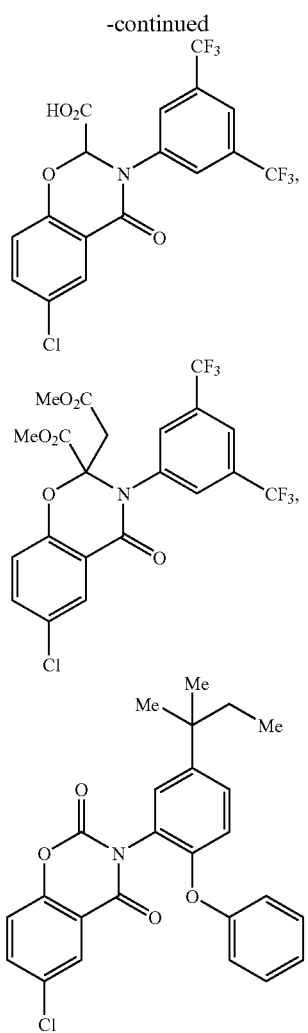

Examples of the "arene" in "an arene which may have one or more substituents in addition to the group represented by formula —O-A wherein A has the same meaning as that defined above and the group represented by formula —X-E wherein each of X and E has the same meaning as that defined above" in the definition of ring Z include a monocyclic or fused heterocyclic aromatic hydrocarbon, and include, for example, benzene ring, naphthalene ring, anthracene ring, phenanthrene ring, and acenaphylene ring. $C_6$ to $C_{10}$ arenes such as benzene ring, naphthalene ring and the like are preferred, benzene ring and naphthalene ring are more preferred, and benzene ring is most preferred.

Examples of the substituent in the definition of "an arene which may have one or more substituents in addition to the group represented by formula —O-A wherein A has the same meaning as that defined above and the group represented by formula —X-E wherein each of X and E has the same meaning as that defined above" in the aforementioned definition of ring Z include similar groups to the substituent explained for the definition "which may be substituted." The position of substituents existing on the arene is not particularly limited, and when two or more substituents exist, they may be the same or different.

When "an arene which may have one or more substituents in addition to the group represented by formula —O-A wherein A has the same meaning as that defined above and the group represented by formula —X-E wherein each of X and E has the same meaning as that defined above" in the aforementioned definition of ring Z is "a benzene ring which may have one or more substituents in addition to the group represented by formula —O-A wherein A has the same meaning as that defined above and the group represented by formula —X-E wherein each of X and E has the same meaning as that defined above," "a benzene ring which has one to two substituents in addition to the group represented by formula —O-A wherein A has the same meaning as that defined above and the group represented by formula —X-E wherein each of X and E has the same meaning as that defined above" is preferred, and "a benzene ring which has one substituent in addition to the group represented by formula —O-A wherein A has the same meaning as that defined above and the group represented by formula —X-E wherein each of X and E has the same meaning as that defined above" is more preferred. Preferred examples of said substituents include groups selected from the following Substituent Group γ-1z. A halogen atom and tert-butyl group [(1,1-dimethyl)ethyl group] are more preferred, and a halogen atom is most preferred.

[Substituent Group γ-1z] halogen atom, tert-butyl group, 2-phenylethen-1-yl group, trifluoromethyl group, phenyl group, and 3-thienyl group [thiophen-3-yl group]

When "an arene which may have one or more substituents in addition to the group represented by formula —O-A wherein A has the same meaning as that defined above and the group represented by formula —X-E wherein each of X and E has the same meaning as that defined above" in the aforementioned definition of ring Z is "a benzene ring which may have one or more substituents in addition to the group represented by formula —O-A wherein A has the same meaning as that defined above and the group represented by formula —X-E wherein each of X and E has the same meaning as that defined above," it is most preferable that one substituent exists and locates on the position of $R^z$ when the following partial formula (Iz-1) in the general formula containing ring Z

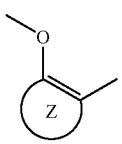

(Iz-1)

is represented by the following formula (Iz-2).

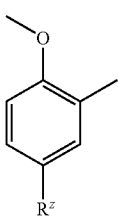

(Iz-2)

In this embodiment, said substituents can be defined as $R^z$. Preferred examples of $R^z$ include a group selected from the following Substituent Group γ-2z. A halogen atom and tert-butyl group are more preferred, and a halogen atom is most preferred.

[Substituent Group γ-2z] a halogen atom, tert-butyl group, 2-phenylethen-1-yl group, trifluoromethyl group, phenyl group, and 3-thienyl group [thiophen-3-yl group]

When "an arene which may have one or more substituents in addition to the group represented by formula —O-A wherein A has the same meaning as that defined above and the group represented by formula —X-E wherein each of X and E has the same meaning as that defined above" in the aforementioned definition of ring Z is "a naphthalene ring which may have one or more substituents in addition to the group represented by formula —O-A wherein A has the same meaning as that defined above and the group represented by formula —X-E wherein each of X and E has the same meaning as that defined above," naphthalene ring is preferred.

Examples of the "hetero arene" in "a hetero arene which may have one or more substituents in addition to the group represented by formula —O-A wherein A has the same meaning as that defined above and the group represented by formula —X-E wherein each of X and E has the same meaning as that defined above" in the aforementioned definition of ring Z include a monocyclic or a fused polycyclic aromatic heterocyclic rings containing at least one of 1 to 3 kinds of heteroatoms selected from oxygen atom, sulfur atom and nitrogen atom and the like as ring-constituting atoms (ring forming atoms), and include, for example, furan ring, thiophene ring, pyrrole ring, oxazole ring, isoxazole ring, thiazole ring, isothiazole ring, imidazole ring, pyrazole ring, 1,2,3-oxadiazole ring, 1,2,3-thiadiazole ring, 1,2,3-triazole ring, pyridine ring, pyridazine ring, pyrimidine ring, pyrazine ring, 1,2,3-triazine ring, 1,2,4-triazine ring, 1H-azepine ring, 1,4-oxepine ring, 1,4-thiazepine ring, benzofuran ring, isobenzofuran ring, benzo[b]thiophene ring, benzo[c]thiophene ring, indole ring, 2H-isoindole ring, 1H-indazole ring, 2H-indazole ring, benzoxazole ring, 1,2-benzisoxazole ring, 2,1-benzisoxazole ring, benzothiazole ring, 1,2-benzisothiazole ring, 2,1-benzisothiazole ring, 1,2,3-benzoxadiazol ring, 2,1,3-benzoxadiazol ring, 1,2,3-benzothiadiazole ring, 2,1,3-benzothiadiazole ring, 1H-benzotriazole ring, 2H-benzotriazole ring, quinoline ring, isoquinoline ring, cinnoline ring, quinazoline ring, quinoxaline ring, phthalazine ring, naphthyridine ring, 1H-1,5-benzodiazepine ring, carbazole ring, α-carboline ring, β-carboline ring, γ-carboline ring, acridine ring, phenoxazine ring, phenothiazine ring, phenazine ring, phenanthridine ring, phenanthroline ring, thianthrene ring, indolizine ring, and phenoxathiine ring, which are 5 to 14-membered monocyclic or fused polycyclic aromatic heterocyclic rings.

Examples of the aryl group of "an aryl group which may be substituted" in the definition of E include similar groups to the aryl group in the definition of the aforementioned "hydrocarbon group," and $C_6$ to $C_{10}$ aryl groups such as phenyl group, 1-naphthyl group, 2-naphthyl group and the like are preferred, and phenyl group is most preferred.

Examples of the substituent in the definition of "an aryl group which may be substituted" in the definition of E include similar groups to the substituent explained for the definition "which may be substituted." The position of substituents existing on the aryl group is not particularly limited, and when two or more substituents exist, they may be the same or different.

When "an aryl group which may be substituted" in the aforementioned definition of E is "a phenyl group which may be substituted," "a mono-substituted phenyl group" and "a di-substituted phenyl group" are preferred, and "a di-substituted phenyl group" is more preferred.

When "an aryl group which may be substituted" in the aforementioned definition of E is "a di-substituted phenyl group," preferred examples of the group include groups represented by the following Substituent Group δ-1e.

[Substituent Group δ-1e] 3,5-bis(trifluoromethyl)phenyl group, 3,5-dichlorophenyl group, 2-chloro-5-(trifluoromethyl)phenyl group, 3,5-bis[(1,1-dimethyl)ethyl]phenyl group, 2,5-bis(trifluoromethyl)phenyl group, 3-methoxy-5-(trifluoromethyl)phenyl group, 2-methoxy-5-(trifluoromethyl)phenyl group, 2-chloro-4-(trifluoromethyl)phenyl group, 5-(1,1-dimethyl)propyl-2-phenoxyphenyl group, and 2-(4-methoxyphenoxy)-5-(trifluoromethyl)phenyl group When "an aryl group which may be substituted" in the aforementioned definition of E is "a di-substituted phenyl group," "a 2,5-di-substituted phenyl group," and "a 3,5-di-substituted phenyl group" are preferred.

When "an aryl group which may be substituted" in the aforementioned definition of E is "a 2,5-di-substituted phenyl group," preferred examples of the group include groups represented by the following Substituent Group δ-2e.

[Substituent Group δ-2e] 2-chloro-5-(trifluoromethyl)phenyl group, 2,5-bis(trifluoromethyl)phenyl group, 2-methoxy-5-(trifluoromethyl)phenyl group, and 2-(4-methoxyphenoxy)-5-(trifluoromethyl)phenyl group When "an aryl group which may be substituted" in the aforementioned definition of E is "a 2,5-di-substituted phenyl group," "a 2,5-di-substituted phenyl group wherein at least one of said substituents is trifluoromethyl group" is more preferred, a group selected from the following Substituent Group δ-3e is further preferred, and 2,5-bis(trifluoromethyl)phenyl group is most preferred.

[Substituent Group δ-3e] 2-chloro-5-(trifluoromethyl)phenyl group, 2,5-bis(trifluoromethyl)phenyl group, 2-methoxy-5-(trifluoromethyl)phenyl group, and 2-(4-methoxyphenoxy)-5-(trifluoromethyl)phenyl group When "an aryl group which may be substituted" in the aforementioned definition of E is "a 3,5-di-substituted phenyl group," preferred examples of the group include groups represented by the following Substituent Group δ-4e.

[Substituent Group δ-4e] 3,5-bis(trifluoromethyl)phenyl group, 3,5-dichlorophenyl group, 3,5-bis[(1,1-dimethyl)ethyl]phenyl group, and 3-methoxy-5-(trifluoromethyl)phenyl group When "an aryl group which may be substituted" in the aforementioned definition of E is "a 3,5-di-substituted phenyl group," "a 3,5-di-substituted phenyl group wherein at least one of said substituents is trifluoromethyl group" is more preferred, a group selected from the following Substituent Group δ-5e is further preferred, and 3,5-bis(trifluoromethyl)phenyl group is most preferred.

[Substituent Group δ-5e] 3,5-bis(trifluoromethyl)phenyl group and 3-methoxy-5-(trifluoromethyl)phenyl group When "an aryl group which may be substituted" in the aforementioned definition of E is "a mono-substituted phenyl group," preferred examples of the group include biphenyl-4-yl group.

Examples of the "heteroaryl group" in "a heteroaryl group which may be substituted" in the definition of E include similar groups to the "monocyclic heteroaryl group" and "fused polycyclic heteroaryl group" in the definition of the aforementioned "heterocyclic group." A 5-membered heteroaryl group is preferred, and thiazolyl group is most preferred.

Examples of the substituent in the definition of "a heteroaryl group which may be substituted" in the aforementioned definition of E include similar groups to the substituent explained for the definition "which may be substituted." The position of substituents existing on the heteroaryl group is not particularly limited, and when two or more substituents exist, they may be the same or different.

When "a heteroaryl group which may be substituted" in the aforementioned definition of E is "a thiazolyl group which may be substituted," "a thiazol-2-yl group which may be substituted" is more preferred, "a di-substituted thiazol-2-yl group" is further preferred, and 4-[(1,1-dimethyl)ethyl]-5-[(2,2-dimethyl)propionyl]thiazol-2-yl group is most preferred.

Compounds represented by the aforementioned general formula (I-1) are explained in details.

Examples of the substituent in the definition of "an acyl group which may be substituted (provided that unsubstituted acetyl group and unsubstituted acryloyl group are excluded)" in the definition of $A^1$ include similar groups to the substituent explained for the definition "which may be substituted." The position of substituents existing on the acyl group is not particularly limited, and when two or more substituents exist, they may be the same or different.

Examples of the acyl group of "an acyl group which may be substituted (provided that unsubstituted acetyl group and unsubstituted acryloyl group are excluded)" in the definition of $A^1$ include similar groups to the acyl group in the aforementioned definition.

Unsubstituted acetyl group and unsubstituted acryloyl group are excluded as "an acyl group which may be substituted" in the definition of $A^1$.

A group selected from the following "substituent group $\omega^1$" is preferred as "an acyl group which may be substituted (provided that unsubstituted acetyl group and unsubstituted acryloyl group are excluded)" in the definition of $A^1$, and a heterocyclic ring-carbonyl group which may be substituted, a phosphono group which may be substituted, and a carbamoyl group which may be substituted are more preferred.

[Substituent Group $\omega^1$] a hydrocarbon-carbonyl group which may be substituted, a heterocyclic ring-carbonyl group which may be substituted, a hydrocarbon-oxy-carbonyl group which may be substituted, a hydrocarbon-sulfonyl group which may be substituted, a sulfamoyl group which may be substituted, a sulfo group which may be substituted, a phosphono group which may be substituted, and a carbamoyl group which may be substituted When "an acyl group which may be substituted" in the definition of $A^1$ is "a heterocyclic ring-carbonyl group which may be substituted," examples of said heterocyclic ring group include similar groups to the heterocyclic ring group in the aforementioned definition.

When "an acyl group which may be substituted" in the definition of $A^1$ is "a heterocyclic ring-carbonyl group which may be substituted," preferred examples of the group include groups represented by the following Substituent Group $\delta^1$-1a.

[Substituent Group $\delta^1$-1a] nicotinoyl group [(pyridin-3-yl)carbonyl group], isonicotinoyl group [(pyridin-4-yl)carbonyl group], (pyrrolidin-1-yl)carbonyl group, (morpholin-4-yl)carbonyl Group [morpholino carbonyl group], (4-methylpiperazin-1-yl)carbonyl group, [4-(ethoxycarbonyl)piperidin-1-yl]carbonyl group, and (4-carboxypiperidin-1-yl)carbonyl group When "an acyl group which may be substituted" in the definition of $A^1$ is "a heterocyclic ring-carbonyl group which may be substituted," "a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom" is more preferred, (pyrrolidin-1-yl)carbonyl group, (morpholin-4-yl)carbonyl group, (4-methylpiperazin-1-yl)carbonyl group, [4-(ethoxycarbonyl)piperidin-1-yl]carbonyl group and (4-carboxypiperidin-1-yl) carbonyl group are further preferred, and (morpholin-4-yl) carbonyl group is most preferred.

When "an acyl group which may be substituted" in the definition of $A^1$ is "a phosphono group which may be substituted," phosphono group and dibenzylphosphono group are preferred, and phosphono group is more preferred.

When "an acyl group which may be substituted" in the definition of $A^1$ is "a carbamoyl group which may be substituted," preferred examples of the group include groups represented by the following Substituent Group $\delta^1$-2a.

[Substituent Group $\delta^1$-2a] N-isopropylcarbamoyl group, N-benzylcarbamoyl group, N-(ethoxycarbonylmethyl)carbamoyl group, N-(carbonylmethyl)carbamoyl group, N-(1-methoxycarbonylethyl)carbamoyl group, N-(1-methoxycarbonyl-2-phenylethyl)carbamoyl group, N-[1-methoxycarbonyl-2-(tert-butoxycarbonyl)ethyl]carbamoyl group, N-({n-[1-(tert-butoxycarbonyl)-2-phenylethyl]carbamoyl}methyl)carbamoyl group, N-{[n-(1-carboxy-2-phenylethyl)carbamoyl]methyl}carbamoyl group, N-({n-[1,2-di(tert-butoxycarbonyl)ethyl]carbamoyl}methyl)carbamoyl group, N-{[n-(1,2-dicarboxyethyl)carbamoyl]methyl}carbamoyl group, N-({n-[1,5-di(tert-butoxycarbonyl)pentyl]carbamoyl}methyl) carbamoyl group, N-[(4-methylsulfanyl)phenyl] carbamoyl group, N,N-dimethylcarbamoyl group, N,N-diethylcarbamoyl group, N-methyl-N-phenylcarbamoyl group, N,N-bis[(ethoxycarbonyl)methyl]carbamoyl group, and N,N-bis(carboxymethyl)carbamoyl group When "an acyl group which may be substituted" in the definition of $A^1$ is "a carbamoyl group which may be substituted," "a N,N-di-substituted carbamoyl group" is more preferred, and N,N-dimethylcarbamoyl group, N,N-diethylcarbamoyl group, N-methyl-N-phenylcarbamoyl group, N,N-bis[(ethoxycarbonyl)methyl]carbamoyl group and N,N-bis(carboxymethyl)carbamoyl group are further preferred.

When "an acyl group which may be substituted" in the definition of $A^1$ is "a hydrocarbon-carbonyl group which may be substituted," examples of said hydrocarbon group include similar groups to the hydrocarbon group in the aforementioned definition.

When "an acyl group which may be substituted" in the definition of $A^1$ is "a hydrocarbon-carbonyl group which may be substituted," preferred examples of the group include groups represented by the following Substituent Group $\delta^1$-3a.

[Substituent Group $\delta^1$-3a] pivaloyl group [(2,2-dimethyl)propionyl group], valeryl group, decanoyl group, benzoyl group, 2-acetoxybenzoyl group, phenylacetyl group, (3,4-methylenedioxyphenyl)acetyl group, methoxyacetyl group, acetoxyacetyl group, phenoxyacetyl group, (4-chlorophenoxy)acetyl group, (2,3-dichlorophenoxy)acetyl group, 2-phenoxypropionyl group, 2-(4-chlorophenoxy)isobutyryl group, (tert-butoxycarbonyl)acetyl group, 3-(benzyloxycarbonyl)propionyl group, 3-(piperidinocarbonyl)propionyl group, (acetylamino)acetyl group, [(benzyloxycarbonyl)amino]acetyl Group, [(tert-butoxycarbonyl)amino]acetyl Group, aminoacetyl group, 2-[(tert-butoxycarbonyl)amino]isovaleryl group, 2-aminoisovaleryl group, 2-[(tert-butoxycarbonyl)amino]-4-methylvaleryl group, 2-amino-4-methylvaleryl group, 2-[(tert-butoxycarbonyl)amino]-3-phenylpropionyl group, 2-amino-3-phenylpropionyl group, 2-[(tert-butoxycarbonyl)amino]-3-(tert-butoxycarbonyl)propionyl group, 2-[(tert-butoxycarbonyl)amino]-4-(tert-butoxycarbonyl)butyryl group, 2-amino-4-carboxybutyryl group, 2,6-bis[(tert-butoxycarbonyl)amino]hexanoyl group, 2,6-diaminohexanoyl group, 2-{2-[(tert-butoxycarbonyl)

amino]-3-phenylpropionyl}amino-4-methylvaleryl group, 2-(2-amino-3-phenylpropionyl)amino-4-methylvaleryl group, 2-{2,3-bis[(tert-butoxycarbonyl)amino]propionyl}amino-4-methylvaleryl group, 2-(2-amino-3-carboxypropionyl)amino-4-methylvaleryl group, 2-{2,6-bis[(tert-butoxycarbonyl)amino]hexanoyl}amino-4-methylvaleryl group, 2-(2,6-diaminohexanoyl)amino-4-methylvaleryl group, 2-(2-amino-4-methylvaleryl)amino-3-phenylpropionyl group, and 2-(2-amino-3-carboxypropionyl)amino-3-phenylpropionyl group When "an acyl group which may be substituted" in the definition of $A^1$ is "a hydrocarbon-oxy-carbonyl group which may be substituted," examples of said hydrocarbon group include similar groups to the hydrocarbon group in the aforementioned definition.

When "an acyl group which may be substituted" in the definition of $A^1$ is "a hydrocarbon-oxy-carbonyl group which may be substituted," preferred examples of the group include methoxycarbonyl group.

When "an acyl group which may be substituted" in the definition of $A^1$ is "a hydrocarbon-sulfonyl group which may be substituted," examples of said hydrocarbon group include similar groups to the hydrocarbon group in the aforementioned definition.

When "an acyl group which may be substituted" in the definition of $A^1$ is "a hydrocarbon-sulfonyl group which may be substituted," preferred examples of the group include methanesulfonyl group [mesyl group], propanesulfonyl group, isopropylsulfonyl group and p-toluenesulfonyl group [tosyl group].

When "an acyl group which may be substituted" in the definition of $A^1$ is "a sulfamoyl group which may be substituted," preferred examples of the group include N,N-dimethylsulfamoyl group.

When "an acyl group which may be substituted" in the definition of $A^1$ is "a sulfo group which may be substituted," preferred examples of the group include sulfo group.

When "an acyl group which may be substituted" in the definition of $A^1$ is "a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom" or "a N,N-di-substituted carbamoyl group," these compounds can be commonly defined as "a N,N-di-substituted carbamoyl group (two substituents of said carbamoyl group may combine to each other, together with the nitrogen atom to which they bind, to form a nitrogen-containing heterocyclic group which may be substituted)." In this embodiment, preferred examples of the group include (pyrrolidin-1-yl)carbonyl group, (morpholin-4-yl)carbonyl group, (4-methylpiperazin-1-yl)carbonyl group, (4-ethoxypiperidin-1-yl)carbonyl group, (4-carboxypiperidin-1-yl)carbonyl group, N,N-dimethylcarbamoyl group, N,N-diethylcarbamoyl group, N-methyl-N-phenylcarbamoyl group, N,N-bis[(ethoxycarbonyl)methyl]carbamoyl group and N,N-bis(carboxymethyl)carbamoyl group, and most preferred examples include (morpholin-4-yl)carbonyl group.

Examples of the substituent in the definition of "a $C_1$ to $C_6$ alkyl group which may be substituted" in the definition of $A^1$ include similar groups to the substituent explained for the definition "which may be substituted." The position of substituents existing on the alkyl group is not particularly limited, and when two or more substituents exist, they may be the same or different.

Examples of the $C_1$ to $C_6$ alkyl group of "a $C_1$ to $C_6$ alkyl group which may be substituted" in the definition of $A^1$ include, for example, methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-ethylbutyl, and 1-ethyl-1-methylpropyl, which are $C_1$ to $C_6$ straight chain or branched chain alkyl groups.

Preferred examples of "a $C_1$ to $C_6$ alkyl group which may be substituted" in the definition of $A^1$ include groups represented by the following Substituent Group $\delta^1$-4a.

[Substituent Group $\delta^1$-4a] ethyl group, isopropyl group, methoxymethyl group, acetoxymethyl group, (pivaloyloxy)methyl group, 1-(ethoxycarbonyloxy)ethyl group, [(piperidinocarbonyl)oxy]methyl group [{[(piperidin-1-yl)carbonyl]oxy}methyl group], [(morpholinocarbonyl)oxy]methyl group [{[(morpholin4-yl)carbonyl]oxy}methyl group], ({[4-(ethoxycarbonyl)piperidin-1-yl]carbonyl}oxy)methyl group, {[(4-carboxypiperidin-1-yl)carbonyl]oxy}methyl group, ({N,N-bis[(ethoxycarbonyl)methyl]carbamoyl}oxy)methyl group, {[N,N-bis(carboxymethyl)carbamoyl]oxy}methyl group, 2-hydroxyethyl group, (ethoxycarbonyl)methyl group, carboxymethyl group, (benzyloxycarbonyl)methyl group, 3,4,5,6-tertaacetoxy-tetrahydropyran-2-yl group, and N-phthalylmethyl group An acyl-oxy-methylene group is more preferred as "a $C_1$ to $C_6$ alkyl group which may be substituted" in the definition of $A^1$, and acetoxymethyl group, (pivaloyloxy)methyl group, 1-(ethoxycarbonyloxy)ethyl group, [(piperidinocarbonyl)oxy]methyl group, [(morpholinocarbonyl)oxy]methyl group, ({[4-(ethoxycarbonyl)piperidin-1-yl]carbonyl}oxy)methyl group, {[(4-carboxypiperidin-1-yl)carbonyl]oxy}methyl group, ({N,N-bis [(ethoxycarbonyl)methyl]carbamoyl}oxy)methyl group and {[N,N-bis(carboxymethyl)carbamoyl]oxy}methyl group are further preferred.

$A^1$ may bind to —CONH— group to form a cyclic structure which may be substituted. In this embodiment, preferred examples of the compound represented by the general formula (I-1) include compounds represented by the following formula.

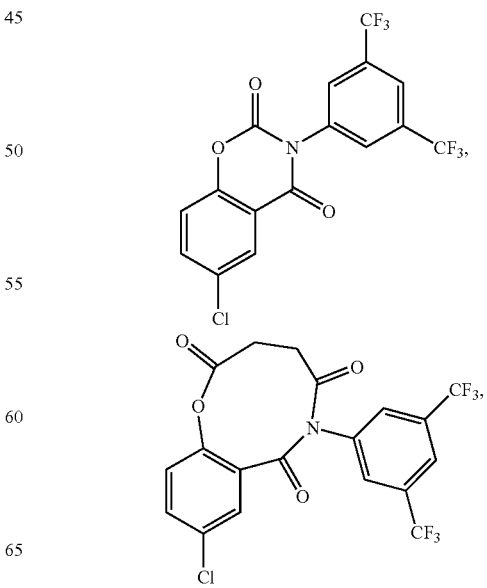

-continued

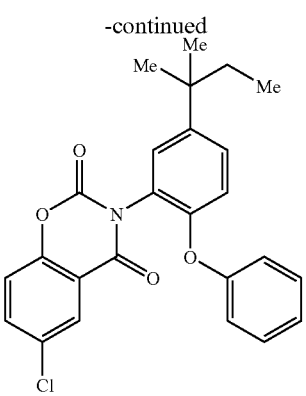

Examples of the "arene" in "an arene which may have one or more substituents in addition to the group represented by formula —O-$A^1$ wherein $A^1$ has the same meaning as that defined above and the group represented by formula —CONH-$E^1$ wherein $E^1$ has the same meaning as that defined above" in the definition of ring $Z^1$ include a monocyclic or fused heterocyclic aromatic hydrocarbon, and include, for example, benzene ring, naphthalene ring, anthracene ring, phenanthrene ring, and acenaphylene ring. $C_6$ to $C_{10}$ arenes such as benzene ring, naphthalene ring and the like are preferred, benzene ring and naphthalene ring are more preferred, and benzene ring is most preferred.

Examples of the substituent in the definition of "an arene which may have one or more substituents in addition to the group represented by formula —O-$A^1$ wherein $A^1$ has the same meaning as that defined above and the group represented by formula —CONH-$E^1$ wherein $E^1$ has the same meaning as that defined above" in the aforementioned definition of ring $Z^1$ include similar groups to the substituent explained for the definition "which may be substituted." The position of substituents existing on the arene is not particularly limited, and when two or more substituents exist, they may be the same or different.

When "an arene which may have one or more substituents in addition to the group represented by formula —O-$A^1$ wherein $A^1$ has the same meaning as that defined above and the group represented by formula —CONH-$E^1$ wherein $E^1$ has the same meaning as that defined above" in the aforementioned definition of ring $Z^1$ is "a benzene ring which may have one or more substituents in addition to the group represented by formula —O-$A^1$ wherein $A^1$ has the same meaning as that defined above and the group represented by formula —CONH-$E^1$ wherein $E^1$ has the same meaning as that defined above," "a benzene ring which has one to two substituents in addition to the group represented by formula —O-$A^1$ wherein $A^1$ has the same meaning as that defined above and the group represented by formula —CONH-$E^1$ wherein $E^1$ has the same meaning as that defined above" is preferred, and "a benzene ring which has one substituent in addition to the group represented by formula —O-$A^1$ wherein $A^1$ has the same meaning as that defined above and the group represented by formula —CONH-$E^1$ wherein $E^1$ has the same meaning as that defined above" is more preferred. Preferred examples of said substituents include groups selected from the following Substituent Group $\gamma^1$-1z. A halogen atom and tert-butyl group [(1,1-dimethyl)ethyl group] are more preferred, and a halogen atom is most preferred.

[Substituent Group $\gamma^1$-1z] a halogen atom, tert-butyl group, 2-phenylethen-1-yl group, trifluoromethyl group, phenyl group, and 3-thienyl group [thiophen-3-yl group]

When "an arene which may have one or more substituents in addition to the group represented by formula —O-$A^1$ wherein $A^1$ has the same meaning as that defined above and the group represented by formula —CONH-$E^1$ wherein $E^1$ has the same meaning as that defined above" in the aforementioned definition of ring $Z^1$ is "a benzene ring which may have one or more substituents in addition to the group represented by formula —O-$A^1$ wherein $A^1$ has the same meaning as that defined above and the group represented by formula —CONH-$E^1$ wherein $E^1$ has the same meaning as that defined above," it is most preferable that one substituent exists and locates on the position of $R^{z1}$ when the following partial formula (Iz$^1$-1) in the general formula containing ring $Z^1$

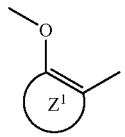

(Iz$^1$-1)

is represented by the following formula (Iz$^1$-2).

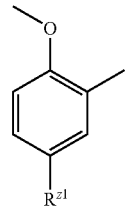

(Iz$^1$-2)

In this embodiment, said substituents can be defined as $R^{z1}$. Preferred examples of $R^{z1}$ include a group selected from the following Substituent Group $\gamma^1$-2z. A halogen atom and tert-butyl group are more preferred, and a halogen atom is most preferred.

[Substituent Group $\gamma^1$-2z] a halogen atom, tert-butyl group, 2-phenylethen-1-yl group, trifluoromethyl group, phenyl group, and 3-thienyl group [thiophen-3-yl group]

When "an arene which may have one or more substituents in addition to the group represented by formula —O-$A^1$ wherein $A^1$ has the same meaning as that defined above and the group represented by formula —CONH-$E^1$ wherein $E^1$ has the same meaning as that defined above" in the aforementioned definition of ring $Z^1$ is "a naphthalene ring which may have one or more substituents in addition to the group represented by formula —O-$A^1$ wherein $A^1$ has the same meaning as that defined above and the group represented by formula —CONH-$E^1$ wherein El has the same meaning as that defined above," naphthalene ring is preferred.

Examples of the "hetero arene" in "a hetero arene which may have one or more substituents in addition to the group represented by formula —O-$A^1$ wherein $A^1$ has the same meaning as that defined above and the group represented by formula —CONH-$E^1$ wherein $E^1$ has the same meaning as that defined above" in the aforementioned definition of ring $Z^1$ include a monocyclic or a fused polycyclic aromatic heterocyclic rings containing at least one of 1 to 3 kinds of heteroatoms selected from oxygen atom, sulfur atom and nitrogen atom and the like as ring-constituting atoms (ring forming atoms), and include, for example, furan ring, thiophene ring, pyrrole ring, oxazole ring, isoxazole ring, thiazole ring, isothiazole ring, imidazole ring, pyrazole ring, 1,2,3-oxadiazole ring, 1,2,3-thiadiazole ring, 1,2,3-triazole ring, pyridine ring, pyridazine ring, pyrimidine ring, pyrazine ring, 1,2,3-triazine ring, 1,2,4-triazine ring, 1H-azepine ring, 1,4-oxepine ring, 1,4-thiazepine ring, benzofuran ring, isobenzofuran ring, benzo[b]thiophene ring, benzo[c]thiophene ring, indole ring, 2H-isoindole ring, 1H-indazole ring, 2H-indazole ring, benzoxazole ring, 1,2-benzisoxazole ring, 2,1-benzisoxazole ring, benzothiazole ring, 1,2-benzisothiazole ring, 2,1-benzisothiazole ring, 1,2,3-benzoxadiazol ring, 2,1,3-benzoxadiazol ring, 1,2,3-benzothiadiazole ring, 2,1,3-benzothiadiazole ring, 1H-benzotriazole ring, 2H-benzotriazole ring, quinoline ring, isoquinoline ring, cinnoline ring, quinazoline ring, quinoxaline ring, phthalazine ring, naphthyridine ring, 1H-1,5-benzodiazepine ring, carbazole ring, α-carboline ring, β-carboline ring, γ-carboline ring, acridine ring, phenoxazine ring, phenothiazine ring, phenazine ring, phenanthridine ring, phenanthroline ring, thianthrene ring, indolizine ring, and phenoxathiine ring, which are 5 to 14-membered monocyclic or fused polycyclic aromatic heterocyclic rings.

Examples of the aryl group of "an aryl group which may be substituted" in the definition of $E^1$ include similar groups to the aryl group in the definition of the aforementioned "hydrocarbon group," and $C_6$ to $C_{10}$ aryl groups such as phenyl group, 1-naphthyl group, 2-naphthyl group and the like are preferred, and phenyl group is most preferred.

Examples of the substituent in the definition of "an aryl group which may be substituted" in the definition of $E^1$ include similar groups to the substituent explained for the definition "which may be substituted." The position of substituents existing on the aryl group is not particularly limited, and when two or more substituents exist, they may be the same or different.

When "an aryl group which may be substituted" in the aforementioned definition of $E^1$ is "a phenyl group which may be substituted," "a mono-substituted phenyl group" and "a di-substituted phenyl group" are preferred, and "a di-substituted phenyl group" is more preferred.

When "an aryl group which may be substituted" in the aforementioned definition of $E^1$ is "a di-substituted phenyl group," preferred examples of the group include groups represented by the following Substituent Group δ-1e.

[Substituent Group $δ^1$-1e] 3,5-bis(trifluoromethyl)phenyl Group, 3,5-dichlorophenyl Group, 2-chloro-5-(trifluoromethyl)phenyl Group, 3,5-bis[(1,1-dimethyl)ethyl]phenyl Group, 2,5-bis(trifluoromethyl)phenyl Group, 3-methoxy-5-(trifluoromethyl)phenyl Group, 2-methoxy-5-(trifluoromethyl)phenyl Group, 2-chloro-4-(trifluoromethyl)phenyl Group, 5-(1,1-dimethyl)propyl-2-phenoxyphenyl Group, and 2-(4-methoxyphenoxy)-5-(trifluoromethyl)phenyl Group When "an aryl group which may be substituted" in the aforementioned definition of $E^1$ is "a di-substituted phenyl group," "a 2,5-di-substituted phenyl group," and "a 3,5-di-substituted phenyl group" are preferred.

When "an aryl group which may be substituted" in the aforementioned definition of $E^1$ is "a 2,5-di-substituted phenyl group," preferred examples of the group include groups represented by the following Substituent Group $δ^1$-2e.

[Substituent Group $δ^1$-2e] 2-chloro-5-(trifluoromethyl)phenyl Group, 2,5-bis(trifluoromethyl)phenyl Group, 2-methoxy-5-(trifluoromethyl)phenyl Group, and 2-(4-methoxyphenoxy)-5-(trifluoromethyl)phenyl Group When "an aryl group which may be substituted" in the aforementioned definition of $E^1$ is "a 2,5-di-substituted phenyl group," "a 2,5-di-substituted phenyl group wherein at least one of said substituents is trifluoromethyl group" is more preferred, a group selected from the following Substituent Group $δ^1$-3e is further preferred, and 2,5-bis(trifluoromethyl)phenyl group is most preferred.

[Substituent Group $δ^1$-3e] 2-chloro-5-(trifluoromethyl)phenyl Group, 2,5-bis(trifluoromethyl)phenyl Group, 2-methoxy-5-(trifluoromethyl)phenyl Group, and 2-(4-methoxyphenoxy)-5-(trifluoromethyl)phenyl Group When "an aryl group which may be substituted" in the aforementioned definition of $E^1$ is "a 3,5-di-substituted phenyl group," preferred examples of the group include groups represented by the following Substituent Group $δ^1$-4e.

[Substituent Group $δ^1$-4e] 3,5-bis(trifluoromethyl)phenyl Group, 3,5-dichlorophenyl Group, 3,5-bis[(1,1-dimethyl)ethyl]phenyl Group, and 3-methoxy-5-(trifluoromethyl)phenyl Group When "an aryl group which may be substituted" in the aforementioned definition of $E^1$ is "a 3,5-di-substituted phenyl group," "a 3,5-di-substituted phenyl group wherein at least one of said substituents is trifluoromethyl group" is more preferred, a group selected from the following Substituent Group $δ^1$-5e is further preferred, and 3,5-bis(trifluoromethyl)phenyl group is most preferred.

[Substituent Group $δ^1$-5e] 3,5-bis(trifluoromethyl)phenyl Group and 3-methoxy-5-(trifluoromethyl)phenyl Group When "an aryl group which may be substituted" in the aforementioned definition of $E^1$ is "a mono-substituted phenyl group," preferred examples of the group include biphenyl-4-yl group.

Examples of the "heteroaryl group" in "a heteroaryl group which may be substituted" in the definition of $E^1$ include similar groups to the "monocyclic heteroaryl group" and "fused polycyclic heteroaryl group" in the definition of the aforementioned "heterocyclic group." A 5-membered heteroaryl group is preferred, and thiazolyl group is most preferred.

Examples of the substituent in the definition of "a heteroaryl group which may be substituted" in the aforementioned definition of $E^1$ include similar groups to the substituent explained for the definition "which may be substituted." The position of substituents existing on the heteroaryl group is not particularly limited, and when two or more substituents exist, they may be the same or different.

When "a heteroaryl group which may be substituted" in the aforementioned definition of $E^1$ is "a thiazolyl group which may be substituted," "a thiazol-2-yl group which may be substituted" is more preferred, "a di-substituted thiazol-2-yl group" is further preferred, and 4-[(1,1-dimethyl)ethyl]-5-[(2,2-dimethyl)propionyl]thiazol-2-yl group is most preferred.

Among the compound represented by the general formula (I), preferred compounds are those other than "substituted benzoic acid derivatives represented by the following general formula (X-1) and/or compounds represented by the following Compound Group φ-1."

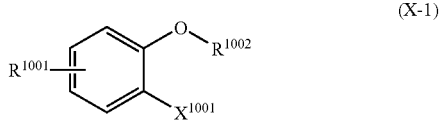

(X-1)

wherein $R^{1001}$ represents the following general formula (X-2):

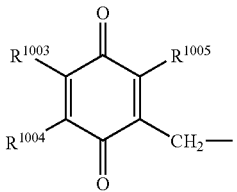

(X-2)

or the following general formula (X-3):

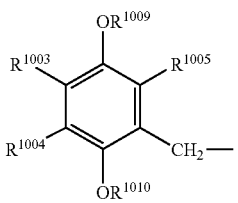

(X-3)

wherein each of $R^{1003}$, $R^{1004}$ and $R^{1005}$ independently represents hydrogen atom, an alkyl group having from 1 to 6 carbons or an alkoxy group having from 1 to 6 carbons, each of $R^{1009}$ and $R^{1010}$ independently represents hydrogen atom, an alkyl group having from 1 to 6 carbons, or an acyl group having from 2 to 11 carbons;

$R^{1002}$ represents hydrogen atom, a lower alkyl group having from 1 to 6 carbons, which may be substituted, an aryl group having from 6 to 12 carbons, which may be substituted, a heteroaryl group having from 4 to 11 carbons, which may be substituted, an aralkyl group having from 7 to 14 carbons, which may be substituted, a heteroarylalkyl group having from 5 to 13 carbons, which may be substituted, or an acyl group having from 2 to 11 carbons;

$X^{1001}$ represents carboxy group which may be esterified or amidated.

[Compound Group φ-1]

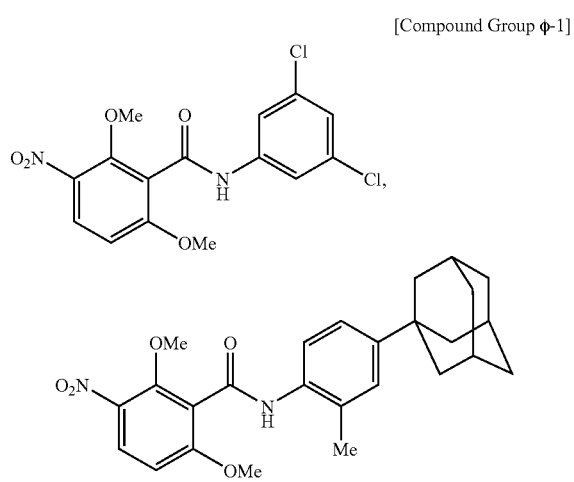

Each compound defined by the aforementioned general formula (I-1) or a pharmacologically acceptable salt thereof, or a hydrate thereof or a solvate thereof is novel, and uses of the compounds according to the present invention relating to chemical substances are not limited.

The compounds represented by the aforementioned general formulas (I) and (I-1) may form salts. Examples of pharmacologically acceptable salts include, when acidic groups exist, metal salts such as lithium salt, sodium salt, potassium salt, magnesium salt, calcium salts, or ammonium salts such as ammonium salt, methylammonium salt, dimethylammonium salt, trimethylammonium salt, dicyclohexylammonium salt, and when basic groups exist, mineral acid salts such as hydrochloride, oxalate, hydrosulfate, nitrate, phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, lactate. Salts may sometimes be formed with amino acids such as glycine. As active ingredients of the medicament of the present invention, pharmacologically acceptable salts may also be suitably used.

The compounds or salts thereof represented by the aforementioned general formulas (I) and (I-1) may exist as hydrates or solvates. As active ingredients of the medicament of the present invention, any of the aforementioned substances may be used. Furthermore, the compounds represented by the aforementioned general formulas (I) and (I-1) may sometimes have one or more asymmetric carbons, and may exist as steric isomers such as optically active substance and diastereomer. As active ingredients of the medicament of the present invention, pure forms of stereoisomers, arbitrary mixture of enantiomers or diastereomers, and racemates may be used.

Furthermore, when the compounds represented by the general formulas (I) and (I-1) have, for example, 2-hydroxypyridine form, the compounds may exist as 2-pyridone form which is a tautomer. As active ingredients of the medicament of the present invention, pure forms of tautomers or a mixture thereof may be used. When the compounds represented by the general formulas (I) and (I-1) have olefinic double bonds, the configuration may be in either E or Z, and as active ingredients of the medicament of the present invention, geometrical isomer in either of the configurations or a mixture thereof may be used.

Examples of the compounds included in the general formulas (I) and (I-1) as active ingredients of the medicaments of the present invention are shown below. However, the active ingredients of the medicaments of the present invention are not limited to the compound set out below.

The abbreviations used in the following tables have the following meanings.

Me: methyl group, Et: ethyl group.

| Compound Number | 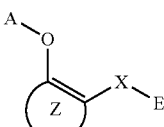 | X | E |
|---|---|---|---|
| 1 | 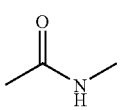 | 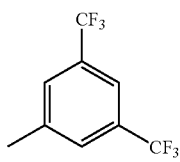 | 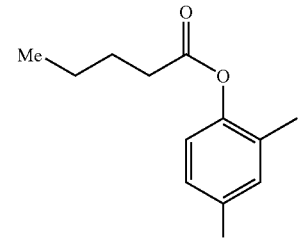 |
| 2 | 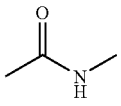 | 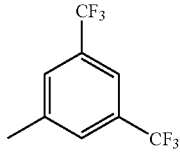 | 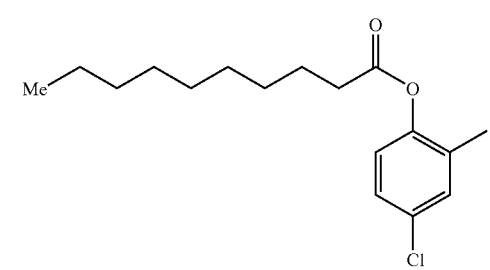 |
| 3 | 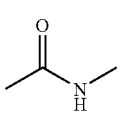 | 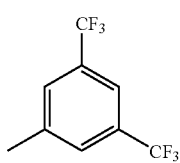 | 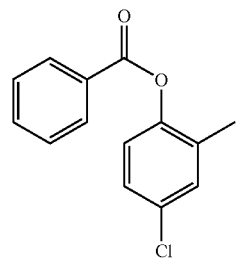 |
| 4 | 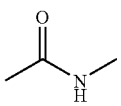 | 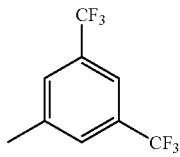 | |

-continued

| Compound Number | | X | E |
|---|---|---|---|
| 5 | 2-acetoxybenzoic acid ester of 4-chloro-2-methylphenol | -C(=O)NH- | 3,5-bis(trifluoromethyl)phenyl |
| 6 | nicotinic acid ester of 4-chloro-2-methylphenol | -C(=O)NH- | 3,5-bis(trifluoromethyl)phenyl |
| 7 | isonicotinic acid ester of 4-chloro-2-methylphenol | -C(=O)NH- | 3,5-bis(trifluoromethyl)phenyl |
| 8 | phenylacetic acid ester of 4-chloro-2-methylphenol | -C(=O)NH- | 3,5-bis(trifluoromethyl)phenyl |

-continued

| Compound Number | A-O-[Z]-X-E / A-O-[Z]-Me | X | E |
|---|---|---|---|
| 9 | benzo[1,3]dioxol-5-yl-CH₂-C(=O)-O-(4-Cl-2-Me-phenyl) | -C(=O)-NH- | 3,5-bis(CF₃)phenyl |
| 10 | MeO-CH₂-C(=O)-O-(4-Cl-2-Me-phenyl) | -C(=O)-NH- | 3,5-bis(CF₃)phenyl |
| 11 | Me-C(=O)-O-CH₂-C(=O)-O-(4-Cl-2-Me-phenyl) | -C(=O)-NH- | 3,5-bis(CF₃)phenyl |
| 12 | PhO-CH₂-C(=O)-O-(4-Cl-2-Me-phenyl) | -C(=O)-NH- | 3,5-bis(CF₃)phenyl |

-continued
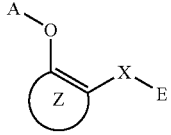
| Compound Number | | X | E |
|---|---|---|---|
| 13 | 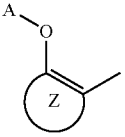 | 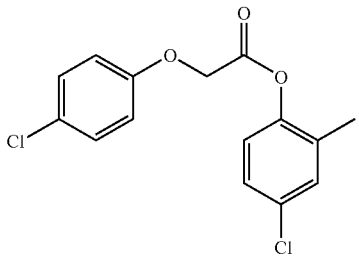 | 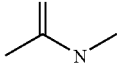 |
| 14 | 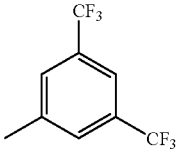 | 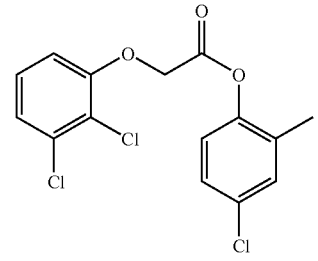 | 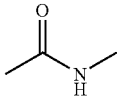 |
| 15 | 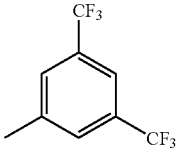 | 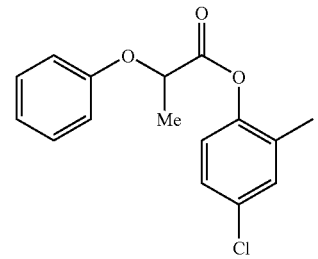 | 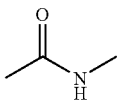 |
| 16 | 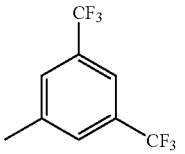 | 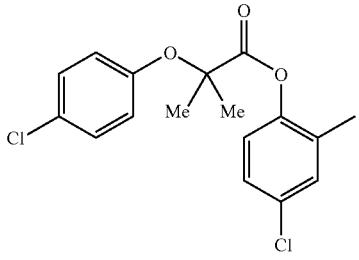 | 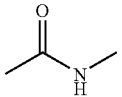 |

-continued
| Compound Number | | X | E |
|---|---|---|---|
| 17 | 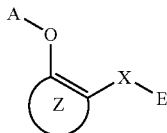 | 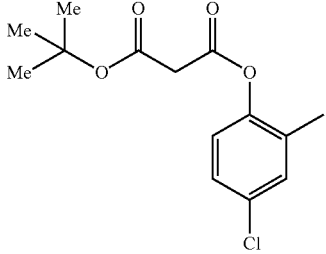 | 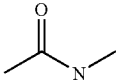 |
| 18 | 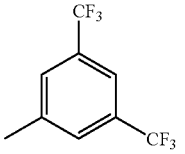 | 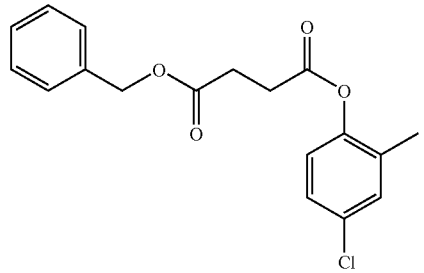 | 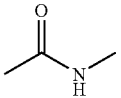 |
| 19 | 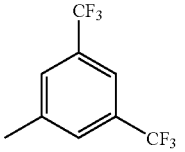 | 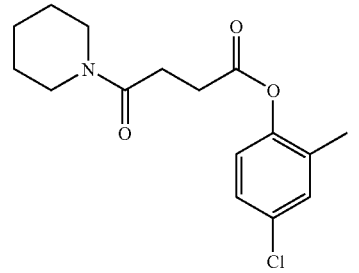 | 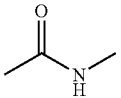 |
| 20 | 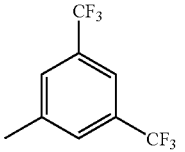 | 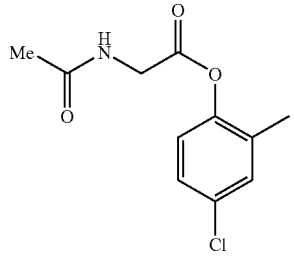 | 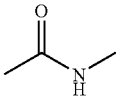 |

-continued
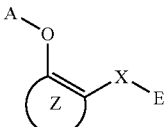
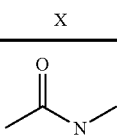
| Compound Number | | X | E |
|---|---|---|---|
| 21 | 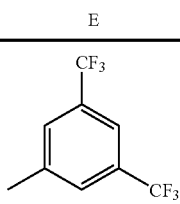 | 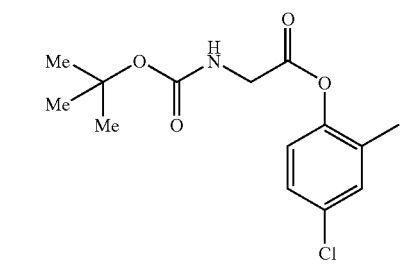 | 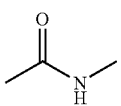 |
| 22 | 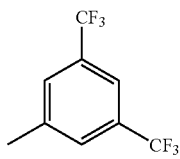 | 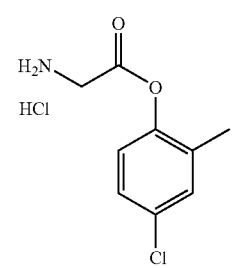 | 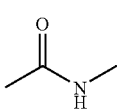 |
| 23 | 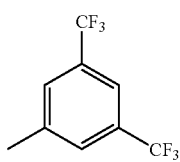 | 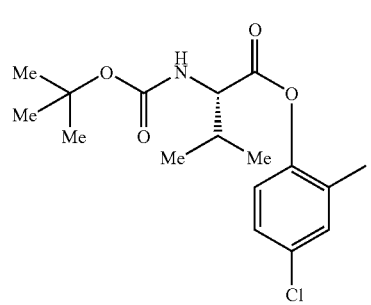 | 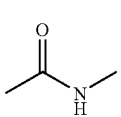 |
| 24 | 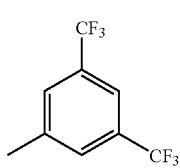 | | |

-continued

| Compound Number | (structure with A-O-Z and methyl) | X | E |
|---|---|---|---|
| 25 | L-Val ester (HCl·H₂N-CH(iPr)-C(O)O-) on 4-chloro-2-methylphenyl | -C(O)-NH- (acetamide linker) | 3,5-bis(trifluoromethyl)phenyl |
| 26 | Boc-Leu ester on 4-chloro-2-methylphenyl | -C(O)-NH- | 3,5-bis(trifluoromethyl)phenyl |
| 27 | L-Leu ester (HCl·H₂N-) on 4-chloro-2-methylphenyl | -C(O)-NH- | 3,5-bis(trifluoromethyl)phenyl |
| 28 | Boc-Phe ester on 4-chloro-2-methylphenyl | -C(O)-NH- | 3,5-bis(trifluoromethyl)phenyl |

-continued

| Compound Number | A | X | E |
|---|---|---|---|
| 29 | L-Phenylalaninate, HCl salt, on 4-chloro-2-methylphenyl | -C(O)-NH- | 3,5-bis(trifluoromethyl)phenyl |
| 30 | N-Boc-L-aspartic acid β-tert-butyl ester, on 4-chloro-2-methylphenyl | -C(O)-NH- | 3,5-bis(trifluoromethyl)phenyl |
| 31 | N-Boc-L-glutamic acid γ-tert-butyl ester, on 4-chloro-2-methylphenyl | -C(O)-NH- | 3,5-bis(trifluoromethyl)phenyl |
| 32 | L-glutamic acid, on 4-chloro-2-methylphenyl | -C(O)-NH- | 3,5-bis(trifluoromethyl)phenyl |

-continued

| Compound Number | [structure with A-O, Z ring, X-E] | X | E |
|---|---|---|---|
| 33 | Boc-Lys(Boc)-O-(4-chloro-2-methylphenyl) | CH₃C(O)NH– | 3,5-bis(trifluoromethyl)phenyl |
| 34 | H-Lys-O-(4-chloro-2-methylphenyl)·2HCl | CH₃C(O)NH– | 3,5-bis(trifluoromethyl)phenyl |
| 35 | Boc-Phe-Leu-O-(4-chloro-2-methylphenyl) | CH₃C(O)NH– | 3,5-bis(trifluoromethyl)phenyl |

-continued
| Compound Number | 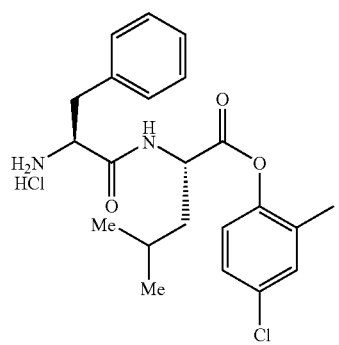 | X | E |
|---|---|---|---|
| 36 | 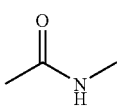 | 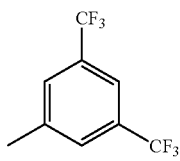 | 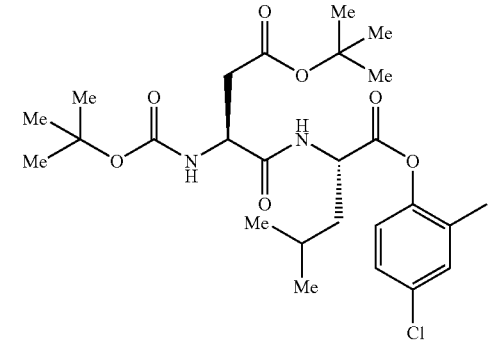 |
| 37 | 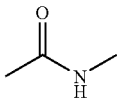 | 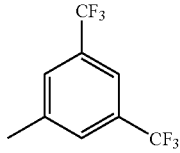 | 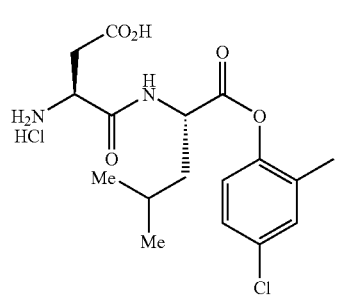 |
| 38 | 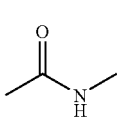 | 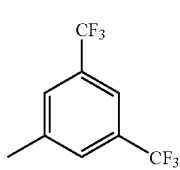 | 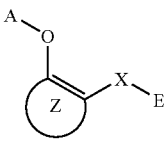 |

-continued
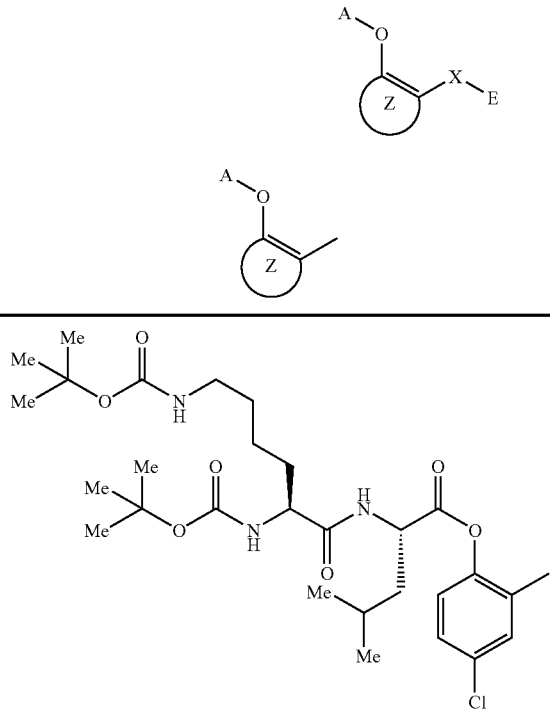
| Compound Number | | X | E |
|---|---|---|---|
| 39 | 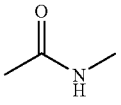 | 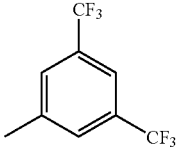 | 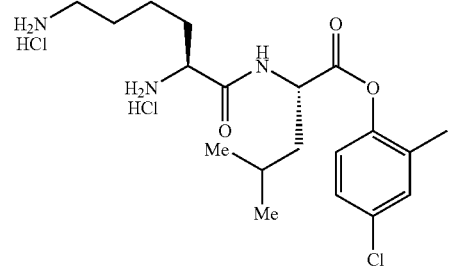 |
| 40 | 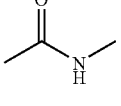 | 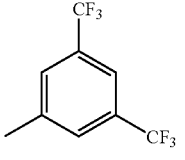 | 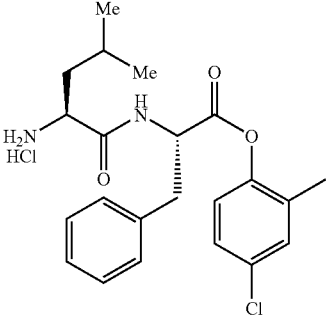 |
| 41 | 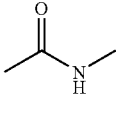 | 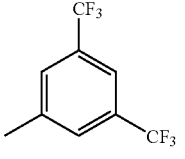 | 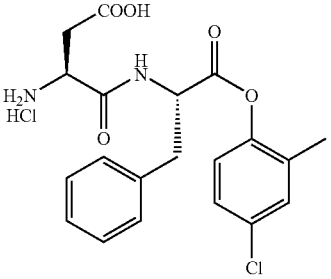 |
| 42 | 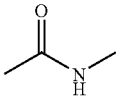 | 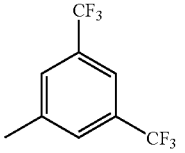 | |

-continued
| Compound Number | 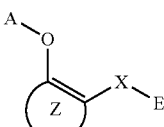 | X | E |
|---|---|---|---|
| 43 | 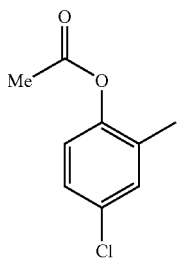 | 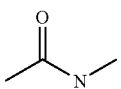 | 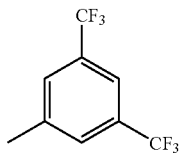 |
| 44 | 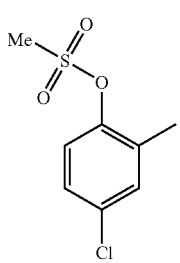 | 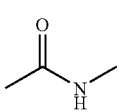 | 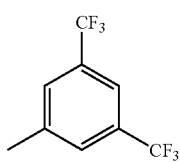 |
| 45 | 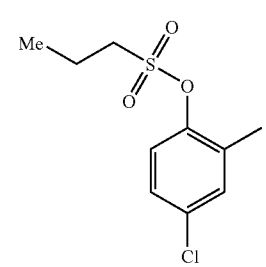 | 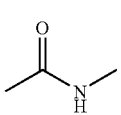 | 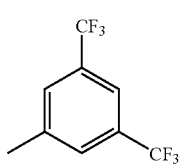 |
| 46 | 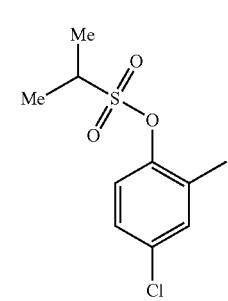 | 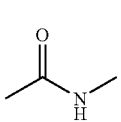 | 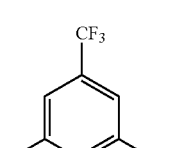 |

-continued

| Compound Number | (A-O-Z-X-E structure; A-O-Z-Me shown) | X | E |
|---|---|---|---|
| 47 | 4-chloro-2-methylphenyl 4-methylbenzenesulfonate | -C(=O)-NH- | 3,5-bis(trifluoromethyl)phenyl |
| 48 | 4-chloro-2-methylphenyl dimethylsulfamate | -C(=O)-NH- | 3,5-bis(trifluoromethyl)phenyl |
| 49 | 4-chloro-2-methylphenyl hydrogen sulfate | -C(=O)-NH- | 3,5-bis(trifluoromethyl)phenyl |
| 50 | dibenzyl 4-chloro-2-methylphenyl phosphate | -C(=O)-NH- | 3,5-bis(trifluoromethyl)phenyl |

-continued
| Compound Number | 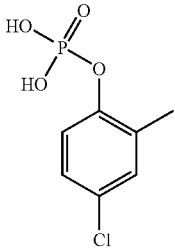 | X | E |
|---|---|---|---|
| 51 | 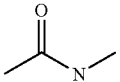 | 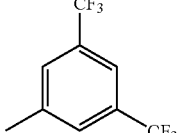 | 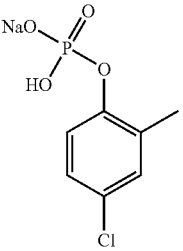 |
| 52 | 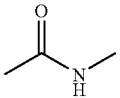 | 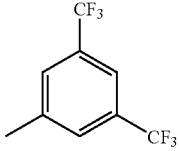 | 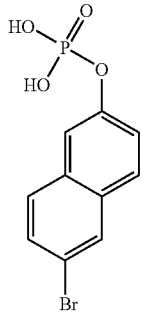 |
| 53 | 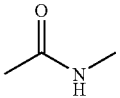 | 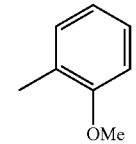 | 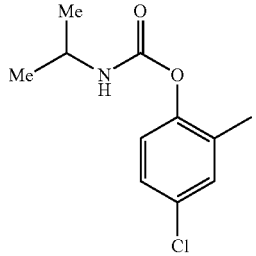 |
| 54 | 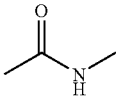 | 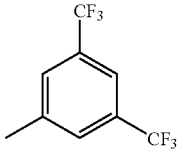 | 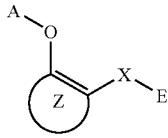 |

-continued

| Compound Number | [A-O-Z with methyl] | X | E |
|---|---|---|---|
| 55 | benzyl-NH-C(=O)-O- attached to 2-methyl-4-chlorophenyl | -C(=O)-NH- | 3,5-bis(CF₃)phenyl |
| 56 | EtO₂C-CH₂-NH-C(=O)-O- attached to 2-methyl-4-chlorophenyl | -C(=O)-NH- | 3,5-bis(CF₃)phenyl |
| 57 | HO₂C-CH₂-NH-C(=O)-O- attached to 2-methyl-4-chlorophenyl | -C(=O)-NH- | 3,5-bis(CF₃)phenyl |
| 58 | MeO₂C-CH(Me)-NH-C(=O)-O- attached to 2-methyl-4-chlorophenyl (S-config) | -C(=O)-NH- | 3,5-bis(CF₃)phenyl |

| Compound Number | Z | X | E |
|---|---|---|---|
| 59 | 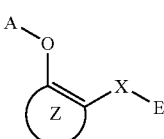 | 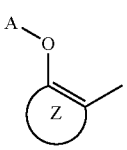 |  |
| 60 | 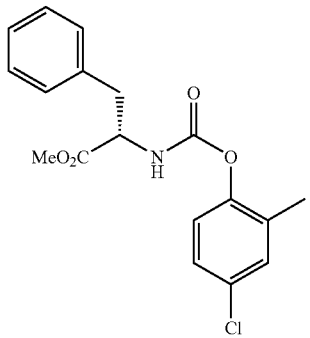 | 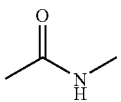 | 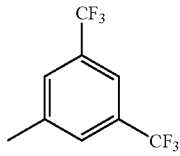 |
| 61 | 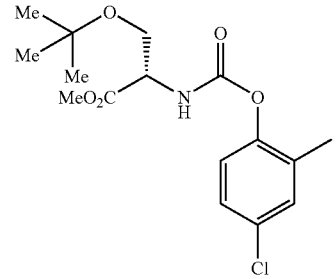 | 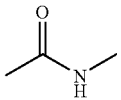 | 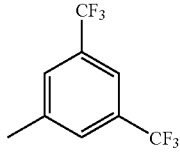 |
| 62 | 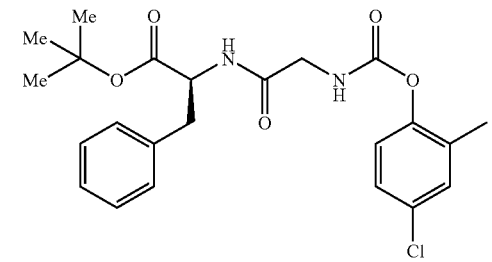 | 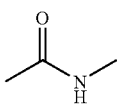 | 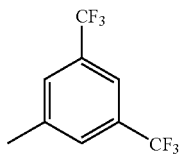 |

-continued
| Compound Number | | X | E |
|---|---|---|---|
| 63 | 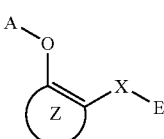 | 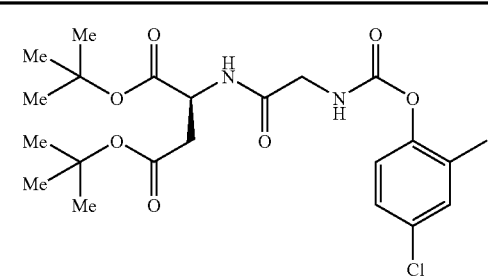 | 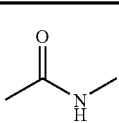 |
| 64 | 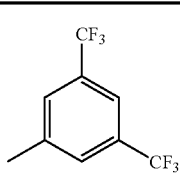 | 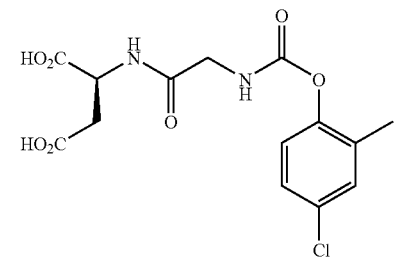 | 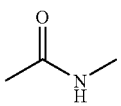 |
| 65 | 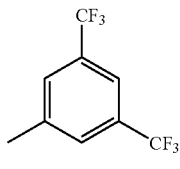 | 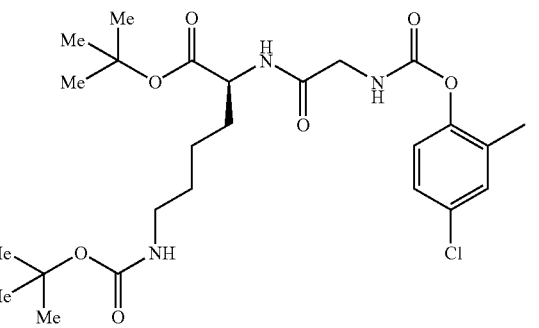 | 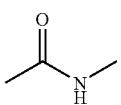 |
| 66 | 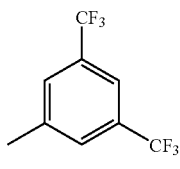 | 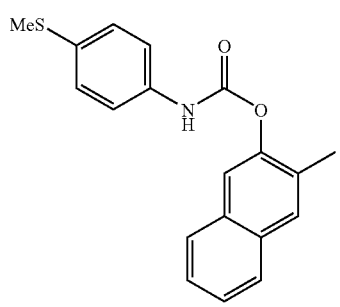 | 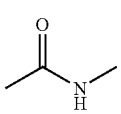 |

-continued

| Compound Number | | X | E |
|---|---|---|---|
| 67 | Me-N(Me)-C(=O)-O-[2-methyl-4-chloro-phenyl] | -C(=O)-NH- | 3,5-bis(CF₃)-phenyl |
| 68 | Et-N(Et)-C(=O)-O-[2-methyl-4-chloro-phenyl] | -C(=O)-NH- | 3,5-bis(CF₃)-phenyl |
| 69 | Ph-N(Me)-C(=O)-O-[2-methyl-4-chloro-phenyl] | -C(=O)-NH- | 3,5-bis(CF₃)-phenyl |
| 70 | pyrrolidin-1-yl-C(=O)-O-[2-methyl-4-chloro-phenyl] | -C(=O)-NH- | 3,5-bis(CF₃)-phenyl |

-continued
| Compound Number | 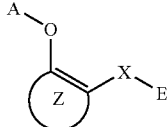 | X | E |
|---|---|---|---|
| 71 | 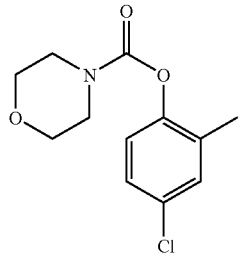 | | 3,5-bis(CF$_3$)phenyl |
| 72 | 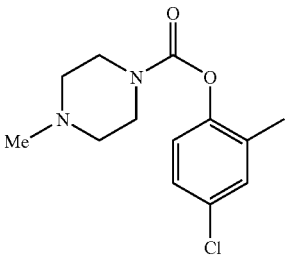 | | 3,5-bis(CF$_3$)phenyl |
| 73 | 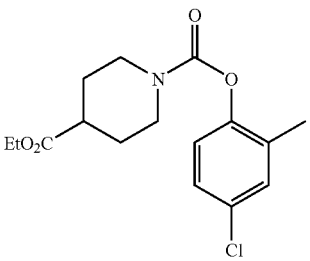 | | 3,5-bis(CF$_3$)phenyl |
| 74 | 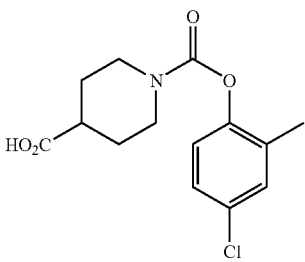 | | 3,5-bis(CF$_3$)phenyl |
| 75 | 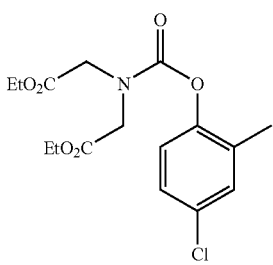 | | 3,5-bis(CF$_3$)phenyl |

-continued
| Compound Number | 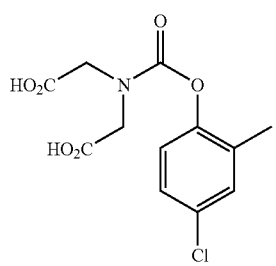 | X | E |
|---|---|---|---|
| 76 | 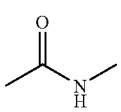 | 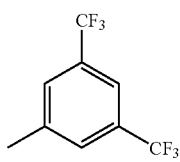 | 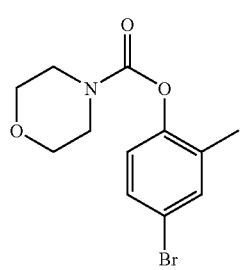 |
| 77 | 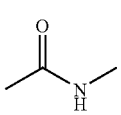 | 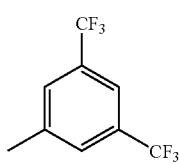 | 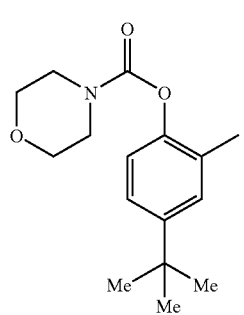 |
| 78 | 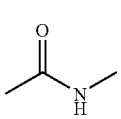 | 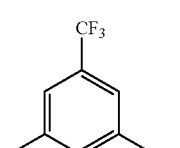 | 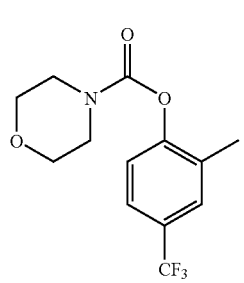 |
| 79 | 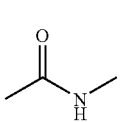 | 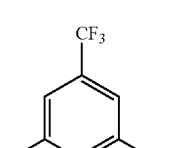 | 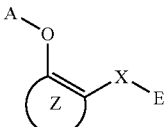 |

-continued
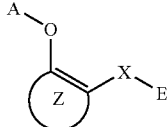
| Compound Number | 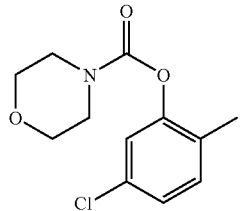 | X | E |
|---|---|---|---|
| 80 | 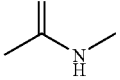 | 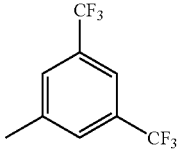 | 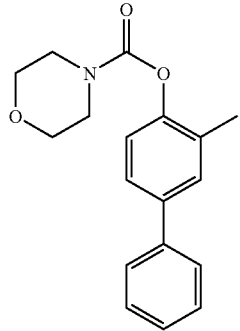 |
| 81 | 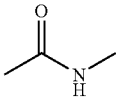 | 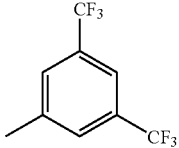 | 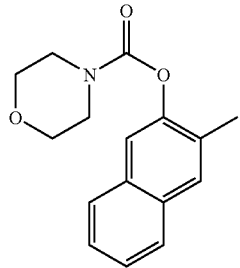 |
| 82 | 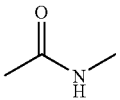 | 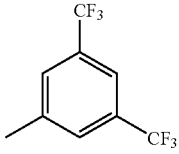 | 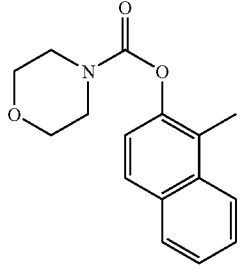 |
| 83 | 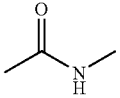 | 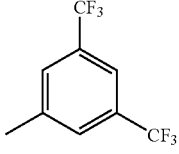 | |

-continued
| Compound Number | 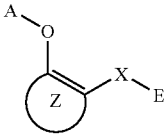 | X | E |
|---|---|---|---|
| 84 | 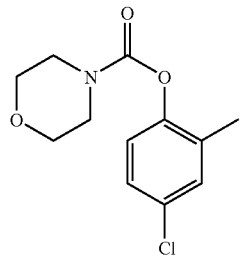 | 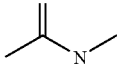 | 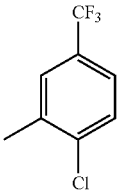 |
| 85 | 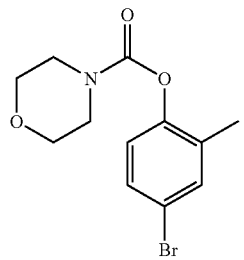 | 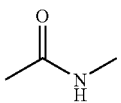 | 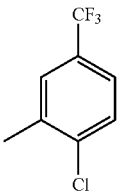 |
| 86 | 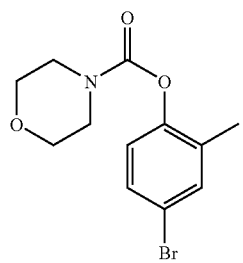 |  | 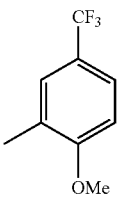 |
| 87 | 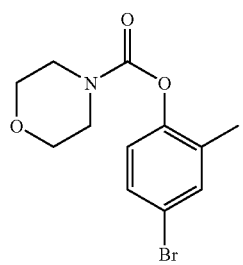 |  | 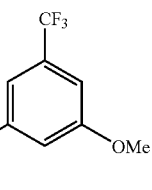 |
| 88 | 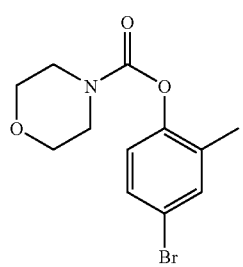 | 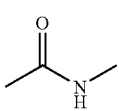 | 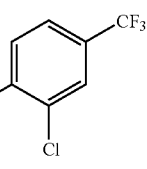 |

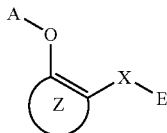

-continued
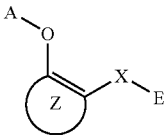
| Compound Number | 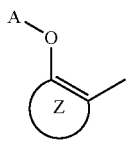 | X | E |
|---|---|---|---|
| 94 | 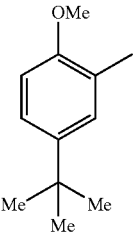 | 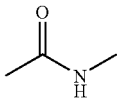 | 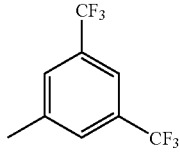 |
| 95 | 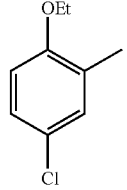 | 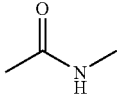 | 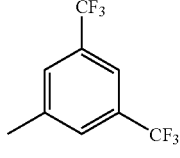 |
| 96 | 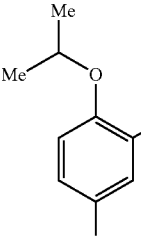 | 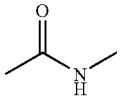 | 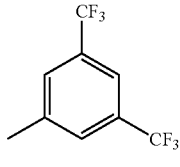 |
| 97 | 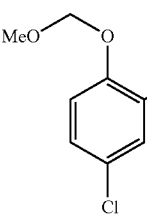 | 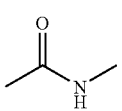 | 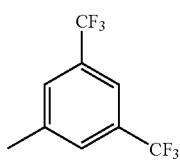 |
| 98 | 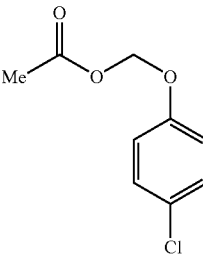 | 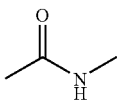 | 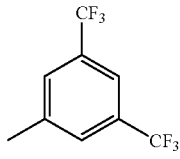 |

-continued
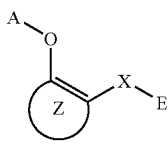
| Compound Number | 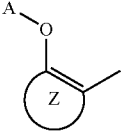 | X | E |
|---|---|---|---|
| 99 | 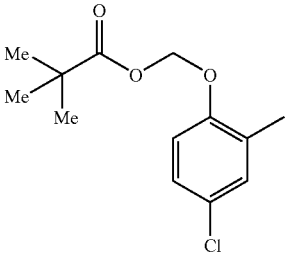 | 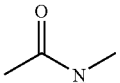 | 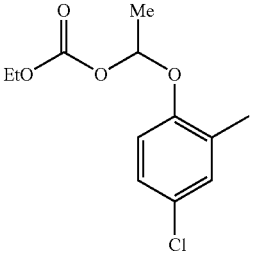 |
| 100 | 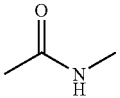 | 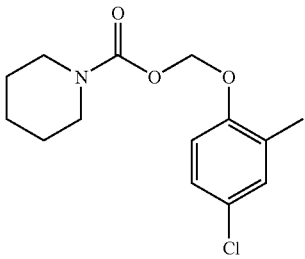 | 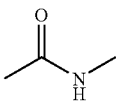 |
| 101 | 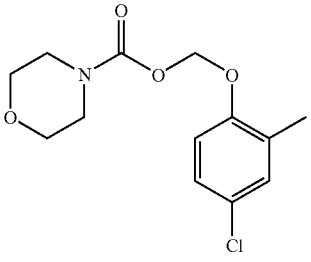 | 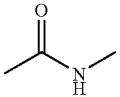 | 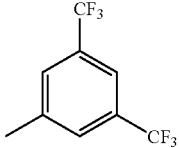 |
| 102 | 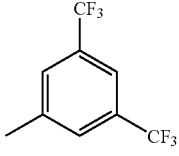 | 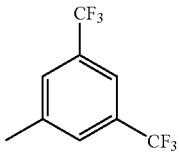 | 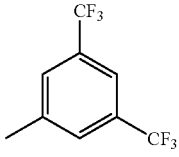 |

-continued
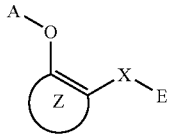
| Compound Number | | X | E |
|---|---|---|---|
| 103 | 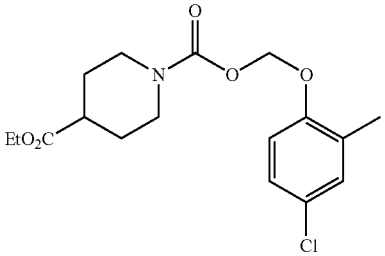 | 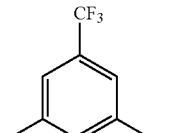 | 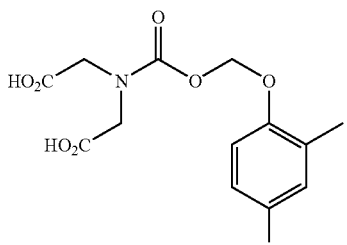 |
| 104 | 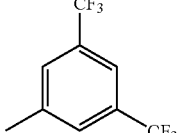 | 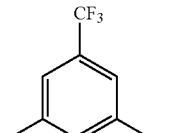 | 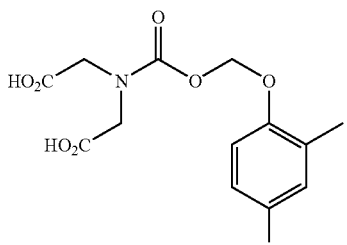 |
| 105 | 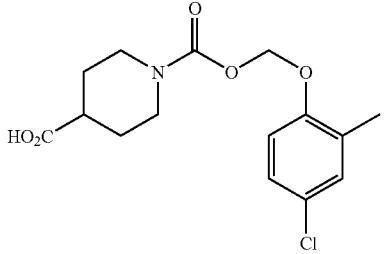 | 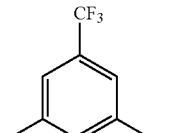 | 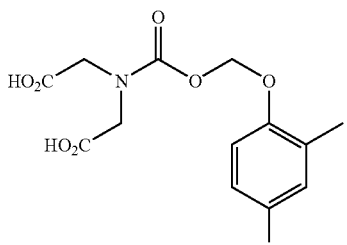 |
| 106 | 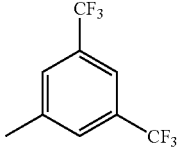 | 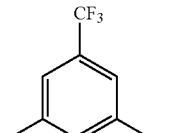 | 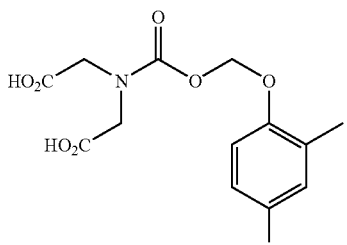 |
| 107 | 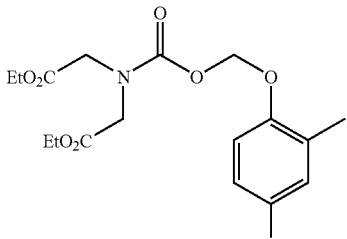 | 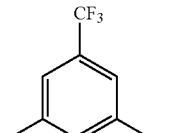 | 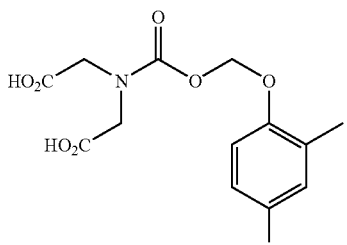 |

-continued

| Compound Number | A-O-[Z]-CH3 | X | E |
|---|---|---|---|
| 108 | EtO2C-CH2-O-(2-methyl-4-chlorophenyl) | -C(O)-NH- | 3,5-bis(CF3)phenyl |
| 109 | HO2C-CH2-O-(2-methyl-4-chlorophenyl) | -C(O)-NH- | 3,5-bis(CF3)phenyl |
| 110 | BnO-C(O)-CH2-O-(2-methyl-4-chlorophenyl) | -C(O)-NH- | 3,5-bis(CF3)phenyl |
| 111 | phthalimido-CH2-O-(2-methyl-4-chlorophenyl) | -C(O)-NH- | 3,5-bis(CF3)phenyl |

-continued

| Compound Number | [Z ring with A-O and methyl substituent] | X | E |
|---|---|---|---|
| 112 | tetra-acetyl glucopyranosyl-O-(4-chloro-2-methylphenyl) | -C(O)-N(H)- | 3,5-bis(trifluoromethyl)phenyl |
| 113 | 6-chloro-3-[3,5-bis(trifluoromethyl)phenyl]-2H-benzo[e][1,3]oxazine-2,4(3H)-dione | | |
| 114 | 9-chloro-5-[3,5-bis(trifluoromethyl)phenyl]-benzoxonane trione | | |
| 115 | methyl 6-chloro-3-[3,5-bis(trifluoromethyl)phenyl]-4-oxo-3,4-dihydro-2H-benzo[e][1,3]oxazine-2-carboxylate | | |

-continued
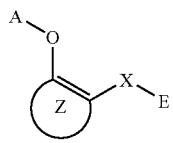
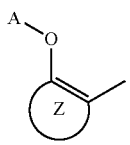
| Compound Number | | X | E |
|---|---|---|---|
| 116 | 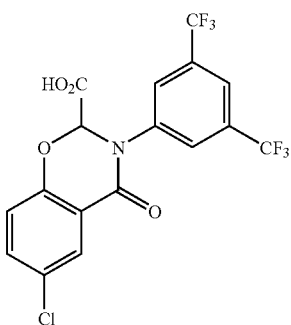 | | |
| 117 | 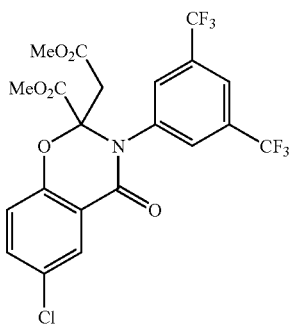 | | |
| 118 | 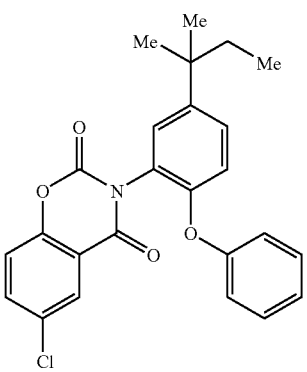 | | |
| 119 | 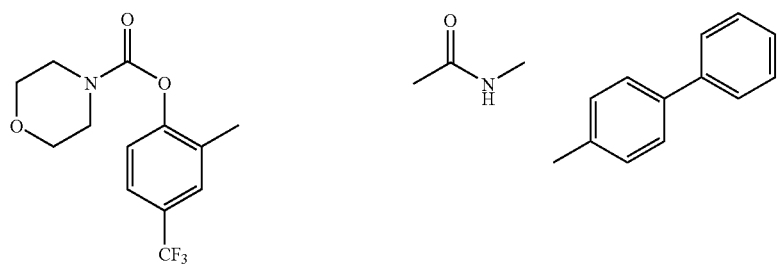 | | |

-continued

| Compound Number | | X | E |
|---|---|---|---|
| 120 | (dibenzyl phosphate ester of 4-chloro-2-methylphenol) | -NHC(O)CH₃- | 2,5-bis(trifluoromethyl)-4-methylphenyl |
| 121 | (phosphate ester of 4-chloro-2-methylphenol) | -NHC(O)CH₃- | 2,5-bis(trifluoromethyl)-4-methylphenyl |
| 122 | (sodium phosphate ester of 4-chloro-2-methylphenol) | -NHC(O)CH₃- | 2,5-bis(trifluoromethyl)-4-methylphenyl |
| 123 | (dibenzyl phosphate ester of 4-chloro-2-methylphenol) | -NHC(O)CH₃- | 4-chloro-2-methyl-5-(trifluoromethyl)phenyl |

-continued
| Compound Number | | X | E |
|---|---|---|---|
| 124 | 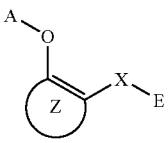 | 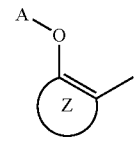 | 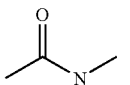 |
| 125 | 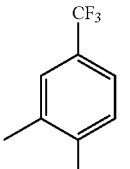 | 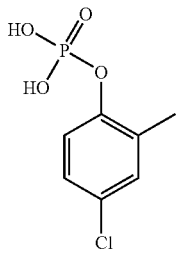 |  |
| 126 | 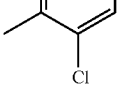 | 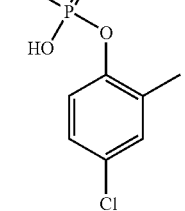 | 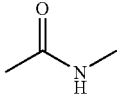 |
| 127 | 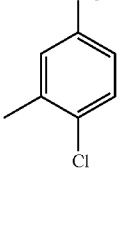 | 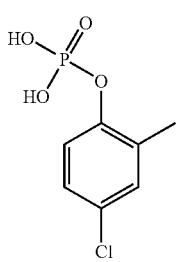 | 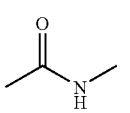 |

-continued

| Compound Number | [A-O-Z-CH3 structure] | X | E |
|---|---|---|---|
| 128 | 4-chloro-2-methylphenyl with NaO,HO-P(=O)-O- | -C(=O)-NH- | 2-methyl-4-tert-butyl-thiazol-5-yl C(=O)-C(Me)3 |
| 129 | 4-bromo-2-methylphenyl with morpholine-N-C(=O)-O- | -C(=O)-NH- | 3,5-bis(CF3)-phenyl (with Me) |
| 130 | 4,6-dibromo-2-methylphenyl with morpholine-N-C(=O)-O- | -C(=O)-NH- | 3,5-bis(CF3)-phenyl (with Me) |
| 131 | 2-methylphenyl with 2-hydroxybenzoate ester | -C(=O)-NH- | 3,5-bis(CF3)-phenyl (with Me) |
| 132 | 2-methylphenyl with morpholine-N-C(=O)-O- | -C(=O)-NH- | 3,5-bis(CF3)-phenyl (with Me) |

-continued
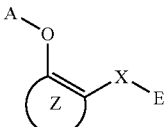
| Compound Number | 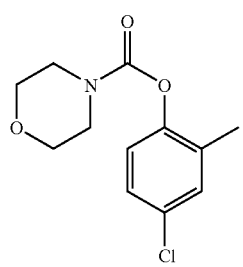 | X | E |
|---|---|---|---|
| 133 | 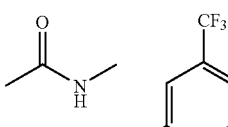 | 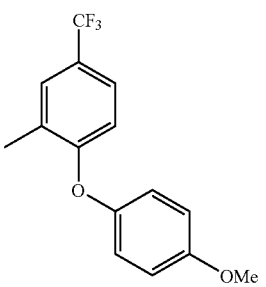 | 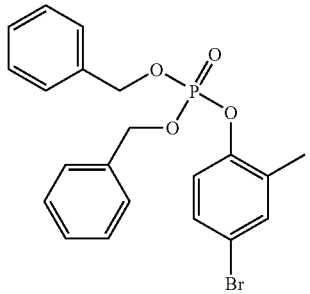 |
| 134 | 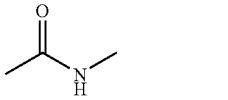 | 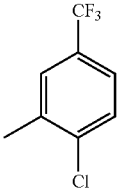 | 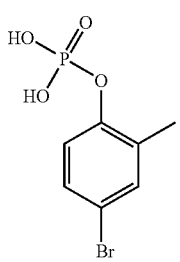 |
| 135 |  | 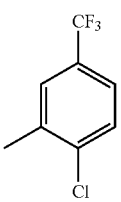 | 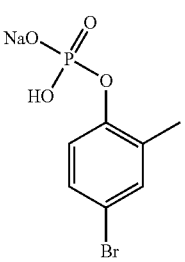 |
| 136 | 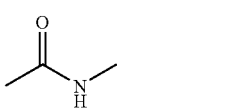 | | 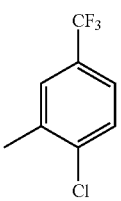 |

-continued
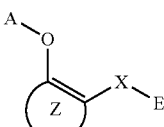
| Compound Number | 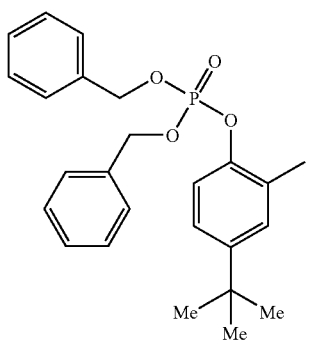 | X | E |
|---|---|---|---|
| 137 | 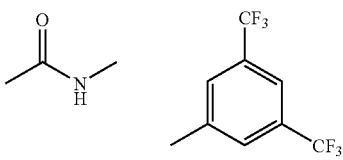 | 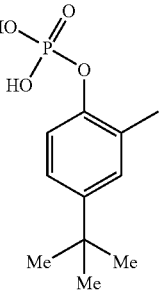 | 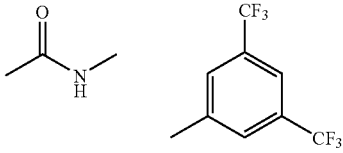 |
| 138 | 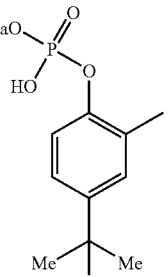 | 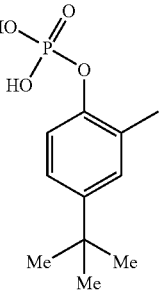 | 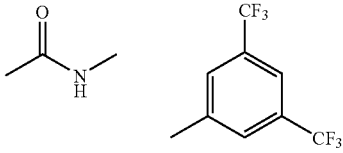 |
| 139 | 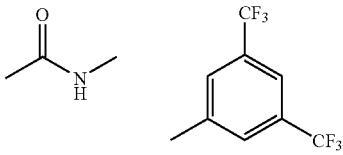 | 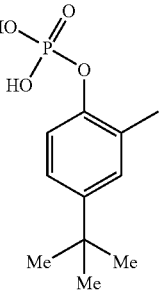 | 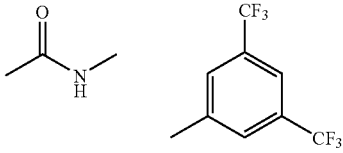 |
| 140 | 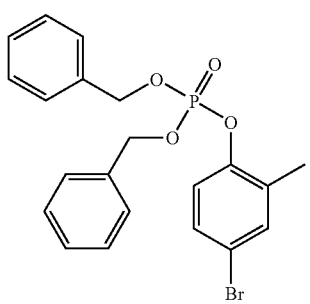 | 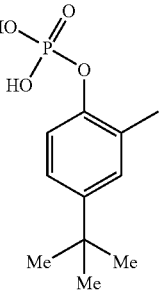 | 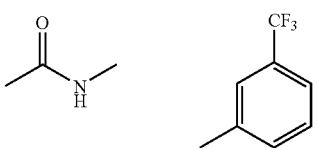 |

-continued

| Compound Number | | X | E |
|---|---|---|---|
| 141 | 2-methyl-4-bromophenyl dihydrogen phosphate | -C(=O)-NH- | 2,5-bis(trifluoromethyl)phenyl |
| 142 | sodium 2-methyl-4-bromophenyl hydrogen phosphate | -C(=O)-NH- | 2,5-bis(trifluoromethyl)phenyl |
| 143 | dibenzyl 2-methyl-4-bromophenyl phosphate | -C(=O)-NH- | 3,5-di-tert-butylphenyl |
| 144 | 2-methyl-4-bromophenyl dihydrogen phosphate | -C(=O)-NH- | 3,5-di-tert-butylphenyl |

-continued
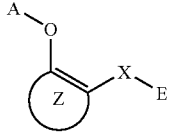
| Compound Number | | X | E |
|---|---|---|---|
| 145 | 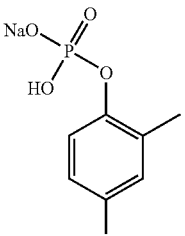 | 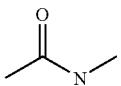 | 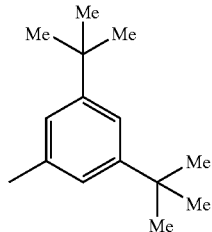 |
| 146 | 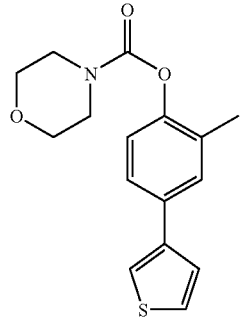 | 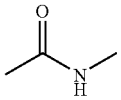 | 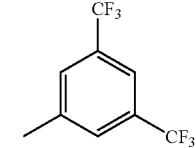 |
| 147 | 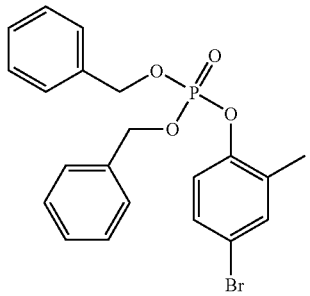 | 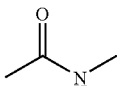 | 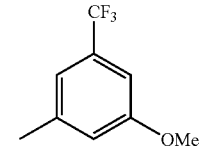 |
| 148 | 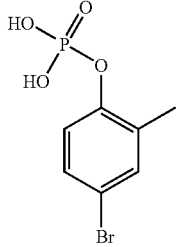 | 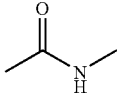 | 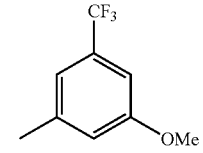 |

-continued
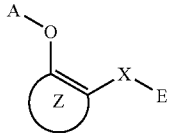
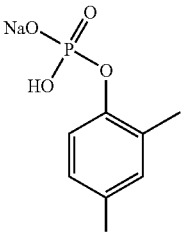
| Compound Number | | X | E |
|---|---|---|---|
| 149 | 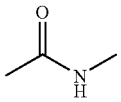 | 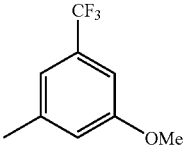 | 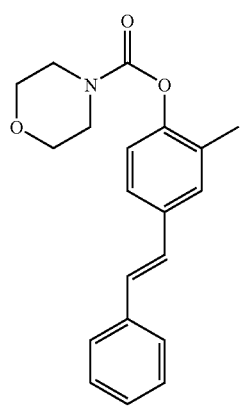 |
| 150 | 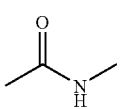 | 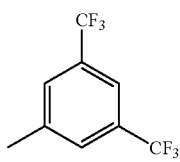 | 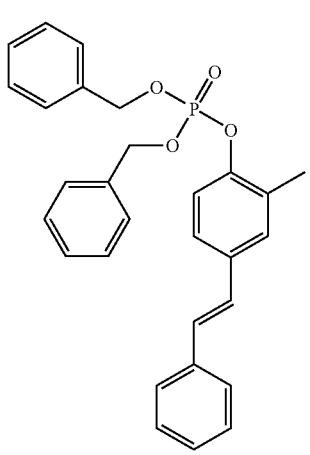 |
| 151 | 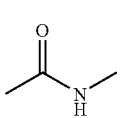 | 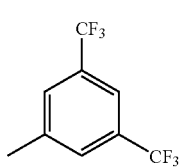 | |

The compounds represented by the general formula (I) can be prepared, for example, by methods shown bellow. First, hydroxyaryl derivatives corresponding to the compounds wherein A is hydrogen atom in the general formula (I), which are used as precursors of the compounds represented by the general formula (I), are prepared by the following methods such as <Method 1> to <Method 5>, and then, the compounds represented by the general formula (I) can be prepared by acylation or alkylation of the hydroxy group of said hydroxyaryl derivatives by the following methods such as <Method 6>.

<Method 1>

The compounds represented by the general formula (I), wherein A is hydrogen atom and X is —CONH— (the hydrogen atom on the nitrogen may be substituted) can be prepared, for example, by a method described in the reaction scheme 1.

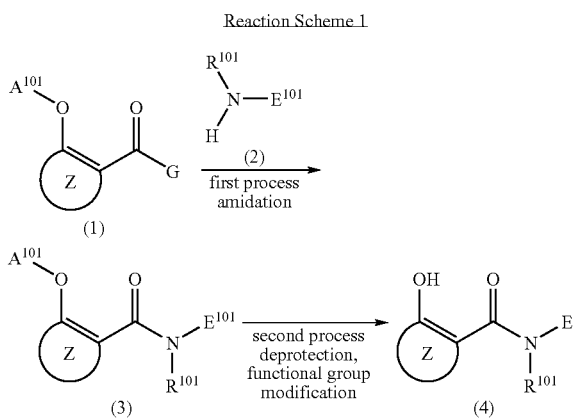

Reaction Scheme 1 wherein each of ring Z, and E has the same meaning as that defined in the general formula (I), $A^{101}$ represents a hydrogen atom or protecting groups of hydroxy group (preferably, an alkyl group such as methyl group and the like; an aralkyl group such as benzyl group and the like; an acetyl group, an alkoxyalkyl group such as methoxymethyl group and the like; a substituted silyl group such as trimethylsilyl group or the like), $R^{101}$ represents a hydrogen atom, a $C_1$ to $C_6$ alkyl group or the like, $E^{101}$ represents E or precursor of E in the definition of the general formula (I), G represents a hydroxy group, halogen atoms (preferably, a chlorine atom), a hydrocarbonoxy group (preferably, an aryl-oxy group which may be substituted by halogen atom), an acyl-oxy group, an imido-oxy group or the like.

(First Step)

The amide (3) can be prepared by dehydrocondensation of the carboxylic acid derivative (1) and the amine (2). This reaction is carried out at a reaction temperature of from 0° C. to 180° C., without solvent or in an aprotic solvent, in the presence of an acid halogenating agent or a dehydrocondensing agent, and in the presence or absence of a base.

As the halogenating agent, examples include, for example, thionyl chloride, thionyl bromide, sulfuryl chloride, phosphorus oxychloride, phosphorus trichloride, phosphorus pentachloride or the like. When $A^{101}$ is hydrogen atom, phosphorus trichloride is preferable, and when $A^{101}$ is acetyl group or the like, phosphorus oxychloride is preferable. As the dehydrocondensing agent, examples include, for example, N,N'-dicyclohexylcarbodiimide, 1-ethyl-3-(3-dimethylaminopropyl)carbodiimide hydrochloride, diphenylphosphorylazide or the like. As the base, examples include inorganic bases such as sodium carbonate, potassium carbonate, sodium hydrogencarbonate or the like, or organic bases such as pyridine, triethylamine, N,N'-diethylaniline or the like. As the aprotic solvent, examples include dichloromethane, dichloroethane, chloroform, tetrahydrofuran, 1,4-dioxane, benzene, toluene, monochlorobenzene, o-dichlorobenzene, N,N'-dimethylformamide, N-methylpyrrolidone or the like, when the reaction is carried out in the presence of the acid halogenating agent, particularly, toluene, monochlorobenzene, o-dichlorobenzene are preferable.

A target compound can also be prepared, for example, by a method or similar method described in Journal of Medicinal Chemistry, (USA), 1998, Vol. 41, No. 16, p. 2939-2945, in which the acid chloride is prepared and isolated beforehand from carboxylic acid, then the result is made to react with an amine having $E^{101}$.

When G is hydroxy group, the reaction condition described in Archiv der Pharmazie, (Germany), 1998, Vol. 331, No. 1, p. 3-6 can be used as a preferred reaction condition.

Kinds of carboxylic acid derivative (1) and amine (2) are not particularly limited, and new compounds synthesized by referring to well-known preparation method described in the literature or commercially available reagents can be used for the aforementioned reaction.

(Second Step)

When the amide (3) has a protecting group and/or has a favorable substituent for functional group modification, for example, an amino group and a protected amino group or its precursor; a carboxy group and a protected carboxy group or its precursor; a hydroxy group and a protected hydroxy group or its precursor, the compound (4) can be prepared by a reaction for deprotection and/or functional group modification in this step. Various well-known methods can be used for the reaction. For the reaction of deprotection and functional group modification, for example, methods described in "Protective Groups in Organic Syntheses", (USA), Theodra W. Green, Peter G. M. Wuts, Eds., Third edition, April in 1999, John Wiley & Sons, and "Handbook of Reagents for Organic Synthesis", (USA), 4 Volumes, June in 1999, John Wiley & Sons can be used, and for the reaction of functional group modification, for example, methods described in "Palladium Reagents in Organic Syntheses", (USA), Richard F. Heck, 1985, Academic Press, and "Palladium Reagents and Catalysts: Innovations in Organic Synthesis", (USA), J. Tsuji, 1999, John Wiley & Sons, or the like can be used.

The aforementioned methods are applicable by appropriately combining raw materials even for the compounds wherein X is other connecting group, for example, —SO$_2$NH—, —NHCO—, —NHSO$_2$—, —CONHCH$_2$—, —CONHCH$_2$CH$_2$—, —CONHCH$_2$CONH—, —CONHNHCO—, —CONHNH CH$_2$—, —COO—, —CONHNH—; wherein the hydrogen atom on said connecting group may be substituted.

<Method 2>

The compounds represented by the general formula (I), wherein A is hydrogen atom and X is —CH$_2$NH— can be prepared, for example, by a method described in the reaction scheme 2.

Reaction Scheme 2

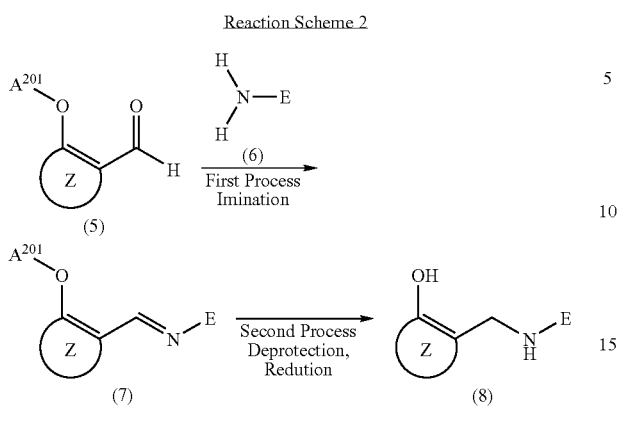

wherein each of ring Z, and E has the same meaning as that defined in the general formula (I), $A^{201}$ represents a hydrogen atom or protecting groups of hydroxy group (preferably, an alkyl group such as methyl group and the like; an aralkyl group such as benzyl group and the like; an acetyl group, an alkoxyalkyl group such as methoxymethyl group and the like; a substituted silyl group such as trimethylsilyl group or the like).

The imine derivative of the formula (7) can be prepared by dehydrocondensation of the aldehyde (5) and the amine (6). This reaction is carried out at a reaction temperature of from 0° C. to 100° C. in a solvent, in the presence or absence of a dehydrating agent. As the dehydrating agent, examples include anhydrous magnesium sulfate, molecular sieves or the like. As the solvent, examples include inert solvent, and tetrahydrofuran, 1,4-dioxane, methanol, ethanol or the like are preferable.

The aforementioned methods are applicable by appropriately combining raw materials even for the compounds wherein X is other connecting group, for example, —CONHN=CH—, —CH=NNHCO—, —CHNNH—; wherein the hydrogen atom on said connecting group may be substituted.

When $A^{201}$ of the imine derivative (7) is a protecting group of hydroxy group, the compound wherein $A^{201}$ is hydrogen atom can be prepared by a reaction for deprotection. Various well-known methods can be used for the reaction, and for example, methods described in "Protective Groups in Organic Syntheses", (USA), Theodra W. Green, Peter G. M. Wuts, Eds., Third edition, April in 1999, John Wiley & Sons, and "Handbook of Reagents for Organic Synthesis", (USA), 4 Volumes, June in 1999, John Wiley & Sons, or the like can be used.

The target compound (8) can be prepared by reduction of the imine derivative (7). This reaction is carried out at a reaction temperature of from 0° C. to 100° C. in a solvent, in the presence of a reducing agent. As the reducing agent, examples include sodium borohydride, lithium borohydride or the like. As the solvent, examples include inert solvent, and tetrahydrofuran, 1,4-dioxane, methanol, ethanol or the like are preferable. This reaction can also be carried out by a method of catalytic hydrogenation. As the catalyst, examples include palladium carbon, platinum carbon, palladium hydroxide, palladium black or the like. As solvent, examples include inert solvent, and tetrahydrofuran, 1,4-dioxane, methanol, ethanol or the like are preferable. The reaction is carried out at a reaction temperature of from 0° C. to 200° C., and the hydrogen pressure may be an ordinary pressure or a positive pressure.

<Method 3>

The compounds represented by the general formula (I), wherein X is —CH=CH— (the hydrogen atom on said connecting group may be substituted), can be prepared, for example, by methods described in the reaction scheme 3-1 or the reaction scheme 3-2.

Reaction Scheme 3-1

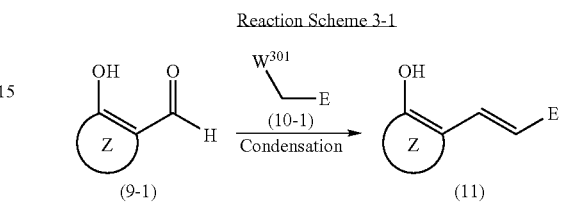

wherein each of ring Z and E has the same meaning as that defined in the general formula (I), $W^{301}$ represents O,O'-dihydrocarbon-phosphono group or triarylphosphonium group.

The target compound (11) can be prepared by dehydrocondensation of the aldehyde (9-1) and the phosphorus compound (10-1). This reaction is carried out in a solvent at a reaction temperature of from 0° C. to the boiling point of the solvent, in the presence of a base. As the base, examples include inorganic base such as sodium carbonate, potassium carbonate, sodium hydrogencarbonate or the like, or organic base such as pyridine, triethylamine, N,N-diethylaniline or the like. As the solvent, examples include inert solvent, and tetrahydrofuran, 1,4-dioxane, methanol, ethanol, water or the like are preferable.

Reaction Scheme 3-2

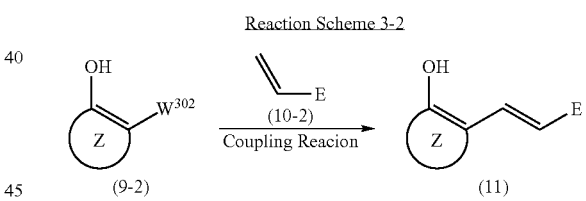

wherein E has the same meaning as that defined in the general formula (I), $W^{302}$ represents halogen atoms (preferably, iodine atom and bromine atom), (trifluoromethanesulfonyl)oxy group and the like.

The target compound (11) can be prepared by reacting the halogenated compound (9-2) with the styrene compound (10-2) in the presence of a transition-metal complex catalyst. This reaction is carried out in a solvent at a reaction temperature of from 0° C. to the boiling point of the solvent, in the presence or absence of a ligand and/or a base. As the transition-metal complex catalyst, examples include palladium catalyst such as palladium acetate and dichlorobis(triphenylphosphine) palladium. As the ligand, examples include phosphine ligand such as triphenylphosphine. As the base, examples include inorganic base such as sodium carbonate, potassium carbonate, and sodium hydrogen carbonate, or organic base such as pyridine, triethylamine, and N,N-diethylaniline. As the solvent, examples include inert solvents, and N,N-dimethylformamide, tetrahydrofuran, 1,4-dioxane or the like are preferable.

<Method 4>

The compounds represented by the general formula (I), wherein X is —COCH=CH— and —COCH$_2$CH$_2$— (the hydrogen atom on said connecting group may be substituted), can be prepared, for example, by a method described in the reaction scheme 4.

Reaction Scheme 4

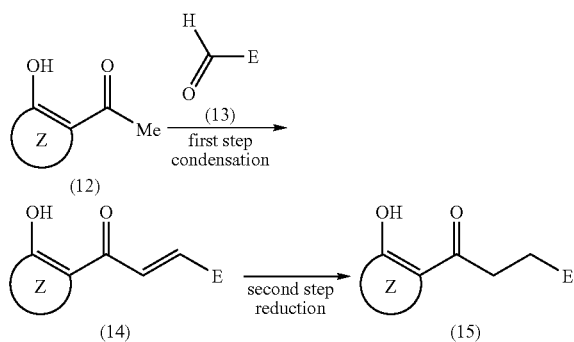

wherein each of rings Z and E has the same meaning as that defined in the general formula (I).

The target compound enone (14) can be prepared by dehydrocondensation of the ketone (12) and the aldehyde (13). This reaction is carried out in a solvent at a reaction temperature of from 0° C. to the boiling point of the solvent, in the presence of a base. As the base, examples include inorganic base such as sodium hydroxide, potassium hydroxide, sodium carbonate, potassium carbonate, sodium hydrogencarbonate or the like, or organic base such as pyridine, triethylamine, N,N-diethylaniline or the like. Examples include inert solvent, and tetrahydrofuran, 1,4-dioxane, methanol, ethanol, water or the like are preferable.

Next, the target compound (15) can be prepared by reduction of the enone (14). This reaction is carried out at a reaction temperature of from 0° C. to 100° C. in solvent, in the presence of a reducing agent. As the reducing agent, examples include sodium borohydride, lithium borohydride or the like. As the solvent, examples include inert solvent, and tetrahydrofuran, 1,4-dioxane, methanol, ethanol or the like are preferable. Moreover, this reaction is carried out by a method of catalytic hydrogenation also. As the catalyst, examples include palladium carbon, platinum carbon, palladium hydroxide, palladium black or the like. As solvent, examples include inert solvent, and tetrahydrofuran, 1,4-dioxane, methanol, ethanol or the like are preferable. The reaction is carried out at a reaction temperature of from 0° C. to 200° C., and the hydrogen pressure is at normal pressure or applied pressure.

<Method 5>

The compounds represented by the general formula (I), wherein X is —NHCONH— (the hydrogen atom on said connecting group may be substituted), can be prepared, for example, by a method described in the reaction scheme 5.

Reaction Scheme 5

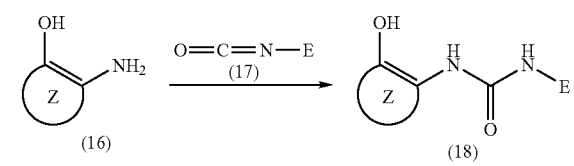

wherein each of ring Z and E has the same meaning as that defined in the general formula (I).

First, the target compound urea (18) can be prepared by reacting the amine (16) with the isocyanate (17). This reaction is carried out in a solvent at a reaction temperature of from 0° C. to the boiling point of the solvent, in the presence or absence of a base. As the base, examples include inorganic base such as sodium hydroxide, potassium hydroxide, sodium carbonate, potassium carbonate, sodium hydrogencarbonate or the like, or organic base such as pyridine, triethylamine, N,N-diethylaniline or the like. Examples include inert solvent, and tetrahydrofuran, 1,4-dioxane, methanol, ethanol, water or the like are preferable.

The target compounds represented by the general formula (I), wherein A represents an acyl group which may be substituted (provided that unsubstituted acetyl group and unsubstituted acryloyl group are excluded) or a $C_1$ to $C_6$ alkyl group which may be substituted, or A may bind to connecting group X to form a cyclic structure which may be substituted, can be prepared by acylation or alkylation of the hydroxyaryl derivatives (19) obtained by each of the aforementioned methods, wherein A is hydrogen atom in the general formula (I) (Reaction Scheme 6).

Reaction Scheme 6

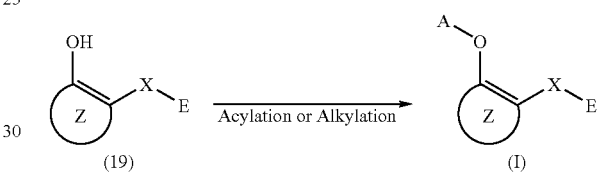

wherein each of A, X and E has the same meaning as that defined in the general formula (I).

Various well-known methods can be used for acylation or alkylation of the hydroxyaryl derivatives (19).

Examples of the acylation of the hydroxyaryl derivatives (19) include, for example, dehydrocondensation with carboxylic acids, substitution by acid halides, acid anhydrides, sulfonic acid halides, sulfonic acid anhydrides, phosphonic acid halides, phosphonic acid anhydrides or the like, addition with isocyanates, isothiocyanates, sulfur trioxide or the like. Examples of the alkylation of the hydroxyaryl derivatives (19) include, for example, substitution by halogenated alkyl groups.

Dehydrocondensation of the hydroxyaryl derivative (19) and the carboxylic acid is carried out at a reaction temperature of from 0° C. to 180° C., without solvent or in an aprotic solvent, in the presence of an acid halogenating agent or a dehydrocondensing agent, and in the presence or absence of a base. As the halogenating agent, examples include, for example, thionyl chloride, thionyl bromide, sulfuryl chloride, phosphorus oxychloride, phosphorus trichloride, phosphorus pentachloride or the like. As the dehydrocondensing agent, examples include, for example, N,N'-dicyclohexylcarbodiimide, 1-ethyl-3-(3-dimethylaminopropyl)carbodiimide hydrochloride, diphenylphosphorylazide or the like. As the base, examples include inorganic bases such as sodium carbonate, potassium carbonate, sodium hydrogencarbonate or the like, or organic bases such as pyridine, triethylamine, N,N-diethylaniline or the like. As the aprotic solvent, examples include dichloromethane, dichloroethane, chloroform, tetrahydrofuran, 1,4-dioxane, benzene, toluene, monochlorobenzene, o-dichlorobenzene, N,N-dimethylformamide, N-methylpyrrolidone or the like, when the reaction is carried out in the presence of the acid halogenating agent, particularly, toluene, monochlorobenzene, o-dichlorobenzene are preferable.

Substitution of the hydroxyaryl derivative (19) and the acid halide, acid anhydride, sulfonic acid halide, sulfonic acid anhydride, phosphonic acid halide, phosphonic acid anhydride or the like is carried out at a reaction temperature of from −50° C. to 180° C., without solvent or in an aprotic solvent, in the presence or absence of a base. As the base, examples include inorganic bases such as sodium carbonate, potassium carbonate, sodium hydrogencarbonate or the like, or organic bases such as pyridine, triethylamine, N,N-diethylaniline or the like. As the aprotic solvent, examples include dichloromethane, dichloroethane, chloroform, tetrahydrofuran, 1,4-dioxane, benzene, toluene, monochlorobenzene, o-dichlorobenzene, N,N-dimethylformamide, N-methylpyrrolidone or the like.

For example, the compounds represented by the general formula (I), wherein A is (morpholin-4-yl)carbonyl group can be prepared by reacting the hydroxyaryl derivative (19) with (morpholin-4-yl)carbonyl chloride in tetrahydrofuran in the presence of triethylamine and 4-dimethylaminopyridine.

The compounds represented by the general formula (I), wherein A is dibenzylphosphono group can be prepared by reacting the hydroxyaryl derivative (19) with dibenzyl phosphite in carbon tetrachloride in the presence of diisopropylethylamine and 4-dimethylaminopyridine.

The compounds represented by the general formula (I), wherein A is sulfo group can be prepared by reacting the hydroxyaryl derivative (19) with sulfur trioxide-pyridine complex in pyridine.

Furthermore, when the hydroxyaryl derivative (19) wherein X is —CONH— group and ethyl chloroformate are refluxed in pyridine, a compound wherein the hydroxy group and —CONH— group on the ring Z are bound via a carbonyl group can be obtained.

Addition of the hydroxyaryl derivative (19) and the isocyanate, isothiocyanate, sulfur trioxide or the like is carried out at a reaction temperature of from −50° C. to 180° C., without solvent or in an aprotic solvent, in the presence or absence of a base. As the base, examples include inorganic bases such as sodium carbonate, potassium carbonate, sodium hydrogencarbonate or the like, or organic bases such as pyridine, triethylamine, N,N-diethylaniline or the like. As the aprotic solvent, examples include dichloromethane, dichloroethane, chloroform, tetrahydrofuran, 1,4-dioxane, benzene, toluene, monochlorobenzene, o-dichlorobenzene, N,N-dimethylformamide, N-methylpyrrolidone or the like.

Substitution of the hydroxyaryl derivative (19) and the halogenated alkyl group is carried out at a reaction temperature of from −50° C. to 180° C., without solvent or in an aprotic solvent, in the presence or absence of a base. As the base, examples include inorganic bases such as sodium carbonate, potassium carbonate, sodium hydrogencarbonate or the like, or organic bases such as pyridine, triethylamine, N,N-diethylaniline or the like. As the aprotic solvent, examples include dichloromethane, dichloroethane, chloroform, tetrahydrofuran, 1,4-dioxane, benzene, toluene, monochlorobenzene, o-dichlorobenzene, N,N-dimethylformamide, N-methylpyrrolidone or the like.

Each of the aforementioned reaction using the hydroxyaryl derivative (19) may be carried out after conversion of (19) to a sodium salt thereof or a potassium salt thereof.

When the compounds represented by the general formula (I) prepared thus have a protecting group and/or has a favorable substituent for functional group modification, for example, an amino group and a protected amino group or its precursor; a carboxy group and a protected carboxy group or its precursor; a hydroxy group and a protected hydroxy group or its precursor, a reaction for deprotection and/or functional group modification can be carried out. Various well-known methods can be used for the reaction. For the reaction of deprotection and functional group modification, for example, methods described in "Protective Groups in Organic Syntheses", (USA), Theodra W. Green, Peter G. M. Wuts, Eds., Third edition, April in 1999, John Wiley & Sons, and "Handbook of Reagents for Organic Synthesis", (USA), 4 Volumes, June in 1999, John Wiley & Sons can be used, and for the reaction of functional group modification, for example, methods described in "Palladium Reagents in Organic Syntheses", (USA), Richard F. Heck, 1985, Academic Press, and "Palladium Reagents and Catalysts: Innovations in Organic Synthesis", (USA), J. Tsuji, 1999, John Wiley & Sons, or the like can be used.

Furthermore, the compounds represented by the general formula (I-1) can be prepared similar to the general formula (I).

The compounds represented by the general formulas (I) and (I-1) prepared by the aforementioned methods can be isolated and purified by methods widely known by those skilled in the art, for example, extraction, precipitation, fractional chromatography, fractional crystallization, suspension and washing, and recrystallization. Furthermore, each of the pharmaceutically acceptable salt of the compound of the present invention, the hydrate thereof and the solvate thereof can be prepared by methods widely known by those skilled in the art.

In the examples of the specification, preparation methods of typical compounds included in the general formulas (I) and (I-1) are explained in details. Therefore, those skilled in the art can prepare any compound fall within the general formulas (I) and (I-1) by referring to the explanations of the aforementioned general preparation methods and those of specific preparation methods of the examples, by choosing appropriate reaction raw materials, reaction reagents, and reaction conditions, and by adding appropriate modification and alteration of these methods, if necessary.

The compounds of the present invention represented by the general formulas (I) and (I-1) have inhibitory action against NF-κB activation and inhibitory action against the production and release of inflammatory cytokines, and are useful as active ingredients of pharmaceutical compositions such as NF-κB inhibitor and inflammatory cytokine release inhibitor. The aforementioned medicament can be suitably used as an expression inhibitor of genes of one or more substances selected from a group comprising tumor necrosis factor (TNF), interleukin-1, interleukin-2, interleukin-6, interleukin-8, granulocyte colony-stimulating factor, interferon β, cell adhesion factor ICAM-1, VCAM-1, and ELAM-1, nitricoxide synthetase, major histocompatibility antigen family class I, major histocompatibility antigen family class II, β2-microglobulin, immunoglobulin light chain, serum amyloid A, angiotensinogen, complement B, complement C4, c-myc, transcript derived from HIV gene, transcript derived from HTLV gene, transcript derived from simian virus 40 gene, transcript derived from cytomegalovirus gene, and transcript derived from adenovirus gene. Moreover, the medicament of the present invention is useful for preventive and/or therapeutic treatment of diseases caused by NF-κB activation and inflammatory cytokine overproduction.

The compounds of the present invention represented by the general formulas (I) and (I-1) have inhibitory action against production and release of the target inflammatory cytokine and inhibitory action against production of inflammatory cell adhesion molecules, without affecting other signal transfer pathway, i.e., without causing serious side effects. NF-κB activation is induced by an external stimulation, and as a result, proteins such as inflammatory cytokine are expressed. Among the inflammatory cytokines, TNF-α and interleukin (IL)-1 are particularly considered to be responsible for chronicity of inflammation, because gene expression itself is regulated positively by NF-κB to form positive feedback loop (TNF-α→NF-κB→TNF-α) (18$^{th}$ Meeting of The Japanese Inflammatory Society, Symposium "Mechanism of Antirheumatic Pharmaceutical composition and New Development" Tokyo, 2000). Accordingly, the compounds of the present invention can be used as medicaments having very high effectiveness for inflammatory diseases advanced in a chronic stage and diseases caused by TNF-α and IL-1.

More specifically, the medicament of the present invention may be used for preventive and/or therapeutic treatment of the following diseases wherein NF-κB activation and/or inflammatory cytokine is believed to be involved, for example, autoimmune diseases such as chronic rheumatism, osteoarthritis, systematic lupus erythematosus, systematic scleroderma, polymyositis, Sjoegren's syndrome, vasculitis syndrome, antiphospholipid syndrome, Still's disease, Behcet's disease, periarteritis nodosa, ulcerative colitis, Crohn's disease, active chronic hepatitis, glomerulonephritis, and chronic nephritis, chronic pancreatitis, gout, atherosclerosis, multiple sclerosis, arteriosclerosis, endothelial hypertrophy, psoriasis, psoriatic arthritis, contact dermatitis, atopic dermatitis, allergic disease such as pollinosis, asthma, bronchitis, interstitial pneumonia, lung disease involving granuloma, chronic obstructive lung disease, chronic pulmonary thromboembolism, inflammatory colitis, insulin resistance, obesity, diabetes and its complications (nephropathy, retinopathy, neurosis, hyperinsulinemia, arteriosclerosis, hypertention, peripheral vessel obstruction, etc.) diseases involving abnormal vascular proliferation such as hyperlipemia, retinopathy, and pneumonia, Alzheimer's disease, encephalomyelitis, acute hepatitis, chronic hepatitis, drug induced toxic hepatopathy, alcoholic hepatitis, viral hepatitis, icterus, cirrhosis hepatic insufficiency, atrial myxoma, Caslemann's syndrome, mesangial nephritis, kidney cancer, lung cancer, liver cancer, breast cancer, uterine cancer, pancreatic cancer, other solid cancer, sarcoma, osteosarcoma, metastatic invasion of cancer, canceration of inflammatory focus, cancerous cachexia, metastasis of cancer, leukemia such as acute myeloblastic leukemia, multiple myeloma, Lennert's lymphoma, malignant lymphoma, development of carcinostatic resistance of cancer, canceration of foci such as viral hepatitis and cirrhosis, canceration from polyp of colon, brain tumor, nervous tumor, sarcoidosis, endotoxic shock, sepsis, cytomegaloviral pneumonia, cytomegaloviral retinopathy, adenoviral cold, adenoviral pool fever, adenoviral ophthalmia, conjunctivitis, AIDS, uveitis, diseases or complications provoked by infections of other bacteria, viruses, and mycetes, complications after surgery such as generalized inflammatory symptoms, restenosis after percutaneous tubal coronary artery plastic surgery, reperfusion disorders after vascular occulusion opening such as ischemia reperfusion disorders, organ transplantation rejection and reperfusion disorders of heart, liver, kidney and the like, pruritus, periodontal disease, anorexia, malaise, chronic fatigue syndrome and the like. Furthermore, inflammatory cytokine and NF-κB are involved in differentiation and activation of osteoclast, and consequently, the medicament of the present invention is also useful for preventive and/or therapeutic treatment of metabolic bone diseases or the like such as osteoporosis and osteocarcinomic pain or the like. The medicament may also be used for prevention of deterioration of an organ during organ conservation before transplantation.

As the active ingredient of the medicament on the present invention, one or more kinds of substances selected from the group consisting of the compound represented by the general formulas (I) and (I-1), and a pharmacologically acceptable salt thereof, and a hydrate thereof and a solvate thereof may be used. The aforementioned substance, per se, may be administered as the medicament of the present invention, however, preferably, the medicament of the present invention is provided in the form of a pharmaceutical composition comprising the aforementioned substance which is an active ingredient together with one or more pharmacologically acceptable pharmaceutical additives. In the aforementioned pharmaceutical compositions, a ratio of the active ingredient to the pharmaceutical additives is 1 weight % to 90 weight %. Some of the compounds represented by the general formulas (I) and (I-1) change to other compounds having inhibitory activity against NF-κB activation after transmigration into blood by oral administration and by chemical modification such as hydrolysis by actions of an esterase in blood. The compounds having these properties can be used as so-called "prodrugs." It should be noted that the aforementioned mode of use falls within the scope of the present invention.

The pharmaceutical compositions of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration, or subcutaneous administration, drip infusions, suppositories, percutaneous absorbent, transmucosal absorption preparations, nasal drops, ear drops, instillation, and inhalants. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the active ingredient, and further binders, disintegrator, lubricant, colorant, corrigent are added, if necessary, to manufacture preparations in the forms of tablets, coating tablets, granules, powders, capsules and the like by ordinary procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used which are approved to be added to ordinary pharmaceuticals. As the corrigent, cocoa powder, menthol, aromatic acid, peppermint oil, d-borneol, cinnamon powder and the like can be used. These tables and granules may be applied with sugarcoating, gelatin coating, or an appropriate coating, if necessary. Preservatives, antioxidant and the like may be added, if required.

For liquid preparations for oral administration such as emulsions, syrups, suspensions, and solutions, ordinary used inactive diluents, for example, water or vegetable oil may be used. For these preparations, besides inactive diluents, adjuvants such as wetting agents, suspending aids, sweating agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the composition are prepared in the form of injections, carriers such as, for example, diluents including water, ethanol, macrogol, propylene glycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt, glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream gel, or paste and the like may be applied by a common method to an ordinary support. As the support, fabric made of cotton, span rayon, and synthetic fibers or nonwoven fabric, and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. It is preferred to increase or decrease the above dose appropriately depending on the age, pathological conditions, and symptoms of a patient. The above dose may be administered once a day or 2 to 3 times a day as divided portions with appropriate intervals, or intermittent administration for every several days may be applied. When the medicament is used as an injection, the dose may be 0.001 to 100 mg per day for an adult as the weight of the compound of the present invention.

EXAMPLES

The present invention will be explained more specifically with reference to the following examples. However the scope of the present invention is not limited to the following examples. The compound number in the following examples correspond to those in the table shown above. And the commercially available compounds, which were purchased and used for the examinations, are contained in these examples. As for such compounds, the suppliers of the reagents and the catalog code numbers are shown.

Example 1

Preparation of the Compound of Compound No. 1.

(1) 5-Chloro-2-hydroxy-N-[3,5-bis(trifluoromethyl)phenyl] benzamide.

A mixture of 5-chlorosalicylic acid(6.90 g, 40 mmol), 3,5-bis(trifluoromethyl)aniline(9.16 g, 40 mmol), phosphorus trichloride(1.74 mL, 20 mmol) and toluene(80 mL) was refluxed for 3 hours under argon atmosphere. After the reaction mixture was cooled to room temperature, it was diluted with ethyl acetate (240 mL). After the ethyl acetate layer was washed successively with water and brine, dried over anhydrous magnesium sulfate, the residue obtained by evaporation of the solvent under reduced pressure was purified by column chromatography on silica gel (n-hexane:ethyl acetate=4:1) to give the title compound (13.12 g, 85.5%) as a light yellow solid.

$^1$H-NMR(DMSO-$d_6$): δ 7.05(1H, d, J=8.7 Hz), 7.49(1H, dd, J=8.7, 2.7 Hz), 7.85(1H, s), 7.87(1H, d, J=2.7 Hz), 8.45 (2H, s), 10.85(1H, s), 11.39(1H, s).

This compound was obtained also by using monochlorobenzene instead of toluene as the reaction solvent (Yield: 85.5%).

When the method described in Example 1(1) is referred in the following examples, phosphorus trichloride was used as the acid halogenating agent. As the reaction solvent, solvents such as monochlorobenzene, toluene or the like were used.

(2) 5-Chloro-2-pivaloyloxy-N-[3,5-bis(trifluoromethyl)phenyl]benzamide (Compound No. 1).

A solution of 5-chloro-2-hydroxy-N-[3,5-bis(trifluoromethyl)phenyl]-benzamide(0.20 g, 0.52 mmol) in tetrahydrofuran(3 mL) was added to a suspension of 60% sodium hydride(21.8 mg, 0.55 mmol) in tetrahydrofuran (3 mL) under ice bath, and the mixture was stirred for 5 minutes. Then, pivaloyl chloride(71 μL, 0.57 mmol) was added and the mixture was stirred for 10 minutes. The reaction mixture was poured into water and extracted with ethyl acetate. After the ethyl acetate layer was washed successively with water and brine, dried over anhydrous sodium sulfate, the residue obtained by evaporation of the solvent under reduced pressure was washed with isopropyl ether/n-hexane under suspension to give the title compound (195 mg, 80.2%) as a white crystal.

$^1$H-NMR(DMSO-$d_6$): δ 1.21(9H, s), 7.35(1H, d, J=8.7 Hz), 7.70(1H, dd, J=8.7, 2.7 Hz), 7.85(2H, d, J=2.4 Hz), 8.36(2H, s), 11.10(1H, s).

Example 2

Preparation of the Compound of Compound No. 2.

1-(3-Dimethylaminopropyl)-3-ethylcarbodiimide hydrochloride (it is abbreviated as WSC.HCl hereafter.; 150 mg, 0.8 mmol) was added to a solution of 5-chloro-2-hydroxy-N-[3,5-bis(trifluoromethyl)phenyl]benzamide (compound of Example 1(1); 200 mg, 0.5 mmol) and valeric acid(80 mg, 0.8 mmol) in dichloromethane(5 mL) under argon atmosphere, and the mixture was stirred at room temperature for 1 hour. After the reaction mixture was diluted with ethyl acetate, washed successively with water and brine, dried over anhydrous sodium sulfate, the residue obtained by evaporation of the solvent under reduced pressure was purified by column chromatography on silica gel(n-hexane:ethyl acetate=6:1) to give the title compound(250 mg, 100%) as a white powder.

$^1$H-NMR(CDCl$_3$): δ 0.89(3H, t, J=7.5 Hz), 1.38(2H, sext, J=7.5 Hz), 1.70(2H, q, J=7.5 Hz), 2.62(2H, t, J=7.5 Hz), 7.11(1H, d, J=8.9 Hz), 7.46(1H, dd, J=8.7, 2.4 Hz), 7.63(1H, s), 7.72(1H, d, J=2.4 Hz), 8.07(2H, s), 8.49(1H, brs).

Example 3

Preparation of the Compound of Compound No. 3.

Decanoyl chloride(70 μL, 0.339 mmol) was added to a solution of 5-chloro-2-hydroxy-N-[3,5-bis(trifluoromethyl)phenyl]benzamide(compound of Example 1(1); 100 mg, 0.261 mmol) and triethylamine(50 μL, 0.359 mmol) in N,N-dimethylformamide(1.5 mL) under argon atmosphere, and the mixture was stirred at room temperature for 1 hour. Water was added to the reaction mixture and it was extracted with ethyl acetate. After the ethyl acetate layer was washed successively with water and brine, dried over anhydrous sodium sulfate, the residue obtained by evaporation of the solvent under reduced pressure was purified by column chromatography on silica gel(n-hexane:ethyl acetate=4:1) to give the title compound(125 mg, 89.3%) as a colorless oil.

$^1$H-NMR(CDCl$_3$): δ 0.87(3H, t, J=7.2 Hz), 1.21-1.33(12H, m), 1.65-1.75(2H, m), 2.61(2H, t, J=7.2 Hz), 7.13(1H, d, J=9.0 Hz), 7.50(1H, dd, J=8.7, 2.4 Hz), 7.66(1H, s), 7.80(1H, d, J=2.4 Hz), 8.09(2H, s), 8.38(1H, s).

Example 4

Preparation of the Compound of Compound No. 4.

Benzoyl chloride(64 μL, 0.55 mmol) was added to a solution of 5-chloro-2-hydroxy-N-[3,5-bis(trifluoromethyl)phenyl]benzamide(compound of Example 1(1); 192 mg, 0.5 mmol) and pyridine(47 mg, 0.6 mmol) in tetrahydrofuran(5 mL) under ice cooling, and the mixture was stirred at room temperature for 2 hours. 2N Hydrochloric acid(1 mL) and water(50 mL) were added to the reaction mixture and it was extracted with ethyl acetate. After the ethyl acetate layer was washed successively with water and brine, dried over anhydrous sodium sulfate, the residue obtained by evaporation of the solvent under reduced pressure was purified by column chromatography on silica gel(dichloromethane:methanol=95:5) to give the title compound(226 mg, 92.7%) as a light yellow solid.

$^1$H-NMR(DMSO-d$_6$): δ 7.53-7.58(3H, m), 7.70-7.76(1H, m), 7.78(1H, dd, J=9.0, 3.0 Hz), 7.80(1H, s), 7.94(1H, d, J=2.7 Hz), 8.07-8.10(2H, m), 8.25(2H, s), 11.13(1H, s).

Example 5

Preparation of the Compound of Compound No. 5.

5-Chloro-2-hydroxy-N-[3,5-bis(trifluoromethyl)phenyl]benzamide (compound of Example 1(1); 0.20 g, 0.52 mmol) was dissolved in tetrahydrofuran(5 mL). Oetylsalicyloyl chloride(0.124 g, 0.62 mmol) and triethylamine(0.2 mL, 1.43 mmol) were added, and the mixture was stirred at room temperature for 3 hours. The reaction mixture was poured into diluted hydrochloric acid and extracted with ethyl acetate. After the ethyl acetate layer was washed with brine, dried over anhydrous sodium sulfate, the residue obtained by evaporation of the solvent under reduced pressure was purified by column chromatography on silica gel(n-hexane:ethyl acetate=3:1), and washed with isopropyl ether/n-hexane under suspension to give the title compound(236.7 mg, 83.4%) as a white powder.

$^1$H-NMR(DMSO-d$_6$): δ 2.13(3H, s), 7.29(1H, dd, J=8.4, 1.2 Hz), 7.45(1H, td, J=7.8, 1.2 Hz), 7.48(1H, d, J=8.7 Hz), 7.76(1H, td, J=8.4, 1.8 Hz), 7.77(1H, dd, J=8.4, 2.4 Hz), 7.82(1H, s), 7.94(1H, d, J=2.4 Hz), 8.16(1H, dd, J=7.8, 1.5 Hz), 8.29(2H, s), 11.12(1H, s).

Example 6

Preparation of the Compound of Compound No. 6.

Triethylamine(80 μL, 0.547 mmol) and Nicotinoyl chloride hydrochloride(492 mg, 0.274 mmol) were added to a solution of 5-chloro-2-hydroxy-N-[3,5-bis(trifluoromethyl)phenyl]benzamide(compound of Example 1(1); 100 mg, 0.261mmol) in N,N-dimethylformamide(1.5 mL), and the mixture was stirred at room temperature for 1 hour. Water was added to the reaction mixture and it was extracted with ethyl acetate. After the ethyl acetate layer was washed successively with water and brine, dried over anhydrous sodium sulfate, the residue obtained by evaporation of the solvent under reduced pressure was purified by column chromatography on silica gel(n-hexane:ethyl acetate=4:1) to give the title compound(120 mg, 94.5%) as a white solid.

$^1$H-NMR(DMSO-d$_6$): δ 7.60(1H, d, J=8.7 Hz), 7.62(1H, ddd, J=8.1, 4.8, 0.9 Hz), 7.81(1H, dd, J=8.7, 2.7 Hz), 7.81 (1H, s), 7.98(1H, d, J=2.4 Hz), 8.26(2H, s), 8.43(1H, ddd, J=8.1, 2.1, 1.5 Hz), 8.88(1H, dd, J=4.8, 1.5 Hz), 9.23(1H, dd, J=2.1, 0.9 Hz), 11.16(1H, s).

Example 7

Preparation of the Compound of Compound No. 7.

Using 5-chloro-2-hydroxy-N-[3,5-bis(trifluoromethyl)phenyl]-benzamide(compound of Example 1(1)) and isonicotinoyl chloride hydrochloride as the raw materials, the same operation as the Example 6 gave the title compound.

Yield: 55.9%.

$^1$H-NMR(DMSO-d$_6$): δ 7.60(1H, d, J=8.7 Hz), 7.81(1H, dd, J=8.7, 2.7 Hz), 7.82(1H, s), 7.96(2H, dd, J=4.5, 1.8 Hz), 7.99(1H, d, J=2.7 Hz), 8.26(2H, s), 8.85(2H, dd, J=4.5, 1.8 Hz), 11.16(1H, s).

Example 8

Preparation of the Compound of Compound No. 8.

Using 5-chloro-2-hydroxy-N-[3,5-bis(trifluoromethyl)phenyl]-benzamide(compound of Example 1(1)) and phenylacetyl chloride as the raw materials, the same operation as the Example 3 gave the title compound.

Yield: 71.0%.

$^1$H-NMR(CDCl$_3$): δ 3.89(2H, s), 7.03-7.09(1H, m), 7.12-7.17(3H, m), 7.22-7.27(3H, m), 7.51(1H, dd, J=9.0, 3.0 Hz), 7.63(1H, s), 7.77(1H, d, J=3.0 Hz), 7.82(2H, s), 7.91(1H, s).

Example 9

Preparation of the Compound of Compound No. 9.

3,4-Methylenedioxyphenylacetic acid(103.1 mg, 0.57 mmol), WSC.HCl(0.13 g, 0.68 mmol) and 4-dimethylaminopyridine(10 mg) were added to a solution of 5-chloro-2-hydroxy-N-[3,5-bis(trifluoromethyl)phenyl]benzamide (compound of Example 1(1); 0.20 g, 0.52 mmol) in tetrahydrofuran(5 mL), and the mixture was stirred for 5 hours. The reaction mixture was poured into diluted hydrochloric acid and extracted with ethyl acetate. After the ethyl acetate layer was washed successively with water and brine, dried over anhydrous sodium sulfate, the residue obtained by evaporation of the solvent under reduced pressure was purified by column chromatography on silica gel(n-hexane:ethyl acetate=3:1) to give the title compound(228 mg, 80.4%) as a white crystal.

$^1$H-NMR(DMSO-d$_6$): δ 3.83(2H, s), 5.89(2H, s), 6.56-6.73(2H, m), 6.79(1H, d, J=1.2 Hz), 7.37(1H, d, J=8.4 Hz), 7.71(1H, dd, J=8.7, 2.4 Hz), 7.85(2H, d, J=2.7 Hz), 8.32(2H, s), 11.01(1H, s).

Example 10

Preparation of the Compound of Compound No. 10

Using 5-chloro-2-hydroxy-N-[3,5-bis(trifluoromethyl) phenyl]-benzamide(compound of Example 1(1)) and methoxyacetic acid as the raw materials, the same operation as the Example 9 gave the title compound.
Yield: 63.4%.
$^1$H-NMR(CDCl$_3$): δ 3.55(3H, s), 4.38(2H, s), 7.37(1H, d, J=9.0 Hz), 7.56(1H, dd, J=9.0, 2.7 Hz), 7.67(1H, s), 8.16(1H, d, J=2.7 Hz), 8.22(2H, s), 9.28(1H, s).

Example 11

Preparation of the Compound of Compound No. 11.

Using 5-chloro-2-hydroxy-N-[3,5-bis(trifluoromethyl) phenyl]-benzamide(compound of Example 1(1)) and acetyloxyacetyl chloride as the raw materials, the same operation as the Example 3 gave the title compound.
Yield: 52.4%.
$^1$H-NMR(CDCl$_3$): δ 2.18(3H, s), 4.84(2H, s), 7.18(1H, d, J=8.4 Hz), 7.52(1H, dd, J=9.0, 2.7 Hz), 7.67(1H, s), 7.83(1H, d, J=2.7 Hz), 8.17(2H, s), 8.31(1H, s).

Example 12

Preparation of the Compound of Compound No. 12.

Using 5-chloro-2-hydroxy-N-[3,5-bis(trifluoromethyl) phenyl]-benzamide(compound of Example 1(1)) and phenoxyacetyl chloride as the raw materials, the same operation as the Example 3 gave the title compound.
Yield: 52.6%.
$^1$H-NMR(CDCl$_3$): δ 4.94(2H, s), 6.89-7.02(3H, m), 7.21-7.29(3H, m), 7.55(1H, dd, J=8.7, 2.4 Hz), 7.64(1H, s), 7.94(1H, d, J=2.4 Hz), 8.10(2H, s), 8.63(1H, s).

Example 13

Preparation of the Compound of Compound No. 13.

Using 5-chloro-2-hydroxy-N-[3,5-bis(trifluoromethyl) phenyl]-benzamide(compound of Example 1(1)) and 4-chlorophenoxyacetic acid as the raw materials, the same operation as the Example 9 gave the title compound.
Yield: 34.1%.
$^1$H-NMR(CDCl$_3$): δ 4.91(2H, s), 6.85(2H, d, J=8.7 Hz), 7.17(2H, d, J=9.0 Hz), 7.24(1H, d, J=8.4 Hz), 7.56(1H, dd, J=8.7, 2.1 Hz), 7.67(1H, s), 7.86(1H, d, J=2.4 Hz), 8.08(2H, s), 8.42(1H, s).

Example 14

Preparation of the Compound of Compound No. 14.

Using 5-chloro-2-hydroxy-N-[3,5-bis(trifluoromethyl) phenyl]-benzamide(compound of Example 1(1)) and 2,3-dichlorophenoxyacetic acid as the raw materials, the same operation as the Example 9 gave the title compound.
Yield: 10.6%.
$^1$H-NMR(CDCl$_3$): δ 4.99(2H, s), 6.90(1H, dd, J=8.1, 1.5 Hz), 7.03(1H, t, J=8.1 Hz), 7.12(1H, dd, J=8.1, 1.5 Hz), 7.23(1H, d, J=9.0 Hz), 7.56(1H, dd, J=9.0, 2.4 Hz), 7.65(1H, s), 7.87(1H, d, J=2.4 Hz), 8.08(2H, s), 8.49(1H, s).

Example 15

Preparation of the Compound of Compound No. 15.

Using 5-chloro-2-hydroxy-N-[3,5-bis(trifluoromethyl) phenyl]-benzamide(compound of Example 1(1)) and 2-phenoxypropionyl chloride as the raw materials, the same operation as the Example 3 gave the title compound.
Yield: 80.6%.
$^1$H-NMR(CDCl$_3$): δ 1.74(3H, d, J=6.9 Hz), 5.02(1H, q, J=6.9 Hz), 6.86-6.96(3H, m), 7.16-7.23(3H, m), 7.52(1H, dd, J=8.7, 2.4 Hz), 7.63(1H, s), 7.95(1H, d, J=2.4 Hz), 8.11(2H, s), 8.75(1H, s).

Example 16

Preparation of the Compound of Compound No. 16.

Using 5-chloro-2-hydroxy-N-[3,5-bis(trifluoromethyl) phenyl]-benzamide(compound of Example 1(1)) and 2-(4-chlorophenoxy)isobutyric acid as the raw materials, the same operation as the Example 9 gave the title compound.
Yield: 95.7%.
$^1$H-NMR(CDCl$_3$): δ 1.69(6H, s), 6.77(2H, d, J=9.0 Hz), 7.13(2H, d, J=9.0 Hz), 7.36(1H, dd, J=8.7, 2.4 Hz), 7.59(1H, s), 8.07(2H, s), 8.14(1H, d, J=2.4 Hz), 9.13(1H, s).

Example 17

Preparation of the Compound of Compound No. 17.

Using 5-chloro-2-hydroxy-N-[3,5-bis(trifluoromethyl) phenyl]-benzamide(compound of Example 1(1)) and malonic acid mono tert-butyl ester as the raw materials, the same operation as the Example 2 gave the title compound.
Yield: 29.2%.
$^1$H-NMR(CDCl$_3$): δ 1.42(9H, s), 3.65(2H, s), 7.19(1H, d, J=8.7 Hz), 7.53(1H, dd, J=8.7, 2.4 Hz), 7.66(1H, brs), 8.10(1H, d, J=2.4 Hz), 8.25(2H, s), 9.07(1H, brs).

Example 18

Preparation of the Compound of Compound No. 18.

Using 5-chloro-2-hydroxy-N-[3,5-bis(trifluoromethyl) phenyl]-benzamide(compound of Example 1(1)) and succinic acid mono benzyl ester as the raw materials, the same operation as the Example 2 gave the title compound.
Yield: 99.3%.
$^1$H-NMR(CDCl$_3$): δ 2.81-2.93(4H, m), 5.09(2H, s), 7.12 (1H, d, J=8.7 Hz), 7.27-7.34(5H, m), 7.48(1H, dd, J=8.7, 2.4 Hz), 7.65(1H, s), 7.88(1H, m), 8.20(2H, s), 8.58(1H, brs).

Example 19

Preparation of the Compound of Compound No. 19.

Using 5-chloro-2-hydroxy-N-[3,5-bis(trifluoromethyl)phenyl]-benzamide(compound of Example 1(1)) and succinic acid mono piperidinamide as the raw materials, the same operation as the Example 2 gave the title compound.

Yield: 97.5%.

$^1$H-NMR(CDCl$_3$): δ 1.45-1.67(6H, m), 2.77-2.89(4H, m), 3.39-3.49(4H, m), 7.32(1H, d, J=8.7 Hz), 7.47(1H, dd, J=8.7, 2.7 Hz), 7.62(1H, s), 8.04(1H, dd, J=2.7, 0.6 Hz), 8.38(2Hs), 9.73(1H, s).

Example 20

Preparation of the Compound of Compound No. 20.

Using 5-chloro-2-hydroxy-N-[3,5-bis(trifluoromethyl)phenyl]-benzamide(compound of Example 1(1)) and N-acetylglycine as the raw materials, the same operation as the Example 2 gave the title compound.

Yield: 95.0%.

$^1$H-NMR(CDCl$_3$): δ 2.04(3H, s), 4.17(2H, d, J=5.4 Hz), 6.17(1H, m), 7.16(1H, d, J=8.7 Hz), 7.50(1H, dd, J=8.7, 2.4 Hz), 7.61(1H, brs), 7.83(1H, d, J=2.4 Hz), 8.24(2H, s), 8.78(1H, brs).

Example 21

Preparation of the Compound of Compound No. 21.

Using 5-chloro-2-hydroxy-N-[3,5-bis(trifluoromethyl)phenyl]-benzamide(compound of Example 1(1)) and N-(benzyloxycarbonyl)glycine as the raw materials, the same operation as the Example 9 gave the title compound.

Yield: 74.4%.

$^1$H-NMR(CDCl$_3$): δ 4.19(2H, d, J=6.0 Hz), 5.12(2H, s), 5.36(1H, t, J=5.7 Hz), 7.16(1H, d, J=8.7 Hz), 7.32(5H, s), 7.53(1H, dd, J=8.7, 2.4 Hz), 7.67(1H, s), 7.86(1H, d, J=2.4 Hz), 8.21(2H, s), 8.40(1H, s).

Example 22

Preparation of the Compound of Compound No. 22.

Using 5-chloro-2-hydroxy-N-[3,5-bis(trifluoromethyl)phenyl]-benzamide(compound of Example 1(1)) and N-(tert-butoxycarbonyl)glycine as the raw materials, the same operation as the Example 2 gave the title compound.

Yield: 70.9%.

$^1$H-NMR(CDCl$_3$): δ 1.41(9H, s), 4.10(2H, d, J=6.0 Hz), 5.16(1H, brt, J=6.0 Hz), 7.15(1H, d, J=8.7 Hz), 7.50(1H, dd, J=8.7, 2.4 Hz), 7.65(1H, s), 7.89(1H, s), 8.23(2H, s), 8.74(1H, brs).

Example 23

Preparation of the Compound of Compound No. 23.

4N Hydrogen chloride/ethyl acetate solution(8 mL) was added to 2-[N-(tert-butoxycarbonyl)glycyl]oxy-5-chloro-N-[3,5-bis(trifluoromethyl)phenyl]-benzamide(Compound No. 22; 146 mg, 0.27 mmol), and the mixture was stirred at room temperature for 1 hour. The residue obtained by evaporation of the solvent under reduced pressure was crystallized from n-hexane/ethyl acetate to give the title compound(110.7 mg, 85.9%) as a white powder.

$^1$H-NMR(DMSO-d$_6$): δ 4.09(2H, brs), 7.42(1H, dd, J=8.7, 1.8 Hz), 7.79(1H, dd, J=8.7, 2.7 Hz), 7.88(1H, s), 8.01(1H, d, 2.7 Hz), 8.41(2H, s), 8.44-8.62(3H, brs), 11.21(1H, brd, J=8.1 Hz).

Example 24

Preparation of the Compound of Compound No. 24.

N-(tert-butoxycarbonyl)-L-valine(135.8 mg, 0.62 mmol), WSC.HCl(0.20 g, 1.04 mmol), 4-dimethylaminopyridine(10 mg) and N-methyl-2-pyrrolidinone(1.5 mL) were added to a solution of 5-chloro-2-hydroxy-N-[3,5-bis(trifluoromethyl)phenyl]-benzamide(compound of Example 1(1); 0.20 g, 0.52 mmol) in tetrahydrofuran(3 mL), and the mixture was stirred at room temperature for 1.5 hours. The reaction mixture was poured into water and extracted with ethyl acetate. After the ethyl acetate layer was washed with water and brine, dried over anhydrous sodium sulfate, the residue obtained by evaporation of the solvent under reduced pressure was purified by column chromatography on silica gel(n-hexane:ethyl acetate=4:1) to give the title compound (277.2 mg, 91.4%) as a white solid.

$^1$H-NMR(CDCl$_3$): δ 1.06(3H, d, J=6.9 Hz), 1.11(3H, d, J=6.9 Hz), 1.37(9H, s), 2.24(1H, m), 4.16(1H, t, J=6.9 Hz), 5.00(1H, d, J=6.9 Hz), 7.22(1H, d, J=9.0 Hz), 7.50(1H, dd, J=8.7, 2.7 Hz), 7.66(1H, s), 8.01(1H, d, J=2.4 Hz), 8.26(2H, s), 8.96(1H, s).

Example 25

Preparation of the Compound of Compound No. 25.

4N Hydrogen chloride/ethyl acetate solution(2 mL) was added to 2-[N-(tert-butoxycarbonyl)-L-valyl]oxy-5-chloro-N-[3,5-bis(trifluoromethyl)phenyl]-benzamide(Compound No. 24; 226.1 mg, 0.39 mmol), and the mixture was stirred at room temperature for 16 hours. The residue obtained by evaporation of the solvent under reduced pressure was washed with isopropyl ether/n-hexane under suspension to give the title compound(199.8 mg, 93.6%) as a white powder.

$^1$H-NMR(DMSO-d$_6$): δ 0.99(3H, d, J=6.9 Hz), 1.01(1H, d, J=6.9 Hz), 2.26-2.35(1H, m), 4.20-4.25(1H, m), 7.42(1H, d, J=8.7 Hz), 7.78(1H, dd, J=8.7, 2.7 Hz), 7.87(1H, s), 7.97(1H, d, J=2.7 Hz), 8.39(2H, s), 8.54(3H, s), 11.21(1H, s).

Example 26

Preparation of the Compound of Compound No. 26.

Using 5-chloro-2-hydroxy-N-[3,5-bis(trifluoromethyl)phenyl]-benzamide(compound of Example 1(1)) and N-(tert-butoxycarbonyl)-L-leucine as the raw materials, the same operation as the Example 24 gave the title compound.

Yield: 96.6%.

$^1$H-NMR(CDCl$_3$): δ 0.93(3H, d, J=6.0 Hz), 0.95(3H, d, J=6.0 Hz), 1.37(9H, s), 1.58-1.79(3H, m), 4.31-4.38(1H, m), 4.92(1H, d, J=6.6 Hz), 7.20(1H, d, J=8.7 Hz), 7.50(1H, dd, J=8.7, 2.7 Hz), 7.65(1H, s), 7.99(1H, d, d=2.7 Hz), 8.27(2H, s), 8.91(1H, s).

Example 27

Preparation of the Compound of Compound No. 27.

Using 2-[N-(tert-butoxycarbonyl)-L-leucyl]oxy-5-chloro-N-[3,5-bis(trifluoromethyl)phenyl]-benzamide(Compound No. 26) as the raw material, the same operation as the Example 25 gave the title compound.
Yield: 89.9%.
$^1$H-NMR(DMSO-$d_6$): δ 0.77-0.81(6H, m), 1.63(1H, q, J=7.2 Hz), 1.73-1.81(2H, m), 4.18(1H, s), 7.46(1H, d, J=8.7 Hz), 7.79(1H, dd, J=8.7, 2.4 Hz), 7.88(1H, s), 7.96(1H, d, J=2.4 Hz), 8.43(2H, s), 8.69(1H, s), 11.28(1H, s).

Example 28

Preparation of the Compound of Compound No. 28.

Using 5-chloro-2-hydroxy-N-[3,5-bis(trifluoromethyl)phenyl]-benzamide(compound of Example 1(1)) and N-(tert-butoxycarbonyl)-L-phenylalanine as the raw materials, the same operation as the Example 24 gave the title compound.
Yield: 91.9%.
$^1$H-NMR(CDCl$_3$): δ 1.32(9H, s), 3.18(1H, d, J=7.2 Hz), 3.19(1H, d, J=6.9 Hz), 4.61(1H, td, J=7.2, 6.6 Hz), 5.00(1H, d, J=6.3 Hz), 6.84(1H, d, J=8.7 Hz), 7.23-7.36(5H, m), 7.44(1H, dd, J=9.0, 3.0 Hz), 7.65(1H, s), 8.02(1H, d, J=2.4 Hz), 8.23(2H, s), 8.91(1H, s).

Example 29

Preparation of the Compound of Compound No. 29.

Using 2-[N-(tert-butoxycarbonyl)-L-phenylalanyl]oxy-5-chloro-N-[3,5-bis(trifluoromethyl)-phenyl]benzamide (Compound No. 28) as the raw material, the same operation as the Example 25 gave the title compound.
Yield: 78.1%.
$^1$H-NMR(DMSO-$d_6$): δ 3.16(1H, dd, J=14.7, 6.9 Hz), 3.31(1H, d, J=14.7, 6.9 Hz), 4.60(1H, s), 7.22-7.35(6H, m), 7.78(1H, dd, J=8.7, 2.4 Hz), 7.88(1H, s), 7.99(1H, d, J=2.7 Hz), 8.41(2H, s), 8.66(3H, s), 11.21(1H, s).

Example 30

Preparation of the Compound of Compound No. 30.

Using 5-chloro-2-hydroxy-N-[3,5-bis(trifluoromethyl)phenyl]-benzamide(compound of Example 1(1)) and N-(tert-butoxycarbonyl)-L-aspartic acid β-(tert-butyl) ester as the raw materials, the same operation as the Example 24 gave the title compound.
Yield: 87.6%.
$^1$H-NMR(CDCl$_3$): δ 1.42(9H, s), 1.42(9H, s), 2.77(1H, dd, J=17.1, 4.8 Hz), 3.05(1H, dd, J=17.1, 4.8 Hz), 4.67-4.74(1H, m), 5.68(1H, d, J=8.4 Hz), 7.18(1H, d, J=9.0 Hz), 7.52(1H, dd, J=8.4, 2.4 Hz), 7.66(1H, s), 8.07(1H, d, J=2.4 Hz), 8.36(2H, s), 8.93(1H, s).

Example 31

Preparation of the Compound of Compound No. 31.

Using 5-chloro-2-hydroxy-N-[3,5-bis(trifluoromethyl)phenyl]-benzamide(compound of Example 1(1)) and N-(tert-butoxycarbonyl)-L-glutamic acid γ-(tert-butyl) ester as the raw materials, the same operation as the Example 24 gave the title compound.
Yield: 83.3%.
$^1$H-NMR(CDCl$_3$): δ 1.38(9H, s), 1.41(9H, s), 2.05-2.26(2H, m), 2.42-2.48(2H, m), 4.34-4.41(1H, m), 5.39(1H, d, J=6.9 Hz), 7.24-7.27(1H, m), 7.51(1H, dd, J=8.7, 2.7 Hz), 7.65(1H, s), 8.00(1H, d, J=2.7 Hz), 8.28(2H, s), 9.02(1H, s).

Example 32

Preparation of the Compound of Compound No. 32.

Using 2-[N-(tert-butoxycarbonyl)-γ-O-(tert-butyl)-α-L-glutamyl]oxy-5-chloro-N-[3,5-bis(trifluoromethyl)phenyl]benzamide(Compound No. 31) as the raw material, the same operation as the Example 25 gave the title compound.
Yield: 78.1%.
$^1$H-NMR(CD$_3$OD): δ 2.17-2.29(1H, m), 2.35-2.47(1H, m), 2.63(2H, t, J=7.5 Hz), 4.32(1H, t, J=6.6 Hz), 7.35-7.38(1H, m), 7.68(1H, dd, J=8.7, 2.7 Hz), 7.72(1H, s), 7.89-7.91(1H, m), 8.32(2H, s).

Example 33

Preparation of the Compound of Compound No. 33.

Using 5-chloro-2-hydroxy-N-[3,5-bis(trifluoromethyl)phenyl]-benzamide(compound of Example 1(1)) and N$^α$,N$^ε$-di(tert-butoxycarbonyl)-L-lysine as the raw materials, the same operation as the Example 24 gave the title compound.
Yield: 87.8%.
$^1$H-NMR(CDCl$_3$): δ 1.38(9H, s), 1.43(9H, s), 1.46-1.49(4H, m), 1.88-1.93(2H, m), 3.03-3.17(2H, m), 4.27(1H, dd, J=13.2, 6.0 Hz), 4.58-4.62(1H, m), 5.57(1H, d, J=5.7 Hz), 7.21(1H, d, J=8.7 Hz), 7.50(1H, dd, J=9.0, 2.7 Hz), 7.65(1H, s), 7.99(1H, d, J=2.1 Hz), 8.28(2H, s), 9.04(1H, s).

Example 34

Preparation of the Compound of Compound No. 34.

Using 5-chloro-2-[N$^α$,N$^ε$-di(tert-butoxycarbonyl)-L-lysyl]oxy-N-[3,5-bis(trifluoromethyl)phenyl]benzamide (Compound No. 33) as the raw material, the same operation as the Example 25 gave the title compound.
Yield: 95.8%.
$^1$H-NMR(DMSO-$d_6$): δ 1.55(4H, br s), 1.91-2.02(2H, m), 2.72(2H, d, J=4.5 Hz), 4.23(1H, br s), 7.49(1H, d, J=8.4 Hz), 7.79(1H, dd, J=8.7, 2.7 Hz), 7.87(1H, s), 8.00(1H, d, J=2.4 Hz), 8.01(3H, br s), 8.45(2H, s), 8.88(3H, br s), 11.34(1H, s).

Example 35

Preparation of the Compound of Compound No. 35.

Using 5-chloro-2-hydroxy-N-[3,5-bis(trifluoromethyl)phenyl]-benzamide(compound of Example 1(1)) and N-[N-(tert-butoxycarbonyl)-L-phenylalanyl]-L-leucine as the raw materials, the same operation as the Example 24 gave the title compound.
Yield: 32.6%.
$^1$H-NMR(CDCl$_3$): δ 0.87(3H, d, J=6.3 Hz), 0.90(3H, d, J=6.3 Hz), 1.38(9H, s), 1.54-1.73(3H, m), 3.00(1H, dd, J=14.1, 7.2 Hz), 3.07(1H, dd, J=13.8, 6.9 Hz), 4.44-4.51(1H, m), 4.88(1H, br s), 6.49(1H, d, J=2.4 Hz), 7.12-7.28(7H, m), 7.50(1H, dd, J=8.7, 2.7 Hz), 7.66(1H, s), 7.98(1H, d, J=2.7 Hz), 8.33(2H, s), 8.96(1H, s).

Example 36

Preparation of the Compound of Compound No. 36.

Using 2-{N-[N-(tert-butoxycarbonyl)-L-phenylalanyl]-L-leucyl}oxy-5-chloro-N-[3,5-bis(trifluoromethyl)phenyl]benzamide(compound No. 35) as the raw material, the same operation as the Example 25 gave the title compound.
Yield: 84.3%.
$^1$H-NMR(DMSO-d$_6$): δ 0.77(6H, t, J=6.0 Hz), 1.53-1.67 (3H, m), 2.92(1H, dd, J=14.1, 8.1 Hz), 3.12(1H, dd, J=14.4, 5.4 Hz), 4.06(1H, br s), 4.51-4.56(1H, m), 7.23-7.28(6H, m), 7.75(1H, dd, J=8.7, 2.4 Hz), 7.84(1H, s), 7.90(1H, d, J=2.4 Hz), 8.23(3H, s), 8.40(2H, s), 9.12(1H, d, J=7.2 Hz), 11.22 (1H, s).

Example 37

Preparation of the Compound of Compound No. 37.

Using 5-chloro-2-hydroxy-N-[3,5-bis(trifluoromethyl)phenyl]-benzamide(compound of Example 1(1)) and N-[N-(tert-butoxycarbonyl)-β-O-(tert-butyl)-α-L-aspartyl]-L-leucine as the raw materials, the same operation as the Example 24 gave the title compound.
Yield: 31.2%.
$^1$H-NMR(CDCl$_3$): δ 0.90(3H, d, J=6.0 Hz), 0.95(3H, d, J=6.0 Hz), 1.37(9H, s), 1.43(9H, s), 1.69-1.78(3H, m), 2.60 (1H, dd, J=17.1, 7.5 Hz), 2.78(1H, dd, J=17.1, 4.5 Hz), 4.45-4.54(2H, m), 5.52(1H, d, J=7.2 Hz), 7.18(1H, d, J=8.7 Hz), 7.23-7.27(1H, m), 7.49(1H, dd, J=9.0, 2.4 Hz), 7.66(1H, s), 7.95(1H, d, J=2.4 Hz), 8.30(2H, s), 8.91(1H, s).

Example 38

Preparation of the Compound of Compound No. 38.

Using 2-{N-[N-(tert-butoxycarbonyl)-β-O-(tert-butyl)-α-L-aspartyl]-L-leucyl}oxy-5-chloro-N-[3,5-bis(trifluoromethyl)phenyl]benzamide(Compound No. 37) as the raw material, the same operation as the Example 25 gave the title compound.
Yield: 76.5%.
$^1$H-NMR(DMSO-d$_6$): δ 0.75(6H, t, J=6.6 Hz), 1.53-1.69 (3H, m), 2.72-2.89(2H, m), 3.49(2H, br s), 4.14(1H, br s), 4.43-4.51(1H, m), 7.28(1H, d, J=8.7 Hz), 7.70-7.74(1H, m), 7.87(1H, s), 7.89(1H, d, J=2.7 Hz), 8.30(3H, s), 8.42(2H, s), 9.05(1H, d, J=6.9 Hz), 11.23(1H, s).

Example 39

Preparation of the Compound of Compound No. 39.

Using 5-chloro-2-hydroxy-N-[3,5-bis(trifluoromethyl)phenyl]-benzamide(compound of Example 1(1)) and N-[N$^α$,N$^ε$-di(tert-butoxycarbonyl)-L-lysyl]-L-leucine as the raw materials, the same operation as the Example 24 gave the title compound.
Yield: 44.5%.
$^1$H-NMR(CDCl$_3$): δ 0.93(3H, d, J=6.0 Hz), 0.98(3H, d, J=6.0 Hz), 1.33-1.40(5H, m), 1.40(9H, s), 1.44(9H, s), 1.72-1.85(4H, m), 2.87-2.93(2H, m), 4.01-4.07(1H, m), 4.56-4.61 (2H, m), 5.22(1H, br s), 6.65(1H, br s), 7.17(1H, d, J=8.4 Hz), 7.48(1H, dd, J=8.7, 2.7 Hz), 7.64(1H, s), 7.87(1H, s), 8.33 (2H, s), 9.58(1H.s).

Example 40

Preparation of the Compound of Compound No. 40.

Using 2-{N-[N$^α$,N$^ε$-di(tert-butoxycarbonyl)-L-lysyl]-L-leucyl}oxy-5-chloro-N-[3,5-bis(trifluoromethyl)phenyl]benzamide(Compound No. 39) as the raw material, the same operation as the Example 25 gave the title compound.
Yield: 86.8%.
$^1$H-NMR(DMSO-d$_6$): δ 0.73(3H, d, J=6.3 Hz), 0.76(3H, d, J=6.3 Hz), 1.41-1.79(9H, m), 2.67-2.76(2H, m), 3.86(1H, br s), 4.45-4.51(1H, m), 7.27(1H, d, J=8.7 Hz), 7.74(1H, dd, J=8.7, 2.7 Hz), 7.88(1H, s), 7.90(1H, d, J=2.4 Hz), 8.00(3H, s), 8.37(3H, s), 8.45(2H, s), 9.14(1H, d, J=7.2 Hz), 11.32(1H, s).

Example 41

Preparation of the Compound of Compound No. 41

(1) 2-{N-[N-(tert-Butoxycarbonyl)-L-leucyl]-L-phenylalanyl}oxy-5-chloro-N-[3,5-bis(trifluoromethyl)phenyl]benzamide.
Using 5-chloro-2-hydroxy-N-[3,5-bis(trifluoromethyl)phenyl]-benzamide(compound of Example 1(1)) and N-[N-(tert-butoxycarbonyl)-L-leucyl]-L-phenylalanine as the raw materials, the same operation as the Example 24 gave the title compound.
Yield: 38.5%.
$^1$H-NMR(CDCl$_3$): δ 0.93(6H, s), 1.41(9H, s), 1.65-1.79 (4H, m), 3.34(2H, d, J=7.5 Hz), 4.54-4.62(1H, m), 5.11(1H, d, J=7.2 Hz), 5.18(1H, d, J=7.2 Hz), 7.21-7.28(5H, m), 7.47 (1H, dd, J=8.4, 2.4 Hz), 7.52(1H, s), 7.60(1H, d, J=2.4 Hz), 7.64(1H, d, J=7.8 Hz), 7.91(2H, s), 9.06(1H, s).

(2) 5-Chloro-2-[N-(L-leucyl)-L-phenylalanyl]oxy-N-[3,5-bis(trifluoromethyl)phenyl]-benzamide hydrochloride(Compound No. 41).
Using 2-{N-[N-(tert-butoxycarbonyl)-L-leucyl]-L-phenylalanyl}oxy-5-chloro-N-[3,5-bis(trifluoromethyl)phenyl]benzamide as the raw material, the same operation as the Example 25 gave the title compound.
Yield: 71.7%.
$^1$H-NMR(DMSO-d$_6$): δ 0.66(3H, d, J=6.0 Hz), 0.71(3H, d, J=6.0 Hz), 1.55-1.61(1H, m), 1.70-1.79(3H, m), 3.06(1H, dd, J=13.8, 10.2 Hz), 3.25(1H, dd, J=13.8, 4.8 Hz), 4.08(1H, m), 4.73-4.80(1H, m), 7.21-7.27(1H, m), 7.29-7.35(2H, m), 7.42 (2H, d, J=7.2 Hz), 7.45(1H, d, J=2.7 Hz), 7.68(1H, dd, J=8.7, 2.7 Hz), 7.79(1H, s), 8.33(2H, s), 8.57(3H, s), 9.08(1H, d, J=8.1 Hz), 11.09(1H, s).

Example 42

Preparation of the Compound of Compound No. 42.

(1) 2-{N-[N-(tert-Butoxycarbonyl)-β-O-(tert-butyl)-α-L-aspartyl]-L-phenylalanyl}oxy-5-chloro-N-[3,5-bis(trifluoromethyl)phenyl]benzamide.
Using 5-chloro-2-hydroxy-N-[3,5-bis(trifluoromethyl)phenyl]-benzamide(compound of Example 1(1)) and N-[N-(tert-butoxycarbonyl)-β-O-(tert-butyl)-α-L-aspartyl]-L-phenylalanine as the raw materials, the same operation as the Example 24 gave the title compound.

Yield: 19.6%.

$^1$H-NMR(CDCl$_3$): δ 1.40(9H, s), 1.44(9H, s), 2.78(1H, dd, J=17.4, 4.5 Hz), 3.02(1H, dd, J=17.1, 4.8 Hz), 3.39(2H, d, J=7.5 Hz), 4.82-4.85(1H, m), 5.07-5.15(1H, m), 5.83(1H, d, J=8.7 Hz), 7.13(1H, d, J=8.7 Hz), 7.29(5H, m), 7.48(1H, dd, J=8.7, 2.7 Hz), 7.50(1H, s), 7.57(1H, d, J=7.8 Hz), 7.69(1H, d, J=1.8 Hz), 7.88(2H, s), 9.07(1H, s).

(2) 2-[N-(α-L-aspartyl)-L-phenylalanyl]oxy-5-chloro-N-[3, 5-bis(trifluoromethyl)-phenyl]benzamide hydrochloride (Compound No. 42).

Using 2-{N-[N-(tert-butoxycarbonyl)-β-O-(tert-butyl)-α-L-aspartyl]-L-phenylalanyl}oxy-5-chloro-N-[3,5-bis(trifluoromethyl)phenyl]benzamide as the raw material, the same operation as the Example 25 gave the title compound.

Yield: 67.4%.

$^1$H-NMR(DMSO-d$_6$): δ 2.82-2.96(2H, m), 3.11-3.17(1H, m), 3.24-3.31(1H, m), 4.60-4.68(1H, m), 4.88-4.95(1H, m), 6.97(1H, d, J=8.7 Hz), 7.18-7.23(1H, m), 7.26-7.36(4H, m), 7.44(1H, dd, J=9.0, 2.7 Hz), 7.80(1H, s), 7.98(1H, d, J=3.0 Hz), 8.31(4H, s), 9.13(1H, d, J=7.8 Hz), 11.12(1H, s), 12.04 (1H, s).

Example 43

Preparation of the Compound of Compound No. 43.

(1) 5-Chloro-2-hydroxy-N-[3,5-bis(trifluoromethyl)phenyl] benzamide 1 Sodium Salt.

2N Aqueous sodium hydroxide(5 mL, 10 mmol) was added to a solution of 5-chloro-2-hydroxy-N-[3,5-bis(trifluoromethyl)phenyl]benzamide(compound of Example 1(1); 3.84 g, 10 mmol) in ethanol(100 mL), and the mixture was stirred at room temperature for 1 minute. The solvent was evaporated under reduced pressure to give the title compound(4.06 g, 100%) as a white solid.

$^1$H-NMR(DMSO-d$_6$): δ 6.43(1H, d, J=8.7 Hz), 6.97(1H, dd, J=8.7, 3.0 Hz), 7.59(1H, s), 7.62(1H, d, J=3.0 Hz), 8.29 (2H, s).

(2) 5-Chloro-2-(methoxycarbonyl)oxy-N-[3,5-bis(trifluoromethyl)phenyl]benzamide (Compound No. 43).

Methyl chloroformate(42 μL, 0.54 mmol) was added to a solution of 5-chloro-2-hydroxy-N-[3,5-bis(trifluoromethyl) phenyl]benzamide 1 sodium salt(200 mg, 0.49 mmol) in tetrahydrofuran(5 mL) under ice cooling, and the mixture was stirred at room temperature for 10 minutes. The reaction mixture was poured into water and extracted with ethyl acetate. After the ethyl acetate layer was washed successively with water and brine, dried over anhydrous sodium sulfate, the residue obtained by evaporation of the solvent under reduced pressure was washed with n-hexane under suspension to give the title compound(171.2 mg, 78.6%) as a white solid.

$^1$H-NMR(DMSO-d$_6$): δ 3.80(3H, s), 7.48(1H, d, J=8.7 Hz), 7.74(1H, dd, J=8.7, 2.7 Hz), 7.87(1H, s), 7.92(1H, d, J=2.7 Hz), 8.36(2H, s), 11.11(1H, s).

Example 44

Preparation of the Compound of Compound No. 44.

Triethylamine(0.15 mL, 1.07 mmol) and methanesulfonyl chloride(45 μL, 0.58 mmol) were added to a solution of 5-chloro-2-hydroxy-N-[3,5-bis(trifluoromethyl)-phenyl] benzamide(compound of Example 1(1); 0.20 g, 0.52 mmol) in tetrahydrofuran (4 mL), and the mixture was stirred at room temperature for 10 minutes. The reaction mixture was poured into water and extracted with ethyl acetate. After the ethyl acetate layer was washed with brine, dried over anhydrous sodium sulfate, the residue obtained by evaporation of the solvent under reduced pressure was purified by column chromatography on silica gel(n-hexane:ethyl acetate=3:1→2:1) to give the title compound(214.3 mg, 89.2%) as a white crystal.

$^1$H-NMR(DMSO-d$_6$): δ 3.43(3H, s), 7.59(1H, d, J=8.7 Hz), 7.77(1H, dd, J=9.0, 2.7 Hz), 7.87(1H, s), 7.91(1H, d, J=3.0 Hz), 8.36(2H, s), 11.14(1H, s).

Example 45

Preparation of the Compound of Compound No. 45.

Using 5-chloro-2-hydroxy-N-[3,5-bis(trifluoromethyl) phenyl]-benzamide(compound of Example 1(1)) and 1-propanesulfonyl chloride as the raw materials, the same operation as the Example 44 gave the title compound.

Yield: 86.1%.

$^1$H-NMR(DMSO-d$_6$): δ 0.91(3H, t, J=7.2 Hz), 1.71-1.83 (2H, m), 3.52-3.57(2H, m), 7.53(1H, d, J=8.7 Hz), 7.75(1H, dd, J=8.7, 2.7 Hz), 7.86(1H, s), 7.88(1H, d, J=3.0 Hz), 8.36 (2H, s), 11.16(1H, s).

Example 46

Preparation of the Compound of Compound No. 46.

Using 5-chloro-2-hydroxy-N-[3,5-bis(trifluoromethyl) phenyl]-benzamide(compound of Example 1(1)) and 2-propanesulfonyl chloride as the raw materials, the same operation as the Example 44 gave the title compound.

Yield: 59.7%.

$^1$H-NMR(CDCl$_3$): δ 1.57(6H, d, J=6.9 Hz), 3.54-3.68(1H, m), 7.41(1H, d, J=8.7 Hz), 7.54(1H, dd, J=8.7, 2.7 Hz), 7.67 (1H, s), 7.87(1H, d, J=2.7 Hz), 8.21(2H, s), 9.10(1H, s).

Example 47

Preparation of the Compound of Compound No. 47.

Using 5-chloro-2-hydroxy-N-[3,5-bis(trifluoromethyl) phenyl]-benzamide(compound of Example 1(1)) and para-toluenesulfonyl chloride as the raw materials, the same operation as the Example 44 gave the title compound.

Yield: 84.8%.

$^1$H-NMR(DMSO-d$_6$): δ 2.19(3H, s), 7.24(2H, d, J=8.4 Hz), 7.36(1H, d, J=8.7 Hz), 7.60(2H, d, J=8.4 Hz), 7.73(1H, dd, J=8.7, 2.7 Hz), 7.77(1H, d, J=2.7 Hz), 7.86(1H, s), 8.19 (2H, s), 10.80(1H, s).

Example 48

Preparation of the Compound of Compound No. 48.

N,N-Dimethylsulfamoyl chloride(52 μL, 0.48 mmol) was added to a solution of 5-chloro-2-hydroxy-N-[3,5-bis(trifluoromethyl)phenyl]benzamide 1 sodium salt(compound of Example 43(1); 0.20 g, 0.49 mmol) in tetrahydrofuran(4 mL) under ice cooling, and the mixture was stirred at room temperature for 12 hours. Further N,N-dimethylsulfamoyl chloride(40 μL, 0.37 mmol) was added, and the mixture was stirred at 60° C. for 6 hours. The reaction mixture was poured into water and extracted with ethyl acetate. After the ethyl acetate layer was washed with brine, dried over anhydrous sodium sulfate, the residue obtained by evaporation of the solvent under reduced pressure was purified by column chromatography on silica gel(n-hexane:ethyl acetate=4:1) to give the title compound (230.7 mg, 95.9%) as a white crystal.

$^1$H-NMR(DMSO-d$_6$): δ 2.85(6H, s), 7.53(1H, d, J=8.7 Hz), 7.74(1H, dd, J=9.0, 2.7 Hz), 7.86(2H, d, J=2.7 Hz), 8.38(2H, s), 11.16(1H, s).

Example 49

Preparation of the Compound of Compound No. 49.

Sulfur trioxide pyridine complex(664 mg, 4 mmol) was added to a solution of 5-chloro-2-hydroxy-N-[3,5-bis(trifluoromethyl)phenyl]benzamide (compound of Example 1(1); 0.4 g, 1 mmol) in pyridine(10 mL), and the mixture was stirred at room temperature for 8 hours under argon atmosphere. The residue obtained by evaporation of the solvent under reduced pressure was diluted with ethyl acetate (15 mL). After the ethyl acetate layer was washed successively with water and brine, dried over sodium sulfate, the residue obtained by evaporation of the solvent under reduced pressure was crystallized from n-hexane/chloroform to give the title compound (425 mg, 87.9%) as a white powder.

$^1$H-NMR(DMSO-d$_6$): δ 7.51(1H, d, J=8.7 Hz), 7.61(1H, dd, J=8.7, 2.7 Hz), 7.70(1H, d, J=2.7 Hz), 7.85(1H, s), 8.36 (2H, s), 11.04(1H, s).

Example 50

Preparation of the Compound of Compound No. 50.

Carbon tetrachloride (401 mg, 5.6 mmol), diisopropylethylamine (141 mg, 1.1 mmol), dimethylaminopyridine (catalytic amount) and dibenzyl phosphite (198 mg, 0.7 mmol) were added successively to a solution of 5-chloro-2-hydroxy-N-[3,5-bis(trifluoromethyl)phenyl]benzamide (compound of Example 1(1); 0.2 g, 0.5 mmol) in acetonitrile (8 mL) at 0° C. under argon atmosphere, and the mixture was stirred at the same temperature for 40 minutes. The reaction mixture was diluted with ethyl acetate (50 mL). After the ethyl acetate layer was washed successively with 2N hydrochloric acid, water and brine, dried over anhydrous sodium sulfate, the residue obtained by evaporation of the solvent under reduced pressure was purified by column chromatography on silica gel (n-hexane:ethyl acetate=3:1) to give the title compound (338 mg, 100%) as a white powder.

$^1$H-NMR(CDCl$_3$): δ 5.04-5.17(4H, m), 7.15(1H, dd, J=9.0, 1.2 Hz), 7.22-7.33(11H, m), 7.61(1H, s), 7.85(1H, dd, J=2.7, 0.9 Hz) 8.20(2H, s), 9.25(1H, s).

Example 51

Preparation of the Compound of Compound No. 51.

Palladium hydroxide on carbon(10 mg) was added to a solution of 5-chloro-2-(dibenzylphosphono)oxy-N-[3,5-bis (trifluoromethyl)phenyl]benzamide (Compound No. 50; 100 mg, 0.16 mmol) in ethyl acetate(10 mL), and the mixture was stirred at room temperature for 1 hour under hydrogen atmosphere. The reaction mixture was filtered through celite, and the solvent was evaporated under reduced pressure to give the title compound (78 mg, 100%) as a white powder.

$^1$H-NMR(DMSO-d$_6$): δ 7.41(1H, dd, J=9.0, 1.2 Hz), 7.63 (1H, dd, J=9.0,2.7 Hz), 7.70(1H, d, J=3.0 Hz), 7.84(1H, brs), 8.40(2H, s), 11.35(1H, brs).

Example 52

Preparation of the Compound of Compound No. 52

Sodium ethoxide (18 mg, 0.3 mmol) was added to a solution of 5-chloro-2-phosphonooxy-N-[3,5-bis(trifluoromethyl)phenyl]benzamide(Compound No. 51; 102 mg, 0.2 mmol) in ethanol(2 mL), and the mixture was stirred at room temperature for 30 minutes. The residue obtained by evaporation of the solvent under reduced pressure was crystallized from n-hexane/ethyl acetate to give the title compound(110 mg, 100%) as a light brown powder.

$^1$H-NMR(DMSO-d$_6$): δ 7.30(1H, d, J=8.7 Hz), 7.52(1H, dd, J=8.7, 2.7 Hz), 7.63(1H, d, J=2.7 Hz), 7.77(1H, brs), 8.52(2H, s).

Example 53

The Compound of Compound No. 53

This compound is a commercially available compound.
Supplier: Nakarai tesk.
Catalog code number: 238-22.

Example 54

Preparation of the Compound of Compound No. 54

Triethyamine (0.055 mL, 0.39 mmol) and isopropyl isocyanate (33.3 mg, 0.39 mmol) were added to a solution of 5-chloro-2-hydroxy-N-[3,5-bis(trifluoromethyl)-phenyl] benzamide(compound of Example 1(1); 0.10 g, 0.26 mmol) in tetrahydrofuran(2 mL) at 0° C. under argon atmosphere, and the mixture was stirred at room temperature overnight. 1N Hydrochloric acid was added to the reaction mixture and it was extracted with ethyl acetate. After the ethyl acetate layer was washed with brine, dried over anhydrous sodium sulfate, the residue obtained by evaporation of the solvent under reduced pressure was washed with n-hexane/ethyl acetate under suspension to give the title compound(33 mg, 27.0%) as a white powder.

1H-NMR(CDCl$_3$): δ 1.21(6H, d, J=6.3 Hz), 3.84-3.93(1H, m), 5.24(1H, d, J=7.2 Hz), 7.07(1H, d, J=8.7 Hz), 7.40(1H, dd, J=8.7, 2.7 Hz), 7.61(1H, s), 7.72(1H, d, J=2.4 Hz), 8.09 (2H, s), 9.08(1H, s).

Example 55

Preparation of the Compound of Compound No. 55

Using 5-chloro-2-hydroxy-N-[3,5-bis(trifluoromethyl) phenyl]-benzamide(compound of Example 1(1)) and benzyl isocyanate as the raw materials, the same operation as the Example 54 gave the title compound.
Yield: 48.2%.

$^1$H-NMR(DMSO-d$_6$): δ 4.21(2H, d, J=6.0 Hz), 7.12-7.15 (3H, m), 7.20-7.23(2H, m), 7.34(1H, d, J=8.7 Hz), 7.65(1H, dd, J=8.7, 2.7 Hz), 7.80(1H, d, J=2.7 Hz), 7.85(1H, s), 8.40 (2H, s), 8.41(1H, t, J=6.3 Hz), 11.03(1H, s).

Example 56

Preparation of the Compound of Compound No. 56

Using 5-chloro-2-hydroxy-N-[3,5-bis(trifluoromethyl) phenyl]benzamide (compound of Example 1(1)) and ethyl 2-isocyanatoacetate as the raw materials, the same operation as the Example 54 gave the title compound.

Yield: 40.3%.

$^1$H-NMR(DMSO-d$_6$): δ 1.12(3H, t, J=7.2 Hz), 3.76(2H, d, J=6.0 Hz), 4.02(2H, q, J=7.2 Hz), 7.31(1H, d, J=9.0 Hz), 7.65(1H, dd, J=8.7, 2.7 Hz), 7.80(1H, d, J=3.0 Hz), 7.84(1H, s), 8.30(1H, t, J=6.0 Hz), 8.37(2H, s), 10.98(1H, s).

Example 57

Preparation of the Compound of Compound No. 57

Water(0.1 mL) and concentrated sulfuric acid(3 drops) were added to a solution of 5-chloro-2-{N-[(ethoxycarbonyl)methyl]carbamoyl}oxy-N-[3,5-bis(trifluoromethyl)-phenyl]benzamide(Compound No. 56; 70 mg, 0.14 mmol) in tetrahydrofuran(3 mL), and the mixture was stirred at 60° C. for 11 hours. After the reaction mixture was cooled to room temperature, it was poured into ice and water, and extracted with ethyl acetate. After the ethyl acetate layer was washed successively with water and brine, dried over anhydrous sodium sulfate, the residue obtained by evaporation of the solvent under reduced pressure was washed with isopropyl ether/n-hexane under suspension to give the title compound(61.4 mg, 93.2%) as a white crystal.

$^1$H-NMR(DMSO-d$_6$): δ 3.68(2H, d, J=6.0 Hz), 7.31(1H, d, J=9.0 Hz), 7.65(1H, dd, J=9.0, 2.7 Hz), 7.79(1H, d, J=2.7 Hz), 7.83(1H, s), 8.19(1H, d, J=6.0 Hz), 8.36(2H, s), 10.98(1H, s), 12.62(1H, brs).

Example 58

Preparation of the Compound of Compound No. 58

Using 5-chloro-2-hydroxy-N-[3,5-bis(trifluoromethyl)phenyl]-benzamide(compound of Example 1(1)) and methyl (S)-(-)-2-isocyanatopropionate as the raw materials, the same operation as the Example 54 gave the title compound.

Yield: 62.5%.

$^1$H-NMR(CDCl$_3$): δ 1.46(3H, d, J=7.2 Hz), 3.75(3H, s), 4.37(1H, m), 5.92(1H, d, J=7.8 Hz), 7.13(1H, d, J=8.7 Hz), 7.47(1H, dd, J=8.7, 2.7 Hz), 7.64(1H, s), 7.82(1H, d, J=2.7 Hz), 8.15(2H, s), 8.78(1H, s).

Example 59

Preparation of the Compound of Compound No. 59

Using 5-chloro-2-hydroxy-N-[3,5-bis(trifluoromethyl)phenyl]-benzamide(compound of Example 1(1)) and methyl (S)-(-)-2-isocyanato-3-phenylpropionate as the raw materials, the same operation as the Example 54 gave the title compound.

Yield: 53.0%.

$^1$H-NMR(CDCl$_3$): δ 3.15(2H, dd, J=6.0, 4.2 Hz), 3.75(3H, s), 4.66(1H, dt, J=7.2, 6.0 Hz), 5.74(1H, d, J=8.1 Hz), 7.04-7.08(3H, m), 7.20-7.27(3H, m), 7.45(1H, dd, J=8.7, 2.7 Hz), 7.63(1H, s), 7.81(1H, d, J=2.7 Hz), 8.11(2H, s), 8.72(1H, s).

Example 60

Preparation of the Compound of Compound No. 60

Using 5-chloro-2-hydroxy-N-[3,5-bis(trifluoromethyl)phenyl]-benzamide(compound of Example 1(1)) and methyl (S)-(-)-2-isocyanato-3-(tert-butoxy)propionate as the raw materials, the same operation as the Example 54 gave the title compound.

Yield: 26.0%.

$^1$H-NMR(DMSO-d$_6$): δ 3.51(2H, d, J=5.1 Hz), 3.57(3H, s), 4.17(1H, dt, J=8.4, 5.1 Hz), 7.30(1H, d, J=8.7 Hz), 7.65(1H, dd, J=8.7, 2.7 Hz), 7.80(1H, d, J=2.7 Hz), 7.83(1H, s), 8.27(1H, d, J=8.1 Hz), 8.39(2H, s), 10.94(1H, s).

Example 61

Preparation of the Compound of Compound No. 61

L-Phenylalanine (tert-butyl) ester hydrochloride(159.4 mg, 0.62 mmol), 1-hydroxybenzotriazole(83.6 mg, 0.62 mmol) and WSC.HCl(158.2 mg, 0.82 mmol) were added to a solution of 2-[N-(carboxymethyl)carbamoyl]oxy-5-chloro-N-[3,5-bis(trifluoromethyl)phenyl]-benzamide(Compound No. 57; 0.20 g, 0.41 mmol) in N-methyl-2-pyrrolidinone(4 mL) under ice cooling, and the mixture was stirred at room temperature for 4 hours. The reaction mixture was poured into water and extracted with ethyl acetate. After the ethyl acetate layer was washed successively with water and brine, dried over anhydrous sodium sulfate, the residue obtained by evaporation of the solvent under reduced pressure was purified by column chromatography on silica gel(n-hexane:ethyl acetate=3:2→1:1), and crystallized by n-hexane to give the title compound(157.9 mg, 56.0%) as a white solid.

$^1$H-NMR(CDCl$_3$): δ 1.40(9H, s), 2.96-2.99(2H, m), 3.86 (2H, d, J=5.7 Hz), 4.72(1H, dt, J=7.5, 6.0 Hz), 6.12(1H, m), 6.35(1H, m), 7.06-7.12(3H, m), 7.20-7.26(3H, m), 7.44(1H, dd, J=8.7, 2.4 Hz), 7.62(1H, s), 7.79(1H, d, J=2.4 Hz), 8.15 (2H, s), 9.00(1H, s).

Example 62

Preparation of the Compound of Compound No. 62

4N Hydrogen chloride/ethyl acetate solution(1 mL) was added to (S)-2-[N-({N-[1-(tert-butoxycarbonyl)-2-phenylethyl]carbamoyl}methyl)carbamoyl]oxy-5-chloro-N-[3,5-bis(trifluoromethyl)phenyl]benzamide(Compound No. 61; 106 mg, 0.15 mmol), and the mixture was stirred at room temperature for 4 hours. Isopropyl ether/n-hexane was added to the reaction mixture and the separated powder was filtered to give the title compound(81 mg, 83.2%) as a white powder.

$^1$H-NMR(DMSO-d$_6$): δ 2.84(1H, dd, J=13.8, 9.0 Hz), 3.01 (1H, dd, J=13.8, 5.1 Hz), 3.60(1H, t, J=6.6 Hz), 4.37-4.45 (1H, m), 7.15-7.26(5H, m), 7.30(1H, d, J=8.4 Hz), 7.65(1H, dd, J=8.7, 2.7 Hz), 7.80(1H, d, J=3.0 Hz), 7.83(1H, s), 8.05 (1H, t, J=9.0 Hz), 8.18(1H, d, J=7.8 Hz), 8.36(2H, s), 10.98 (1H, s).

Example 63

Preparation of the Compound of Compound No. 63

Using 2-[N-(carboxymethyl)carbamoyl]oxy-5-chloro-N-[3,5-bis(trifluoromethyl)phenyl]-benzamide(Compound No. 57) and L-aspartic acid di(tert-butyl) ester hydrochloride as the raw materials, the same operation as the Example 61 gave the title compound.

Yield: 35.7%.

$^1$H-NMR(DMSO-d$_6$): δ 1.36(18H, s), 2.46-2.54(1H, m), 2.62(1H, dd, J=16.5, 6.0 Hz), 3.64(2H, d, J=6.0 Hz), 4.46(1H, dt, J=7.5, 6.6 Hz), 7.31(1H, d, J=8.7 Hz), 7.65(1H, dd, J=9.0, 2.4 Hz), 7.80(1H, d, J=2.7 Hz), 7.83(1H, s), 8.11(1H, t, J=6.0 Hz), 8.20(1H, d, J=8.4 Hz), 8.37(2H, s), 10.97(1H, s).

Example 64

Preparation of the Compound of Compound No. 64

Using (S)-2-[N-({N-[1,2-di(tert-butoxycarbonyl)ethyl] carbamoyl}-methyl)carbamoyl]oxy-5-chloro-N-[3,5-bis(trifluoromethyl)phenyl]benzamide (Compound No. 63) as the raw material, the same operation as the Example 62 gave the title compound.

Yield: 74.0%.

$^1$H-NMR(DMSO-d$_6$): δ 2.56(1H, dd, J=16.5, 6.6 Hz), 2.66 (1H, dd, J=16.5, 5.7 Hz), 3.65(2H, d, J=6.0 Hz), 4.53(1H, dt, J=8.1, 6.3 Hz), 7.32(1H, d, J=8.7 Hz), 7.65(1H, dd, J=8.7, 3.0 Hz), 7.79(1H, d, J=2.7 Hz), 7.83(1H, s), 8.09(1H, t, J=6.3 Hz), 8.23(1H, d, J=8.1 Hz), 8.37(2H, s), 10.97(1H, s), 12.2-12.9(2H, br).

Example 65

Preparation of the Compound of Compound No. 65

Using 2-[N-(carboxymethyl)carbamoyl]oxy-5-chloro-N-[3,5-bis(trifluoromethyl)phenyl]-benzamide(Compound No. 57) and N$^ε$-(tert-butoxy)carbonyl-L-lysine (tert-butyl) ester hydrochloride as the raw materials, the same operation as the Example 61 gave the title compound.

Yield: 14.3%.

$^1$H-NMR(DMSO-d$_6$): δ 1.18-1.43(4H, m), 1.36(9H, s), 1.37(9H, s), 1.51-1.64(2H, m), 2.84(1H, t, J=6.6 Hz), 2.86 (1H, t, J=6.3 Hz), 3.64-3.68(2H, m), 4.02-4.10(1H, m), 6.71 (1H, m), 7.32(1H, d, J=8.7 Hz), 7.65(1H, dd, J=8.7, 2.7 Hz), 7.80(1H, d, J=2.7 Hz), 7.82(1H, s), 8.01-8.06(2H, m), 8.37 (2H, s), 10.93(1H, s).

Example 66

The Compound of Compound No. 66

This compound is a commercially available compound.
Supplier: Sigma-Aldrich.
Catalog code number: S71824-6.

Example 67

Preparation of the Compound of Compound No. 67

N,N-Dimethylcarbamoyl chloride(304 μL, 3.3 mmol) was added to a solution of 5-chloro-2-hydroxy-N-[3,5-bis(trifluoromethyl)phenyl]benzamide(compound of Example 1(1); 1.15 g, 3 mmol) and pyridine(285 mg, 3.6 mmol) in tetrahydrofuran(10 mL) under ice cooling, and the mixture was stirred at room temperature for 3.5 hours. Triethylamine(0.5 mL, 3.6 mmol), N,N-dimethylcarbamoyl chloride (304 μL, 3.3 mmol) and 4-dimethylaminopyridine(110 mg, 0.9 mmol) were added to the reaction mixture, and the mixture was stirred at room temperature for further 20 hours. 2N Hydrochloric acid(6 mL) and water(30 mL) were added to the reaction mixture and it was extracted with ethyl acetate. After the ethyl acetate layer was washed successively with water and brine, dried over anhydrous sodium sulfate, the solvent was evaporated under reduced pressure to give the title compound(1.29 g, 94.2%) as a white solid.

$^1$H-NMR(DMSO-d$_6$): δ 2.81(3H, s), 2.98(3H, s), 7.36(1H, d, J=8.7 Hz), 7.66(1H, dd, J=8.7, 2.4 Hz), 7.80(1H, d, J=2.4 Hz), 7.84(1H, s), 8.35(1H, s), 11.03(1H, s).

Example 68

Preparation of the Compound of Compound No. 68

N,N-Diethylcarbamoyl chloride(80 μL, 0.63 mmol) was added to a solution of 5-chloro-2-hydroxy-N-[3,5-bis(trifluoromethyl)phenyl]benzamide(compound of Example 1(1); 0.20 g, 0.52 mmol) in pyridine(3 mL), and the mixture was stirred at 60° C. for 4 hours. The reaction mixture was poured into 2N hydrochloric acid and extracted with ethyl acetate. After the ethyl acetate layer was washed successively with water and brine, dried over anhydrous sodium sulfate, the residue obtained by evaporation of the solvent under reduced pressure was crystallized by isopropyl ether/n-hexane to give the title compound (231.2 mg, 92.1%) as a white crystal.

$^1$H-NMR(CDCl$_3$): δ 1.16(3H, t, J=7.2 Hz), 1.20(3H, t, J=7.2 Hz), 3.41(2H, q, J=7.2 Hz), 3.45(2H, q, J=7.2 Hz), 7.05(1H, d, J=9.0 Hz), 7.44(1H, dd, J=9.0, 2.7 Hz), 7.62(1H, s), 7.70(1H, d, J=2.7 Hz), 8.09(2H, s), 9.25(1H, s).

Example 69

Preparation of the Compound of Compound No. 69

N-Methyl-N-phenylcarbamoyl chloride(105.8 mg, 0.62 mmol), triethylamine(0.2 mL, 1.43 mmol) and 4-dimethylaminopyridine(10 mg) were added to a solution of 5-chloro-2-hydroxy-N-[3,5-bis(trifluoromethyl)phenyl]benzamide (compound of Example 1(1); 0.20 g, 0.52 mmol) in tetrahydrofuran (3 mL), and the mixture was stirred at room temperature for 3 hours. The reaction mixture was poured into diluted hydrochloric acid and extracted with ethyl acetate. After the ethyl acetate layer was washed successively with water and brine, dried over anhydrous sodium sulfate, the residue obtained by evaporation of the solvent under reduced pressure was washed with isopropyl ether/n-hexane under suspension to give the title compound (239.3 mg, 89.0%) as a white powder.

$^1$H-NMR(DMSO-d$_6$): δ 3.28(3H, s), 7.15-7.34(5H, m), 7.39(1H, d, J=8.4 Hz), 7.66(1H, dd, J=8.7, 2.4 Hz), 7.81(1H, d, J=2.4 Hz), 7.87(1H, s), 8.34(2H, s), 11.00(1H, s).

Example 70

Preparation of the Compound of Compound No. 70

Using 5-chloro-2-hydroxy-N-[3,5-bis(trifluoromethyl) phenyl]-benzamide(compound of Example 1(1)) and 1-pyrrolidinecarbonyl chloride as the raw materials, the same operation as the Example 69 gave the title compound.

Yield: 70.4%.

$^1$H-NMR(DMSO-d$_6$): δ 1.71-1.81(4H, m), 3.19(2H, t, J=6.6 Hz), 3.45(2H, t, J=6.6 Hz), 7.37(1H, d, J=8.7 Hz), 7.66(1H, dd, J=8.7, 2.7 Hz), 7.79(1H, d, J=2.4 Hz), 7.85(1H, s), 8.34(2H, s), 11.03(1H, s).

Example 71

Preparation of the Compound of Compound No. 71

Morpholine-4-carbonyl chloride(73 μL, 0.62 mmol), triethylamine(0.2 mL, 1.43 mmol) and 4-dimethylaminopyridine(10 mg) were added to a solution of 5-chloro-2-hydroxy- N-[3,5-bis(trifluoromethyl)phenyl]benzamide(compound of Example 1(1); 0.20 g, 0.52 mmol) in tetrahydrofuran(3 mL), and the mixture was stirred at room temperature for 2 hours. The reaction mixture was poured into diluted hydrochloric acid and extracted with ethyl acetate. After the ethyl acetate layer was washed successively with water and brine, dried over anhydrous sodium sulfate, the residue obtained by evaporation of the solvent under reduced pressure was washed with isopropyl ether/n-hexane under suspension to give the title compound(237.2 mg, 91.8%) as a white powder.

$^1$H-NMR(DMSO-d$_6$): δ 3.35(4H, s), 3.54(4H, s), 7.37(1H, d, J=9.0 Hz), 7.68(1H, dd, J=9.0, 3.0 Hz), 7.83(1H, d, J=2.7 Hz), 7.87(1H, s), 8.39(2H, s), 11.06(1H, s).

Example 72

Preparation of the Compound of Compound No. 72

Using 5-chloro-2-hydroxy-N-[3,5-bis(trifluoromethyl)phenyl]-benzamide(compound of Example 1(1)) and 4-methylpiperazine-1-carbonyl chloride as the raw materials, the same operation as the Example 69 gave the title compound.
Yield: 69.9%.
$^1$H-NMR(CDCl$_3$): δ 2.28(3H, s), 2.34-2.44(4H, m), 3.60-3.73(4H, m), 7.02(1H, d, J=9.0 Hz), 7.33(1H, dd, J=8.7, 2.7 Hz), 7.61(1H, s), 7.65(1H, d, J=2.4 Hz), 8.05(2H, s), 9.18(1H, s).

Example 73

Preparation of the Compound of Compound No. 73

A solution of ethyl isonipecotate (786 mg, 5.00 mmol) and triethylamine (506 mg, 5.00 mmol) in dichloroethane (5 mL) was added to a solution of triphosgene (549 mg, 1.85 mmol) in dichloroethane (10 mL), and the mixture was stirred at room temperature for 1 hour. The residue obtained by evaporation of the reaction mixture under reduced pressure was dissolved in tetrahydrofuran (10 mL). A solution of 5-chloro-2-hydroxy-N-[3,5-bis(trifluoromethyl)phenyl]benzamide (compound of Example 1(1); 1.92 g, 5.00 mmol) in tetrahydrofuran (10 mL), triethylamine (549 mg, 5.00 mmol) and 4-dimethylaminopyridine (100 mg) were added to the solution under ice cooling, and the mixture was stirred at room temperature for 32 hours. The reaction mixture was washed with diluted hydrochloric acid and the residue obtained by evaporation of the solvent under reduced pressure was purified by column chromatography on silica gel(n-hexane:ethyl acetate=3:1) to give the title compound(1.814 g, 64.0%) as a white crystal.
$^1$H-NMR(CDCl$_3$): δ 1.25(3H, t, J=7.2 Hz), 1.63-1.73(2H, m), 1.95-2.00(2H, m), 2.48-2.58(1H, m), 3.05-3.13(1H, m), 3.18-3.25(1H, m), 4.08-4.18(2H, m), 4.15(2H, q, J=7.2 Hz), 7.05(1H, d, J=9.0 Hz), 7.42(1H, dd, J=9.0, 3.0 Hz), 7.62(1H, s), 7.69(1H, d, J=2.7 Hz), 8.06(2H, s), 9.13(1H, s).

Example 74

Preparation of the Compound of Compound No. 74

Water(0.6 mL) and concentrated sulfuric acid(20 drops) were added to a solution of 5-chloro-2-{[4-(ethoxycarbonyl)piperidin-1-yl]carbonyl}oxy-N-[3,5-bis(trifluoromethyl)-phenyl]benzamide(Compound No. 73; 504 mg, 0.889 mmol) in tetrahydrofuran(10 mL), and the mixture was stirred at 60° C. for 5 hours. After the reaction mixture was cooled to room temperature, it was poured into ice and water, and the separated solid was filtered and recrystallized from ethyl acetate/n-hexane to give the title compound(419.8 mg, 87.6%) as a white crystal.

$^1$H-NMR(DMSO-d$_6$): δ 1.24-1.34(1H, m), 1.39-1.51(1H, m), 1.77(2H, d, J=12.3 Hz), 2.38-2.46(1H, m), 2.90(1H, t, J=11.4 Hz), 3.08(1H, t, J=12.0 Hz), 3.80(1H, d, J=12.0 Hz), 4.02-4.07(1H, m), 7.36(1H, d, J=9.0 Hz), 7.66(1H, dd, J=8.7, 2.7 Hz), 7.80(1H, d, J=2.4 Hz), 7.82(1H, s), 8.36(2H, s), 11.03(1H, s), 12.21(1H, brs).

Example 75

Preparation of the Compound of Compound No. 75

Using 5-chloro-2-hydroxy-N-[3,5-bis(trifluoromethyl)phenyl]-benzamide(compound of Example 1(1)) and diethyl iminodiacetate as the raw materials, the same operation as the Example 73 gave the title compound.
Yield: 64.4%.
$^1$H-NMR(DMSO-d$_6$): δ 1.11(1H, t, J=7.5 Hz), 1.13(1H, t, J=6.9 Hz), 4.01(2H, q, J=7.2 Hz), 4.02(2H, q, J=6.9 Hz), 4.08(2H, s), 4.27(2H, s), 7.29(1H, d, J=9.0 Hz), 7.67(1H, dd, J=8.7, 2.4 Hz), 7.80(1H, d, J=2.4 Hz), 7.84(1H, s), 8.37(2H, s), 10.98(1H, s).

Example 76

Preparation of the Compound of Compound No. 76

Using 2-{N,N-bis[(ethoxycarbonyl)methyl]carbamoyl}oxy-5-chloro-N-[3,5-bis(trifluoromethyl)phenyl]benzamide(Compound No. 75) as the raw material, the same operation as the Example 74 gave the title compound.
Yield: 36.5%.
$^1$H-NMR(DMSO-d$_6$): δ 3.98(2H, s), 4.18(2H, s), 7.28(1H, d, J=8.7 Hz), 7.67(1H, dd, J=8.7, 2.7 Hz), 7.79(1H, d, J=2.7 Hz), 7.82(1H, s), 8.35(2H, s), 10.96(1H, s), 12.75(2H, brs).

Example 77

Preparation of the Compound of Compound No. 77

(1) 5-Bromo-2-hydroxy-N-[3,5-bis(trifluoromethyl)phenyl]benzamide
Using 5-bromosalicylic acid and 3,5-bis(trifluoromethyl)aniline as the raw materials, the same operation as the Example 1(1) gave the title compound.
Yield: 88.5%.
$^1$H-NMR(DMSO-d$_6$): δ 6.98(1H, d, J=8.8 Hz), 7.59(1H, dd, J=8.8, 2.8 Hz), 7.83(1H, s), 7.98(1H, d, J=2.8 Hz), 8.43(2H, s), 10.82(1H, s), 11.37(1H, s).

(2) 5-Bromo-2-(morpholinocarbonyl)oxy-N-[3,5-bis(trifluoromethyl)phenyl]benzamide (Compound No. 77)
Using 5-bromo-2-hydroxy-N-[3,5-bis(trifluoromethyl)phenyl]benzamide and morpholine-4-carbonyl chloride as the raw materials, the same operation as the Example 71 gave the title compound.
Yield: 87.1%.
$^1$H-NMR(CDCl$_3$): δ 3.59-3.70(8H, m), 7.01(1H, d, J=8.7 Hz), 7.55(1H, dd, J=8.7, 2.4 Hz), 7.63(1H, s), 7.80(1H, d, J=2.1 Hz), 8.05(2H, s), 8.99(1H, s).

Example 78

Preparation of the Compound of Compound No. 78

(1) 5-[(1,1-Dimethyl)ethyl]salicylic acid
Sulfamic acid (1.76 g, 18.1 mmol) and sodium dihydrogenphosphate (7.33 g, 47 mmol) were added to a solution of 5-[(1,1-dimethyl)ethyl]-2-hydroxybenzaldehyde (2.15 g, 12.1 mmol) in 1,4-dioxane(100 mL) and water(40 mL). A solution of sodium chlorite(1.76 g, 15.5 mmol) in water(10 mL) was added to the mixture under ice cooling, and it was stirred for 1 hour. Then, sodium sulfite(1.80 g, 14.3 mmol) was added to the mixture, and it was stirred for 30 minutes. Concentrated hydrochloric acid was added to the reaction mixture, and pH was adjusted to 1. The residue obtained by evaporation of 1,4-dioxane under reduced pressure was extracted with ethyl acetate. The organic layer was washed with water and brine, and dried over anhydrous magnesium sulfate. The residue obtained by evaporation of the solvent under reduced pressure was washed with n-hexane under suspension to give the title compound(1.81 g, 77.4%) as a white powder.

$^1$H-NMR(DMSO-$d_6$): δ 1.26(9H, s), 6.90(1H, d, J=9.0 Hz), 7.58(1H, dd, J=8.7, 2.4 Hz), 7.75(1H, d, J=2.4 Hz), 11.07(1H, brs).

(2) 5-[(1,1-Dimethyl)ethyl]ethyl-2-hydroxy-N-[3,5-bis(trifluoromethyl)phenyl]-benzamide Using 5-[(1,1-dimethyl)ethyl]salicylic acid and 3,5-bis(trifluoromethyl)aniline as the raw materials, the same operation as the Example 1(1) gave the title compound.

Yield: 53.8%.

$^1$H-NMR(DMSO-$d_6$):1.30(9H, s), 6.96(1H, d, J=8.7 Hz), 7.50(1H, dd, J=8.7, 2.4 Hz), 7.82(1H, d, J=2.4 Hz), 7.83(1H, s), 8.46(2H, s), 10.80(1H, s) 11.12(1H, s).

(3) 5-[(1,1-Dimethyl)ethyl]-2-[(morpholinocarbonyl)oxy]-N-[3,5-bis(trifluoromethyl)-phenyl]benzamide(Compound No. 78)

Using 5-[(1,1-dimethyl)ethyl]-2-hydroxy-N-[3,5-bis(trifluoromethyl)-phenyl]benzamide and morpholine-4-carbonyl chloride as the raw materials, the same operation as the Example 71 gave the title compound.

Yield: 95.0%.

$^1$H-NMR(CDCl$_3$): δ 1.35(9H, s) 3.60-3.67(8H, m), 7.05 (1H, d, J=8.4 Hz), 7.54(1H, dd, J=8.7, 2.4 Hz), 7.64(1H, s), 7.74(1H, d, J=2.7 Hz), 8.12(2H, s), 9.02(1H, s).

Example 79

Preparation of the Compound of Compound No. 79

(1) 2-Hydroxy-5-trifluoromethyl-N-[3,5-bis(trifluoromethyl)phenyl]benzamide

Using 2-hydroxy-5-(trifluoromethyl)benzoic acid and 3,5-bis(trifluoromethyl)aniline as the raw materials, the same operation as the Example 1(1) gave the title compound.

Yield: 44.7%.

$^1$H-NMR(CDCl$_3$, δ ):7.17(1H, d, J=9.0 Hz) 7.72-7.75(2H, m), 7.86(1H, s), 8.17(2H, s), 8.35(1H, s) 11.88(1H, s).

[2-Hydroxy-5-(trifluoromethyl)benzoic acid: Refer to "Chemical and Pharmaceutical Bulletin", 1996, Vol. 44, No. 4, p. 734-745.]

(2) 2-(Morpholinocarbonyl)oxy-5-trifluoromethyl-N-[3,5-bis(trifluoromethyl)phenyl]-benzamide(Compound No. 79)

Using 2-hydroxy-5-trifluoromethyl-N-[3,5-bis(trifluoromethyl)-phenyl]benzamide and morpholine-4-carbonyl chloride as the raw materials, the same operation as the Example 71 gave the title compound.

Yield: 83.6%.

$^1$H-NMR(DMSO-$d_6$): δ 3.30-3.38(2H, m), 3.48-3.58(6H, m), 7.59(1H, d, J=8.4 Hz), 7.87(1H, s), 8.01(1H, ddd, J=8.4, 2.4, 0.6 Hz), 8.13(1H, d, J=2.1 Hz), 8.39(2H, s), 11.14(1H, s).

Example 80

Preparation of the Compound of Compound No. 80

(1) 4-Chloro-2-hydroxy-N-[3,5-bis(trifluoromethyl)phenyl]benzamide

Using 4-chlorosalicylic acid and 3,5-bis(trifluoromethyl)aniline as the raw materials, the same operation as the Example 1(1) gave the title compound.

Yield: 55.8%.

$^1$H-NMR(DMSO-$d_6$): δ 7.05-7.08(2H, m), 7.84-7.87(2H, m), 8.45(2H, s), 10.84(1H, s) 11.64(1H, brs).

(2) 4-Chloro-2-(morpholinocarbonyl)oxy-N-[3,5-bis(trifluoromethyl)phenyl]benzamide (Compound No. 80)

Using 4-chloro-2-hydroxy-N-[3,5-bis(trifluoromethyl)phenyl]benzamide and morpholine-4-carbonyl chloride as the raw materials, the same operation as the Example 71 gave the title compound.

Yield: 84.1%.

$^1$H-NMR(CDCl$_3$): δ 3.56-3.68(8H, m), 7.18(1H, d, J=1.8 Hz), 7.35(1H, dd, J=8.4, 1.8 Hz), 7.64(1H, s), 7.67(1H, d, J=8.4 Hz), 8.08(2H, s), 8.91(1H, s).

Example 81

Preparation of the Compound of Compound No. 81

(1) 2-Hydroxy-5-iodo-N-[3,5-bis(trifluoromethyl)phenyl]benzamide

Using 5-iodosalicylic acid and 3,5-bis(trifluoromethyl)aniline as the raw materials, the same operation as the Example 1(1) gave the title compound.

Yield: 62.2%.

$^1$H-NMR(DMSO-$d_6$): δ 6.86(1H, d, J=8.4 Hz), 7.74(1H, dd, J=8.7, 2.4 Hz), 7.84(1H, s), 8.13(1H, d, J=2.1 Hz), 8.84 (2H, s), 10.82(1H, s), 11.41(1H, s).

(2) 2-Hydroxy-5-phenyl-N-[3,5-bis(trifluoromethyl)phenyl]benzamide

Tetrakis(triphenylphosphine)palladium (16 mg, 0.0014 mmol) was added to a solution of 2-hydroxy-5-iodo-N-[3,5-bis(trifluoromethyl)phenyl]benzamide (200 mg, 0.42 mmol) in 1,2-dimethoxyethane (3 mL) under argon atmosphere, and the mixture was stirred at room temperature for 5 minutes. Then dihydroxyphenylborane (57 mg, 0.47 mmol) and 1 mmol/L aqueous sodium carbonate (1.3 mL) were added and the mixture was refluxed for 2 hours. After the reaction mixture was cooled to room temperature, it was poured into diluted hydrochloric acid and extracted with ethyl acetate. After the ethyl acetate layer was washed successively with water and brine, dried over anhydrous sodium sulfate, the residue obtained by evaporation of the solvent under reduced pressure was purified by column chromatography on silica gel (n-hexane:ethyl acetate=6:1→3:1) to give the title compound (109 mg, 61.1%) as a white crystal.

$^1$H-NMR(DMSO-$d_6$): δ 7.12(1H, d, J=8.7 Hz), 7.33-7.38 (1H, m), 7.48(2H, t, J=7.5 Hz), 7.67-7.70(2H, m), 7.79(1H, dd, J=8.4, 2.4 Hz), 7.87(1H, s), 8.17(1H, d, J=2.4 Hz), 8.49 (2H, s), 10.92(1H, s), 11.41(1H, s).

(3) 2-(Morpholinocarbonyl)oxy-5-phenyl-N-[3,5-bis(trifluoromethyl)phenyl]benzamide (Compound No. 81)

Using 2-hydroxy-5-phenyl-N-[3,5-bis(trifluoromethyl)phenyl]benzamide and morpholine-4-carbonyl chloride as the raw materials, the same operation as the Example 71 gave the title compound.

Yield: 91.4%.
¹H-NMR(DMSO-d₆): δ 3.30-3.39(2H, m), 3.48-3.61(6H, m), 7.39-7.45(2H, m), 7.49-7.54(2H, m), 7.76-7.79(2H, m), 7.85(1H, s), 7.90(1H, dd, J=8.7, 2.4 Hz), 8.01(1H, d, J=2.4 Hz), 8.43(2H, s), 11.05(1H, s).

Example 82

Preparation of the Compound of Compound No. 82

(1) 3-Hydroxy-N-[3,5-bis(trifluoromethyl)phenyl]-2-naphthamide
Using 3-hydroxynaphthalene-2-carboxylic acid and 3,5-bis(trifluoromethyl)aniline as the raw materials, the same operation as the Example 1(1) gave the title compound.
Yield: 46.9%.
¹H-NMR(DMSO-d₆): δ 7.36-7.41(2H, m), 7.50-7.55(1H, m), 7.79(1H, d, J=8.2 Hz), 7.85(1H, d, J=0.6 Hz), 7.96(1H, d, J=8.0 Hz), 8.51(2H, s), 10.98(1H, s), 11.05(1H, s).

(2) 3-(Morpholinocarbonyl)oxy-N-[3,5-bis(trifluoromethyl)phenyl]-2-naphthamide (Compound No. 82)
Using 3-hydroxy-N-[3,5-bis(trifluoromethyl)phenyl]-2-naphthamide and morpholine-4-carbonyl chloride as the raw materials, the same operation as the Example 71 gave the title compound.
Yield: 81.2%.
¹H-NMR(DMSO-d₆): δ 3.42-3.65(8H, m), 7.59-7.70(2H, m), 7.82-7.87(2H, m), 7.99(1H, d, J=7.8 Hz), 8.09(1H, d, J=7.8 Hz), 8.38(1H, s), 8.46(2H, s), 11.15(1H, s).

Example 83

Preparation of the Compound of Compound No. 83

(1) 2-Hydroxy-N-[3,5-bis(trifluoromethyl)phenyl]-1-naphthamide
Using 2-hydroxynaphthalene-1-carboxylic acid and 3,5-bis(trifluoromethyl)aniline as the raw materials, the same operation as the Example 1(1) gave the title compound.
Yield: 30.2%.
¹H-NMR(DMSO-d₆): δ 7.27(1H, d, J=8.8 Hz), 7.32-7.38 (1H, m), 7.45-7.50(1H, m), 7.72(1H, d, J=8.5 Hz), 7.82-7.93 (3H, m), 8.50(1H, s), 10.28(1H, s), 11.07(1H, brs).

(2) 2-(Morpholinocarbonyl)oxy-N-[3,5-bis(trifluoromethyl)phenyl]-1-naphthamide (Compound No. 83)
Using 3-hydroxy-N-[3,5-bis(trifluoromethyl)phenyl]-2-naphthamide and morpholine-4-carbonyl chloride as the raw materials, the same operation as the Example 71 gave the title compound.
Yield: 98.0%.
¹H-NMR(CDCl₃): δ 3.43-3.67(8H, m) 7.25(1H, d, J=9.0 Hz), 7.54-7.65(2H, m), 7.69(1H, s), 7.92(1H, d, 7.8, 2.1 Hz), 7.98(1H, d, J=9.0 Hz), 8.08(1H, d, 8.1, 1.2 Hz), 8.20(2H, s), 8.92(1H, s).

Example 84

Preparation of the Compound of Compound No. 84

(1) 5-Chloro-N-[2-chloro-5-(trifluoromethyl)phenyl]-2-hydroxybenzamide.
Using 5-chlorosalicylic acid and 2-chloro-5-(trifluoromethyl)aniline as the raw materials, the same operation as the Example 1(1) gave the title compound.

Yield: 49.1%.
¹H-NMR(DMSO-d₆): δ 7.09(1H, d, J=9.0 Hz), 7.53(1H, dd, J=9.0, 3.0 Hz), 7.55(1H, dd, J=8.4, 2.7 Hz), 7.83(1H, d, J=8.4 Hz), 7.98(1H, d, J=3.0 Hz), 8.88(1H, d, J=2.7 Hz), 11.14(1H, s), 12.39(1H, s).

(2) 5-Chloro-N-[2-chloro-5-(trifluoromethyl)phenyl]-2-[(morpholinocarbonyl)oxy]-benzamide (Compound No. 84)
Using 5-chloro-N-[2-chloro-5-(trifluoromethyl)phenyl]-2-hydroxybenzamide and morpholine-4-carbonyl chloride as the raw materials, the same operation as the Example 71 gave the title compound.
Yield: 95.1%.
¹H-NMR(CDCl₃): δ 3.54-3.68(8H, m), 7.14(1H, d, J=8.7 Hz), 7.35-7.39(1H, m), 7.50(1H, dd, J=8.7, 2.7 Hz), 7.54(1H, d, J=8.4 Hz), 7.84(1H, d, J=2.7 Hz), 8.61(1H, s), 8.87(1H, d, J=1.8 Hz).

Example 85

Preparation of the Compound of Compound No. 85

(1) 5-Bromo-N-[2-chloro-5-(trifluoromethyl)phenyl]-2-hydroxybenzamide
Using 5-bromosalicylic acid and 2-chloro-5-(trifluoromethyl)aniline as the raw materials, the same operation as the Example 1(1) gave the title compound.
Yield: 34.2%.
¹H-NMR(DMSO-d₆): δ 7.04(1H, d, J=8.7 Hz), 7.56(1H, ddd, J=8.1, 2.4, 1.2 Hz), 7.64(1H, dd, J=8.7, 2.7 Hz), 7.83 (1H, dd, J=8.1, 1.2 Hz), 8.11(1H, d, J=2.7 Hz), 8.87(1H, d, J=2.4 Hz), 11.12(1H, s), 12.42(1H, s).

(2) 5-Bromo-N-[2-chloro-5-(trifluoromethyl)phenyl]-2-[(morpholinocarbonyl)oxy]-benzamide(Compound No. 85)
Using 5-bromo-N-[2-chloro-5-(trifluoromethyl)phenyl]-2-hydroxybenzamide and morpholine-4-carbonyl chloride as the raw materials, the same operation as the Example 71 gave the title compound.
Yield: 68.1%.
¹H-NMR(DMSO-d₆): δ 3.30-3.75, (8H, m), 7.29(1H, d, J=8.4 Hz), 7.67(1H, dd, J=8.4, 1.8 Hz), 7.78(1H, dd, J=8.4, 2.4 Hz), 7.83(1H, d, J=8.4), 7.91(1H, d, J=2.4 Hz), 8.04(1H, d, J=2.1 Hz) 10.39(1H, s).

Example 86

Preparation of the Compound of Compound No. 86

(1) 5-Bromo-2-hydroxy-N-[2-methoxy-5-(trifluoromethyl)phenyl]benzamide
Using 5-bromosalicylic acid and 2-methoxy-5-(trifluoromethyl)aniline as the raw materials, the same operation as the Example 1(1) gave the title compound.
Yield: 71.3%.
¹H-NMR(DMSO-d₆): δ 3.99(3H, s), 7.03(1H, d, J=9.0 Hz), 7.30(1H, d, J=8.7 Hz), 7.47-7.51(1H, m), 7.61(1H, dd, J=9.0, 2.4 Hz), 8.10(1H, d, J=2.4 Hz), 8.82(1H, d, J=2.1 Hz) 11.03(1H, s), 12.19(1H, s).

(2) 5-Bromo-N-[2-methoxy-5-(trifluoromethyl)phenyl]-2-[(morpholinocarbonyl)oxy]-benzamide(Compound No. 86)
Using 5-bromo-2-hydroxy-N-[2-methoxy-5-(trifluoromethyl)phenyl]benzamide and morpholine-4-carbonyl chloride as the raw materials, the same operation as the Example 71 gave the title compound.
Yield: 94.9%.

¹H-NMR(CDCl₃): δ 3.52-3.65(8H, m), 3.94(3H, s), 6.98 (1H, d, J=9.0 Hz), 7.10(1H, d, J=8.4 Hz), 7.37-7.41(1H, m), 7.62(1H, dd, J=8.7, 2.7 Hz), 7.89(1H, d, J=2.4 Hz), 8.52(1H, s), 8.84(1H, d, J=1.8 Hz).

Example 87

Preparation of the Compound of Compound No. 87

(1) 5-Bromo-2-hydroxy-N-[3-methoxy-5-(trifluoromethyl) phenyl]benzamide

Using 5-bromosalicylic acid and 3-methoxy-5-(trifluoromethyl)aniline as the raw materials, the same operation as the Example 1(1) gave the title compound.

Yield: 58.8%.
¹H-NMR(DMSO-d₆): δ 3.85(3H, s), 6.98(1H, d, J=8.7 Hz), 7.03(1H, s), 7.57-7.61(2H, m), 7.77(1H, s), 8.00(1H, d, J=2.4 Hz), 10.57(1H, s), 11.56(1H, s).

(2) 5-Bromo-N-[3-methoxy-5-(trifluoromethyl)phenyl]-2-[(morpholinocarbonyl)oxy]-benzamide(Compound No. 87)

Using 5-bromo-2-hydroxy-N-[3-methoxy-5-(trifluoromethyl)phenyl]benzamide and morpholine-4-carbonyl chloride as the raw materials, the same operation as the Example 71 gave the title compound.

Yield: 85.8%.
¹H-NMR(CDCl₃): δ 3.56-3.66(8H, m), 3.87(3H, s), 6.92 (1H, m), 7.03(1H, d, J=8.7 Hz), 7.23(1H, m), 7.57-7.61(2H, m), 7.83(1H, d, J=2.7 Hz), 8.54(1H, s).

Example 88

Preparation of the Compound of Compound No. 88

(1) 5-Bromo-N-[2-chloro-4-(trifluoromethyl)phenyl]-2-hydroxybenzamide

Using 5-bromosalicylic acid and 2-chloro-4-(trifluoromethyl)aniline as the raw materials, the same operation as the Example 1(1) gave the title compound.

Yield: 34.9%.
¹H-NMR(DMSO-d₆): δ 7.04(1H, d, J=8.7 Hz), 7.64(1H, dd, J=8.7, 2.7 Hz), 7.79(1H, dd, J=9.0, 2.1 Hz), 7.99(1H, d, J=2.1 Hz), 8.11(1H, d, J=2.4 Hz), 8.73(1H, d, J=9.0 Hz), 11.15(1H, s), 12.42(1H, s).

(2) 5-Bromo-N-[2-chloro-4-(trifluoromethyl)phenyl]-2-[(morpholinocarbonyl)oxy]-benzamide(Compound No. 88)

Using 5-bromo-N-[2-chloro-4-(trifluoromethyl)phenyl]-2-hydroxybenzamide and morpholine-4-carbonyl chloride as the raw materials, the same operation as the Example 71 gave the title compound.

Yield: 93.5%.
¹H-NMR(CDCl₃): δ 3.54-3.68(8H, m), 7.08(1H, d, J=8.7 Hz), 7.61(1H, d, J=9.0 Hz), 7.66(1H, dd, J=8.4, 2.4 Hz), 7.69(1H, d, J=1.8 Hz), 7.99(1H, d, J=2.4 Hz), 8.65(1H, s), 8.70(1H, d, J=8.7 Hz).

Example 89

Preparation of the Compound of Compound No. 89

(1) 5-Chloro-N-(3,5-dichlorophenyl)-2-hydroxybenzamide

Using 5-chlorosalicylic acid and 3,5-dichloroaniline as the raw materials, the same operation as the Example 1(1) gave the title compound.

Yield: 41.2%.
¹H-NMR(DMSO-d₆): δ 7.03(1H, d, J=9.0 Hz), 7.36-7.37 (1H, m), 7.48(1H, dd, J=8.7, 2.7 Hz), 7.83-7.84(3H, m), 10.56(1H, s), 11.44(1H, s).

(2) 5-Chloro-N-(3,5-dichlorophenyl)-2-[(morpholinocarbonyl)oxy]benzamide(Compound No. 89)

Using 5-chloro-N-(3,5-dichlorophenyl)-2-hydroxybenzamide and morpholine-4-carbonyl chloride as the raw materials, the same operation as the Example 71 gave the title compound.

Yield: 83.2%.
¹H-NMR(DMSO-d₆): δ 3.33(2H, s), 3.53(6H, s), 7.34-7.37(2H, m), 7.65(1H, dd, J=8.7, 2.7 Hz), 7.74-7.76(3H, m), 10.74(1H, s).

Example 90

Preparation of the Compound of Compound No. 90

(1) 5-Bromo-N-{3,5-bis[(1,1-dimethyl)ethyl]phenyl}-2-hydroxybenzamide

Using 5-bromosalicylic acid and 3,5-bis[(1,1-dimethyl)ethyl]aniline as the raw material, the same operation as the Example 1(1) gave the title compound.

Yield: 45.2%.
¹H-NMR(DMSO-d₆, δ ):1.30(18H, s), 6.95(1H, d, J=8.7 Hz), 7.20(1H, t, J=1.5 Hz), 7.56(2H, d, J=1.5 Hz), 7.58(1H, dd, J=8.7, 2.4 Hz), 8.12(1H, d, J=2.7 Hz), 10.39(1H, s), 11.98(1H, s).

(2) 5-Bromo-N-{3,5-bis[(1,1-dimethyl)ethyl]phenyl}-2-[(morpholinocarbonyl)oxy]-benzamide(Compound No. 90)

Using 5-bromo-N-{3,5-bis[(1,1-dimethyl)ethyl]phenyl}-2-hydroxybenzamide and morpholine-4-carbonyl chloride as the raw materials, the same operation as the example 71 gave the title compound.

Yield: 93.6%.
¹H-NMR(CDCl₃): δ 1.33(18H, s), 3.54-3.64(8H, m), 7.05 (1H, d, J=8.4 Hz), 7.22(1H, t, J=1.5 Hz), 7.44(2H, d, J=1.5 Hz), 7.59(1H, dd, J=8.7, 2.7 Hz), 7.87(1H, d, J=2.1 Hz), 8.13(1H, s).

Example 91

Preparation of the Compound of Compound No. 91

(1) 5-Chloro-2-hydroxy-N-[2,5-bis(trifluoromethyl)phenyl]benzamide

Using 5-chlorosalicylic acid and 2,5-bis(trifluoromethyl) aniline as the raw material, the same operation as the Example 1(1) gave the title compound.

Yield: 3.6%.
¹H-NMR(CDCl₃): δ 7.03(1H, d, J=8.7 Hz), 7.43-7.48(2H, m), 6.61(1H, d, J=8.1 Hz), 7.85(1H, d, J=8.4 Hz), 8.36(1H, brs), 8.60(1H, s), 11.31(1H, s).

(2) 5-Chloro-2-(morpholinocarbonyl)oxy-N-[2,5-bis(trifluoromethyl)phenyl]benzamide (Compound No. 91)

Using 5-chloro-2-hydroxy-N-[2,5-bis(trifluoromethyl) phenyl]benzamide and morpholine-4-carbonyl chloride as the raw materials, the same operation as the Example 71 gave the title compound.

Yield: 92.1%.
¹H-NMR(CDCl₃): δ 3.55-3.69(8H, m), 7.12(1H, d, J=8.7 Hz), 7.50(1H, dd, J=8.4,2.4 Hz), 7.57(1H, d, J=8.4 Hz), 7.81 (1H, d, J=8.4 Hz), 7.82(1H, d, J=2.7 Hz), 8.41(1H, s), 8.59 (1H, s).

Example 92

Preparation of the Compound of Compound No. 92

(1) 4-Bromo-2,2,6,6-tetramethyl-3,5-heptanedione(α-Bromo-dipivaloylmethane)

N-bromosuccinimide(965.8 mg, 5.42 mmol) was added to a solution of 2,2,6,6-tetramethyl-3,5-heptanedione (dipivaloylmethane; 1.00 g, 5.42 mmol) in carbon tetrachloride(10 mL), and the mixture was refluxed for 2 hours. After the reaction mixture was cooled to room temperature, the insoluble matter was filtered off, and the filtrate was evaporated under reduced pressure to give the title compound(1.42 g, quant.) as a white crystal.

$^1$H-NMR(CDCl$_3$): δ 1.27(18H, s), 5.67(1H, s).

(2) 2-Amino-4-[(1,1-dimethyl)ethyl]-5-[(2,2-dimethyl)propionyl]thiazole

A mixture of 4-bromo-2,2,6,6-tetramethyl-3,5-heptanedione (α-bromo-dipivaloylmethane; 1.42 g, 5.40 mmol), thiourea(451.8 mg, 5.94 mmol) and ethanol(15 mL) was refluxed for 2 hours. After the reaction mixture was cooled to room temperature, it was poured into saturated aqueous sodium hydrogen carbonate and extracted with ethyl acetate. After the ethyl acetate layer was washed successively with water and brine, dried over anhydrous sodium sulfate, the residue obtained by evaporation of the solvent under reduced pressure was crystallized by dichloromethane/n-hexane to give the title compound(1.23 g, 94.5%) as a white crystal.

$^1$H-NMR(CDCl$_3$): δ 1.26(9H, s), 1.29(9H, s), 5.03(2H, s).

(3) 5-Chloro-N-{4-[(1,1-dimethyl)ethyl]-5-[(2,2-dimethyl)propionyl]thiazol-2-yl}-2-hydroxybenzamide A mixture of 5-chlorosalicylic acid (143.6 mg, 0.83 mmol), 2-amino-4-[(1,1-dimethyl)ethyl]-5-[(2,2-dimethyl)propionyl]thiazole (200.0 mg, 0.83 mmol), phosphorus trichloride (40 μL, 0.46 mmol) and chlorobenzene (4 mL) was refluxed for 3 hours. After the reaction mixture was cooled to room temperature, the residue obtained by concentration of the solvent under reduced pressure was purified by column chromatography on silica gel(n-hexane:ethyl acetate=3:1) to give the title compound(159.1 mg, 48.4%) as a white powder.

$^1$H-NMR(CDCl$_3$): δ 1.33(9H, s), 1.35(9H, s), 6.99(1H, d, J=8.7 Hz), 7.43(1H, dd, J=9.0, 2.7 Hz), 7.70(1H, d, J=2.7 Hz), 10.52(2H, br).

(4) 5-Chloro-N-{4-[(1,1-dimethyl)ethyl]-5-[(2,2-dimethyl)propionyl]thiazol-2-yl}-2-[(morpholinocarbonyl)oxy]benzamide(Compound No. 92)

Using 5-chloro-N-{4-[(1,1-dimethyl)ethyl]-5-[(2,2-dimethyl)propionyl]-thiazol-2-yl}-2-hydroxybenzamide and morpholine-4-carbonyl chloride as the raw materials, the same operation as the Example 71 gave the title compound.

Yield: 93.1%.

$^1$H-NMR(CDCl$_3$): δ 1.32(9H, s), 1.33(9H, s), 3.60(2H, brs), 3.75(2H, brs), 3.83(4H, brs), 7.21(1H, d, J=8.4 Hz), 7.54(1H, dd, J=8.4, 2.7 Hz), 8.01(1H, d, J=2.7 Hz), 9.78(1H, brs).

Example 93

Preparation of the Compound of Compound No. 93

A mixture of 5-chloro-2-hydroxy-N-[3,5-bis(trifluoromethyl)phenyl]benzamide 1 sodium salt(compound of Example 43(1); 203 mg, 0.50 mmol), methyl iodide(85 mg, 0.60 mmol) and N,N-dimethylformamide(5 mL) was stirred at 60° C. for 2 hours. The residue obtained by evaporation of the solvent under reduced pressure was purified by column chromatography on silica gel(n-hexane:ethyl acetate=3:1) to give the title compound(156.9 mg, 79.1%) as a white crystal.

$^1$H-NMR(DMSO-d$_6$): δ 3.89(3H, s), 7.25(1H, d, J=8.7 Hz), 7.60(1H, dd, J=9.0, 2.7 Hz), 7.66(1H, d, J=2.7 Hz), 7.84(1H, s), 8.43(2H, s), 10.83(1H, s).

Example 94

Preparation of the Compound of Compound No. 94

Using 5-[(1,1-dimethyl)ethyl]-2-methoxybenzoic acid and 3,5-bis(trifluoromethyl)aniline as the raw materials, the same operation as the Example 1(1) gave the title compound.

Yield: 75.0%.

$^1$H-NMR(DMSO-d$_6$): δ 1.29(9H, s), 3.89(3H, s), 7.13(1H, d, J=8.7 Hz), 7.63(1H, dd, J=8.7, 2.7 Hz), 7.65(1H, d, J=2.4 Hz), 7.80(1H, s), 8.47(2H, s), 10.70(1H, s).

Example 95

Preparation of the Compound of Compound No. 95

Using 5-chloro-2-hydroxy-N-[3,5-bis(trifluoromethyl)phenyl]benzamide 1 sodium salt (compound of Example 43(1)) and ethyl iodide as the raw materials, the same operation as the Example 93 gave the title compound.

Yield: 70.7%.

$^1$H-NMR(DMSO-d$_6$): δ 1.34(3H, t, J=6.9 Hz), 4.16(4H, q, J=6.9 Hz), 7.23(1H, d, J=9.0 Hz), 7.57(1H, dd, J=9.0, 2.7 Hz), 7.65(1H, d, J=2.7 Hz), 7.83(1H, s), 8.40(2H, s), 10.80(1H, s).

Example 96

Preparation of the Compound of Compound No. 96

Isopropyl bromide(60 μL, 0.64 mmol) and potassium carbonate(143.7 mg, 1.04 mmol) were added to a solution of 5-chloro-2-hydroxy-N-[3,5-bis(trifluoromethyl)-phenyl]benzamide (compound of Example 1(1); 0.20 g, 0.52 mmol) in N,N-dimethylformamide (4 mL), and the mixture was stirred at 60° C. for 6 hours. After the reaction mixture was cooled to room temperature, it was poured into water and extracted with ethyl acetate. After the ethyl acetate layer was washed successively with water and brine, dried over anhydrous sodium sulfate, the residue obtained by evaporation of the solvent under reduced pressure was purified by column chromatography on silica gel (n-hexane:ethyl acetate=4:1) to give the title compound(164.9 mg, 74.5%) as a white crystal.

$^1$H-NMR(CDCl$_3$): δ 1.55(6H, d, J=6.0 Hz), 4.85(1H, m), 7.00(1H, d, J=9.0 Hz), 7.46(1H, dd, J=8.7, 2.7 Hz), 7.63(1H, s), 8.14(2H, s), 8.26(1H, d, J=2.7 Hz), 10.47(1H, s).

Example 97

Preparation of the Compound of Compound No. 97

A solution of 5-chloro-2-hydroxy-N-[3,5-bis(trifluoromethyl)-phenyl]benzamide(compound of Example 1(1); 0.20 g, 0.52 mmol) in tetrahydrofuran(2 mL) was added to a suspension of 60% sodium hydride(41.6 mg, 1.04 mmol) in N,N-dimethylformamide(1 mL), and the mixture was stirred at room temperature for 10 minutes. Then, chloromethyl methyl ether (50 μL, 0.65 mmol) was added and the mixture was further stirred at room temperature for 3 hours. The reaction mixture was poured into diluted hydrochloric acid and extracted with ethyl acetate. After the ethyl acetate layer was washed with brine, dried over anhydrous sodium sulfate, the residue obtained by evaporation of the solvent under reduced pressure was purified by column chromatography on silica gel(n-hexane:ethyl acetate=4:1→3:1) to give the title compound(44.5 mg, 20.0%) as a white crystal.
¹H-NMR(DMSO-d₆): δ 3.38(3H, s), 5.30(2H, s), 7.31(1H, d, J=9.0 Hz), 7.57(1H, dd, J=8.7, 2.7 Hz), 7.66(1H, d, J=2.7 Hz), 7.84(1H, s), 8.41(2H, s), 10.93(1H, s).

Example 98

Preparation of the Compound of Compound No. 98

A mixture of 5-chloro-2-hydroxy-N-[3,5-bis(trifluoromethyl)phenyl]benzamide 1 sodium salt(compound of Example 43(1); 406 mg, 1.00 mmol), acetic acid bromomethyl ester(184 mg, 1.20 mmol), sodium iodide(30 mg, 0.20 mmol) and N,N-dimethylformamide(5 mL) was heated at 50° C. for 1 hour under argon atmosphere. The residue obtained by evaporation of the solvent under reduced pressure was purified by column chromatography on silica gel(n-hexane:ethyl acetate=3:1) to give the title compound(281.3 mg, 61.7%) as a white crystal.
¹H-NMR(DMSO-d₆): δ 2.05(3H, s), 5.82(2H, s), 7.40(1H, d, J=8.7 Hz), 7.64(1H, dd, J=8.7, 2.7 Hz), 7.70(1H, d, J=2.7 Hz), 7.85(1H, s), 8.38(2H, s), 10.88(1H, s).

Example 99

Preparation of the Compound of Compound No. 99

Using 5-chloro-2-hydroxy-N-[3,5-bis(trifluoromethyl)phenyl]benzamide 1 sodium salt(compound of Example 43(1)) and pivalic acid chloromethyl ester as the raw materials, the same operation as the Example 98 gave the title compound.
Yield: 71.3%.
¹H-NMR(CDCl₃): δ 1.13(9H, s), 5.97(2H, s), 7.17(1H, d, J=9.0 Hz), 7.51(1H, dd, J=8.7, 2.7 Hz), 7.64(1H, s), 8.24(1H, d, J=2.7 Hz), 8.32(2H, s), 9.84(1H, s).

Example 100

Preparation of the Compound of Compound No. 100

A solution of 5-chloro-2-hydroxy-N-[3,5-bis(trifluoromethyl)-phenyl]benzamide (compound of Example 1(1); 0.2 g, 0.5 mmol), carbonic acid 1-chloroethyl ethyl ester(119 mg, 0.8 mmol), potassium tert-butoxide(88 mg, 0.5 mmol) and 18-crown-6 (catalytic amount) in acetonitrile(8 mL) was stirred at 60° C. for 8 hours under argon atmosphere. After the reaction mixture was cooled to room temperature, it was diluted with ethyl acetate. After the ethyl acetate solution was washed successively with water and brine, dried over anhydrous sodium sulfate, the residue obtained by evaporation of the solvent under reduced pressure was purified by column chromatography on silica gel(n-hexane:ethyl acetate=3:1) to give the title compound(56 mg, 21.5%) as a white powder.
¹H-NMR(CDCl₃): δ 1.24(3H, t, J=7.2 Hz), 1.85(3H, d, J=5.4 Hz), 4.01-4.27(2H, m), 6.50(1H, q, J=5.4 Hz), 7.11(1H, d, J=9.0 Hz), 7.48(1H, dd, J=9.0, 2.7 Hz), 7.64(1H, d, J=0.9 Hz), 8.14(1H, d, J=2.7 Hz), 8.19(2H, s), 9.83(1H, brs).

Example 101

Preparation of the Compound of Compound No. 101

(1) 1-[(Chloromethoxy)carbonyl]piperidine
Piperidine(1.06 g, 12.5 mmol) was added to a solution of chloroformic acid chloromethyl ester(645 mg, 5 mmol) in n-hexane (15 mL) at 0° C. under argon atmosphere, and the mixture was stirred at the same temperature for 30 minutes. The reaction mixture was diluted with ethyl acetate. After the ethyl acetate solution was washed successively with 1N hydrochloric acid(20 mL), water and brine, dried over anhydrous magnesium sulfate, the solvent was evaporated under reduced pressure to give the title compound(796 mg, 89.6%) as a colorless oil.
¹H-NMR(CDCl₃): δ 1.54-1.63(6H, m), 3.43-3.47(4H, m), 5.80(2H, s).

(2) 5-Chloro-2-[(piperidinocarbonyl)oxy]methoxy-N-[3,5-bis(trifluoromethyl)phenyl]-benzamide(Compound No. 101)
Using 5-chloro-2-hydroxy-N-[3,5-bis(trifluoromethyl)phenyl]benzamide 1 sodium salt (compound of Example 43(1)) and 1-[(chloromethoxy)carbonyl]piperidine as the raw materials, the same operation as the Example 98 gave the title compound.
Yield: 86.2%.
¹H-NMR(CDCl₃): δ 1.38-1.58(6H, m), 3.34(4H, t, J=5.7 Hz), 5.93(2H, s), 7.12(1H, d, J=9.0 Hz), 7.50(1H, dd, J=8.7, 2.7 Hz), 7.62(1H, s), 8.22(1H, d, J=2.7 Hz), 8.41(2H, s), 10.07(1H, s).

Example 102

Preparation of the Compound of Compound No. 102

(1) 4-[(Chloromethoxy)carbonyl]morpholine
Using chloroformic acid chloromethyl ester and morpholine as the raw materials, the same operation as the Example 101(1) gave the title compound as a crude product, and the crude product was used for the next reaction without further purification.

(2) 5-Chloro-2-[(morpholinocarbonyl)oxy]methoxy-N-[3,5-bis(trifluoromethyl)phenyl]-benzamide(Compound No. 102)
Using 5-chloro-2-hydroxy-N-[3,5-bis(trifluoromethyl)phenyl]benzamide 1 sodium salt (compound of Example 43(1)) and 4-[(chloromethoxy)carbonyl]morpholine as the raw materials, the same operation as the Example 98 gave the title compound.
Yield: 61.5%.
¹H-NMR(CDCl₃): δ 3.40-3.42(4H, m), 3.55-3.58(4H, m), 5.95(2H, s), 7.12(1H, d, J=8.7 Hz), 7.50(1H, dd, J=9.0, 2.7 Hz), 7.63(1H, s), 8.22(1H, d, J=2.7 Hz), 8.38(2H, s), 10.00 (1H, s).

Example 103

Preparation of the Compound of Compound No. 103

(1) Ethyl 1-[(chloromethoxy)carbonyl]isonipecotate
Using chloroformic acid chloromethyl ester and ethyl isonipecotate as the raw materials, the same operation as the Example 101(1) gave the title compound as a crude product, and the crude product was used for the next reaction without further purification.

(2) 5-Chloro-2-({[4-(ethoxycarbonyl)piperidin-1-yl]carbonyl}oxy)methoxy-N-[3,5-bis(trifluoromethyl)phenyl]benzamide(Compound No. 103)
Using 5-chloro-2-hydroxy-N-[3,5-bis(trifluoromethyl)phenyl]benzamide 1 sodium salt (compound of Example 43(1)) and ethyl 1-[(chloromethoxy)carbonyl]isonipecotate as the raw materials, the same operation as the Example 98 gave the title compound.
Yield: 65.7%.
¹H-NMR(CDCl₃): δ 1.24(3H, t, J=7.2 Hz), 1.49-1.61(2H, m), 1.82(2H, m), 2.38-2.48(1H, m), 2.81-2.98(2H, m), 3.87-

3.98(2H, m), 4.12(2H, q, J=7.2 Hz), 5.89(1H, d, J=6.3 Hz), 5.98(1H, d, J=6.6 Hz), 7.12(1H, d, J=8.7 Hz), 7.50(1H, dd, J=8.7, 2.7 Hz), 7.62(1H, s), 8.22(1H, d, J=2.7 Hz), 8.39(2H, s), 10.03(1H, s).

Example 104

Preparation of the Compound of Compound No. 104

2N Aqueous sodium hydroxide(0.25 mL, 0.5 mmol) was added to a solution of 5-chloro-2-({[4-(ethoxycarbonyl)piperidin-1-yl]carbonyl}oxy)methoxy-N-[3,5-bis(trifluoromethyl)phenyl]benzamide(Compound No. 103; 149 mg, 0.25 mmol) in methanol(5 mL), and the mixture was stirred at 50° C. for 30 minutes. After the reaction mixture was cooled to room temperature, it was poured into diluted hydrochloric acid, and the separated solid was filtered. After the solid was washed with water, it was recrystallized from ethyl acetate/n-hexane to give the title compound(76.0 mg, 53.4%) as a white crystal.

$^1$H-NMR(DMSO-$d_6$): δ 1.28-1.39(2H, m), 1.75(2H, d, J=12.3 Hz), 2.36-2.41(1H, m), 2.78-2.95(2H, m), 3.80(2H, d, J=13.5 Hz), 5.83(2H, d, J=5.1 Hz), 7.43(1H, d, J=9.3 Hz), 7.64(1H, dd, J=9.0, 2.7 Hz), 7.71(1H, d, J=2.4 Hz), 7.84(1H, s), 8.39(2H, s), 10.80(1H, s).

Example 105

Preparation of the Compound of Compound No. 105

(1) Diethyl N-[(chloromethoxy)carbonyl]iminodiacetate

Using chloroformic acid chloromethyl ester and diethyl iminodiacetate as the raw materials, the same operation as the Example 101(1) gave the title compound as a crude product, and the crude product was used for the next reaction without further purification.

(2) 2-({N,N-bis[(ethoxycarbonyl)methyl]carbamoyl}oxy)methoxy-5-chloro-N-[3,5-bis(trifluoromethyl)phenyl]benzamide(Compound No. 105)

Using 5-chloro-2-hydroxy-N-[3,5-bis(trifluoromethyl)phenyl]benzamide 1 sodium salt (compound of Example 43(1)) and diethyl N-[(chloromethoxy)carbonyl]iminodiacetate as the raw materials, the same operation as the Example 98 gave the title compound.

Yield: 38.6%.

$^1$H-NMR(CDCl$_3$): δ 1.16(3H, t, J=7.2 Hz), 1.20(3H, t, J=7.2 Hz), 3.99(2H, q, J=7.2 Hz), 4.01(2H, s), 4.07(2H, s), 4.08(2H, q, J=7.2 Hz), 5.97(2H, s), 7.10(1H, d, J=9.0 Hz), 7.47(1H, dd, J=9.0, 2.7 Hz), 7.61(1H, s), 8.19(1H, d, J=2.7 Hz), 8.37(2H, s), 9.82(1H, s).

Example 106

Preparation of the Compound of Compound No. 106

Using 2-({N,N-bis[(ethoxycarbonyl)methyl]carbamoyl}oxy)methoxy-5-chloro-N-[3,5-bis(trifluoromethyl)phenyl]benzamide(Compound No. 105) as the raw material, the same operation as the Example 104 gave the title compound.

Yield: 98.3%.

$^1$H-NMR(DMSO-$d_6$): δ 3.96(2H, s), 4.02(2H, s), 5.84(2H, s), 7.34(1H, d, J=9.0 Hz), 7.59(1H, dd, J=8.7, 2.4 Hz), 7.72(1H, d, J=2.7 Hz), 7.84(1H, s), 8.40(2H, s), 10.77(1H, s), 12.77(2H, brs).

Example 107

Preparation of the Compound of Compound No. 107

Using 5-chloro-2-hydroxy-N-[3,5-bis(trifluoromethyl)phenyl]benzamide 1 sodium salt (compound of Example 43(1)) and 2-bromoethanol as the raw materials, the same operation as the Example 98 gave the title compound.

Yield: 69.0%.

$^1$H-NMR(CDCl$_3$): δ 2.10(1H, t, J=4.8 Hz), 4.18-4.22(2H, m), 4.33(2H, t, J=4.8 Hz), 6.96(1H, d, J=8.7 Hz), 7.44(1H, dd, J=8.7, 2.7 Hz), 7.59(1H, s), 8.21(1H, d, J=2.7 Hz), 8.35(2H, s), 10.54(1H, s).

Example 108

Preparation of the Compound of Compound No. 108

A mixture of 5-chloro-2-hydroxy-N-[3,5-bis(trifluoromethyl)phenyl]-benzamide(compound of Example 1(1); 600 mg, 1.6 mmol), potassium carbonate (1.10 g, 8.0 mmol), ethyl chloroacetate (383 mg, 3.2 mmol) and acetone (10 mL) was refluxed for 1 hour under argon atmosphere. After the reaction mixture was cooled to room temperature, the insoluble matter was filtered off, and the residue obtained by concentration of the filtrate under reduced pressure was diluted with ethyl acetate (15 mL). After the ethyl acetate layer was washed successively with water and brine, dried over anhydrous sodium sulfate, the residue obtained by evaporation of the solvent under reduced pressure was purified by column chromatography on silica gel(n-hexane:ethyl acetate=3:1) to give the title compound(427 mg, 58.1%) as a white powder.

$^1$H-NMR(CDCl$_3$): δ 1.38(3H, t, J=7.2 Hz), 4.41(2H, q, J=7.2 Hz), 4.79(2H, s), 6.86(1H, d, J=8.7 Hz), 7.46(1H, dd, J=8.7, 2.7 Hz), 7.62(1H, s), 8.27(1H, d, J=2.7H), 8.52(2H, s), 10.88(1H, brs).

Example 109

Preparation of the Compound of Compound No. 110

Using 5-chloro-2-hydroxy-N-[3,5-bis(trifluoromethyl)phenyl]-benzamide(compound of Example 1(1)) and benzyl chloroacetate as the raw materials, the same operation as the Example 108 gave the title compound.

Yield: 30.3%.

$^1$H-NMR(CDCl$_3$): δ 4.82(2H, s), 5.35(2H, s), 6.84(1H, d, J=8.7 Hz), 7.38-7.41(6H, m), 7.63(1H, brs), 8.28(1H, d, J=2.7 Hz), 8.54(2H, s), 10.86(1H, brs).

Example 110

Preparation of the Compound of Compound No. 109

Sodium hydroxide(66.7 mg, 1.6 mmol) was added to a solution of 2-[(benzyloxy)carbonyl]methoxy-5-chloro-N-[3,5-bis(trifluoromethyl)phenyl]-benzamide(Compound No. 110; 430 mg, 0.8 mmol) in a mixed solvent of methanol/water(5 mL+5 mL), and the mixture was stirred at 60° C. for 40 minutes. After the reaction mixture was cooled to room temperature, the residue obtained by evaporation of the solvent under reduced pressure was diluted with ethyl acetate. After the ethyl acetate solution was washed successively with 2N hydrochloric acid, water and brine, dried over anhydrous sodium sulfate, the residue obtained by evaporation of the solvent under reduced pressure was crystallized from n-hexane/ethyl acetate to give the title compound(310 mg, 86.8%) as a white powder.
$^1$H-NMR(DMSO-d$_6$): δ 4.95(2H, s), 7.28(1H, d, J=8.7 Hz), 7.65(1H, dd, J=8.7, 2.7 Hz), 7.85(1H, brs), 7.90(1H, d, J=2.7 Hz), 8.53(2H, s), 11.12(1H, s).

Example 111

Preparation of the Compound of Compound No. 111

Using 5-chloro-2-hydroxy-N-[3,5-bis(trifluoromethyl)phenyl]benzamide 1 sodium salt(compound of Example 43(1)) and N-(chloromethyl)phthalimide as the raw materials, the same operation as the Example 98 gave the title compound.
Yield: 80.7%.
$^1$H-NMR(CDCl$_3$): δ 5.94(2H, s), 7.36(1H, d, J=8.7 Hz), 7.70(1H, dd, J=8.7, 2.7 Hz), 7.62(1H, s), 7.78-7.85(2H, m), 7.90-7.96(2H, m), 8.17(1H, d, J=2.7 Hz), 8.37(2H, s), 9.90(1H, s).

Example 112

Preparation of the Compound of Compound No. 112

Using 5-chloro-2-hydroxy-N-[3,5-bis(trifluoromethyl)phenyl]-benzamide(compound of Example 1(1)) and 2,3,4,6-tetra-O-acetyl-α-D-glucopyranosyl bromide as the raw materials, the same operation as the Example 108 gave the title compound.
Yield: 26.9%.
$^1$H-NMR(CDCl$_3$): δ 1.99(3H, s), 2.03(3H, s), 2.05(3H, s), 2.06(3H, s), 3.92(1H, ddd, J=10.2, 5.4, 2.4 Hz), 4.11-4.16(1H, m), 4.33(1H, dd, J=12.6, 5.7 Hz), 5.15-5.21(1H, m), 5.30-5.40(3H, m), 7.08(1H, d, J=8.7 Hz), 7.48(1H, dd, J=8.7, 2.7 Hz), 7.67(1H, s), 8.18(1H, d, J=2.7 Hz), 8.26(2H, s), 9.27(1H, s).

Example 113

The Compound of Compound No. 113

This compound is a commercially available compound.
Supplier: Maybridge.
Catalog code number: RDR03099.
$^1$H-NMR(DMSO-d$_6$): δ 7.67(1H, dd, J=8.1, 1.2 Hz), 7.99(1H, dd, J=9.9, 2.7 Hz), 8.01(1H, s), 8.27(2H, s), 8.35(1H, s).

Example 114

Preparation of the Compound of Compound No. 114

Succinic acid dichloride(121 mg, 0.8 mmol) was added to a solution of 5-chloro-2-hydroxy-N-[3,5-bis(trifluoromethyl)phenyl]benzamide(compound of Example 1(1); 0.2 g, 0.5 mmol) and triethylamine(0.5 mL) in dichloromethane(8 mL) under ice cooling and argon atmosphere, and the mixture was stirred at room temperature for 1 hour. The reaction mixture was diluted with ethyl acetate. After the ethyl acetate solution was washed successively with 2N hydrochloric acid, water and brine, dried over anhydrous sodium sulfate, the residue obtained by evaporation of the solvent under reduced pressure was purified by column chromatography on silica gel(n-hexane:ethyl acetate=3:1) to give the title compound (161 mg, 66%) as a light yellow powder.
$^1$H-NMR(CDCl$_3$): δ 2.25(1H, dt, J=13.5, 10.0 Hz), 2.55(1H, ddd, J=18.0, 10.0, 1.8 Hz), 2.75(1H, ddd, J=13.5, 9.3, 2.4 Hz), 2.99(1H, dt, J=18.9, 9.3 Hz), 7.07(1H, d, J=8.7 Hz), 7.58(1H, dd, J=8.7, 2.7 Hz), 7.88(2H, s), 8.00(1H, d, J=2.7 Hz), 8.01(1H, s).

Example 115

Preparation of the Compound of Compound No. 115

Using 5-chloro-2-hydroxy-N-[3,5-bis(trifluoromethyl)phenyl]-benzamide(compound of Example 1(1)) and methyl dichloroacetate as the raw materials and using acetonitrile as the solvent, the same operation as the Example 108 gave the title compound.
Yield: 79.1%.
$^1$H-NMR(CDCl$_3$): δ 3.77(3H, s), 5.99(1H, s), 7.11(1H, d, J=8.7 Hz), 7.52(1H, dd, J=8.7, 2.4 Hz), 7.87(1H, s), 7.95(2H, s), 7.99(1H, d, J=2.4 Hz).

Example 116

Preparation of the Compound of Compound No. 116

Using 6-chloro-3,4-dihydro-4-oxo-3-[3,5-bis(trifluoromethyl)phenyl]-2H-1,3-benzoxazine-2-carboxylic acid methyl ester (Compound No. 115) as the raw material, the same operation as the Example 110 gave the title compound.
Yield: 89.4%.
$^1$H-NMR(CDCl$_3$): δ 6.02(1H, s), 7.12(1H, d, J=8.7 Hz), 7.53(1H, dd, J=8.7, 2.4 Hz), 7.87(1H, br), 7.95(2H, s), 7.99(1H, brs).

Example 117

Preparation of the Compound of Compound No. 117

Metal sodium (1.2 mg) was added to anhydrous methanol (2.0 mL), and dissolved by stirring at room temperature under argon atmosphere. 5-chloro-2-hydroxy-N-[3,5-bis(trifluoromethyl)phenyl]benzamide(compound of Example 1(1); 200 mg, 0.521 mmol) was added to the solution. Dimethyl acetylene dicarboxylate (81 mg, 0.573 mmol) was further added dropwise to the solution for 40 minutes, and the mixture was stirred at room temperature for 48 hours. Brine was added to the reaction mixture and it was extracted with tetrahydrofuran. After the tetrahydrofuran layer was dried over anhydrous sodium sulfate, the residue obtained by evaporation of the solvent under reduced pressure was purified by column chromatography on silica gel(n-hexane:ethyl acetate=4:1) to give the title compound(141 mg, 51.5%) as a white solid.
$^1$H-NMR(CDCl$_3$): δ 3.14(1H, d, J=16.2 Hz), 3.25(1H, d, J=16.2 Hz), 3.39(3H, s), 3.79(3H, s), 7.05(1H, d, J=8.7 Hz), 7.50(1H, dd, J=8.7, 2.4 Hz), 7.93(1H, d, J=2.7 Hz), 7.94(2H, s).

Example 118

Preparation of the Compound of Compound No. 118

(1) 5-Chloro-N-[5-(1,1-dimethyl)propyl-2-phenoxyphenyl]-2-hydroxybenzamide
Using 5-chlorosalicylic acid and 5-(1,1-dimethyl)propyl-2-phenoxyaniline as the raw materials, the same operation as the Example 1(1) gave the title compound.

Yield: 65.2%.

$^1$H-NMR(CDCl$_3$): δ 0.69(3H, t, J=7.6 Hz), 1.29(6H, s), 1.64(2H, q, J=7.6 Hz), 6.91(1H, dd, J=1.7, 7.6 Hz), 6.96(1H, d, J=8.9 Hz), 7.03(2H, d, J=8.9 Hz), 7.10(1H, dt, J=1.7, 7.6 Hz), 7.16(1H, dt, J=1.7, 7.6 Hz), 7.31-7.40(4H, m), 8.42(1H, dd, J=2.0, 7.9 Hz), 8.53(1H, br.s) 11.94(1H, s).

(2) 6-Chloro-3-[5-(1,1-dimethyl)propyl-2-phenoxyphenyl]-3,4-dihydro-2H-1,3-benzoxazine-2,4-dione(Compound No. 118)

A mixture of 5-chloro-N-[5-(1,1-dimethyl)propyl-2-phenoxyphenyl]-2-hydroxybenzamide(99 mg, 0.24 mmol), ethyl chloroformate(25 μL, 0.26 mmol) and pyridine(1 mL) was refluxed for 1 hour. After the reaction mixture was cooled to room temperature, the residue obtained by evaporation of the solvent under reduced pressure was purified by column chromatography on silica gel (n-hexane:ethyl acetate=10:1) to give the title compound(46 mg, 43.6%) as a white solid.

$^1$H-NMR(CDCl$_3$): δ 0.65(3H, t, J=7.5 Hz), 1.24(6H, s), 1.59(2H, q, J=7.5 Hz), 6.96(3H, m), 7.18-7.29(4H, m), 7.33 (1H, dd, J=8.0, 1.6 Hz), 7.40(1H, dt, J=8.4, 1.5 Hz), 7.65(1H, dd, J=8.7, 2.4 Hz), 8.06(1H, d, J=2.4 Hz).

Example 119

Preparation of the Compound of Compound No. 119

Using N-(4-biphenyl)-2-hydroxy-5-(trifluoromethyl)benzamide and morpholine-4-carbonyl chloride as the raw materials, the same operation as the Example 71 gave the title compound.

Yield: 88.9%.

$^1$H-NMR(DMSO-d$_6$): δ 3.29-3.38(2H, m), 3.48-3.58(6H, m), 7.31-7.37(1H, m), 7.44-7.49(2H, m), 7.57(1H, d, J=8.4 Hz), 7.67-7.71(4H, m), 7.79(2H, d, J=8.7 Hz), 7.95(1H, dd, J=9.0, 2, 4 Hz), 8.02(1H, d, J=1.5 Hz), 10.60(1H, s).

[N-(4-Biphenyl)-2-hydroxy-5-(trifluoromethyl)benzamide: Refer to International Patent Publication WO99/65449 pamphlet.]

Example 120

Preparation of the Compound of Compound No. 120

Using 5-chloro-2-hydroxy-N-[2,5-bis(trifluoromethyl) phenyl]-benzamide(compound of Example 91(1)) and dibenzyl phosphite as the raw materials, the same operation as the Example 50 gave the title compound.

Yield: 90.6%.

$^1$H-NMR(DMSO-d$_6$): δ 5.14(2H, d, J=8.4 Hz), 5.15(2H, d, J=7.5 Hz), 7.29-7.35(10H, m), 7.43(1H, dd, J=8.7, 0.9 Hz), 7.64(1H, dd, J=8.7, 2.7 Hz), 7.74(1H, d, J=2.1 Hz), 7.91(1H, d, J=8.1 Hz), 8.05(1H, d, J=8.4 Hz), 8.09(1H, s), 10.61(1H, s).

Example 121

Preparation of the Compound of Compound No. 121

Using 5-chloro-2-(dibenzylphosphono)oxy-N-[2,5-bis (trifluoromethyl)-phenyl]benzamide(Compound No. 120) as the raw material, the same operation as the Example 51 gave the title compound.

Yield: 95.7%.

$^1$H-NMR(DMSO-d$_6$): δ 7.47(1H, dd, J=8.7, 0.9 Hz), 7.63-7.68(2H, m), 7.90(1H, d, J=8.4 Hz), 8.05(1H, d, J=8.1 Hz), 8.15(1H, s), 10.38(1H, s).

Example 122

Preparation of the Compound of Compound No. 122

Using 5-chloro-2-phosphonooxy-N-[2,5-bis(trifluoromethyl)phenyl]-benzamide(Compound No. 121) as the raw material, the same operation as the Example 52 gave the title compound.

Yield: 93.8%.

$^1$H-NMR(DMSO-d$_6$): δ 7.40(1H, dd, J=8.7, 0.9 Hz) 7.52 (1H, dd, J=8.7, 3.0 Hz), 7.59(1H, d, J=3.0 Hz), 7.86(1H, d, J=8.4 Hz), 7.98(1H, s), 8.02(1H, d, J=8.4 Hz), 11.95(1H, s).

Example 123

Preparation of the Compound of Compound No. 123

Using 5-chloro-N-[2-chloro-5-(trifluoromethyl)phenyl]-2-hydroxybenzamide-(compound of Example 84(1)) and dibenzyl phosphite as the raw materials, the same operation as the Example 50 gave the title compound.

Yield: 99.1%.

$^1$H-NMR(DMSO-d$_6$): δ 5.13(2H, d, J=8.1 Hz), 5.14(2H, d, J=8.1 Hz), 7.27-7.33(10H, m), 7.43(1H, d, J=9.3 Hz), 7.61-7.66(2H, m), 7.77-7.80(2H, m), 8.19(1H, s), 10.43(1H, s).

Example 124

Preparation of the Compound of Compound No. 124

Using 5-chloro-N-[2-chloro-5-(trifluoromethyl)phenyl]-2-[(dibenzylphosphono)-oxy]benzamide (Compound No. 123) as the raw material, the same operation as the Example 51 gave the title compound.

Yield: 95.8%.

$^1$H-NMR(DMSO-d$_6$): δ 7.52(1H, d, J=8.7 Hz), 7.60(1H, dd, J=8.1, 2.1 Hz), 7.66(1H, dd, J=8.7, 3.0 Hz), 7.79-7.82(2H, m), 8.44(1H, s), 10.31(1H, s).

Example 125

Preparation of the Compound of Compound No. 125

Using 5-chloro-N-[2-chloro-5-(trifluoromethyl)phenyl]-2-(phosphonooxy)-benzamide (Compound No. 124) as the raw material, the same operation as the Example 52 gave the title compound.

Yield: 90.2%.

$^1$H-NMR(DMSO-d$_6$): δ 7.48(1H, dd, J=9.0, 3.0 Hz) 7.53 (1H, dd, J=8.7, 2.1 Hz), 7.58(1H, d, J=8.7 Hz), 7.69-7.72(2H, m), 8.36(1H, d, J=2.1 Hz), 11.70(1H, s).

Example 126

Preparation of the Compound of Compound No. 126

Using 5-chloro-N-{4-[(1,1-dimethyl)ethyl]-5-[(2,2-dimethyl)-propionyl]thiazol-2-yl}-2-hydroxybenzamide(compound of Example 92(3)) and dibenzyl phosphite as the raw materials, the same operation as the Example 50 gave the title compound.

Yield: 100.0%.

$^1$H-NMR(DMSO-d$_6$): δ 1.21(9H, s), 1.25(9H, s), 5.09(2H, d, J=8.4 Hz), 5.11(2H, d, J=7.8 Hz) 7.23-7.38(11H, m), 7.63 (1H, dd, J=8.7, 2.7 Hz), 7.82(1H, dd, J=2.7, 0.9 Hz), 13.00 (1H, s).

Example 127

Preparation of the Compound of Compound No. 127

Using 5-chloro-2-(dibenzylphosphono)oxy-N-{4-[(1,1-dimethyl)ethyl]-5-[(2,2-dimethyl)-propionyl]thiazol-2-yl}benzamide(Compound No. 126) as the raw material, the same operation as the Example 51 gave the title compound.
Yield: 98.1%.
$^1$H-NMR(DMSO-d$_6$): δ 1.26(9H, s), 1.28(9H, s), 7.43(1H, dd, J=8.7, 1.2 Hz), 7.61(1H, dd, J=8.7, 2.7 Hz), 7.67(1H, d, J=2.4 Hz).

Example 128

Preparation of the Compound of Compound No. 128

Using 5-chloro-N-{4-[(1,1-dimethyl)ethyl]-5-[(2,2-dimethyl)-propionyl]thiazol-2-yl}-2-(phosphonooxy)benzamide(Compound No. 127) as the raw material, the same operation as the Example 52 gave the title compound.
Yield: 35.8%.
$^1$H-NMR(DMSO-d$_6$): δ 1.26(9H, s), 1.27(9H, s), 7.37(1H, d, J=9.0 Hz), 7.55(1H, dd, J=9.0, 2.7 Hz), 7.64(1H, d, J=2.4 Hz).

Example 129

Preparation of the Compound of Compound No. 129

(1) 5-Bromo-2-hydroxy-N-[2,5-bis(trifluoromethyl)phenyl]benzamide

Using 5-bromosalicylic acid and 2,5-bis(trifluoromethyl)aniline as the raw materials, the same operation as the Example 1(1) gave the title compound.
Yield: 24.0%.
$^1$H-NMR(DMSO-d$_6$): δ 7.03(1H, d, J=8.7 Hz), 7.65(1H, dd, J=8.7, 2.7 Hz), 7.76(1H, d, J=8.4 Hz), 8.03(1H, d, J=8.1 Hz) 8.11(1H, d, J=2.7 Hz), 8.74(1H, s), 11.02(1H, s), 12.34 (1H, s).

(2) 5-Bromo-2-(morpholinocarbonyl)oxy-N-[2,5-bis(trifluoromethyl)phenyl]benzamide (Compound No. 129)

Using 5-bromo-2-hydroxy-N-[2,5-bis(trifluoromethyl)phenyl]benzamide and morpholine-4-carbonyl chloride as the raw materials, the same operation as the Example 71 gave the title compound.
Yield: 89.4%.
$^1$H-NMR(CDCl$_3$): δ 3.55-3.68(8H, m), 7.06(1H, d, J=9.0 Hz), 7.57(1H, d, J=8.1 Hz), 7.65(1H, dd, J=9.0, 2.7 Hz), 7.81(1H, d, J=8.4 Hz), 7.97(1H, d, J=2.7 Hz), 8.39(1H, s), 8.60(1H, s).

Example 130

Preparation of the Compound of Compound No. 130

(1) 2-Hydroxy-N-[2,5-bis(trifluoromethyl)phenyl]benzamide

A mixture of salicylic acid (6.90 g, 50 mmol), 2,5-bis(trifluoromethyl)-aniline (11.46 g, 50 mmol), phosphorus trichloride(2.18 ml, 25 mmol) and chlorobenzene(150 mL) was refluxed for 4 hours. After the reaction mixture was cooled to room temperature, it was diluted with ethyl acetate. The organic layer was washed with water and brine, and dried over magnesium sulfate. The residue obtained by evaporation of the solvent under reduced pressure was washed with n-hexane to give the title compound(8.4 g, 47.8%) as a white solid.
$^1$H-NMR(CD$_3$OD): δ 7.00-7.06(2H, m), 7.48(1H, dt, J=1.5, 7.5 Hz), 7.74(1H, d, J=8.4 Hz), 8.01-8.08(2H, m), 8.79(1H, s), 11.09(1H, s), 12.03(1H, s).

(2) 3,5-Dibromo-2-hydroxy-N-[2,5-bis(trifluoromethyl)phenyl]benzamide

Iron(3 mg, 0.05 mmol) and bromine(129 μl, 2.5 mmol) were added to a solution of 2-hydroxy-N-[2,5-bis(trifluoromethyl)phenyl]benzamide(175 mg, 0.5 mmol) in carbon tetrachloride(5 mL), and the mixture was stirred at 50° C. for 12 hours. After the reaction mixture was cooled to room temperature, it was washed with saturated aqueous sodium hydrogen carbonate, water and brine, and dried over anhydrous magnesium sulfate. The residue obtained by evaporation of the solvent under reduced pressure was purified by column chromatography on silica gel(n-hexane:ethyl acetate=2:1) to give the title compound(184.2 mg, 72.7%) as a white crystal.
$^1$H-NMR(DMSO-d$_6$): δ 7.92-7.98(1H, m), 8.06(1H, d, J=2.1 Hz), 8.09(1H, d, J=8.4 Hz), 8.22(1H, d, J=2.1 Hz), 8.27-8.32(1H, m), 11.31(1H, s).

(3) 3,5-Dibromo-2-(morpholinocarbonyl)oxy-N-[2,5-bis(trifluoromethyl)phenyl]-benzamide(Compound No. 130)

Using 3,5-dibromo-2-hydroxy-N-[2,5-bis(trifluoromethyl)phenyl]benzamide and morpholine-4-carbonyl chloride as the raw materials, the same operation as the Example 71 gave the title compound.
Yield: 70.6%.
$^1$H-NMR(CDCl$_3$-d$_6$): δ 3.54-3.77(8H, m), 7.58(1H, d, J=8.4 Hz), 7.81(1H, d, J=8.4 Hz), 7.91(1H, d, J=2.1 Hz), 7.94(1H, d, J=2.1 Hz), 8.54(2H, brs).

Example 131

Preparation of the Compound of Compound No. 131

The title compound was obtained from the n-hexane wash described in the Example 130(1) as a white solid (211.7 mg, 0.9%).
$^1$H-NMR(DMSO-d$_6$): δ 6.98(1H, t, J=7.5 Hz), 7.03(1H, d, 8.4 Hz), 7.46-7.60(3H, m), 7.67-7.72(1H, m), 7.80-7.84(2H, m), 7.88-7.91(1H, m), 7.97(1H, dd, J=1.2, 8.1 Hz), 8.02(1H, dd, J=8.1 Hz), 10.23(1H, s), 10.52(1H, s).

Example 132

Preparation of the Compound of Compound No. 132

Using 2-hydroxy-N-[2,5-bis(trifluoromethyl)phenyl]benzamide(compound of Example 130(1)) and morpholine-4-carbonyl chloride as the raw materials, the same operation as the Example 71 gave the title compound.
$^1$H-NMR(CDCl$_3$): δ 3.57-3.71(8H, m), 7.18(1H, d, J=8.4 Hz), 7.37(1H, dt, J=7.8, 1.2 Hz), 7.53-7.59(2H, m), 7.79(1H, d, J=8.4 Hz), 7.84(1H, dd, J=1.5, 7.8 Hz), 8.42(1H, brs), 8.68(1H, s).

Example 133

Preparation of the Compound of Compound No. 133

(1) 5-Chloro-2-hydroxy-N-[2-(4-methoxyphenoxy)-5-(trifluoromethyl)phenyl]-benzamide Using 5-chlorosalicylic acid and 3-amino-4-(4-methoxyphenoxy)-benzotrifluoride as the raw materials, the same operation as the Example 1(1) gave the title compound.
Yield: 88.1%.

$^1$H-NMR(CDCl$_3$): δ 3.85(3H, s) 6.81(1H, d, J=8.5 Hz), 6.97-7.02(3H, m), 7.08(2H, d, J=8.8 Hz), 7.30(1H, m), 7.40 (1H, dd, J=8.8, 1.9 Hz), 7.45(1H, d, J=2.2 Hz), 8.70(1H, s), 8.78(1H, d, J=1.6 Hz), 11.76(1H, s).

(2) 5-Chloro-N-[2-(4-methoxyphenoxy)-5-(trifluoromethyl)phenyl]-2-[(morpholino-carbonyl)oxy]benzamide(Compound No. 133)

Using 5-chloro-2-hydroxy-N-[2-(4-methoxyphenoxy)-5-(trifluoromethyl)-phenyl]benzamide and morpholine-4-carbonyl chloride as the raw materials, the same operation as the Example 71 gave the title compound.

Yield: 60.0%.

$^1$H-NMR(CDCl$_3$): δ 3.37-3.41(2H, m), 3.62(6H, s), 3.83 (3H, s), 6.78(1H, d, J=8.7 Hz), 6.93-7.03(4H, m), 7.11(1H, d, J=8.4 Hz), 7.24-7.28(1H, m), 7.47(1H, dd, J=8.7, 2.4 Hz), 7.86(1H, d, J=2.7 Hz), 8.90-8.93(2H, m).

Example 134

Preparation of the Compound of Compound No. 134

Using 5-bromo-N-[2-chloro-5-(trifluoromethyl)phenyl]-2-hydroxybenzamide(compound of Example 85(1)) and dibenzyl phosphite as the raw materials, the same operation as the Example 50 gave the title compound.

Yield: 89.8%.

$^1$H-NMR(DMSO-d$_6$): δ 5.11(2H, d, J=8.4 Hz), 5.13(2H, d, J=8.7 Hz), 7.23-7.39(11H, m), 7.61-7.64(1H, m), 7.74-7.80 (2H, m), 7.91(1H, m), 8.19(1H, m), 10.45(1H, s).

Example 135

Preparation of the Compound of Compound No. 135

Using 5-bromo-N-[2-chloro-5-(trifluoromethyl)phenyl]-2-[(dibenzylphosphono)oxy]benzamide(Compound No. 134) as the raw material, the same operation as the Example 51 gave the title compound.

Yield: 89.6%.

$^1$H-NMR(DMSO-d$_6$): δ 7.46(1H, dd, J=9.0, 1.2 Hz), 7.61, (1H, dd, J=8.4, 2.1 Hz), 7.78(1H, dd, J=9.0, 2.4 Hz), 7.81(1H, d, J=8.1 Hz), 7.92(1H, d, J=1.8 Hz), 8.44(1H, d, J=1.2 Hz), 10.27(1H, s).

Example 136

Preparation of the Compound of Compound No. 136

Using 5-bromo-N-[2-chloro-5-(trifluoromethyl)phenyl]-2-(phosphonooxy)benzamide(Compound No. 135) as the raw material, the same operation as the Example 52 gave the title compound.

Yield: 100.0%.

$^1$H-NMR(DMSO-d$_6$): δ 7.49(1H, dd, J=8.7, 0.9 Hz), 7.56 (1H, dd, J=8.4, 1.8 Hz), 7.61(1H, dd, J=8.7, 2.4 Hz), 7.73(1H, d, J=8.4 Hz), 7.83(1H, d, J=2.4 Hz), 8.31(1H, d, J=1.5 Hz), 11.96(1H, s).

Example 137

Preparation of the Compound of Compound No. 137

Using 5-[(1,1-dimethyl)ethyl]-2-hydroxy-N-[3,5-bis(trifluoromethyl)-phenyl]benzamide (compound of Example 78(1)) and dibenzyl phosphite as the raw materials, the same operation as the Example 50 gave the title compound.

Yield: 94.4%.

$^1$H-NMR(DMSO-d$_6$): δ 1.32(9H, s), 5.09(2H, d, J=8.1 Hz), 5.10(2H, d, J=7.8 Hz), 7.22-7.36(11H, m), 7.60(1H, dd, J=8.7, 2.4 Hz), 7.65(1H, d, J=2.4 Hz), 7.80(1H, s), 8.39(2H, s), 11.05(1H, s).

Example 138

Preparation of the Compound of Compound No. 138

Using 2-(dibenzylphosphono)oxy-5-[(1,1-dimethyl)ethyl]-N-[3,5-bis(trifluoromethyl)phenyl]-benzamide(Compound No. 137) as the raw material, the same operation as the Example 51 gave the title compound.

Yield: 100.0%.

$^1$H-NMR(DMSO-d$_6$): δ 1.31(9H, s), 7.32(1H, d, J=8.1 Hz), 7.58-7.63(2H, m), 7.82(1H, s), 8.43(2H, s), 11.11(1H, s).

Example 139

Preparation of the Compound of Compound No. 139

Using 5-[(1,1-dimethyl)ethyl]-2-phosphonooxy-N-[3,5-bis(trifluoromethyl)phenyl]benzamide (Compound No. 138) as the raw material, the same operation as the Example 52 gave the title compound.

Yield: 85.0%.

$^1$H-NMR(DMSO-d$_6$): δ 1.29(9H, s), 7.23(1H, d, J=8.7 Hz), 7.48(1H, dd, J=8.7, 2.4 Hz), 7.63(1H, d, J=2.7 Hz), 7.74(1H, s), 8.55(2H, s), 13.47(1H, s).

Example 140

Preparation of the Compound of Compound No. 140

Using 5-bromo-2-hydroxy-N-[2,5-bis(trifluoromethyl)phenyl]-benzamide(compound of Example 129(1)) and dibenzyl phosphite as the raw materials, the same operation as the Example 50 gave the title compound.

Yield: 84.1%.

$^1$H-NMR(DMSO-d$_6$): δ 5.14(2H, d, J=7.8 Hz), 5.15(2H, d, J=7.8 Hz), 7.26-7.39(11H, m), 7.76(1H, dd, J=8.7, 2.1 Hz), 7.87(1H, m), 7.91(1H, d, J=8.7 Hz), 8.05(1H, d, J=7.8 Hz), 8.09(1H, s), 10.61(1H, s).

Example 141

Preparation of the Compound of Compound No. 141

Using 5-bromo-2-(dibenzylphosphono)oxy-N-[2,5-bis(trifluoromethyl)-phenyl]benzamide (Compound No. 140) as the raw material, the same operation as the Example 51 gave the title compound.

Yield: 85.4%.

$^1$H-NMR(DMSO-d$_6$): δ 7.41(1H, d, J=8.4 Hz), 7.75-7.79 (2H, m), 7.90(1H, d, J=7.8 Hz), 8.05(1H, d, J=8.1 Hz), 8.15 (1H, s), 10.42(1H, s).

Example 142

Preparation of the Compound of Compound No. 142

Using 5-bromo-2-phosphonooxy-N-[2,5-bis(trifluoromethyl)phenyl]-benzamide(Compound No. 141) as the raw material, the same operation as the Example 52 gave the title compound.

Yield: 89.3%.
¹H-NMR(DMSO-d₆): δ 7.32(1H, d, J=8.4 Hz), 7.62(1H, dd, J=8.4, 2.7 Hz), 7.69(1H, d, J=2.4 Hz), 7.86(1H, d, J=8.1 Hz), 7.92(1H, s), 8.02(1H, d, J=8.4 Hz), 12.44(1H, s).

Example 143

Preparation of the Compound of Compound No. 143

Using 5-bromo-N-{3,5-bis[(1,1-dimethyl)ethyl]phenyl}-2-hydroxy-benzamide(compound of Example 90(1)) and dibenzyl phosphite as the raw materials, the same operation as the Example 50 gave the title compound.
Yield: 94.7%.
¹H-NMR(DMSO-d₆): δ 1.23(18H, s), 5.08(2H, d, J=8.4 Hz), 5.10(2H, d, J=7.2 Hz), 7.16-7.34(12H, m), 7.65(2H, d, J=1.5 Hz), 7.71(1H, dd, J=9.0, 2.7 Hz), 7.82-7.83(1H, m), 10.43(1H, s).

Example 144

Preparation of the Compound of Compound No. 144

Using 5-bromo-2-(dibenzylphosphono)oxy-N-{3,5-bis [(1, 1-dimethyl)-ethyl]phenyl}benzamide(Compound No. 143) as the raw material, the same operation as the Example 51 gave the title compound.
Yield: 94.8%.
¹H-NMR(DMSO-d₆): δ 1.28(18H, s), 7.15(1H, t, J=1.5 Hz), 7.38(1H, dd, J=8.7, 0.9 Hz), 7.61(2H, d, J=2.1 Hz), 7.70(1H, dd, J=8.7, 2.4 Hz), 7.77(1H, dd, J=2.7, 0.6 Hz), 10.31(1H, s).

Example 145

Preparation of the Compound of Compound No. 145

Using 5-bromo-N-{3,5-bis[(1,1-dimethyl)ethyl]phenyl}-2-(phosphonooxy)benzamide (Compound No. 144) as the raw material, the same operation as the Example 52 gave the title compound.
Yield: 75.7%.
¹H-NMR(DMSO-d₆): δ 1.28(18H, s), 7.11(1H, t, J=1.5 Hz), 7.30(1H, dd, J=8.7, 0.6 Hz), 7.55(1H, dd, J=8.7, 2.7 Hz), 7.72(2H, d, J=2.1 Hz), 7.79(1H, d, J=2.7 Hz), 12.00(1H, s).

Example 146

Preparation of the Compound of Compound No. 146

(1) 2-Hydroxy-5-(3-thienyl)-N-[3,5-bis(trifluoromethyl)phenyl]benzamide
Using 2-hydroxy-5-iodo-N-[3,5-bis(trifluoromethyl)phenyl]-benzamide(compound of Example 81(1)) and 3-thiopheneboronic acid as the raw materials, the same operation as the Example 81(2) gave the title compound.
Yield: 38.7%.
¹H-NMR(DMSO-d₆): δ 7.06(1H, d, J=8.7 Hz), 7.57(1H, dd, J=4.8, 1.5 Hz), 7.66(1H, dd, J=4.8, 3.0 Hz), 7.81-7.84(2H, m), 7.86(1H, s), 8.18(1H, d, J=2.1 Hz), 8.49(2H, s), 10.90 (1H, s), 11.33(1H, s).
(2) 2-(Morpholinocarbonyl)oxy-5-(3-thienyl)-N-[3,5-bis (trifluoromethyl)phenyl]-benzamide(Compound No. 146)
Using 2-hydroxy-5-(3-thienyl)-N-[3,5-bis(trifluoromethyl)phenyl]benzamide and morpholine-4-carbonyl chloride as the raw materials, the same operation as the Example 71 gave the title compound.
Yield: 92.7%.

¹H-NMR(CDCl₃): δ 3.58-3.72(8H, m), 7.05(1H, d, J=8.4 Hz), 7.36(1H, dd, J=4.8, 1.2 Hz) 7.43(1H, dd, J=5.1, 3.0 Hz), 7.48(1H, dd, J=3.0, 1.5 Hz), 7.60-7.64(2H, m), 7.89(1H, d, J=2.7 Hz), 8.09(2H, s), 9.15(1H, s).

Example 147

Preparation of the Compound of Compound No. 147

Using 5-bromo-2-hydroxy-N-[3-methoxy-5-(trifluoromethyl)phenyl]-benzamide(compound of Example 87(1)) and dibenzyl phosphite as the raw materials, the same operation as the Example 50 gave the title compound.
Yield: 77.7%.
¹H-NMR(DMSO-d₆): δ 3.78(3H, s), 5.09(2H, d, J=8.1 Hz), 5.10(2H, d, J=7.5 Hz), 7.00(1H, s), 7.23-7.36(11H, m), 7.56(1H, m), 7.73-7.77(2H, m), 7.87(1H, d, J=1.8 Hz), 10.84 (1H, s).

Example 148

Preparation of the Compound of Compound No. 148

Using 5-bromo-2-(dibenzylphosphono)oxy-N-[3-methoxy-5-(trifluoromethyl)phenyl]-benzamide(Compound No. 147) as the raw material, the same operation as the Example 51 gave the title compound.
Yield: 98.1%.
¹H-NMR(DMSO-d₆): δ 3.83(3H, s), 7.00(1H, s), 7.37(1H, d, J=8.7 Hz), 7.57(1H, s), 7.71-7.77(3H, m), 10.80(1H, s).

Example 149

Preparation of the Compound of Compound No. 149

Using 5-bromo-N-[3-methoxy-5-(trifluoromethyl)phenyl]-2-(phosphonooxy)benzamide (Compound No. 148) as the raw material, the same operation as the Example 52 gave the title compound.
Yield: 98.6%.
¹H-NMR(DMSO-d₆): δ 3.82(3H, s), 6.95(1H, s), 7.26(1H, d, J=8.7 Hz), 7.61(1H, dd, J=8.7, 2.4 Hz), 7.70(1H, s), 7.74 (1H, d, J=2.4 Hz), 7.86(1H, s), 12.62(1H, brs).

Example 150

Preparation of the Compound of Compound No. 150

(1) 2-Hydroxy-5-phenylethenyl-N-[3,5-bis(trifluoromethyl) phenyl]benzamide
A mixture of 2-hydroxy-5-iodo-N-[3,5-bis(trifluoromethyl)phenyl]-benzamide(compound of Example 81(1); 475 mg, 1 mmol), styrene (130 mg, 1.25 mmol), palladium acetate (4.5 mg, 0.02 mmol), tris(ortho-tolyl)phosphine(12.2 mg, 0.04 mmol), diisopropylamine(388 mg, 3 mmol) and N,N-dimethylformamide(2 mL) was refluxed for 8 hours. After the reaction mixture was cooled to room temperature, water was added and the mixture was extracted with ethyl acetate. The ethyl acetate layer was washed with water and brine, and dried over anhydrous magnesium sulfate. The residue obtained by evaporation of the solvent under reduced pressure was purified by column chromatography on silica gel(n-hexane:isopropyl ether=2:1→1:1) to give the title compound (173 mg, 38.3%) as a pale yellow solid.
¹H-NMR(DMSO-d₆): δ 7.04(1H, d, J=8.4 Hz), 7.20-7.29 (3H, m), 7.38(2H, t, J=7.5 Hz), 7.59(2H, d, J=7.5 Hz), 7.72

(1H, dd, J=8.4, 2.1 Hz), 7.86(1H, s), 8.07(1H, d, J=2.1 Hz), 8.49(2H, s), 10.89(1H, s), 11.33(1H, brs).

(2) 2-(Morpholinocarbonyl)oxy-5-phenylethenyl-N-[3,5-bis(trifluoromethyl)phenyl]-benzamide(Compound No. 150)

Using 2-hydroxy-5-phenylethenyl-N-[3,5-bis(trifluoromethyl)-phenyl]benzamide and morpholine-4-carbonyl chloride as the raw materials, the same operation as the Example 71 gave the title compound.

Yield: 99.5%.

$^1$H-NMR(CDCl$_3$): δ 3.61-3.69(8H, m), 7.08-7.12(3H, m), 7.32(1H, d, J=7.2 Hz), 7.36-7.41(2H, m), 7.51-7.53(2H, m), 7.59(1H, dd, J=8.4, 2.4 Hz), 7.65(1H, s), 7.87(1H, d, J=2.1 Hz), 8.11(2H, s), 9.05(1H, s).

Example 151

Preparation of the Compound of Compound No. 151

Using 2-hydroxy-5-phenylethenyl-N-[3,5-bis(trifluoromethyl)-phenyl]benzamide(compound of Example 150(1)) and dibenzyl phosphite as the raw materials, the same operation as the Example 50 gave the title compound.

Yield: 82.0%.

$^1$H-NMR(DMSO-d$_6$): δ 5.12(2H, d, J=8.4 Hz), 5.13(2H, d, J=7.5 Hz), 7.25-7.43(16H, m), 7.63(2H, d, J=7.2 Hz), 7.78-7.82(2H, m), 7.96(1H, s), 8.40(2H, s), 11.17(1H, s).

Test Example

Measurement of Inhibitory Activity Against NκB Activation

Inhibitory activity against NF-κB activation was measured by referring to the method of Hill et al. (Cell, (USA), in 1993, Vol. 73, No. 2, p. 395-406). Using a transfection reagent (Effectene; QIAGEN), the human hepatoma cell strain HepG2 was transfected with a plasmid (pNFκ Luc Reporter Plasmid; STRATAGENE) integrated with an oligonucleotide having five tandem copies of NF-κB binding sequences (TGGGGACTTTCCGC) on a upstream region of firefly luciferase gene (Luc) according to the QIAGEN's protocol, and the cells were incubated for 6 to 24 hours. Then the cells were cultured for 4 hours after the addition of TNF-α (40 ng/ml) in the presence of a test compound, and intracellular luciferase activity was measured by using PicaGene LT (TOYO INK MFG Co., Ltd.) and a chemical luminescence measurement apparatus(SPECTRAFluor Plus; TECAN). The inhibitory ratio was measured as a ratio relative to a value of the luciferase activity in the absence of the test compound. The inhibitory ratios against NF-κB activity in the presence of the test compound at 10 μg/ml and 1 μg/ml are shown in the following table.

| Compound Number | Inhibitory Ratio of NF-κ B Activation(%) | |
|---|---|---|
| | Drug Concentration 10 μg/mL | Drug Concentration 1 μg/mL |
| 1 | 95.8 | 94.9 |
| 2 | 98.6 | 97.9 |
| 3 | 98.4 | 96.1 |
| 4 | 97.5 | 94.2 |
| 5 | 98.0 | 96.1 |
| 6 | 98.1 | 94.4 |
| 7 | 98.8 | 93.9 |
| 8 | 97.9 | 95.0 |
| 9 | 97.3 | 94.6 |
| 10 | 97.4 | 95.3 |
| 11 | 99.2 | 97.3 |
| 12 | 97.5 | 95.5 |
| 13 | 98.7 | 96.6 |
| 14 | 99.4 | 98.9 |
| 15 | 99.1 | 97.9 |
| 16 | 98.4 | 96.6 |
| 17 | 96.8 | 97.0 |
| 18 | 98.1 | 95.4 |
| 19 | 98.8 | 97.9 |
| 20 | 98.1 | 94.8 |
| 21 | 98.7 | 96.7 |
| 22 | 98.7 | 35.3 |
| 23 | 97.3 | 19.8 |
| 24 | 96.8 | 96.3 |
| 25 | 97.2 | 93.4 |
| 26 | 98.9 | 97.8 |
| 27 | 99.2 | 95.8 |
| 28 | 98.4 | 96.4 |
| 29 | 97.5 | 90.2 |
| 30 | 97.0 | 96.4 |
| 31 | 97.2 | 97.2 |
| 32 | 98.8 | 98.0 |
| 33 | 98.6 | 96.6 |
| 34 | 99.5 | 51.9 |
| 35 | 98.3 | 96.9 |
| 36 | 98.7 | 97.8 |
| 37 | 98.1 | 96.6 |
| 38 | 98.6 | 97.8 |
| 39 | 98.4 | 96.7 |
| 40 | 97.5 | 96.2 |
| 41 | 99.1 | 91.4 |
| 42 | 96.9 | 92.7 |
| 43 | 97.6 | 94.9 |
| 44 | 98.6 | 85.9 |
| 45 | 95.4 | 84.7 |
| 46 | 96.3 | 89.5 |
| 47 | 92.5 | 84.7 |
| 48 | 90.4 | 37.9 |
| 49 | 99.0 | 80.1 |
| 50 | 97.1 | 90.7 |
| 51 | 96.6 | 89.7 |
| 52 | 96.5 | 76.3 |
| 53 | 92.0 | 21.5 |
| 54 | 98.0 | 96.0 |
| 55 | 99.1 | 97.1 |
| 56 | 98.9 | 96.8 |
| 57 | 97.2 | 95.4 |
| 58 | 98.8 | 97.9 |
| 59 | 97.8 | 96.2 |
| 60 | 98.9 | 97.7 |
| 61 | 99.2 | 98.6 |
| 62 | 97.8 | 96.8 |
| 63 | 98.2 | 97.1 |
| 64 | 97.5 | 96.3 |
| 65 | 97.3 | 95.8 |
| 66 | 41.4 | 12.2 |
| 68 | 47.4 | 53.0 |
| 69 | 18.7 | 29.7 |
| 70 | 89.6 | 48.1 |
| 71 | 78.0 | 70.6 |
| 72 | 35.2 | 39.4 |
| 74 | 58.1 | 56.2 |
| 75 | 94.9 | 94.3 |
| 76 | 98.2 | 98.9 |
| 77 | 31.0 | 69.7 |
| 79 | 70.2 | 88.1 |
| 80 | 68.4 | 91.4 |
| 81 | 29.2 | 26.4 |
| 83 | 18.0 | 23.5 |
| 85 | 29.8 | 21.4 |
| 86 | 11.9 | 23.4 |
| 87 | 55.4 | 29.7 |
| 89 | 35.9 | 48.3 |
| 92 | 93.9 | 86.3 |
| 93 | 24.0 | 44.3 |

-continued

| Compound Number | Inhibitory Ratio of NF-κ B Activation(%) | |
|---|---|---|
|  | Drug Concentration 10 μg/mL | Drug Concentration 1 μg/mL |
| 94 | 51.7 | 56.1 |
| 95 | 71.4 | 31.3 |
| 96 | 96.1 | 54.1 |
| 97 | 94.4 | 21.6 |
| 98 | 96.6 | 94.9 |
| 99 | 94.7 | 92.3 |
| 100 | 98.5 | 96.1 |
| 101 | 42.8 | 41.0 |
| 102 | 70.0 | 39.1 |
| 103 | 45.9 | 40.4 |
| 104 | 58.8 | 48.4 |
| 105 | 56.0 | 71.8 |
| 106 | 83.5 | 61.0 |
| 107 | 52.1 | 47.4 |
| 109 | 95.9 | 21.0 |
| 110 | 39.2 | 38.5 |
| 111 | 96.0 | 94.3 |
| 112 | 49.5 | 47.2 |
| 113 | 97.9 | 96.8 |
| 114 | 98.5 | 97.2 |
| 115 | 92.2 | 41.8 |
| 116 | 20.1 | 35.1 |
| 117 | 56.7 | 34.8 |
| 118 | 97.4 | 94.0 |
| 119 | >99.9 | >99.9 |
| 122 | >99.9 | >99.9 |
| 125 | >99.9 | >99.9 |
| 128 | >99.9 | >99.9 |
| 130 | N.T. | 18.9 |
| 131 | N.T. | >99.9 |
| 132 | N.T. | 32.3 |
| 133 | 12.5 | N.T. |
| 136 | N.T. | >99.9 |
| 139 | N.T. | 64.3 |
| 142 | N.T. | >99.9 |
| 145 | N.T. | 93.1 |
| 149 | N.T. | >99.9 |

N.T.: not tested

INDUSTRIAL APPLICABILITY

The medicaments of the present invention have inhibitory activity against the activation of transcription factor NF-κB, furthermore they have suppressing activity against the production and release of inflammatory cytokines. Therefore, the medicaments of the present invention are useful as preventive and/or therapeutic agent for treatment of diseases caused by activation of NF-κB and for diseases caused by overproduction of inflammatory cytokines.

What is claimed is:

1. A compound represented by formula (I-1) or a salt thereof:

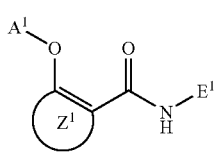

(I-1)

wherein
$A^1$ represents
a 5 to 6-membered non-aromatic heterocyclic ring-carbonyl group which comprises at least one nitrogen atom as ring-constituting atoms (ring forming atoms) of said heterocyclic ring and binds to the carbonyl group at the nitrogen atom, and said heterocyclic ring may be substituted with one or more substituents independently selected from
an alkyl group,
an alkyl-oxy-carbonyl group, and
a carboxy group
$E^1$ represents a mono- or di-substituted phenyl group, wherein the substituents of the mono- and di-substituted phenyl group are independently selected from
a halogen atom;
an alkyl group;
a halogenated alkyl group;
an alkoxy group;
an aryl group;
an aryl-oxy group which may be substituted with an alkoxy group; and
an alkyl-carbonyl group,
ring $Z^1$ represents a benzene ring wherein said benzene ring has one or more substituents independently selected from
a halogen atom;
an alkyl group;
a halogenated alkyl group;
an alkenyl group which may be substituted with an aryl group;
an aryl group; and
a 5-membered heteroaryl group,
in addition to the group represented by formula —O-$A^1$ wherein $A^1$ has the same meaning as that defined above and the group represented by formula —CONH-$E^1$ wherein $E^1$ has the same meaning as that defined above.

2. The compound according to claim 1 or a salt thereof, wherein $E^1$ is a di-substituted phenyl group wherein the substituents of the di-substituted phenyl group are independently selected from
a halogen atom;
an alkyl group;
a halogenated alkyl group;
an alkoxy group; and
a phenyl-oxy group which may be substituted with an alkoxy group.

3. The compound according to claim 1 or a salt thereof, wherein $E^1$ is a di-substituted phenyl group wherein one of the substituents of the di-substituted phenyl group is trifluoromethyl group, and the other substituent is independently selected from
a halogen atom;
an alkyl group;
a halogenated alkyl group;
an alkoxy group; and
a phenyl-oxy group which may be substituted with an alkoxy group.

4. The compound according to claim 1 or a salt thereof, wherein $A^1$ is a 5 to 6-membered non-aromatic heterocyclic ring-carbonyl group wherein said 5 to 6-membered non-aromatic heterocyclic ring is selected from 1-pyrrolidinyl group, piperidino group, morpholino group, and 1-piperazinyl group, and said heterocyclic ring may be substituted with one or more substituents independently selected from
an alkyl group,
an alkyl-oxy-carbonyl group, and
a carboxy group.

5. The compound according to claim 1 or a salt thereof, wherein ring $Z^1$ is a benzene ring wherein said benzene ring has one or more substituents independently selected from a halogen atom;
an alkyl group;
a halogenated alkyl group;
an alkenyl group which may be substituted with a phenyl group,
a phenyl group, and
a 3-thienyl group,
in addition to the group represented by formula —O-$A^1$ wherein $A^1$ has the same meaning as that defined above and the group represented by formula —CONH-$E^1$ wherein $E^1$ has the same meaning as that defined above.

6. The compound according to claim 1 or a salt thereof, wherein
$A^1$ is a (pyrrolidin-1-yl)carbonyl group, a(morpholin-4-yl) carbonyl group, a (4-methylpiperazin-1-yl)carbonyl group, a [4-(ethoxycarbonyl)piperidin-1-yl]carbonyl group or a (4-carboxypiperidin-1-yl)carbonyl group,
$E^1$ is a 3,5-bis(trifluoromethyl)phenyl group, a 3-methoxy-5-(trifluoromethyl)phenyl group, a 2-chloro-5-(trifluoromethyl)phenyl group, a 2,5-bis(trifluoromethyl)phenyl group, a 2-methoxy-5-(trifluoromethyl)phenyl group or a 2-(4-methoxyphenoxy)-5-(trifluoromethyl)phenyl group,
the following partial formula ($Iz^1$-1) in the formula (I-1) containing ring $Z^1$

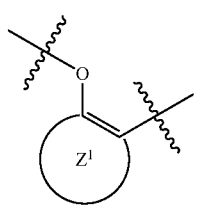
($Iz^1$-1)

is represented by the following formula ($Iz^1$-2),

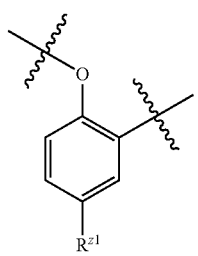
($Iz^1$-2)

wherein $R^{z1}$ represents a halogen atom a tert-butyl group, a 2-phenylethen-1-yl group, a trifluoromethyl group, a phenyl group or a 3-thienyl group.

7. The compound according to claim 6 or a salt thereof, wherein
$A^1$ is a (morpholin-4-yl)carbonyl group,
$E^1$ is a 3,5-bis(trifluoromethyl)phenyl group or a 2,5-bis(trifluoromethyl)phenyl group, and $R^{z1}$ is a halogen atom.

8. The compound according to claim 6 or a salt thereof, wherein $A^1$ is a (morpholin-4-yl)carbonyl group,
$E^1$ is a 3,5-bis(trifluoromethyl)phenyl group, and
$R^{z1}$ is a chlorine atom.

9. The compound according to claim 6 or a salt thereof, wherein
$A^1$ is a (morpholin-4-yl)carbonyl group,
$E^1$ is a 2,5-bis(trifluoromethyl)phenyl group, and
$R^{z1}$ is a bromine atom.

10. The compound according to claim 1 or a salt thereof, wherein
$E^1$ is
a di-substituted phenyl group wherein the substituents of the di-substituted phenyl group are independently selected from
a halogen atom,
an alkyl group,
a halogenated alkyl group,
an alkoxy group, and
a phenyl-oxy group which may be substituted with an alkoxy group;
a 2-methoxy phenyl group; or
a biphenyl-4-yl group.

11. The compound according to claim 1 or a salt thereof, wherein
$E^1$ is a 3,5- or 2,5-di-substituted phenyl group wherein one of the substituents of the 3,5- or 2,5-di-substituted phenyl group is trifluoromethyl group, and the other substituent is independently selected from
a halogen atom;
an alkyl group;
a halogenated alkyl group;
an alkoxy group; and
a phenyl-oxy group which may be substituted with an alkoxy group.

12. The compound according to claim 1 or a salt thereof, wherein
$E^1$ is a 3,5-bis(trifluoromethyl)phenyl group, a 2-chloro-5-(trifluoromethyl)phenyl group, a 2,5-bis(trifluoromethyl)phenyl group, a 3-methoxy-5-(trifluoromethyl)phenyl group, a 2-methoxy-5-(trifluoromethyl)phenyl group or a 2-(4-methoxyphenoxy)-5-(trifluoromethyl)phenyl group.

13. The compound according to claim 1 or a salt thereof, wherein
$A^1$ is a (pyrrolidin-1-yl)carbonyl group, a (morpholin-4-yl)carbonyl group, a (4-methylpiperazin-1-yl)carbonyl group, a [4-(ethoxycarbonyl)piperidin-1-yl]carbonyl group or a (4-carboxypiperidin-1-yl)carbonyl group.

14. The compound according to claim 1 or a salt thereof, wherein
the following partial formula ($Iz^1$-1) in the general formula containing ring $Z^1$

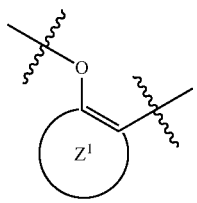
($Iz^1$-1)

is represented by the following formula (Iz$^1$-2),

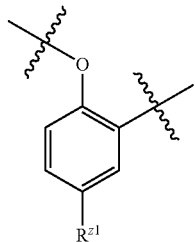

(Iz$^1$-2)

wherein R$^1$ represents
  a halogen atom,
  an alkyl group,
  a halogenated alkyl group,
  an alkenyl group which may be substituted with a phenyl group,
  a phenyl group, or
  a 3-thienyl group.

15. The compound according to claim 14 or a salt thereof, wherein
R$^{z1}$ is atom, a halogen atom, a tert-butyl group, a 2-phenylethen-1-yl group, a trifluoromethyl group, a phenyl group or a 3-thienyl group.

* * * * *